US007723029B2

(12) United States Patent
Huang et al.

(10) Patent No.: US 7,723,029 B2
(45) Date of Patent: *May 25, 2010

(54) BIOCHIPS INCLUDING ION TRANSPORT DETECTING STRUCTURES AND METHODS OF USE

(75) Inventors: Mingxian Huang, San Diego, CA (US); David Rothwarf, La Jolla, CA (US); Jia Xu, San Diego, CA (US); Xiaobo Wang, San Diego, CA (US); Lei Wu, San Diego, CA (US); Antonio Guia, San Diego, CA (US)

(73) Assignee: Aviva Biosciences Corporation, San Diego, CA (US)

( * ) Notice: Subject to any disclaimer, the term of this patent is extended or adjusted under 35 U.S.C. 154(b) by 525 days.

This patent is subject to a terminal disclaimer.

(21) Appl. No.: 11/153,825

(22) Filed: Jun. 15, 2005

(65) Prior Publication Data

US 2005/0266478 A1 Dec. 1, 2005

Related U.S. Application Data

(63) Continuation of application No. 10/642,014, filed on Aug. 16, 2003, now abandoned, which is a continuation-in-part of application No. 10/351,019, filed on Jan. 23, 2003, now abandoned.

(60) Provisional application No. 60/351,849, filed on Jan. 24, 2002, provisional application No. 60/380,007, filed on May 4, 2002.

(51) Int. Cl.
*C12Q 1/68* (2006.01)

(52) U.S. Cl. .......................................... 435/6

(58) Field of Classification Search ........................ None
See application file for complete search history.

(56) References Cited

U.S. PATENT DOCUMENTS

| 3,364,087 | A | 1/1968 | Solomon et al. |
|---|---|---|---|
| 3,410,979 | A | 11/1968 | Larson |
| 4,055,799 | A | 10/1977 | Coster et al. |
| 4,160,645 | A | 7/1979 | Ullman |
| 4,275,149 | A | 6/1981 | Litman et al. |
| 4,318,980 | A | 3/1982 | Boguslaski et al. |
| 4,324,255 | A | 4/1982 | Barach et al. |
| 4,454,032 | A | 6/1984 | Dupont |
| 4,894,343 | A | 1/1990 | Tanaka et al. |
| 4,894,443 | A | 1/1990 | Greenfield et al. |
| 5,079,169 | A | 1/1992 | Chu et al. |
| 5,364,744 | A | 11/1994 | Buican et al. |
| 5,389,215 | A | 2/1995 | Horiuchi et al. |
| 5,422,272 | A | 6/1995 | Papp et al. |
| 5,506,141 | A | 4/1996 | Weinreb et al. |
| 5,585,277 | A | 12/1996 | Bowie et al. |
| 5,612,474 | A | 3/1997 | Patel |
| 5,653,939 | A | 8/1997 | Hollis et al. |
| 5,661,035 | A | 8/1997 | Tsien et al. |
| 5,679,582 | A | 10/1997 | Bowie et al. |
| 5,840,041 | A | 11/1998 | Petter et al. |
| 5,846,396 | A | 12/1998 | Zanzucchi et al. |
| 5,858,666 | A | 1/1999 | Weiss |
| 5,880,071 | A | 3/1999 | Parce et al. |
| 5,883,760 | A | 3/1999 | Yamada et al. |
| 5,932,485 | A | 8/1999 | Schofield |
| 5,948,684 | A | 9/1999 | Weigl et al. |
| 5,972,710 | A | 10/1999 | Weigl et al. |
| 5,981,268 | A | 11/1999 | Kovacs |
| 5,998,129 | A | 12/1999 | Schutze et al. |
| 6,063,260 | A | 5/2000 | Oleson |
| 6,071,702 | A | 6/2000 | Yamamoto et al. |
| 6,107,066 | A | 8/2000 | Tsien et al. |
| 6,117,291 | A | 9/2000 | Olesen et al. |
| 6,120,666 | A | 9/2000 | Jacobson et al. |
| 6,159,749 | A | 12/2000 | Liu |
| 6,171,865 | B1 | 1/2001 | Weigl et al. |
| 6,177,000 | B1 | 1/2001 | Peterson |
| 6,225,059 | B1 | 5/2001 | Ackley et al. |
| 6,251,691 | B1 | 6/2001 | Seul |
| 6,267,872 | B1 | 7/2001 | Akeson et al. |

(Continued)

FOREIGN PATENT DOCUMENTS

EP 1195432 A2 10/2002

(Continued)

OTHER PUBLICATIONS

U.S. Appl. No. 10/351,019, filed Jan. 23, 2003.

(Continued)

*Primary Examiner*—Young J Kim
(74) *Attorney, Agent, or Firm*—Morrison & Foerster LLP

(57) ABSTRACT

The present invention recognizes that the determination of an ion transport function or property using direct detection methods, such as patch-clamps, whole cell recording or single channel recording, are preferable to methods that utilize indirect detection methods, such as FRET based detection system. The present invention provides biochips and methods of use that allow for the direct analysis of ion transport functions or properties using microfabricated structures that can allow for automated detection of one or more ion transport functions or properties. These biochips and methods of use thereof are particularly appropriate for automating the detection of ion transport functions or properties, particularly for screening purposes.

34 Claims, 43 Drawing Sheets

U.S. PATENT DOCUMENTS

| | | | |
|---|---|---|---|
| 6,284,113 | B1 | 9/2001 | Bjornson et al. |
| 6,284,459 | B1 | 9/2001 | Nova et al. |
| 6,315,940 | B1 | 11/2001 | Nisch |
| 6,352,853 | B1 | 3/2002 | King et al. |
| 6,355,491 | B1 | 3/2002 | Zhou et al. |
| 6,387,707 | B1 | 5/2002 | Weigl et al. |
| 6,416,642 | B1 | 7/2002 | Alajoki et al. |
| 6,448,794 | B1 | 9/2002 | Cheng et al. |
| 6,488,829 | B1 * | 12/2002 | Schroeder et al. ...... 204/403.01 |
| 6,613,211 | B1 * | 9/2003 | McCormick et al. ........ 204/601 |
| 6,699,697 | B2 | 3/2004 | Klemic |
| 6,758,961 | B1 | 7/2004 | Vogel |
| 6,766,817 | B2 | 7/2004 | Da Silva |
| 6,936,462 | B1 | 8/2005 | Owen |
| 2002/0006357 | A1 | 1/2002 | McGeoch |
| 2002/0014408 | A1 | 2/2002 | Schroeder |
| 2002/0022219 | A1 | 2/2002 | Clements et al. |
| 2002/0025573 | A1 | 2/2002 | Maher et al. |
| 2002/0053915 | A1 | 5/2002 | Weaver et al. |
| 2002/0063067 | A1 | 5/2002 | Bech |
| 2002/0064841 | A1 | 5/2002 | Klemic et al. |
| 2002/0086280 | A1 | 7/2002 | Lynes |
| 2002/0104757 | A1 | 8/2002 | Schmidt |
| 2002/0108869 | A1 | 8/2002 | Savtchenko |
| 2002/0123134 | A1 | 9/2002 | Huang et al. |
| 2002/0144905 | A1 | 10/2002 | Schmidt et al. |
| 2002/0146845 | A1 | 10/2002 | Parce et al. |
| 2002/0164777 | A1 | 11/2002 | Kelly et al. |
| 2002/0182627 | A1 | 12/2002 | Wang et al. |
| 2002/0195337 | A1 | 12/2002 | Osipchuk et al. |
| 2003/0031829 | A1 | 2/2003 | Tanner et al. |
| 2003/0052002 | A1 | 3/2003 | Vogel et al. |
| 2003/0098248 | A1 | 5/2003 | Vogel et al. |
| 2003/0146091 | A1 | 8/2003 | Vogel et al. |
| 2004/0146849 | A1 | 7/2004 | Huang et al. |

FOREIGN PATENT DOCUMENTS

| | | | |
|---|---|---|---|
| WO | WO 94/25862 | | 10/1994 |
| WO | WO 96/13721 | | 5/1996 |
| WO | WO 98/50791 | A1 | 11/1998 |
| WO | WO 99/19729 | | 4/1999 |
| WO | WO 99/31503 | | 6/1999 |
| WO | WO 99/66329 | | 12/1999 |
| WO | WO 00/25121 | | 5/2000 |
| WO | WO 00/54882 | A1 | 9/2000 |
| WO | WO 00/71742 | A2 | 11/2000 |
| WO | WO 02/004943 | A2 | 1/2001 |
| WO | WO 02/004943 | A3 | 1/2001 |
| WO | WO 01/25769 | A2 | 4/2001 |
| WO | WO 01/27614 | A1 | 4/2001 |
| WO | WO 01/34764 | A2 | 5/2001 |
| WO | WO 01/48474 | A1 | 7/2001 |
| WO | WO 01/59447 | A1 | 8/2001 |
| WO | WO 01/69241 | | 9/2001 |
| WO | WO 01/25769 | A2 | 12/2001 |
| WO | WO 01/25769 | A3 | 12/2001 |
| WO | WO 02/52045 | | 1/2002 |
| WO | WO 02/12986 | A1 | 2/2002 |
| WO | WO 02/16647 | A1 | 2/2002 |
| WO | WO 02/24862 | | 3/2002 |
| WO | WO 02/27909 | A2 | 4/2002 |
| WO | WO 02/28523 | A2 | 4/2002 |
| WO | WO 02/29400 | | 4/2002 |
| WO | WO 02/29402 | A2 | 4/2002 |
| WO | WO 02/29402 | A3 | 4/2002 |
| WO | WO 02/30562 | A1 | 4/2002 |
| WO | WO 02/31505 | A1 | 4/2002 |
| WO | WO 02/31506 | A1 | 4/2002 |
| WO | WO 02/42766 | A2 | 5/2002 |
| WO | WO 02/42766 | A3 | 5/2002 |
| WO | WO 02/059603 | | 8/2002 |
| WO | WO 02/065092 | A2 | 8/2002 |
| WO | WO 02/066596 | | 8/2002 |
| WO | WO 02/075309 | | 9/2002 |
| WO | WO 02/077259 | | 10/2002 |
| WO | WO 03/093494 | | 11/2003 |

OTHER PUBLICATIONS

U.S. Appl. No. 10/642,014, filed Aug. 16, 2003.
Non-Final Office Action for U.S. Appl. No. 10/642,014, date mailed on Feb. 23, 2005.
Response to Office Action for U.S. Appl. No. 10/642,014, filed Aug. 16, 2005.
Non-Final Office Action for U.S. Appl. No. 10/642,014, date mailed on Nov. 22, 2005.
U.S. Appl. No. 60/164,128, filed Nov. 8, 1999, Schmidt.
U.S. Appl. No. 60/322,365, filed Sep. 14, 2000, Schmidt.
U.S. Appl. No. 60/233,800, filed Sep. 19, 2000, Schmidt.
U.S. Appl. No. 60/322,178, filed Sep. 13, 2001, Schmidt.
Gutmann et al., Pharma. Research 16: 402-407 (1999).
Luong et al., Anal. Chem. 73: 1844-1848 (2001).
Wegener et al., Exp. Cell Research 259:158-166 (2000).
Xiao et al., Anal. Chem. 74:5748-5753 (2002).
Xiao et al., Biotechnol. Prog. 19:1000-1005 (2003).
Lindner et al., Microelectronic Engineering 41/42: 75-78 (1998).
Vogler et al., Microelectronic Engineering 53: 149-152 (2000).
Nehr et al., Pflueger Arch., 375:219-278 (1978).
Liem et al., Neurosurgery, 36: 382-392 (1995).
Nehr and Sakman, Scientific American, 266:44-51 (1992).
Sakman and Nehr, Ann. Rev. Physiol., 46:455-472 (1984).
Cahalan and Nehr, Methods in Enzymology, 207:3-14 (1992).
Levis and Rae, Mehods in Enzymology, 207:14-66 (1992).
Armstrong and Gilly, Methods in Enzymology, 207:100-122 (1992).
Heinmann and Conti, Methods in Enzymology, 207:131-148 (1992).
Bean, Methods in Enzymology, 207:181-193 (1992).
Lester, Ann. Rev. Physiol., 53:477-496 (1991).
Hamill and McBride, Ann. Rev. Physiol., 59:621-637 (1997).
Bustamante and Verranda, Brazilian Journal.,31:333-354 (1998).
Martinez-Pardon and Ferrus, Current Topics in Developmental. Biol., 36:303-312 (1998).
Herness, Physiology and Behavior, 69:17-27 (2000).
Wang et al., IEEE Transaction on Industry Applications, 33(3):660-669 (1997).
Cheng et al., Nature Biotechnology, 16:541-546 (1998).
Markx et al., Microbiology, 140:585-591 (1994).
Huang and Pethig, Meas. Sci. Technol., 2:1142-1146 (1991).
Gascoyne et al., IEEE Transactions, 33(3):670-678 (1997).
De Gasperis et al., Biomedical Microdevices, 2:41-49 (1999).
Wang et al., Biochim. Biophys. Acta., 1243:185-194 (1995).
Wang et al., Biophys. J., 74:2689-2701 (1998).
Huang et al., Biophys J., 73:1118-1129 (1997).
Yang et al., Anal. Chem., 71(5):911-918 (1999).
Becker et al., Proc. Natl Acad. Sci. USA, 92:860-864 (1995).
Becker et al., J. Phys. D: Appl. Phys., 27:2659-2662 (1994).
Huang et al., J. Phys. D: Appl. Phys., 26:1528-1535 (1993).
Wang et al., J. Phys. D: Appl. Phys., 26:1278-1285 (1993).
Stephens et al., Bone Marrow Transplantation, 18:777-782 (1996).
Washizu et al., IEEE Trans Ind. Appl., 30:835-843 (1994).
Hughes et al., Biochim. Biophys. Acta., 1425:119-126 (1998).
Morgan et al., Biophys. J., 77:516-525 (1999).
Fuhr et al., Biochim. Biophys. Acta., 1108:215-233 (1992).
Washizu et al., IEEE Trans. Ind. Appl., 26:352-358 (1990).
Fiedler et al., Anal. Chem., 70:1909-1915 (1998).
Muller et al., Biosensors and Bioelectronics, 14:247-256 (1999).
Schnelle et al., Biochim. Biophys. Acta. 1157:127-140 (1993).
Morgan et al., J. Micromech. Microeng., 7:65-70 (1997).
Wang et al., Biophys. J., 72:1887-1899 (1997).
Batra et al., Molecular Immunol., 30:379-386 (1993).
Huston et al., Proc. Natl. Acad. Sci., USA, 85:5879-5883 (1998).
Whitlow et al., Protein Engineering, 6:989-995 (1993).
Newton et al., Biochemistry, 35:545-553 (1996).
Cumber et al., Bioconj. Chem., 3:397-401 (1992).

Ladurner et al., J. Mol. Biol., 273:330-337 (1997).
Ahn et al., J. Microelectromechanical systems, 5:151-158 (1996).
Liakopoulos et al., Transducers 97, pp. 484-488, presented in 1997 international conference on solid state sensors and actuators, Chicago, Jun. 16, 1997.
Safarik and Safarikova, J. Chromotography, 722(B):33-53 (1999).
Fuhr et al., Biochim. Biophys. Acta., 1269:221-232 (1995).
Course Description for MEM System taught by James Klemic.
Protein Chip Data Archive Archive-Yale Gershein Lab, http://entry.eng.yale.edu/genome/yeast/chip Mar. 13, 2001.
Zhu et al., Nature Genetics, 26:283-289 (2000).
About Axon Instruments (Axoclamp and Axopatch Series Microelectrode Amplifiers).
Axon Instruments, Inc. Press Release Apr. 17, 2001.
Micro Vacuum Ltd. A Surface Engineering Approach Towards the Development of Cell Based Biochips, www.microvacuum.com/research/memocs/meeting1/.
Aston-Jones and Siggins, www.acnp.org/GA/GN401000005/CH005.html.
Straub et al., Nature Biotechnology, 19:121-124 (2001).
Chun et al., IEEE, pp. 406-411 (1999).
Erbe et al., App. Phys. Lett., 77(19):3102-3104 (2000).
Tilke et al., Superlattices and Microstructures, 27(5/6):597-601 (2000).
Blick et al., Physics 6 E pp. 821-827 (2000).
Krommer et al., Europhys. Lett., 50(1):101-106 (2000).
Fertig et al., Appl. Phys. Lett., 77(8)1218-1220 (2000).
Islas and Sigworth, J. Gen. Physiol., 117(1):69-68 (2001) (Abstract).
Presentation—Cambridge Healthtech Institutes HTT Expo (High-Throughput Technologies), Philadelphia Jun. 13, 2001.
Automated Patch-Clamp, CeNes Ltd. Homepage.
Vegel, Development of Bioassays for Odorant Molecule Analysis, www.ehrat.ch/topnano21/english/11e.html (Abstract).
Vegel, http://bioweb.psi.ch/abstracts.html (Abstract).
Axon Instruments Inc., Press Release Oct. 30, 2000.
Axon Instruments Inc., Press Release May 25, 2000.
Axon Instruments, Inc., Press Release Aug. 29, 2000.
Patch Clamp-Method of Choice for Receptor Analysis, www.cytion.com/principe.htm.
Summary of Projects in the Laboratory of Dr. Albert Folch.
Liu et al., J. Chromotogr., 891(1):149-156 (2000) (Abstract).
Niwa et al., Anal. Chem., 72(5):949-955 (2000) (Abstract).
Niwa et al., Anal. Chem., 68(11):18650-1870 (1996) (Abstract).
Ryttsen, et al., Biophys. J., 79(4):1993-2001 (2000) (Abstract).
Chiu et al., Science, 283(5409):1892-1895 (Abstract).
Jardemark et al., Anal. Chem., 70(13):2468-1474 (Abstract).
Almers et al., J. Physiol. 312:159-176 (1981).
Costa et al., Biophysical Journal 64:395-401 (1994).
Karnakis et al, Proc. SPIE 4443:150-158 (2001) Abstract.
Dunsky, Proc. SPIE 4443:135-149 (2001) Abstract.
Nishimae, Proc. SPIE 4088:209-211 (2000) Abstract.
Okada, Proc. SPIE 4088:148-153 (2000) Abstract.
Asada, Proc. SPIE 4088:132-135 (2000) Abstract.
Knowles, Proc. SPIE 3888:210-216 (2000) Abstract.
Madou, Proc. SPIE 3877:44-53 (1999) Abstract.
Kreutz, Proc. SPIE 2879:37-44 (1996) Abstract.
Mathes, DDT 8:1022-1024 (2003).
Xiao et al., Anal. Chem 74:1333-1339 (2002).
Wang and Li, Assay and Drug Devel. Technol. 1:1-13 (2003).

* cited by examiner

A

B

C

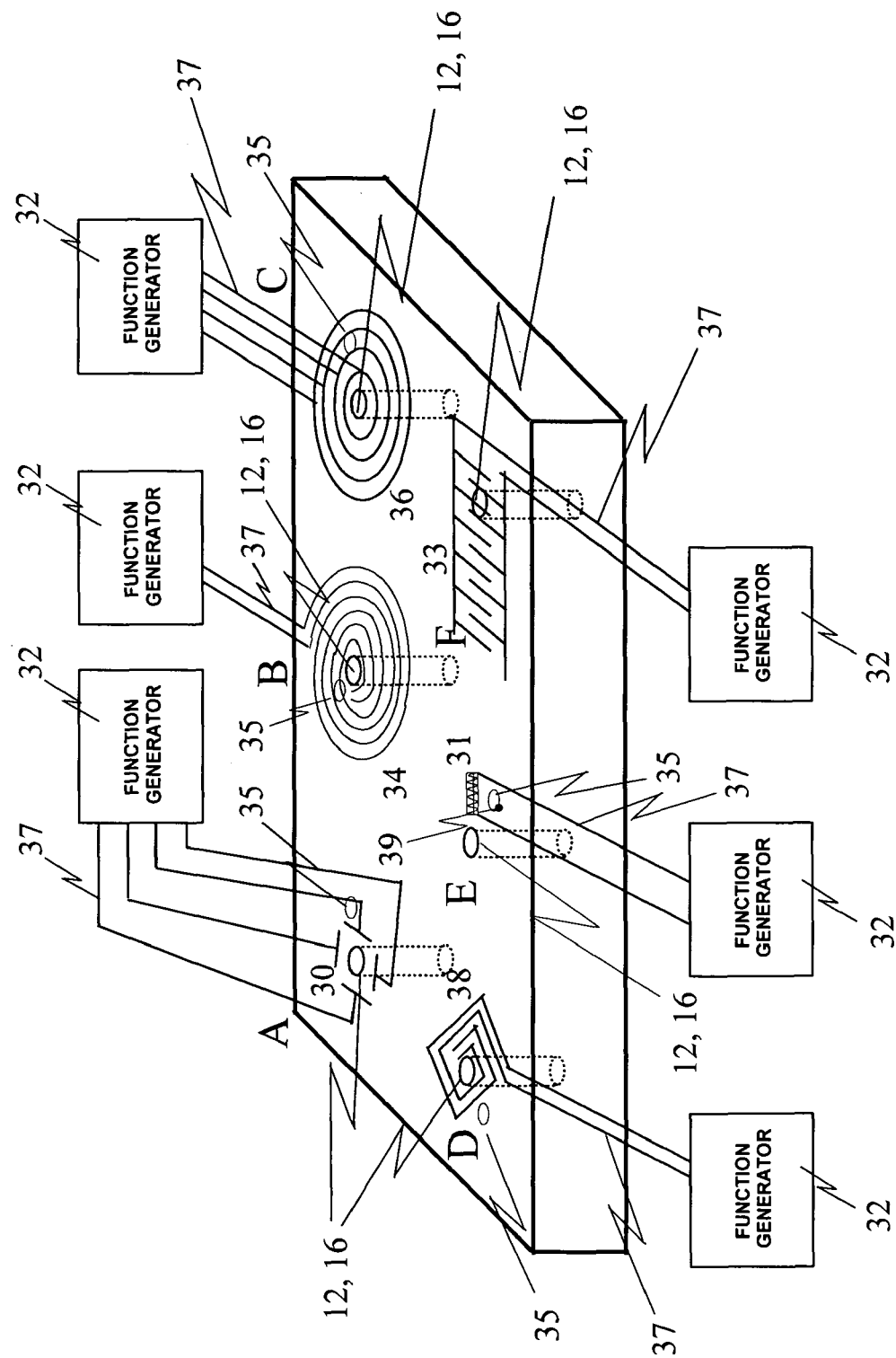
FIG. 3A - F (*) The measurement of device (63) optionally is not within the substrate (10).

⊛ The electrode (60) can be positioned in either configuration.

* Signal source can be AC or DC.
Typically, the signal source is integral to the measuring device, but this is not a requirement.

| | |
|---|---|
| I | Viability Unit |
| II | Ion Transport Unit |
| III | Fluorescence Unit |
| IV | Proteomics Unit |
| V | Genomics Unit |
| VI | Separation of Particles |

(A)

(B)

(A)    (B)

(A)

(B)

(A)

(B)

BIOCHIPS INCLUDING ION TRANSPORT DETECTING STRUCTURES AND METHODS OF USE

This application is a continuation of U.S. patent application Ser. No. 10/642,014 filed Aug. 16, 2003 now abandoned, which is a continuation in part of U.S. application Ser. No. 10/351,019 filed Jan. 23, 2003 now abandoned, naming Mingxian Huang, David Rothwarf, Jia Xu, Xiaobo Wang, Lei Wu and Antonio Guia as inventors, each of which are herein incorporated by reference in its entirety. U.S. application Ser. No. 10/642,014 also claims benefit of priority to U.S. Provisional Application 60/351,849, filed Jan. 24, 2002, naming Xiaobo Wang, Lei Wu, Junquan Xu, Mingxian Huang, Weiping Yang, Jing Chen, Jia Xu, Antonio Guia, and David Rothwarf as inventors; and to U.S. Provisional Application 60/380,007, filed May 4, 2002, naming Xiaobo Wang, Lei Wu, Junquan Xu, Mingxian Huang, Jia Xu, Antonio Guia, and David Rothwarf as inventors, each of which are incorporated by reference in their entirety.

TECHNICAL FIELD

The present invention relates generally to the field of ion transport detection systems and methods, particularly those that relate to the use of biochip technologies. Such biochip technologies can include micromanipulation methods to direct particles, such as cells, to areas on a biochip that have ion transport detection or measuring structures.

BACKGROUND

Ion transports are located within cellular membranes and regulate the flow of ions across the membrane. Ion transports participate in diverse processes, such as generating and timing of action potentials, synaptic transmission, secretion of hormones, contraction of muscles etc. Ion transports are popular candidates for drug discovery, and many known drugs exert their effects via modulation of ion transport functions or properties. For example, antiepileptic compounds such as phenyloin and lamotrigine which block voltage dependent sodium ion transports in the brain, anti-hypertension drugs such as nifedipine and diltiazem which block voltage dependent calcium ion transports in smooth muscle cells, and stimulators of insulin release such as glibenclamide and tolbutamine which block an ATP regulated potassium ion transport in the pancreas.

One popular method of measuring an ion transport function or property is the patch-clamp method, which was first reported by Neher, Sakmann and Steinback (Pflueger Arch. 375:219-278 (1978)). This first report of the patch clamp method relied on pressing a glass pipette containing acetylcholine (Ach) against the surface of a muscle cell membrane, where discrete jumps in electrical current were attributable to the opening and closing of Ach-activated ion transports.

The method was refined by fire polishing the glass pipettes and applying gentle suction to the interior of the pipette when contact was made with the surface of the cell. Seals of very high resistance (between about 1 and about 100 giga ohms) could be obtained. This advancement allowed the patch clamp method to be suitable over voltage ranges which ion transport studies can routinely be made.

A variety of patch clamp methods have been developed, such as whole cell, vesicle, outside-out and inside-out patches (Liem et al., Neurosurgery 36:382-392 (1995)). Additional methods include whole cell patch clamp recordings, pressure patch clamp methods, cell free ion transport recording, perfusion patch pipettes, concentration patch clamp methods, perforated patch clamp methods, loose patch voltage clamp methods, patch clamp recording and patch clamp methods in tissue samples such as muscle or brain (Boulton et al, Patch-Clamp Applications and Protocols, Neuromethods V. 26 (1995), Humana Press, New Jersey).

These and later methods relied upon interrogating one sample at a time using large laboratory apparatus that require a high degree of operator skill and time. Attempts have been made to automate patch clamp methods, but these have met with little success. Alternatives to patch clamp methods have been developed using fluorescent probes, such as cumarin-lipids (cu-lipids) (Tsien et al., U.S. Pat. No. 6,107,066, issued August 2000). These methods rely upon change in polarity of membranes and the resulting motion of cu-lipids across the membrane. This motion allows for detection using fluorescence resonance energy transfer (FRET). Unfortunately, these methods do not measure ion transport directly but measure the change of indirect parameters as a result of ionic flux. For example, the characteristics of the lipid used in the cu-lipid can alter the biological and physical characteristics of the membrane, such as fluidity and polarizability.

Thus, what is needed is a simple device and method to measure ion transport directly. Preferably, these devices would utilize patch clamp detection methods because these types of methods represent a gold standard in this field of study. The present invention provides these devices and methods particularly miniaturized devices and automated methods for the screening of chemicals or other moieties for their ability to modulate ion transport functions or properties.

BRIEF DESCRIPTION OF THE FIGURES

FIG. 1A depicts a biochip of the present invention with a coating. FIG. 1B depicts a cross section of FIG. 1A along "1-1" showing the coating in place. FIG. 1C depicts a biochip not having a coating. Although cylinder-shaped holes (12) are depicted in FIG. 1A-FIG. 1C, the holes can be of any regular or irregular geometry, as long as the holes, with or without the coating (14), allow adequate electric seals or electronic seals (high resistance seals, for example, mega ohms and giga ohms) between the membranes of the particles (for example cells, artificial vesicles, cell fragments) and the substrates or the holes for appropriate electrophysiological measurement of ion transports located in the membranes. For example, in the cross sectional view depicted in FIG. 1A and FIG. 1C, the holes (12) do not have to be vertically straight and can have a funnel shape, as shown in, for example, FIG. 2B. The coating (14) depicted in FIG. 1A and FIG. 1B may be the same or similar material as the substrate (10). For example, the coating (14) can be a functionalized surface having appropriate electric charge, hydrophilicity or hydrophobicity, texture (for example, smoothness) and/or composition, for facilitating or enhancing high-resistance sealing (for example electric seals or electronic seals) between the substrates or holes and the membranes of the particles under electrophysiological measurement. Examples of the coating materials include glass materials and silicon dioxide deposited on the substrate by different methods such chemical vapor deposition and physical vapor deposition (e.g. sputtering or evaporation).

FIG. 2A depicts the biochip of FIG. 1A with a cell (24) engaged thereto. FIG. 2B depicts a substrate (10) with a coating (14), wherein the substrate has been machined or etched to form a funnel shaped structure (20) continuous with a hole in the substrate (10). This funnel shaped structure (20) can allow for less rigorous manufacturing parameters as compared to the straight walled holes (12) depicted in FIG. 2A. A cell (24) is depicted engaged on the structure of FIG. 2B. FIG. 2C depicts the structure of FIG. 2B inverted with a cell (24) engaged thereto. FIG. 2D depicts a structure having a double funnel structure (20, 22) that defines a hole (12) in the substrate (10). FIG. 2E depicts a substrate (10) with a smaller hole (12) with a funnel structure (20) engaged with a cell (24) with electrodes (60, 61) placed on alternate surfaces of the biochip. Although holes of particular shapes and dimensions are depicted, the holes can be of any appropriate shape or dimensions. Shapes of holes can be geometric or non-geometric, such as circular, oval, square, triangular, pentagonal, hexagonal, heptagonal, octagonal or the like. Non-geometrical shapes such as kidney bead or other shapes are also appropriate. Geometric shapes can have the advantage of allowing higher density packing of holes, such as in a honeycomb configuration. The diameter or cross section of the holes at the portion where a particle is contacted can be of any appropriate size, but is preferably between about 0.1 micrometer and about 100 micrometers, more preferably between about 1 micrometer and about 10 micrometers.

FIG. 3 depicts a variety of particle positioning means provided on a biochip of the present invention. The particle positioning means can be provided on the surface of the substrate, coated by a coating or be imbedded within the substrate. FIG. 3A depicts a quadropole electrode structure or electrorotation structure (30) useful for positioning particles (35) at or near a hole (12, 16) wherein the electrical connection leads (37) thereto are operably connected with an electrical signal source (32), such as a sine wave generator (which can also provide signals other than sine waves), to allow modulation of current at the electrode structures to allow positioning of particles (35). FIG. 3B depicts a spiral electrode structure (34), circular in nature, that is useful for positioning particles (35) at or near a hole (12, 16) wherein the depicted electrical connection leads (37) are operably engaged with an electrical signal source (32). The number of spiral electrode structures is preferably three or more, and more preferably between about three and about ten. The electrodes structures are preferably parallel at the tangent. FIG. 3C depicts a concentric electrode structure (36), circular in nature, that is useful for positioning particles (35) at or near a hole (12, 16) wherein the depicted electrical connection leads (37) are operably engaged with an electrical signal source (32). FIG. 3D depicts a square electrode structure (38), square in nature, that is useful for positioning particles (35) at or near a hole (12, 16) wherein the depicted electrical connection leads (37) are operably engaged with an electrical signal source (32). FIG. 3E depicts an electromagnetic electrode (31), that is useful for positioning particles (35) having bound thereto a magnetic moiety (39) at or near a hole (12, 16) wherein the depicted electrical connection leads (37) are operably engaged with an electrical signal source (32). FIG. 3F depicts a traveling wave dielectrophoresis structure (33), that is useful for positioning particles (35) at or near a hole (12, 16) wherein the depicted electrical connection leads (37) are operably engaged with an electrical signal source (32).

FIG. 5A depicts such a structure with a coating (50) over all surfaces. The coating can be made of appropriate materials, such as polymers or functional coatings that can allow for immobilization of materials such as biological moieties or chemical moieties. The coating can also include binding members, such as specific binding members, such as antibodies, that can facilitate the localization or immobilization of particles such as cells at or near the hole (12). In one aspect of the present invention, the coating is made of a polymer that has the characteristic of changing size with temperature. By changing in size (e.g., increasing or decreasing), the polymer can promote the formation of an efficient seal between a particle (24) such as a cell and the hole. In another aspect of the present invention, the substrate can be of any suitable material that provides a surface, including but not limited to one or more plastics, ceramics, metals, fibers, polymers (e.g., polyimide, polyamide, polycarbonate, polypropylene, polyester, mylar, teflon), silicon, silicon dioxide, or glass, and the coating can be a glass coating, silicon, silicon dioxide, that is deposited on the top of the substrate. The glass can optionally be further treated, for example, with chemicals (e.g, acid, base solutions), or by baking or polishing, to improve its electronic sealing properties. In FIG. 5B the coating (52) is depicted as being localized to an area in close proximity to the hole (12) in the substrate. In one aspect of the present invention, the coating in this configuration includes specific binding members present on particles such as cells. In FIG. 5C (54) the coating is depicted as being localized to the hole (12) and optionally surrounding areas. This configuration can promote a strong seal (for example a high resistance seal) between the cell and the hole (12). In one aspect of the present invention, the substrate (10) is made of silicon. The substrate (10) is then heated to make a structure that includes the substrate (10) of silicon and a coating (50) of silicon dioxide. FIG. 5D depicts one aspect of the present invention where the coating (56) is localized in the hole and the surrounding areas on the bottom of the substrate (10). The coating (56) is of material, such as detergent or lipid binding proteins, preferably provided in a matrix such as polymer matrix that can dissolve or weaken membrane lipids or structure. As an example, use of this device to measure ion transport function or properties in eukaryotic cells such as mammalian cells, a cell is pushed or pulled into a hole (12) to achieve appropriate electric sealing, for example a 1 giga-ohm seal, between the cell membrane and the hole. When membrane patch of the cell is pushed or pulled down into the hole to be in contact with the coating (56) the lipid molecules in the membrane that are in contact or in close proximity with the coating (56) will dissolve or weaken by action of the coating (56). As a result, the membrane patch breaks off or is otherwise removed from the cell. This coating (56) serves as a means to rupture a membrane patch for certain whole cell ion transport assay methods. As illustrated here, the coating (50, 52, 54, or 56) of appropriate compositions may serve different purposes or functions such as promoting a strong seal (5C) between the cell and the hole and rupturing (5D) a membrane patch of the cell being assayed. Different coatings may be employed for different purposes. For example, the coating (for example, 54) may be functionalized surfaces having appropriate electric charge (for example, positive or negative charges), hydrophilicity or hydrophobicity, texture (for example, smoothness) and/or composition, which may facilitate and enhance high-resistance sealing between the substrates or holes and the membranes of the particles under electrophysiological measurement. Functionalized surfaces (for example 54) may be the same or similar in composition as the substrate (10), but with appropriate surface properties such as smoothness and electrical charge. The functionalized surfaces may be made by modification of the substrate, such as chemical modification or chemical treatment, by deposition onto a surface (such as, for example, by chemical vapor deposition (CVD), or by physical vapor deposition including, for example, sputtering and evaporation), or by coating a surface (for example, by spin coating). Those skilled in the art of microfabrication can readily choose and determine appropriate procedures and protocols for depositing or coating materials such as glass, silicon dioxide onto the substrates.

FIG. 6B is viewed from the top of FIG. 6A, similar structures can be provided as electrodes (61) as viewed from the bottom of FIG. 6B. The electrodes (61) can be provided in or outside of the funnel structure (22) when present.

In FIG. 9A, a particle (24) such as a cell is engaged with the protrusions or wires (80). This is preferably accomplished by applying a positive or negative force, such as depicted in FIG. 7. The particle, such as a cell, is ruptured, such as through a pulse of force, to form a whole cell configuration. The electrical connection leads (62) from the electrodes (60, 61) connect to a measuring device (63) that can monitor and optionally record the electric properties in the circuit completed as depicted by the dashed line.

FIG. 16 depicts the manufacture and use of needle structures for ion transport function or transport determinations.

FIG. 18 depicts chambers (190) being formed by a top channel (192) and a bottom channel (194) that can be made using appropriate methods such as etching, machining or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel function detecting structure, such as an aperture (195).

FIG. 35 shows the microscopic images of a 150 micron dielectrophoresis positioning structure.

SUMMARY

Figure 1:
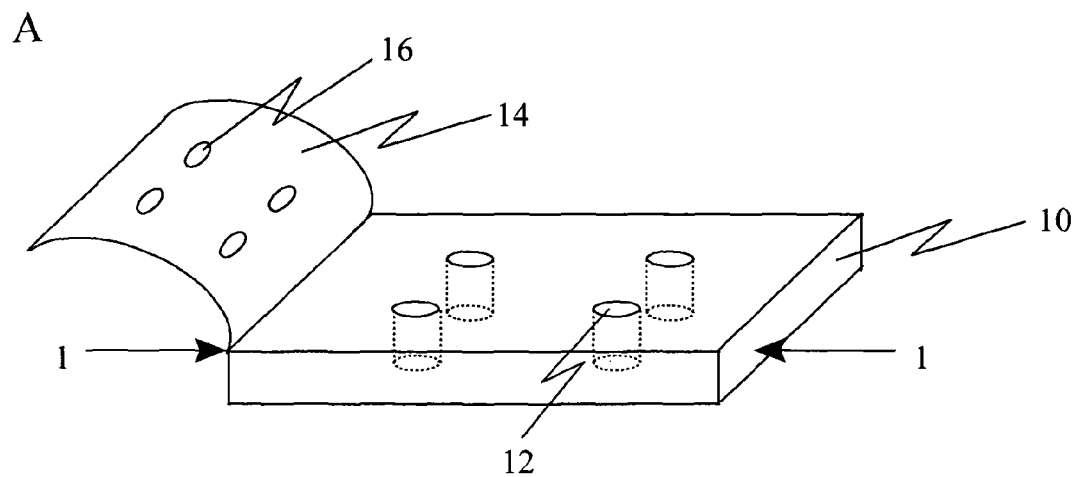
FIG. 1A, FIG. 1B and FIG. 1C depict one aspect of a biochip of the present invention. A substrate (10) made of appropriate material, such as fused silica, glass, silica, $SiO_2$, silicon, rubber, ceramics, PTFE, plastics, polymers or a combination or combinations thereof can define holes (12) that form ion transport measuring means, or at least in part ion transport measuring means, of the present invention. Optionally, a coating (14) such as a polymer coating can be placed on top of the surface of the substrate. The coating can include functional groups to aid in the localization and immobilization particles at or near the holes (12). Such functional groups can include, for example, specific binding members that can facilitate such localization or immobilization of particles. The coating can also define holes (16) that can functionally engage the holes (12) defined by the substrate (10). In one aspect of the present invention, such holes (16) in the coating (14) are preferable because the accuracy and precision for machining or molding such holes in the coating is better suited for the coating (14) rather than the substrate (10). For example, it is more efficient, accurate and precise to manufacture holes in the thin coating (14) rather than the relatively thick substrate (10). This is particularly true when the coating (14) is made of polymers whereas the substrate (10) is made of harder materials that may be less suitable for machining, etching or molding, such as silica.
Figure 1:
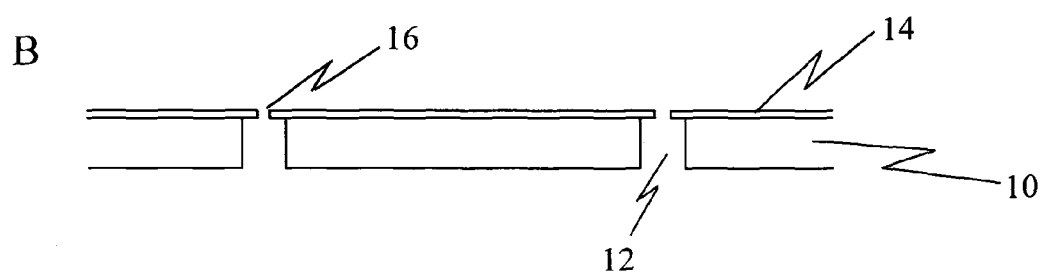
Figure 1:
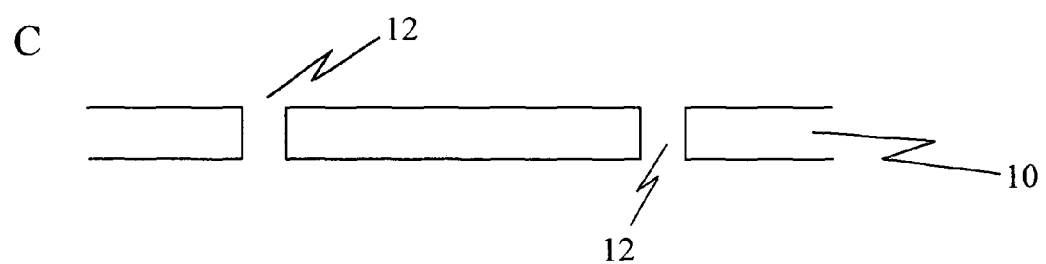

The present invention recognizes that the determination of one or more ion transport functions or properties using direct detection methods, such as patch-clamp, whole cell recording, or single channel recording, are preferable to methods that utilize indirect detection methods, such as fluorescence-based detection systems. The present invention provides biochips and methods of use that allow for the direct analysis of ion transport functions or properties using microfabricated structures that can allow for automated detection of ion transport functions or properties. These biochips and methods of use thereof are particularly appropriate for automating the detection of ion transport functions or properties, particularly for screening purposes.

A first aspect of the present invention is a biochip cell positioning device and methods of use. The biochip preferably includes particle positioning means and ion transport measuring means. The particle positioning means are preferably active upon cells such as eukaryotic cells using appropriate forces, particularly dielectric forces. The ion transport measuring means can be any appropriate, such as but not limited to patch clamp detection means, whole cell detection means, single ion transport detection means and the like.

A second aspect of the present invention is an array of capillaries on a biochip and methods of use. The array of capillaries is preferably microfabricated and integrated onto the chip such that they are useful in ion transport determinations. In one aspect of the present invention, the capillaries can be used as the basis of patch clamp assay methods, whole cell assay methods or single channel assay methods.

A third aspect of the invention is an array of needle electrodes on a biochip and methods of use. The array of needle electrodes is preferably microfabricated such that they are useful in ion transport determinations. These structures are particularly useful in ion transport determinations using whole cells.

A fourth aspect of the invention is an array of holes on a biochip and methods of use. The holes are preferably microfabricated and are useful as part of methods for the determination of one or more ion transport functions or properties. The holes can be used in patch clamp methods such as whole cell or single ion channel methods. In one aspect of the present invention, the holes can be used in whole cell or single ion channel methods, particularly when negative pressure is applied upon a solution through such holes. In another aspect of the present invention, the surface of the substrate around and preferably within the hole is negatively charged and is capable of engaging particles such as biological cells, vesicles, and/or membrane organelles with a high resistance electric seal. In another aspect of the present invention, the surface of the substrate around and preferably within the hole has been treated in acidic and/or basic solutions and is capable of engaging particles such as biological cells, vesicles, and/or membrane organelles with a high resistance electric seal. In one particular embodiment, the substrate or coating material for the biochip is glass, one or more holes is fabricated using laser ablation, and the surface of the substrate or coating around the one or more holes has been treated in acidic and/or basic solutions.

A fifth aspect of the invention is a biochip having ion transport detection structures being "detection channels" with appropriate geometries and dimensions, which are located along the side walls of other microfluidic channels, and methods of use. This type of patch-clamp-in-a-channel technology provides means of efficient simultaneous recording on and fluid delivery to a chip of current invention.

A sixth aspect of the invention is a method for modifying at least a portion of a chip or substrate comprising at least one ion transport measuring means to enhance the electric seal of a particle or a portion thereof with an ion transport measuring means. In one aspect of the present invention, the chip or substrate comprising an ion transport measuring means is modified to become more electronegative and/or more smooth. In another aspect of the present invention, the chip or substrate comprising the ion transport measuring means is modified chemically, such as with different types of acids and bases.

A seventh aspect of the invention is the substrates, biochips, cartridges, apparatuses, and/or devices comprising ion transport measuring means with enhanced electric seal properties.

An eighth aspect of the present invention is a method for storing the substrates, biochips, cartridges, apparatuses, and/or devices comprising ion transport measuring means with enhanced electrical seal properties.

A ninth aspect of the present invention is a method for shipping the substrates, biochips, cartridges, apparatuses, and/or devices comprising ion transport measuring means with enhanced electrical seal properties.

A tenth aspect of the invention is a biochip with ion transport detection structure combined with high information content screening and methods of use. This type of on-chip procedural combination allows for high throughput detection of multiple cellular signals in a time and space-controlled manner that cannot be achieved by existing technologies.

An eleventh aspect of the invention is a biochip with three-dimensionally configured channels that can be microfabricated using sacrificial methodologies such as sacrificial wire methods and methods of use. This method provides an efficient procedure to microfabricate three-dimensional microfluidic structures that could be used for high-density bioassays and lab-on-a-chip systems.

The particle positioning means, particularly for positioning biological cells in an array format for single cell analysis, can be used with significant advantages for cell-based assays over current cell based assays. Current cell based assays analyze and examine a population of cells by measuring averaged, integrated signals and do not allow for assays at the single cell level. The cell positioning means disclosed in this application provides the devices and methods for analyzing individual cellular events in high throughput events. These analyses could be performed by reading out electrical (for example, ion transport assay) and optical signals (for example, fluorescent readout) from individual cells. With the high throughput capability for ion transport assays described in this application, one can begin to analyze intracellular signaling events influencing ion transport functions or properties in a systematic fashion. High throughput proteomics and functional analysis of ion channels can be performed at the single cell level. Furthermore, the devices and methods in the present invention allow the electrophysiological measurement of native cells isolated from tissues (normal or diseased). Such analysis would allow for more accurate determinations of cellular variation as hundreds or thousands of cells could be investigated individually for their biological, pharmacological and physiological responses. Cellular variation has proven to be a factor complicating the scientific analysis of complex systems, for example, in diseases such as arrhythmias, cancer, and nervous system disorders. The present inventions provide devices and methods to address such cellular variations by providing single cell measurement.

In addition, positioning of individual cells in an array format may permit better studies in subcellular organization and microdomain measurements. With the cells positioned, dynamic subcellular locations of cellular compartments, structures and molecules such as receptors and enzymes may be examined. Cells may be engineered to express recombinant ion channels or receptors with appropriate scaffolding proteins or chaperone proteins so that the surface expression of these proteins can be achieved at certain locations in a timed manner. For microdomain measurement of individual cells, various detection technologies such as imaging could be applied. Individual cells are positioned in an array format and the examination of hundreds or even thousands of cells could be performed in a single device for their chemical and biochemical parameters or properties in given subcellular microdomains. These parameters include, but are not limited to, calcium levels, enzyme activity, translocation, membrane and molecular trafficking, pH, and concentrations of specific molecules.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Terms of orientation such as "up" and "down" or "upper" or "lower" and the like refer to orientation of parts during use of a device. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings:

"Dielectrophoresis" is the movement of polarized particles in electrical fields of nonuniform strength. There are generally two types of dielectrophoresis, positive dielectrophoresis and negative dielectrophoresis. In positive dielectrophoresis, particles are moved by dielectrophoretic forces toward the strong field regions. In negative dielectrophoresis, particles are moved by dielectrophoretic forces toward weak field regions. Whether moieties exhibit positive or negative dielectrophoresis depends on whether particles are more or less polarizable than the surrounding medium.

A "dielectrophoretic force" is the force that acts on a polarizable particle in an AC electrical field of non-uniform strength. The dielectrophoretic force $\vec{F}_{DEP}$ acting on a particle of radius r subjected to a non-uniform electrical field can be given, under the dipole approximation, by:

$$\vec{F}_{DEP} = 2\pi \epsilon_m r^3 X_{DEP} \nabla E_{rms}^2$$

where $E_{rms}$ is the RMS value of the field strength, the symbol $\nabla$ is the symbol for gradient-operation, $\epsilon_m$ is the dielectric permittivity of the medium, and $X_{DEP}$ is the particle polarization factor, given by:

$$\chi_{DEP} = \text{Re}\left(\frac{\epsilon_p^* - \epsilon_m^*}{\epsilon_p^* + 2\epsilon_m^*}\right),$$

"Re" refers to the real part of the "complex number". The symbol $\epsilon_x^* = \epsilon_x - j\sigma_x/2\pi f$ is the complex permittivity (of the particle x=p, and the medium x=m) and $j=\sqrt{-1}$. The parameters $\epsilon_p$ and $\sigma_p$ are the effective permittivity and conductivity of the particle, respectively. These parameters may be frequency dependent. For example, a typical biological cell will have frequency dependent, effective conductivity and permittivity, at least, because of cytoplasm membrane polarization. Particles such as biological cells having different dielectric properties (as defined by permittivity and conductivity) will experience different dielectrophoretic forces. The dielectrophoretic force in the above equation refers to the simple dipole approximation results. However, the dielectrophoretic force utilized in this application generally refers to the force generated by non-uniform electric fields and is not limited by the dipole simplification. The above equation for the dielectrophoretic force can also be written as $$\vec{F}_{DEP} = 2\pi \epsilon_m r^3 X_{DEP} V^2 \nabla p(x,y,z)$$

where p(x,y,z) is the square-field distribution for a unit-voltage excitation (Voltage V=1 V) on the electrodes, V is the applied voltage.

"Traveling-wave dielectrophoretic (TW-DEP) force" refers to the force that is generated on particles or molecules due to a traveling-wave electric field. An ideal traveling-wave field is characterized by the distribution of the phase values of AC electric field components, being a linear function of the position of the particle. In this case the traveling wave dielectrophoretic force $\vec{F}_{TW\text{-}DEP}$ on a particle of radius r subjected to a traveling wave electrical field $E=E\cos(2\pi(ft-z/\lambda_0))\vec{a}_x$ (i.e., a x-direction field is traveling along the z-direction) is given, again, under the dipole approximation, by $$\vec{F}_{TW\text{-}DEP} = -\frac{4\pi^2 \varepsilon_m}{\lambda_0} r^3 \zeta_{TW\text{-}DEP} E^2 \cdot \vec{a}_z$$

where E is the magnitude of the field strength, $\varepsilon_m$ is the dielectric permittivity of the medium. $\zeta_{TW\text{-}DEP}$ is the particle polarization factor, given by $$\zeta_{TW\text{-}DEP} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $\varepsilon_x^* = \varepsilon_x - j\sigma_x/2\pi f$ is the complex permittivity (of the particle x=p, and the medium x=m). The parameters $\varepsilon_p$ and $\sigma_p$ are the effective permittivity and conductivity of the particle, respectively. These parameters may be frequency dependent.

A traveling wave electric field can be established by applying appropriate AC signals to the microelectrodes appropriately arranged on a chip. For generating a traveling-wave-electric field, it is necessary to apply at least three types of electrical signals each having a different phase value. An example to produce a traveling wave electric field is to use four phase-quardrature signals (0, 90, 180 and 270 degrees) to energize four linear, parallel electrodes patterned on the chip surfaces. Such four electrodes may be used to form a basic, repeating unit. Depending on the applications, there may be more than two such units that are located next to each other. This will produce a traveling-electric field in the spaces above or near the electrodes. As long as electrode elements are arranged following certain spatially sequential orders, applying phase-sequenced signals will result in establishing traveling electrical fields in the region close to the electrodes.

"Electric field pattern" refers to the field distribution in space or in a region of interest. An electric field pattern is determined by many parameters, including the frequency of the field, the magnitude of the field, the magnitude distribution of the field, and the distribution of the phase values of the field components, the geometry of the electrode structures that produce the electric field, and the frequency and/or magnitude modulation of the field.

"Dielectric properties" of a particle are properties that determine, at least in part, the response of a particle to an electric field. The dielectric properties of a particle include the effective electric conductivity of a particle and the effective electric permittivity of a particle. For a particle of homogeneous composition, for example, a polystyrene bead, the effective conductivity and effective permittivity are independent of the frequency of the electric field at least for a wide frequency range (e.g. between 1 Hz to 100 MHz). Particles that have a homogeneous bulk composition may have net surface charges. When such charged particles are suspended in a medium, electrical double layers may form at the particle/medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent. For moieties of nonhomogeneous composition, for example, a cell, the effective conductivity and effective permittivity are values that take into account the effective conductivities and effective permittivities of both the membrane and internal portion of the cell, and can vary with the frequency of the electric field. In addition, the dielectrophoretic force experience by a particle in an electric field is dependent on its size; therefore, the overall size of particle is herein considered to be a dielectric property of a particle. Properties of a particle that contribute to its dielectric properties include but are not limited to the net charge on a particle; the composition of a particle (including the distribution of chemical groups or moieties on, within, or throughout a particle); size of a particle; surface configuration of a particle; surface charge of a particle; and the conformation of a particle. Particles can be of any appropriate shape, such as geometric or non-geometric shapes. For example, particles can be spheres, non-spherical, rough, smooth, have sharp edges, be square, oblong or the like.

"Magnetic forces" refer to the forces acting on a particle due to the application of a magnetic field. In general, particles have to be magnetic or paramagnetic when sufficient magnetic forces are needed to manipulate particles. For a typical magnetic particle made of super-paramagnetic material, when the particle is subjected to a magnetic field $\vec{B}$, a magnetic dipole $\vec{\mu}$ is induced in the particle $$\vec{\mu} = V_p(\chi_p - \chi_m)\frac{\vec{B}}{\mu_m},$$
$$= V_p(\chi_p - \chi_m)\vec{H}_m$$

where $V_p$ is the particle volume, $X_p$ and $X_m$ are the volume susceptibility of the particle and its surrounding medium, $\mu_m$ is the magnetic permeability of medium, $\vec{H}_m$ is the magnetic field strength. The magnetic force $\vec{F}_{magnetic}$ acting on the particle is determined, under the dipole approximation, by the magnetic dipole moment and the magnetic field gradient:

$$\vec{F}_{magnetic} = -0.5 V_p(X_p - X_m)\vec{H}_m \cdot \nabla \vec{B}_m,$$

where the symbols "·" and "∇" refer to dot-product and gradient operations, respectively. Whether there is magnetic force acting on a particle depends on the difference in the volume susceptibility between the particle and its surrounding medium. Typically, particles are suspended in a liquid, non-magnetic medium (the volume susceptibility is close to zero) thus it is necessary to utilize magnetic particles (its volume susceptibility is much larger than zero). The particle velocity $v_{particle}$ under the balance between magnetic force and viscous drag is given by:

$$v_{particle} = \frac{\vec{F}_{magnetic}}{6\pi r \eta_m}$$

where r is the particle radius and $\eta_m$ is the viscosity of the surrounding medium.

As used herein, "manipulation" refers to moving or processing of the particles, which results in one-, two- or three-dimensional movement of the particle, in a chip format, whether within a single chip or among multiple chips. Non-limiting examples of the manipulations include transportation, focusing, enrichment, concentration, aggregation, trapping, repulsion, levitation, separation, isolation or linear or other directed motion of the particles. For effective manipulation, the binding partner and the physical force used in the method should be compatible. For example, binding partner such as microparticles that can be bound with particles, having magnetic properties are preferably used with magnetic force. Similarly, binding partners having certain dielectric properties, for example, plastic particles, polystyrene microbeads, are preferably used with dielectrophoretic force.

A "sample" is any sample from which particles are to be separated or analyzed. A sample can be from any source, such as an organism, group of organisms from the same or different species, from the environment, such as from a body of water or from the soil, or from a food source or an industrial source. A sample can be an unprocessed or a processed sample. A sample can be a gas, a liquid, or a semi-solid, and can be a solution or a suspension. A sample can be an extract, for example a liquid extract of a soil or food sample, an extract of a throat or genital swab, or an extract of a fecal sample. Samples are can include cells or a population of cells. The population of cells can be a mixture of different cells or a population of the same cell or cell type, such as a clonal population of cells. Cells can be derived from a biological sample from a subject, such as a fluid, tissue or organ sample. In the case of tissues or organs, cells in tissues or organs can be isolated or separated from the structure of the tissue or organ using known methods, such as teasing, rinsing, washing, passing through a grating and treatment with proteases. Samples of any tissue or organ can be used, including mesodermally derived, endodermally derived or ectodermally derived cells. Particularly preferred types of cells are from the heart and blood. Cells include but are not limited to suspensions of cells, cultured cell lines, recombinant cells, infected cells, eukaryotic cells, prokaryotic cells, infected with a virus, having a phenotype inherited or acquired, cells having a pathological status including a specific pathological status or complexed with biological or non-biological entities.

A "blood sample" as used herein can refer to a processed or unprocessed blood sample, for example, it can be a centrifuged, filtered, extracted, or otherwise treated blood sample, including a blood sample to which one or more reagents such as, but not limited to, anticoagulants or stabilizers have been added. An example of blood sample is a buffy coat that is obtained by processing human blood for enriching white blood cells. A blood sample can be of any volume, and can be from any subject such as an animal or human. A preferred subject is a human. Blood samples can be from a given individual or specific or known or unknown condition or pooled samples. Such conditions can be practically inherent or acquired from contact with objects or exposure to environmental conditions, including but not limited to toxins or radiation. Environmental conditions include those provided during medical treatment, including chemotherapy, drug therapy, therapy and radiation therapy. Environmental conditions also include voluntary exposure or ingestion of compounds, including plant extracts, drugs of abuse, pharmaceuticals, food, toxins, ethanol, tobacco products and the like.

A "white blood cell" is a leukocyte, or a cell of the hematopoietic lineage that is not a reticulocyte or platelet and that can be found in the blood of an animal. Leukocytes can include lymphocytes, such as B lymphocytes or T lymphocytes. Leukocytes can also include phagocytic cells, such as monocytes, macrophages, and granulocytes, including basophils, eosinophils and neutrophils. Leukocytes can also comprise mast cells.

A "red blood cell" is an erythrocyte.

"Neoplastic cells" refers to abnormal cells that grow by cellular proliferation more rapidly than normal and can continue to grow after the stimuli that induced the new growth has been withdrawn. Neoplastic cells tend to show partial or complete lack of structural organization and functional coordination with the normal tissue, and may be benign or malignant.

A "malignant cell" is a cell having the properties of locally invasive and destructive growth and metastasis.

A "stem cell" is an undifferentiated cell that can give rise, through one or more cell division cycles, to at least one differentiated cell type.

A "progenitor cell" is a committed but undifferentiated cell that can give rise, through one or more cell division cycles, to at least one differentiated cell type. Typically, a stem cell gives rise to a progenitor cell through one or more cell divisions in response to a particular stimulus or set of stimuli, and a progenitor gives rise to one or more differentiated cell types in response to a particular stimulus or set of stimuli.

An "etiological agent" refers to any etiological agent, such as a bacteria, virus, parasite or prion that can be associated with, such but not limited to infecting, a subject. An etiological agent can cause symptoms or a disease state in the subject it infects. A human etiological agent is an etiological agent that can infect a human subject. Such human etiological agents may be specific for humans, such as a specific human etiological agent, or may infect a variety of species, such as a promiscuous human etiological agent.

"Subject" refers to any organism, such as an animal or a human. An animal can include any animal, such as a feral animal, a companion animal such as a dog or cat, an agricultural animal such as a pig or a cow, or a pleasure animal such as a horse.

A "chamber" is a structure that comprises a chip and that is capable of containing a fluid sample. The chamber may have various dimensions and its volume may vary between 0.001 microliter and 50 milliliter.

A "port" is an opening in the housing of a chamber through which a fluid sample can enter or exit the chamber. A port can be of any dimensions, but preferably is of a shape and size that allows a sample to be dispensed into a chamber by means of a pipette, syringe, or conduit, or other means of dispensing a sample.

A "conduit" is a means for fluid to be transported from one compartment to another compartment of a device of the present invention or to another structure, such as a dispensation or detection device. Preferably a conduit engages a port in the housing of a chamber. A conduit can comprise any material that permits the passage of a fluid through it. Preferably a conduit is tubing, such as, for example, rubber, teflon, or tygon tubing. A conduit can be of any dimensions, but preferably ranges from 10 microns to 5 millimeters in internal diameter.

A "chip" is a solid substrate on which one or more processes such as physical, chemical, biochemical, biological or biophysical processes can be carried out. Such processes can be assays, including biochemical, cellular, and chemical assays; ion transport or ion channel function or activity determinations, separations, including separations mediated by electrical, magnetic, physical, and chemical (including biochemical) forces or interactions; chemical reactions, enzymatic reactions, and binding interactions, including captures. The micro structures or micro-scale structures such as, channels and wells, electrode elements, electromagnetic elements, may be incorporated into or fabricated on the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, for example, from about 1 mm$^2$ to about 0.25 m$^2$. Preferably, the size of the chips is from about 4 mm$^2$ to about 25 cm$^2$ with a characteristic dimension from about 1 mm to about 5 cm. The chip surfaces may be flat, or not flat. The chips with non-flat surfaces may include wells fabricated on the surfaces.

A "biochip" is a chip that is useful for a biochemical, biological or biophysical process. In this regard, a biochip is preferably biocompatible.

"Micro-scale structures" are structures integral to or attached on a chip, wafer, or chamber that have characteristic dimensions of scale for use in microfluidic applications ranging from about 0.1 micron to about 20 mm. Example of micro-scale structures that can be on chips of the present invention are wells, channels, scaffolds, electrodes, electromagnetic units, or microfabricated pumps or valves.

"Separation" is a process in which one or more components of a sample is spatially separated from one or more other components of a sample or a process to spatially redistribute particles within a sample such as a mixture of particles, such as a mixture of cells. A separation can be performed such that one or more particles is translocated to one or more areas of a separation apparatus and at least some of the remaining components are translocated away from the area or areas where the one or more particles are translocated to and/or retained in, or in which one or more particles is retained in one or more areas and at least some or the remaining components are removed from the area or areas. Alternatively, one or more components of a sample can be translocated to and/or retained in one or more areas and one or more particles can be removed from the area or areas. It is also possible to cause one or more particles to be translocated to one or more areas and one or more moieties of interest or one or more components of a sample to be translocated to one or more other areas. Separations can be achieved through the use of physical, chemical, electrical, or magnetic forces. Examples of forces that can be used in separations include but are not limited to gravity, mass flow, dielectrophoretic forces, traveling-wave dielectrophoretic forces, and electromagnetic forces.

"Capture" is a type of separation in which one or more particles is retained in one or more areas of a chip. In the methods of the present application, a capture can be performed when physical forces such as dielectrophoretic forces or electromagnetic forces are acted on the particle and direct the particle to one or more areas of a chip.

An "assay" is a test performed on a sample or a component of a sample. An assay can test for the presence of a component, the amount or concentration of a component, the composition of a component, the activity of a component, the electrical properties of an ion transport protein, etc. Assays that can be performed in conjunction with the compositions and methods of the present invention include, but not limited to, biochemical assays, binding assays, cellular assays, genetic assays, ion transport assay, gene expression assays and protein expression assays.

A "binding assay" is an assay that tests for the presence or the concentration of an entity by detecting binding of the entity to a specific binding member, or an assay that tests the ability of an entity to bind another entity, or tests the binding affinity of one entity for another entity. An entity can be an organic or inorganic molecule, a molecular complex that comprises, organic, inorganic, or a combination of organic and inorganic compounds, an organelle, a virus, or a cell. Binding assays can use detectable labels or signal generating systems that give rise to detectable signals in the presence of the bound entity. Standard binding assays include those that rely on nucleic acid hybridization to detect specific nucleic acid sequences, those that rely on antibody binding to entities, and those that rely on ligands binding to receptors.

A "biochemical assay" is an assay that tests for the composition of or the presence, concentration, or activity of one or more components of a sample.

A "cellular assay" is an assay that tests for or with a cellular process, such as, but not limited to, a metabolic activity, a catabolic activity, an ion transport function or property, an intracellular signaling activity, a receptor-linked signaling activity, a transcriptional activity, a translational activity, or a secretory activity.

An "ion transport assay" is an assay useful for determining ion transport functions or properties and testing for the abilities and properties of chemical entities to alter ion transport functions. Preferred ion transport assays include electrophysiology-based methods which include, but are not limited to patch clamp recording, whole cell recording, perforated patch or whole cell recording, vesicle recording, outside out and inside out recording, single channel recording, artificial membrane channel recording, voltage gated ion transport recording, ligand gated ion transport recording, stretch activated (fluid flow or osmotic) ion transport recording, and recordings on energy requiring ion transporters (such as ATP), non energy requiring transporters, and channels formed by toxins such a scorpion toxins, viruses, and the like. See, generally Neher and Sakman, Scientific American 266: 44-51 (1992); Sakmann and Heher, Ann. Rev. Physiol. 46:455-472 (1984); Cahalan and Neher, Methods in Enzymology 207:3-14 (1992); Levis and Rae, Methods in Enzymology 207:14-66 (1992); Armstrong and Gilly, Methods in Enzymology 207:100-122 (1992); Heinmann and Conti, Methods in Enzymology 207:131-148 (1992); Bean, Methods in Enzymology 207:181-193 (1992); Leim et al., Neurosurgery 36:382-392 (1995); Lester, Ann. Rev. Physiol 53:477-496 (1991); Hamill and McBride, Ann. Rev. Physiol 59:621-631 (1997); Bustamante and Varranda, Brazilian Journal 31:333-354 (1998); Martinez-Pardon and Ferrus, Current Topics in Developmental Biol. 36:303-312 (1998); Herness, Physiology and Behavior 69:17-27 (2000); Aston-Jones and Siggins, www.acnp.org/GA/GN40100005/CH005.html (Feb. 8, 2001); U.S. Pat. No. 6,117,291; U.S. Pat. No. 6,107,066; U.S. Pat. No. 5,840,041 and U.S. Pat. No. 5,661,035; Boulton et al., Patch-Clamp Applications and Protocols, Neuromethods V. 26 (1995), Humana Press, New Jersey; Ashcroft, Ion Channels and Disease, Cannelopathies, Academic Press, San Diego (2000); Sakmann and Neher, Single Channel Recording, second edition, Plenuim Press, New York (1995) and Soria and Cena, Ion Channel Pharmacology, Oxford University Press, New York (1998), each of which is incorporated by reference herein in their entirety.

An "electric sealing" refers to a high-resistance engagement between a particle such as a cell membrane and a measuring device, such as a hole, capillary or needle of the present invention. Preferred resistance of such electric sealing is between about 1 mega ohm and about 100 giga ohms, but that need not be the case. Generally, a large resistance results in decreased noise in the recording signals. For specific types of ion channels (with different magnitude of recording current) appropriate electric sealing in terms of mega ohms or giga ohms can be used A "ligand gated ion transport" refers to ion transporters such as ligand gated ion channels, including extracellular ligand gated ion channels and intracellular ligand gated ion channels, whose activity or function is activated or modulated by the binding of a ligand. The activity or function of ligand gated ion transports can be detected by measuring voltage or current in response to ligands or test chemicals. Examples include but are not limited to $GABA_A$, strychnine-sensitive glycine, nicotinic acetylcholine (Ach), ionotropic glutamate (iGlu), and 5-hydroxytryptamine$_3$ (5-HT$_3$) receptors.

A "voltage gated ion transport" refers to ion transporters such as voltage gated ion channels whose activity or function is activated or modulated by voltage. The activity or function of voltage gated ion transports can be detected by measuring voltage or current in response to different commanding currents or voltages respectively. Examples include but are not limited to voltage dependent $Na^+$ channels.

"Perforated" patch clamp refers to the use of perforation agents such as but not limited to nystatin or amphotericin B to form pores or perforations that are preferably ion-conducting, which allows for the measurement of current, including whole cell current.

An "electrode" is a structure of highly electrically conductive material. A highly conductive material is a material with conductivity greater than that of surrounding structures or materials. Suitable highly electrically conductive materials include metals, such as gold, chromium, platinum, aluminum, and the like, and can also include nonmetals, such as carbon, conductive liquids and conductive polymers. An electrode can be any shape, such as rectangular, circular, castellated, etc. Electrodes can also comprise doped semi-conductors, where a semi-conducting material is mixed with small amounts of other "impurity" materials. For example, phosphorous-doped silicon may be used as conductive materials for forming electrodes.

A "well" is a structure in a chip, with a lower surface surrounded on at least two sides by one or more walls that extend from the lower surface of the well or channel. The walls can extend upward from the lower surface of a well or channel at any angle or in any way. The walls can be of an irregular conformation, that is, they may extend upward in a sigmoidal or otherwise curved or multi-angled fashion. The lower surface of the well or channel can be at the same level as the upper surface of a chip or higher than the upper surface of a chip, or lower than the upper surface of a chip, such that the well is a depression in the surface of a chip. The sides or walls of a well or channel can comprise materials other than those that make up the lower surface of a chip. In this way the lower surface of a chip can comprise a thin material through which electrical (including dielectrophoretic, traveling-wave dielectrophoretic, electromagnetic) forces can be transmitted, and the walls of one or more wells and/or one or more channels can optionally comprise other insulating materials that can prevent the transmission of electrical forces. The walls of a well or a channel of a chip can comprise any suitable material, including silicon, glass, rubber, and/or one or more polymers, plastics, ceramics, or metals.

A "channel" is a structure in a chip with a lower surface and at least two walls that extend upward from the lower surface of the channel, and in which the length of two opposite walls is greater than the distance between the two opposite walls. A channel therefore allows for flow of a fluid along its internal length. A channel can be covered (a "tunnel") or open.

"Continuous flow" means that fluid is pumped or injected into a chamber of the present invention continuously during the separation process. This allows for components of a sample that are not selectively retained on a chip to be flushed out of the chamber during the separation process.

"Binding partner" refers to any substances that both bind to the moieties with desired affinity or specificity and are manipulatable with the desired physical force(s). Non-limiting examples of the binding partners include cells, cellular organelles, viruses, particles, microparticles or an aggregate or complex thereof, or an aggregate or complex of molecules.

A "specific binding member" is one of two different molecules having an area on the surface or in a cavity that specifically binds to and is thereby defined as complementary with a particular spatial and polar organization of the other molecule. A specific binding member can be a member of an immunological pair such as antigen-antibody, can be biotin-avidin or biotin streptavidin, ligand-receptor, nucleic acid duplexes, IgG-protein A, DNA-DNA, DNA-RNA, RNA-RNA, and the like.

A "nucleic acid molecule" is a polynucleotide. A nucleic acid molecule can be DNA, RNA, or a combination of both. A nucleic acid molecule can also include sugars other than ribose and deoxyribose incorporated into the backbone, and thus can be other than DNA or RNA. A nucleic acid can comprise nucleobases that are naturally occurring or that do not occur in nature, such as xanthine, derivatives of nucleobases, such as 2-aminoadenine, and the like. A nucleic acid molecule of the present invention can have linkages other than phosphodiester linkages. A nucleic acid molecule of the present invention can be a peptide nucleic acid molecule, in which nucleobases are linked to a peptide backbone. A nucleic acid molecule can be of any length, and can be single-stranded, double-stranded, or triple-stranded, or any combination thereof. The above described nucleic acid molecules can be made by a biological process or chemical synthesis or a combination thereof.

A "detectable label" is a compound or molecule that can be detected, or that can generate readout, such as fluorescence, radioactivity, color, chemiluminescence or other readouts known in the art or later developed. Such labels can be, but are not limited to, photometric, colorimetric, radioactive or morphological such as changes of cell morphology that are detectable, such as by optical methods. The readouts can be based on fluorescence, such as by fluorescent labels, such as but not limited to, Cy-3, Cy-5, phycoerythrin, phycocyanin, allophycocyanin, FITC, rhodamine, or lanthanides; and by fluorescent proteins such as, but not limited to, green fluorescent protein (GFP). The readout can be based on enzymatic activity, such as, but not limited to, the activity of beta-galactosidase, beta-lactamase, horseradish peroxidase, alkaline phosphatase, or luciferase. The readout can be based on radioisotopes (such as $^{33}P$, $^3H$, $^{14}C$, $^{35}S$, 125I, $^{32}P$ or $^{131}I$. A label optionally can be a base with modified mass, such as, for example, pyrimidines modified at the C5 position or purines modified at the N7 position. Mass modifying groups can be, for examples, halogen, ether or polyether, alkyl, ester or polyester, or of the general type XR, wherein X is a linking group and R is a mass-modifying group. One of skill in the art will recognize that there are numerous possibilities for mass-modifications useful in modifying nucleic acid molecules and oligonucleotides, including those described in Oligonucleotides and Analogues: A Practical Approach, Eckstein, ed. (1991) and in PCT/US94/00193.

A "signal producing system" may have one or more components, at least one component usually being a labeled binding member. The signal producing system includes all of the reagents required to produce or enhance a measurable signal including signal producing means capable of interacting with a label to produce a signal. The signal producing system provides a signal detectable by external means, often by measurement of a change in the wavelength of light absorption or emission. A signal producing system can include a chromophoric substrate and enzyme, where chromophoric substrates are enzymatically converted to dyes, which absorb light in the ultraviolet or visible region, phosphors or fluorescers. However, a signal producing system can also provide a detectable signal that can be based on radioactivity or other detectable signals.

The signal producing system can include at least one catalyst, usually at least one enzyme, and can include at least one substrate, and may include two or more catalysts and a plurality of substrates, and may include a combination of enzymes, where the substrate of one enzyme is the product of the other enzyme. The operation of the signal producing system is to produce a product that provides a detectable signal at the predetermined site, related to the presence of label at the predetermined site.

In order to have a detectable signal, it may be desirable to provide means for amplifying the signal produced by the presence of the label at the predetermined site. Therefore, it will usually be preferable for the label to be a catalyst or luminescent compound or radioisotope, most preferably a catalyst. Preferably, catalysts are enzymes and coenzymes that can produce a multiplicity of signal generating molecules from a single label. An enzyme or coenzyme can be employed which provides the desired amplification by producing a product, which absorbs light, for example, a dye, or emits light upon irradiation, for example, a fluorescer. Alternatively, the catalytic reaction can lead to direct light emission, for example, chemiluminescence. A large number of enzymes and coenzymes for providing such products are indicated in U.S. Pat. No. 4,275,149 and U.S. Pat. No. 4,318,980, which disclosures are incorporated herein by reference. A wide variety of non-enzymatic catalysts that may be employed are found in U.S. Pat. No. 4,160,645, issued Jul. 10, 1979, the appropriate portions of which are incorporated herein by reference.

The product of the enzyme reaction will usually be a dye or fluorescer. A large number of illustrative fluorescers are indicated in U.S. Pat. No. 4,275,149, which is incorporated herein by reference.

An "ion transport" can be any protein or non-protein moiety that modulates, regulates or allows transfer of ions across a membrane, such as a biological membrane or an artificial membrane. Ion transport include but are not limited to ion channels, proteins allowing transport of ions by active transport, proteins allowing transport of ions by passive transport, toxins such as from insects, viral proteins or the like. Viral proteins, such as the M2 protein of influenza virus can form an ion channel on cell surfaces.

A "particle" refers to an organic or inorganic particulate that is suspendable in a solution and can be manipulated by a particle positioning means. A particle can include a cell, such as a prokaryotic or eukaryotic cell, or can be a cell fragment, such as a vesicle or a microsome that can be made using methods known in the art. A particle can also include artificial membrane preparations that can be made using methods known in the art. Preferred artificial membrane preparations are lipid bilayers, but that need not be the case. A particle in the present invention can also be a lipid film, such as a black-lipid film (see, Houslay and Stanley, Dynamics of Biological Membranes, Influence on Synthesis, Structure and Function, John Wiley & Sons, New York (1982)). In the case of a lipid film, a lipid film can be provided over a hole, such as a hole or capillary of the present invention using methods known in the art (see, Houslay and Stanley, Dynamics of Biological Membranes, Influence on Synthesis, Structure and Function, John Wiley & Sons, New York (1982)). A particle preferably includes or is suspected of including at least one ion transport or an ion transport of interest. Particles that do not include an ion transport or an ion transport of interest can be made to include such ion transport using methods known in the art, such as by fusion of particles or insertion of ion transports into such particles such as by detergents, detergent removal, detergent dilution, sonication or detergent catalyzed incorporation (see, Houslay and Stanley, Dynamics of Biological Membranes, Influence on Synthesis, Structure and Function, John Wiley & Sons, New York (1982)). A microparticle, such as a bead, such as a latex bead or magnetic bead, can be attached to a particle, such that the particle can be manipulated by a particle positioning means.

A "microparticle" is a structure of any shape and of any composition that is manipulatable by desired physical force(s). The microparticles used in the methods could have a dimension from about 0.01 micron to about ten centimeters. Preferably, the microparticles used in the methods have a dimension from about 0.1 micron to about several hundred microns. Such particles or microparticles can be comprised of any suitable material, such as glass or ceramics, and/or one or more polymers, such as, for example, nylon, polytetrafluoroethylene (TEFLON™), polystyrene, polyacrylamide, sepaharose, agarose, cellulose, cellulose derivatives, or dextran, and/or can comprise metals. Examples of microparticles include, but are not limited to, plastic particles, ceramic particles, carbon particles, polystyrene microbeads, glass beads, magnetic beads, hollow glass spheres, metal particles, particles of complex compositions, microfabricated free-standing microstructures, etc. The examples of microfabricated free-standing microstructures may include those described in "Design of asynchronous dielectric micromotors" by Hagedorn et al., in Journal of Electrostatics, Volume: 33, Pages 159-185 (1994). Particles of complex compositions refer to the particles that comprise or consists of multiple compositional elements, for example, a metallic sphere covered with a thin layer of non-conducting polymer film.

"A preparation of microparticles" is a composition that comprises microparticles of one or more types and can optionally include at least one other compound, molecule, structure, solution, reagent, particle, or chemical entity. For example, a preparation of microparticles can be a suspension of microparticles in a buffer, and can optionally include specific binding members, enzymes, inert particles, surfactants, ligands, detergents, etc.

"Coupled" means bound. For example, a moiety can be coupled to a microparticle by specific or nonspecific binding. As disclosed herein, the binding can be covalent or noncovalent, reversible or irreversible.

A "cell" refers to a viable or non-viable prokaryotic or eukaryotic cell. A eukaryotic cell can be any eukaryotic cell from any source, such as obtained from a subject, human or non-human, fetal or non-fetal, child or adult, such as from a tissue or fluid, including blood, which are obtainable through appropriate sample collection methods, such as biopsy, blood collection or otherwise. Eukaryotic cells can be provided as is in a sample or can be cell lines that are cultivated in vitro. Differences in cell types also include cellular origin, distinct surface markers, sizes, morphologies and other physical and biological properties.

A "cell fragment" refers to a portion of a cell, such as cell organelles, including but not limited to nuclei, endoplasmic reticulum, mitochondria or golgi apparatus. Cell fragments can include vesicles, such as inside out or outside out vesicles or mixtures thereof. Preparations that include cell fragments can be made using methods known in the art.

A "population of cells" refers to a sample that includes more than one cell or more than one type of cell. For example, a sample of blood from a subject is a population of white cells and red cells. A population of cells can also include a sample including a plurality of substantially homogeneous cells, such as obtained through cell culture methods for a continuous cell lines.

A "population of cell fragments" refers to a sample that includes more than one cell fragment or more than one type of cell fragments. For example, a population of cell fragments can include mitochondria, nuclei, microsomes and portions of golgi apparatus that can be formed upon cell lysis.

A "particle positioning means" refers to a means that is capable of manipulating the position of a particle relative to the X-Y coordinates or X-Y-Z coordinates of a biochip. Positions in the X-Y coordinates are in a plane. The Z coordinate is perpendicular to the plane. In one aspect of the present invention, the X-Y coordinates are substantially perpendicular to gravity and the Z coordinate is substantially parallel to gravity. This need not be the case, however, particularly if the biochip need not be level for operation or if a gravity free or gravity reduced environment is present. Several particle positioning means are disclosed herein, such as but not limited to dielectric structures, dielectric focusing structures, quadropole electrode structures, electrorotation structures, traveling wave dielectrophoresis structures, concentric electrode structures, spiral electrode structures, circular electrode structures, square electrode structures, particle switch structures, electromagnetic structures, DC electric field induced fluid motion structure, acoustic structures, negative pressure structures and the like.

An "ion transport measuring means" refers to a means that is capable of measuring at least one ion transport function, property, or response to various chemical, biochemical or electrical stimuli. For example, holes, apertures, capillaries, needles and other detection structures of the present invention can be used as ion transport measuring means. An ion transport measuring means is preferably positioned on or within a biochip or a chamber. Where an ion transport measuring means refers to a hole or aperture, the use of the terms "ion transport measuring means" "hole" or "aperture" are also meant to encompass the perimeter of the hole or aperture that is in fact a part of the chip or substrate (or coating) surface (or surface of another structure, for example, a channel) and can also include the surfaces that surround the interior space of the hole that is also the chip or substrate (or coating) material or material of another structure that comprises the hole or aperture.

A "hole" is an aperture that extends through a chip. Descriptions of holes found herein are also meant to encompass the perimeter of the hole that is in fact a part of the chip or substrate (or coating) surface, and can also include the surfaces that surround the interior space of the hole that is also the chip or substrate (or coating) material. Thus, in the present invention, where particles are described as being positioned on, at, near, against, or in a hole, or adhering or fixed to a hole, it is intended to mean that a particle contacts the entire perimeter of a hole, such that at least a portion of the surface of the particle lies across the opening of the hole, or in some cases, descends to some degree into the opening of the whole, contacting the surfaces that surround the interior space of the hole.

A "patch clamp detection structure" refers to a structure that is on or within a biochip or a chamber that is capable of measuring at least one ion transport function or property via patch clamp methods.

A "dielectric focusing structure" refers to a structure that is on or within a biochip or a chamber that is capable of modulating the position of a particle in the X-Y or X-Y-Z coordinates of a biochip using dielectric forces or dielectrophoretic forces.

A "quadropole electrode structure" refers to a structure that includes four electrodes arranged around a locus such as a hole, capillary or needle on a biochip and is on or within a biochip or a chamber that is capable of modulating the position of a particle in the X-Y or X-Y-Z coordinates of a biochip using dielectrophoretic forces or dielectric forces generated by such quadropole electrode structures.

An "electrorotation structure" refers to a structure that is on or within a biochip or a chamber that is capable of producing a rotating electric field in the X-Y or X-Y-Z coordinates that can rotate a particle. Preferred electrorotation structures include a plurality of electrodes that are energized using phase offsets, such as 360/N degrees, where N represents the number of electrodes in the electroroation structure (see generally U.S. patent application Ser. No. 09/643,362 entitled "Apparatus and Method for High Throughput Electrorotation Analysis" filed Aug. 22, 2000, naming Jing Cheng et al. as inventors). A rotating electrode structure can also produce dielectrophoretic forces for positioning particles to certain locations under appropriate electric signal or excitation. For example, when N=4 and electrorotation structure corresponds to a quadropole electrode structure.

A "traveling wave dielectrophoresis structure" refers to a structure that is on or within a biochip or a chamber that is capable of modulating the position of a particle in the X-Y or X-Y-Z coordinates of a biochip using traveling wave dielectrophoretic forces (see generally U.S. patent application Ser. No. 09/686,737 filed Oct. 10, 2000, to Xu, Wang, Cheng, Yang and Wu; and U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu).

A "concentric circular electrode structure" refers to a structure having multiple concentric circular electrodes that are on or within a biochip or a chamber that is capable of modulating the position of a particle in the X-Y or X-Y-Z coordinates of a biochip using dielectrophoretic forces.

A "spiral electrode structure" refers to a structure having multiple parallel spiral electrode elements that is on or within a biochip or a chamber that is capable of modulating the position of a particle in the X-Y or X-Y-Z coordinates of a biochip using dielectric forces.

A "square spiral electrode structure" refers to a structure having multiple parallel square spiral electrode elements that are on or within a biochip or a chamber that is capable of modulating the position of a particle in the X-Y or X-Y-Z coordinates of a biochip using dielectrophoretic or traveling wave dielectrophoretic forces.

A "particle switch structure" refers to a structure that is on or within a biochip or a chamber that is capable of transporting particles and switching the motion direction of a particle or particles in the X-Y or X-Y-Z coordinates of a biochip. The particle switch structure can modulate the direction that a particle takes based on the physical properties of the particle or at the will of a programmer or operator (see, generally U.S. application Ser. No. 09/678,263, entitled "Apparatus for Switching and Manipulating Particles and Methods of Use Thereof" filed on Oct. 3, 2000 and naming as inventors Xiaobo Wang, Weiping Yang, Junquan Xu, Jing Cheng, and Lei Wu.

An "electromagnetic structure" refers to a structure that is on or within a biochip or a chamber that is capable of modulating the position of a particle in the X-Y or X-Y-Z coordinates of a biochip using electromagnetic forces. See generally U.S. patent application Ser. No. 09/685,410 filed Oct. 10, 2000, to Wu, Wang, Cheng, Yang, Zhou, Liu and Xu and WO 00/54882 published Sep. 21, 2000 to Zhou, Liu, Chen, Chen, Wang, Liu, Tan and Xu.

A "DC electric field induced fluid motion structure" refers to a structure that is on or within a biochip or a chamber that is capable of modulating the position of a particle in the X-Y or X-Y-Z coordinates of a biochip using DC electric field that produces a fluidic motion.

An "electroosomosis structure" refers to a structure that is on or within a biochip or a chamber that is capable of modulating the position of a particle in the X-Y or X-Y-Z coordinates of a biochip using electroosmotic forces. Preferably, an electroosmosis structure can modulate the positioning of a particle such as a cell or fragment thereof with an ion transport measuring means such that the particle's seal (or the particle's sealing resistance) with such ion transport measuring means is increased.

An "acoustic structure" refers to a structure that is on or within a biochip or a chamber that is capable of modulating the position of a particle in the X-Y or X-Y-Z coordinates of a biochip using acoustic forces. In one aspect of the present invention, the acoustic forces are transmitted directly or indirectly through an aqueous solution to modulate the positioning of a particle. Preferably, an acoustic structure can modulate the positioning of a particle such as a cell or fragment thereof with an ion transport measuring means such that the particle's seal with such ion transport measuring means is increased.

A "negative pressure structure" refers to a structure that is on or within a biochip or a chamber that is capable of modulating the position of a particle in the X-Y or X-Y-Z coordinates of a biochip using negative pressure forces, such as those generated through the use of pumps or the like. Preferably, a negative pressure structure can modulate the positioning of a particle such as a cell or fragment thereof with an ion transport measuring means such that the particle's seal with such ion transport measuring means is increased.

A "horizontal positioning means" refers to a particle positioning means that can position a particle in the X-Y coordinates of a biochip or chamber wherein the Z coordinate is substantially defined by gravity.

A "vertical positioning means" refers to a particle positioning means that can position a particle in the Z coordinate of a biochip or chamber wherein the Z coordinate is substantially defined by gravity.

Other technical terms used herein have their ordinary meaning in the art that they are used, as exemplified by a variety of technical dictionaries.

Introduction

The present invention recognizes that the determination of an ion transport function or property using direct detection methods, such as patch-clamps, are preferable to methods that utilize indirect detection methods, such as fluorescence-based detection system. The present invention provides biochips and methods of use that allow for the direct detection of one or more ion transport functions or properties using microfabricated structures that can allow for automated detection of one or more ion transport functions or properties. These biochips and methods of use thereof are particularly appropriate for automating the detection of ion transport functions or properties, particularly for screening purposes.

In some aspects the present invention can be practiced using a wide variety of cells from different sources. For example, cancer cells can be interogated as to their ion channel activity in the presence and absence of test compounds or in comparison to other cells such as non-cancerous cells or other cancer cells. Also, the present invention can utilize neurons or cells of neuronal origin. For example, neuronal cells derived or obtained from subjects including humans or animals or animals sympomatic for neurodegenerative disorders such as, but not limited to Alzheimer's disease, Parkinson's disease, multiple sclerosis, lateral sclerosis and the like can be interogated as to ion channel activity in the presence and absence of test compounds or in comparison to other cells such as normal neuronal cells or cells from different subjects having the same or different neurodegenerative disorders. Alternatively, stem cells can be investigated as to ion channel activity and compared to other cells or during differentiation of a population of stem cells over time or in the presence or absence of a test compound.

As a non-limiting introduction to the breath of the present invention, the present invention includes several general and useful aspects, including:

1) A biochip cell positioning device and methods of use;
2) An array of capillaries on a biochip, optionally with electrodes, and methods of use thereof;
3) An array of needle electrodes on a biochip and methods of use;
4) An array of holes on a biochip and methods of use;
5) A biochip having ion transport detection structures located along the side of one or more channels;
6) A method for modifying a chip, substrate, surface, or structure that comprises one or more ion transport measuring means to enhance the electric seal of a particle with at least one of the one or more ion transport measuring means;
7) A chip, cartridge, pipette, or capillary comprising at least one ion transport measuring means with enhanced electric seal properties;
8) A method for storing chips, cartridges, pipettes, and capillaries comprising at least one ion transport measuring means with enhanced electrical seal properties;
9) A method for shipping a structure, chip, cartridge, pipette, or capillary comprising at least one ion transport measuring means with enhanced electrical seal properties;
10) A biochip combined with high information content screening methods; and
11) A biochip with three-dimensionally configured channels that can be microfabricated using sacrificial methodologies such as sacrificial wire methods.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I A Biochip Cell Positioning Device and Methods of Use

The present invention includes a biochip that includes a particle positioning means and an ion transport measuring means. The particle positioning means such as, but not limited to dielectric focusing devices, electrorotation devices, dielectrophoresis devices, traveling wave dielectrophoresis devices, or acoustic devices that can precisely position a particle, such as a cell, at or near an ion transport measuring means. Preferred ion transport measuring means include holes or capillaries that can form a seal with the particle, such as a biological membrane, so that an ion transport function or property of the particle can be determined. Coupled with holes or capillaries there can be electrodes that can record electric responses of ion channels.

Biochips in General

Biochips of the present invention generally are made using microfabrication methods such as those generally used in electronic chip manufacture. For example, methods of photolithography, MEMS fabrication, micromachining, molding, casting and other methods can be used. Generally, biochips include a substrate that forms a solid support or platform on which a separation or an assay can take place. Biochips can also include chambers or conduits to allow for the introduction of materials onto the substrate or within the channels of the biochip.

Substrate

The substrate can be of any appropriate material or combination of materials for the manufacture of chips, such as through microfabrication methods used in the semiconductor industry. Preferred materials include, but are not limited to silicon, glass, sintered glass, quartz, silicon-oxide, plastics, ceramics or the like. The substrate is preferably non-porous, but porous materials are also useful, particularly for applications that utilize the transfer of materials through a substrate to take part in methods of the present invention, such as but not limited to binding reactions or detection of binding reactions.

The substrate is preferably of dimensions that are appropriate for microfabrication methods, such as etching, sputtering, masking and the like. The substrate is also preferably of a size appropriate for micromanipulation of particles and for comprising an ion transport measuring means that can be use to determine at least one ion transport function or property such as described in the methods herein. For example, the substrate is preferably thin, such as about a millimeter in thickness, and between about 5 millimeters and about 50 centimeters in length and width, preferably between about 1 centimeter and about 5 centimeters in length and width. However, such sizes are not considered limiting to the present invention. The substrate can be of any appropriate shape, such as geometric or non-geometric shapes, such as square, circular, oblong, elliptical or the like. Preferred shapes include squares, circles, and appropriate polygons.

The substrate can be part of a single layer or multi-layered chip that can have a plurality of functions. For example, a single layer chip can include a variety of structures to perform a variety of functions, particularly particle positioning means. Preferred particle positioning means include, for example, acoustic structures or vibrational structures such as piezoelectric materials as they are known in the art to generate acoustic fields in a sample; dielectric structures such as dielectric focusing structures, quadropole electrode structures, traveling wave dielectrophoresis structures, concentric circular electrode structures, spiral electrode structures, square spiral electrode structures particle switch structures; electrorotational structures; electromagnetic structures; DC electric field induced fluid motion structures, electroosmosis structures or negative pressure structures to move or modulate moieties or particles. Alternatively, these additional structures, such as vibrational structures or dielectric structures can be provided in separate layers of substrate. In this aspect of the present invention, a plurality of substrates can be sandwiched and adhered together and fabricated into a multifunctional chip. The different functional elements can be independently controlled by appropriate controlling devices, such as switches and conductive materials (see, generally U.S. application Ser. No. 09/679,024, entitled "Apparatuses Containing Multiple Active Force Generating Elements and Uses Thereof" filed Oct. 4, 2000, and naming as inventors Xiaobo Wang, Jing Cheng, Lei Wu, Weiping Yang and Junquan Xu).

Coating

The substrate can optionally include a coating. The coating can cover the whole surface of the substrate of a biochip, or portions of the surface of the substrate of the biochip. The coating can be provided as a thin film of appropriate material to prevent direct interaction of particles with the substrate of a biochip. Alternatively, the coating can provide structures, such as holes, that can align with or interact with structural elements on or within the substrate, such as particle positioning means or holes or capillaries (see for example, FIG. 1). Because a coating can be thinner than a substrate, precise micromanufacture of structures, particularly holes, can be done with higher degrees of accuracy or precision when compared with substrates. The film can be of any appropriate material, but is preferably a polymer, such as a plastic. The film can be made by adhering a premade film to a substrate, or can be made on the substrate. In the latter instance, for example, a solution of monomer can be dispensed onto a surface and the monomer polymerized using appropriate methods, such as the use of a polymerizing agent, such as an initiator. In one aspect of the present invention, two or more layers of polymerized materials can be made such that the polymerized layer can be made incrementally thicker using this type of process.

Other examples of coating materials include glass materials and silicon dioxide deposited on the substrate by any practical methods such as chemical vapor deposition and physical vapor deposition (e.g., sputtering or evaporation).

The coating can be a functional layer. A functional layer can include at least one immobilized moiety or ligand. Preferred immobilized moieties include charged groups, nucleic acid molecules, antibodies or receptors. The functional layer, when present, can be provided on the surface of the substrate such as to provide a variety of chemical groups or biological groups that can be utilized in the methods of the present invention. For example, antibodies or cell adhesion molecules or active fragments thereof can be localized at, near or on or within holes, capillaries or needles of the devices of the present invention so that a good electric seal between the particle such as a cell and the device can be achieved.

The functional layer can be of any appropriate material, but is preferably includes at least one of the following materials: a hydrophilic molecular monolayer, a hydrophilic molecular monolayer with functional groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups.

The functional layer can be a sheet of material that is contacted, attached or adhered to the substrate. In addition or in the alternative, the functional layer can be made by modification, such as by chemical modification or chemical treatment (for example, treatment in acid, and/or base for specified lengths of time), of the substrate or coating. Furthermore, the functional layer can be made by spraying, dipping or otherwise contacting liquid or semisolid material onto the substrate, wherein the material is then solidified such as through cooling, gelling, solidifying or polymerization. Another category of methods for producing the functional layer is physical means, in which the biochip is subjected to certain physical treatment. For example, a substrate or a biochip can be subjected to a baking procedure at certain temperature for certain lengths of time, which may result in some changes in surface compositions of the biochip. In another example, a substrate or a biochip surface or a portion of a substrate or biochip surface can be subjected a treatment by applying high energy radiation (including UV radiation), microwave radiation, oxygen plasma, or reactive chemical compounds. In still another example, the surface or the portion of the surface of a biochip made of glass may be subjected to a laser of appropriate wavelength and intensity so that the surface can be smoothed or polished.

The functional layer can have a variety of functional groups that can take part in a variety of chemical or biochemical reactions designed to immobilize particles thereon. Preferred functional groups include but are not limited to aldehydes, carbodiimides, succinimydyl esters, antibodies, receptors and lectins. Materials having these functional groups are known in the art. In addition, methods of making a variety of surfaces having these functional groups are known in the art.

The functional layer can include a moiety or ligand immobilized thereon. Preferred immobilized moieties or ligands include, but are not limited to nucleic acid molecules (such as single stranded or double stranded DNA or RNA or a combination thereof), binding reagents (such as antibodies or active fragments thereof), receptors or other members of binding pair, polypeptides, proteins, carbohydrates, lipids, prokaryotic cells, eukaryotic cells, prions, viruses, parasites, bacteria antibodies, lectins or receptors. Functional layers having such immobilized moieties thereon can be made using a variety of methods. For example, a functional layer with an appropriate functional group can be contacted with a preparation having a moiety to be immobilized thereon. The immobilization of such moieties on a functional layer can be throughout the functional layer or localized using appropriate methods, such as masking. For example, antibodies or cell adhesion molecules or active fragments thereof can be localized at, near or on or within holes, capillaries or needles of the devices of the present invention so that a good electric seal between the particle such as a cell and the device can be achieved.

A coating or a functional layer on the whole surface of a substrate, or on one or more portions of the surface of a substrate may serve any of a number of purposes. In one example, a functional layer (for example, a functionalized or modified surface obtained by chemical treatment or chemical modification) may have appropriate electric charge, hydrophilicity or hydrophobicity, texture (for example, smoothness) and/or composition, facilitating or enhancing high-resistance sealing between the substrates or ion transport measuring means and the membranes or surfaces of particles used for electrophysiological measurement.

In a specific embodiment, the substrate or coating is made of glass or silicon dioxide and the functionalized surface refers to the surface that is obtained by treating the chip with acidic and/or basic solutions. Not intending to be limited to a mechanism of action, such a treatment may result in a change in surface composition, and/or surface texture, and/or surface cleanness, and/or surface electric charge on the substrate and/or on or around the ion transport measuring means. The altered surface properties may improve or facilitate high resistance electric seal or sealing between the substrates or ion transport measuring means and the membranes or the particles under electrophysiological measurement.

In another example, a coating or a functional layer can be used for rupturing a membrane patch of a cell that has been positioned on an ion transport measuring means located on the substrate.

In some preferred embodiments of the present invention, substrates, chips, coatings or any portions thereof can be treated with one or more acids, one or more bases, oxygen plasma, or peroxide to modify the surface of substrates, chips, coatings, or any portions thereof. Alternatively or in addition, the surface of substrates, chips, or coatings or any portions thereof can optionally be heat treated or laser polished. In a particularly preferred embodiment of the present invention, a surface, substrate, chip, coating or any portion thereof can be treated with base to facilitate the formation of an electric seal between a particle and an ion transport measuring means on the surface, substrate, chip, or coating; to enhance an electric seal formed between a particle and an ion transport measuring means that is surrounded by, or located on the substrate, chip or coating; or to improve the probability of forming an electric seal between a particle and an ion transport measuring means that is surrounded by or located on the substrate, chip, or coating.

Whilst the coatings described above may be homogeneous surfaces in the composition, this is not necessarily to be the case. Different coatings may be applied to different portions of a substrate, such as a biochip surface, so that desired effects at different regions of the substrate can be obtained. For example, for a chip with ion channel measurement holes, the regions around the ion channel holes can be modified to facilitate and enhance the high-resistance electronic seal between the chip or the hole and the membrane of a particle (e.g. a cell) under measurement, whilst the regions away from the measurement hole may be modified to prevent the particles (e.g., the cells) to stick.

Chambers

The substrate is preferably provided as part of a chamber that can hold samples, such as fluids. The chamber forms walls around at least a portion of the substrate such that fluid can be stored. Optionally, the chamber can be sealed on all sides, but that need not be the case. In addition, a chamber can be connected to a variety of structures such as ports or conduits to allow fluids or solids such as samples or reagents to enter the chamber, such as through conduits. The fluids or solids are introduced into the chamber by appropriate methods or forces, such as by gravity feed or pumps. The chamber can also include exit structures, such as conduits or ports that allow materials within the chamber to be removed. In one preferred aspect of the present invention, the chamber is a flow through chamber that allows materials to be introduced by way of entry structures such as ports or conduits and materials to be removed by way of exit structures such as ports or conduits.

A chamber of the present invention is a structure that can contain a fluid sample. A chamber can be of any size or dimensions, and preferably can contain a fluid sample of between one nanoliter and 50 milliliters, more preferably between about 1 microliter and about 10 milliliters, and most preferably between about 10 microliters and about 1 milliliter. Preferably, a chamber comprises a chip. A chamber can comprise any suitable material, for example, silicon, glass, metal, ceramics, polymers, plastics, etc. and can be of a rigid or flexible material.

Chambers used in the methods of the present invention can comprise chips, where chips are solid supports on which one or more separations, assays, transportation switching, electrophysiology measurements or capturing procedures can be performed. A chip can comprise one or more metals, ceramics, polymers, copolymers, plastics, rubber, silicon, or glass. A chip can comprise one or more flexible materials. A chip can be from about one $mm^2$ to about 0.25 $m^2$. Preferably, the size of the chips useable in the present methods is from about four $mm^2$ to about 25 $cm^2$. The shape of the chips useable in the present methods can be regular shapes such as square, rectangular, circular, or oval, or can be irregularly shaped. Chips useable in the methods of the present invention can have one or more wells or one or more channels that can be etched into a chip or built onto the surface of a chip. Chips useable in the devices or methods of the present invention can have at least one incorporated ion-channel measurement structure. For example, the ion-channel measurement structure may take the form of an ion-channel measurement hole or aperture (for example, as shown in FIG. 1A-C).

Preferably, in embodiments where the chamber comprises electrodes, the electrodes will be incorporated onto or within the chip, but this is not a requirement of the present invention. Electrodes on a chip can be of any shape, such as rectangular, castellated, triangular, circular, and the like. Electrodes can be arranged in various patterns, for example, spiral, parallel, interdigitated, polynomial, etc. Electrodes can be arranged so that dielectrophoretic forces can be produced to position particles such as cells to desired locations. Electrode arrays can be fabricated on a chip by methods known in the art, for example, electroplating, sputtering, photolithography or etching. Examples of a chip comprising electrodes include, but are not limited to, the dielectrophoresis electrode array on a glass substrate (for example, Dielectrophoretic Manipulation of Particles by Wang et al., in IEEE Transaction on Industry Applications, Vol. 33, No. 3, May/June, 1997, pages 660-669), individually addressable electrode array on a microfabricated bioelectronic chip (e.g., Preparation and Hybridization Analysis of DNA/RNA from *E. coli* on Microfabricated Bioelectronic Chips by Cheng et al., Nature Biotechnology, Vol. 16, 1998, pages 541-546), and the capillary electrophoresis chip (for example, Combination of Sample-Preconcentration and Capillary Electrophoresis On-Chip by Lichtenberg, et al., in Micro Total Analysis Systems 2000 edited by A. van den Berg et al., pages 307-310).

A chamber that comprises a chip useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, for example, tygon or Teflon tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a solution of the present invention that selectively modifies the dielectric properties of one or more moieties in a sample, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

Particle Positioning Means

A biochip of the present invention preferably includes particle positioning means on substrate, within the substrate, partially within the substrate or on within or partially within the coating, although such particle positioning means can be separate from such substrate altogether. These particle positioning means are preferably manufactured using microfabrication methods, such as etching, lithography or masking, but other methods, such as machining or micro-machining can be used. The particle positioning means are active upon a particle, parts of a particle or population of particles, such as a cell, portions of cells, or cells depending on their physical characteristics. Particles can include, for example, cells or portions of cells that are linked directly or indirectly to another particle, such as a bead or microparticle, such as a polymeric bead or magnetic bead. These particles such as cells associated with additional particles can have physical properties different from the cell or cell fragment, such as dielectrophoretic mobility or susceptibility to a magnetic field.

The particle positioning means are preferably arranged such that particles can be mobilized using such particle positioning means so that particles are mobilized and positioned at, on or in close proximity to an ion transport measuring means.

The particle positioning means preferably include at least one structure selected from the group consisting of dielectric focusing structure, quadropole electrode structure, electrorotation structure, traveling wave dielectrophoresis structure, concentric circular electrode structure, spiral electrode structure, square spiral electrode structure, particle switch structure, electromagnetic structure, DC electric field-induced fluid motion structure, AC electric field induced fluid motion structure, electrophoretic structure, electroosmosis structure, acoustic structure or negative pressure structure. One or more of these structures can be integrated into a biochip for use as particle positioning structures or means. In one aspect of the present invention, one or more of these structures can be integral to a chip and can optionally be serviced by the same or different set of electrodes leading to a chip.

Dielectric Structures

A number of dielectrophoretic manipulation methods may be used for manipulating particles or cells in the present invention. For example, dielectrophoretic separation methods may be used for separating or isolating target cells or particles before they are transported to the ion transport determining means for assaying their ion transport properties. The methods that can be used for the dielectrophoretic separation in the present invention include but are not limited to the following: dielectrophoretic techniques, dielectrophoretic migration, dielectrophoretic retention, dielectrophoretic/gravitational field flow fractionation, traveling-wave dielectrophoresis and 2-D dielectrophoresis.

For an electric field of non-uniform magnitude distribution, the dielectrophoretic force on a particle of radius r can be determined, under the dipole approximation, by the following equation:

$$\vec{F}_{DEP} = 2\pi \epsilon_m r^3 X_{DEP} \nabla E_{rms}^2 \qquad (1)$$

where $E_{rms}$ is the RMS value of the field strength, the symbol $\nabla$ is the symbol for gradient-operation, $\epsilon_m$ is the dielectric permittivity of the medium, and $X_{DEP}$ is the particle polarization factor (or dielectrophoretic polarization factor), given by:

$$\chi_{DEP} = \text{Re}\left(\frac{\varepsilon_p^* - \varepsilon_m^*}{\varepsilon_p^* + 2\varepsilon_m^*}\right), \quad (2)$$

"Re" refers to the real part of the "complex number". The symbol $\varepsilon_x^* = \varepsilon_x - j\sigma_x/2\pi f$ is the complex permittivity (of the particle x=p, and the medium x=m) and $j=\sqrt{-1}$. The parameters $\varepsilon_p$ and $\sigma_p$ are the effective permittivity and conductivity of the particle, respectively.

When a particle exhibits a positive dielectrophoretic polarization factor ($X_{DEP}>0$), the particle is moved by dielectrophoretic forces toward regions where the field is the strongest. On the other hand, when a particle exhibits a negative dielectrophoretic polarization factor ($X_{DEP}<0$), the particle is moved by dielectrophoretic forces away from those regions where the field is strongest and toward those regions where the field is weakest.

The traveling wave dielectrophoretic force for an ideal traveling wave field acting on a particle of radius r an subjected to a traveling-wave electrical field $\vec{E}=E\cos(2\pi(ft-z/\lambda_0)\vec{a}_x$ (i.e. the x-component of an E-field traveling in the $\vec{a}_x$-direction, the phase value of the field x-component being a linear function of the position along the z-direction) is given by:

$$\vec{F}_{TW-DEP} = -\frac{4\pi^2 \varepsilon_m}{\lambda_0} r^3 \zeta_{TWD} E^2 \cdot \vec{a}_z \quad (4)$$

where E is the magnitude of the field strength, $\varepsilon_m$ is the dielectric permittivity of the medium. $\zeta_{TWD}$ is the particle traveling-wave dielectrophoretic polarization factor, given by $$\zeta_{TW-DEP} = \text{Im}\left(\frac{\varepsilon_p^* - \varepsilon_m^*}{\varepsilon_p^* + 2\varepsilon_m^*}\right),$$

"Im" refers to the imaginary part of the "complex number". The symbol $\varepsilon_x^* = \varepsilon_x - j\sigma_x/2\pi f$ is the complex permittivity (of the particle x=p, and the medium x=m). The parameters $\varepsilon_p$ and $\sigma_p$ are the effective permittivity and conductivity of the particle, respectively. These parameters may be frequency dependent.

The traveling wave dielectrophoretic force acts on a particle that is either oriented with or against that of the direction of propagation of the traveling-wave field, depending upon whether the traveling wave dielectrophoretic polarization factor is negative or positive. If a particle exhibits a positive traveling wave dielectrophoretic polarization factor ($\xi_{TW-DEP}>0$) at the frequency of operation, the traveling wave dielectrophoretic force will be exerted on the particle in a direction opposite that of the direction in which the electric field travels. On the other hand, if a particle exhibits a negative traveling wave dielectrophoretic polarization factor ($\xi_{TW-DEP}<0$) at the frequency of operation, the traveling wave dielectrophoretic force will be exerted on the particle in the same direction in which the electric field travels.

Thus, the movement of a particle in a non-uniform electric field depends in part on the size (r), permittivity ($\varepsilon_p$), and conductivity ($\sigma_p$) of the particle. The size of a particle in part determines the magnitude of the dielectrophoretic force, whereas the conductivity and permittivity of a particle influence the direction and the magnitude of a particle's movement in a non-uniform field. Accordingly, particles that have different dielectric properties but are subjected to identical electrical fields will experience different dielectrophoretic forces and different traveling wave dielectrophoretic forces.

The following discussion of the dielectric properties of particles is provided as background information for factors to be considered in the selection and derivation of particle suspending media or solution for dielectrophoretic positioning and manipulation of particles such as cells. The applicants provide this model as background only, and expressly do not wish to be limited to any mechanism of action described herein.

The permittivies and conductivities of particles depend upon the composition of the particles. For example, a homogeneous particle such as a polystyrene bead has a single permittivity value that determines the effective permittivity of the bead, and a single conductivity value that determines the effective conductivity of the bead. These properties may be independent of the field frequency in a wide frequency range, for example, between 1 Hz and 100 MHz. Particles that have a homogeneous bulk composition may have net surface charges. When such charged particles are suspended in a medium, electrical double layers may form at the particle/medium interfaces. Externally applied electric field may interact with the electrical double layers, causing changes in the effective conductivity and effective permittivity of the particles. The interactions between the applied field and the electrical double layers are generally frequency dependent. Thus, the effective conductivity and effective permittivity of such particles may be frequency dependent.

In contrast, non-homogeneous particles such as cells have a membrane permittivity and an internal permittivity, and a membrane conductivity and an internal conductivity. The effective permittivity and the effective conductivity of a non-homogeneous particle is dependent on both its membrane properties and its internal properties. The effective permittivity and effective conductivity of a non-homogeneous particle are dependent on the field frequency. Different dielectric models have been developed to represent different cell types. In particular, single-shell modeling has been applied to mammalian cells, in which cells are modeled as conducting spheres (corresponding to cell interiors) surrounded by poorly-conducting thin shells (corresponding to cell membranes). The effective cell dielectric property is then determined by dielectric parameters of the cell interiors and membranes and can be calculated according to:

$$\varepsilon_{cell}^* = \varepsilon_{mem}^* \frac{\left(\frac{r}{r-d}\right)^3 + 2\frac{\varepsilon_{int}^* - \varepsilon_{mem}^*}{\varepsilon_{int}^* + 2\varepsilon_{mem}^*}}{\left(\frac{r}{r-d}\right)^3 - \frac{\varepsilon_{int}^* - \varepsilon_{mem}^*}{\varepsilon_{int}^* + 2\varepsilon_{mem}^*}}$$

Here is the complex permittivity $\varepsilon_x^*$ of a cell (x=cell), or its membrane (x=mem) or its interior (x=int). The parameters r and d refer to the cell radius and membrane thickness, respectively.

The frequency dependence of the dielectrophoretic polarization factor ($X_{DEP}$) and the traveling wave dielectrophoretic polarization factor ($\xi_{TW-DEP}$) of non-homogeneous particles such as cells arises from the frequency dependence of the particles' dielectric properties. The dielectric properties of a mammalian cell are influenced by cell size, membrane thickness, the dielectric properties of the cell membrane, and the dielectric properties of the cell interior. Typically, a viable cell has a poorly-conducting membrane (membrane conductivity is typically small, less than $10^{-4}$ Siemens/m) which encloses a moderately conducting cell interior (interior conductivity is typically high, larger than 0.1 Siemens/m). At low frequencies, the applied field the cell membrane drops across the cell membrane, and the cell membrane dominates the dielectric properties of the whole cell. Under these conditions the cell may have negative values for the dielectrophoretic polarization factor ($X_{DEP}<0$) and exhibit negative dielectrophoresis. As frequency is increased, the applied field gradually penetrates through the cell membrane into the cell interior, and the cell's dielectrophoretic polarization factor changes from negative to positive ($X_{DEP}>0$). In such a frequency range, the interaction between the cell and the applied field tends to cause the cell to exhibit positive values for the traveling wave polarization factor ($\xi_{TW-DEP}>0$). As the frequency is increased further, the cells interior properties (at first the effective conductivity and then the effective permittivity) determine the cell's responses. The cell first exhibits positive values for the dielectrophoresis polarization factor ($X_{DEP}>0$) and then at even higher frequencies exhibits gradually decreasing values for $X_{DEP}$. In this frequency range, the cell exhibits negative values for the traveling wave dielectrophoretic polarization factor ($\xi_{TW-DEP}<0$). The exact frequency ranges for these different regimes of dielectrophoresis and traveling wave dielectrophoresis polarization factors depend on the cell's dielectric properties and the electrical conductivity of the solution in which the cells are suspended.

Some cells, notably bacterial, fungal, and plant cells, have a cell wall in addition to a cell membrane. The dielectric properties of such complex particles are complex, with the electrical permittivities and conductivities of each of the cell wall, cell membrane, and cell interior dominating the dielectrophoretic behavior of the cells at particular field frequencies. The determination of electrical properties of the cell walls of micro-organisms and the dielectrophoretic behavior of cell wall-containing micro-organisms is described in Markx et al. (Microbiology 140: 585-591 (1994)).

The overall size of a particle or a component of a sample also determines its response to an electric field, and thus is herein considered a dielectric property. A sample component's conductivity, permittivity, or size, or any combination of these properties, can be altered by a solution of the present invention.

Electrode arrays can be used to test behavior of particles in suspending solution or media. For example, positive or negative dielectrophoresis of particles can be observed after applying an electric field. For example, a particle suspended in solution can be pipetted onto a polynomial electrode array and a sinusoidal signal at certain frequencies (for example, between about 10 Hz to about 500 MHz) and at certain magnitude (<20 V peak-to-peak) can be applied to the electrodes. Particles that experience positive dielectrophoresis collect at the electrode edges, while components that experience negative dielectrophoresis collect at the central region between the electrodes (Huang and Pethig, Meas. Sci. Technol. 2: 1142-1146 (1991).

Tests for manipulation or positioning of particles by dielectrophoresis can use detectable labels, where at least one particle in a sample is detectably labeled. For example, a biological sample having a population of particles such as cells can be subjected to a dielectrophoretic manipulation procedure, one cell type can be labeled using antibodies that recognize that cell type and not other cell types or components of the sample. The antibodies can be bound to a detectable label, such as, for example, a fluorescent molecule, such as rhodamine, fluorescein, Texas red, phycoerythrin, phycocynanin, green fluorescent protein, cyan fluorescent protein, blue fluorescent protein, yellow fluorescent protein, D.s. red protein, etc. Another cell type can optionally be labeled with a different antibody and a different detectable label. In this way, the positions of the cells carrying the fluorescent labels can be visualized and the quality of dielectrophoretic separation using a buffer of the present invention can be assessed.

The dielectric manipulation and positioning of particles such as cells can also be monitored by loading cells with detectable labels, such as dyes, as they are known in the art. For example, cells can be loaded with BCECF-AM (available from Molecular Probes, Eugene, Oreg.) a flourescein probe that can be taken up by viable cells and there position after dielectric positioning can be determined (Gascoyne et al. IEEE Transcactions 33:670-678 (1997)). A chip on which positioning of particles such as cells has been tested can be viewed microscopically.

Separation, manipulation or positioning of particles in a sample in a chamber can occur through the application of a non-uniform electric field. Preferably, separation, manipulation or positioning of particles occurs on a chip that is part of a chamber, and application of the non-uniform electric field can be by means of controls that are external to a chamber and a chip. One or more power sources or electrical signal generators, which may be capable of varying voltage, frequency, phase, or any combination thereof, can transmit at least one electrical signal to one or more electrodes to create a spatially non-homogeneous alternating electric field. The voltage applied to the electrodes can be in the range of from about 0 to about 100 volts, more preferably from about 0 to about 15 volts, and the frequency of the electrical signal can be in the range of from about 0.01 kHz to about 500 MHz, and preferably from between about 1 kHz to about 20 MHz. These frequencies are exemplary only, as the frequency of the separation, manipulation or positioning of particles will depend upon a dielectric property of the particles to be separated, manipulated or positioned and the conductivity of the solution the particles are suspended in.

Separation, manipulation or positioning of particles by dielectrophoretic forces can occur by any dielectrophoretic mechanism, for example, by dielectrophoretic retention, dielectrophoretic migration, dielectrophoretic/gravitational field flow fractionation, or traveling wave dielectrophoresis-based separation, or 2-D dielectrophoresis. The following examples of separations, manipulations or positionings are given by way of illustration, and not by way of limitation. Dielectrophoretic retention can be employed, in which the particle is selectively retained in one or more areas of the chamber and other components of the sample are optionally washed out of the chamber by fluid flow. In a different approach of dielectrophoretic migration, one or more particles can be dielectrophoretically translocated to one or more areas of a chip and one or more other components of a sample can be dielectrophoretically repelled from those areas. It is also possible to effect a dielectric separation, manipulation or positioning using dielectrophoretic/gravitational field flow fractionation, in which different particles are levitated to different heights, or in which one or more particles is levitated while other particles are directed to one or more locations on the chip, and fluid flow through the chamber comprising the chip carries different sample components out of the chip at different speeds. It is also possible to direct one or more particles out of the chamber using traveling wave dielectrophoresis, to effect a separation, manipulation or positioning from the other components. It is also possible to use 2-dimensional dielectrophoresis in which both dielectrophoretic forces and traveling-wave dielectrophoretic forces are exploited for separation, manipulation or positioning of one or more particles from a sample (De Gasperis et al., Biomedical Microdevices 2: 41-49 (1999)).

Because a sample can comprise components whose behaviors in various dielectric field patterns is unknown, separation of moieties can be achieved and optimized by altering such parameters as electrode geometry, electric field magnitude, and electric field frequency.

The separation can be achieved by collecting and trapping the positive dielectrophoresis-exhibiting moieties on electrode edges while removing other cells with forces such as fluidic forces. Similar methods may be applied for the case of using negative dielectrophoresis-exhibiting particles for selective separation of target cells from cell mixtures where most or many cell types exhibit positive dielectrophoresis. In aspects where dielectrophoretic/gravitational field-flow fractionation, traveling wave dielectrophoresis, or 2-dimensional dielectrophoresis is used, the separation can be achieved by collecting fractions of the sample-sample solution mixture as they "elute" or flow out of, a chamber experiencing fluid flow and dielectrophoretic forces.

There are a number of dielectrophoretic methods for separating and manipulating cells, bioparticles and moieties from a sample mixture. These methods include, but not limited to, dielectrophoretic migration, dielectrophoretic retention, dielectrophoretic/gravitational field flow fractionation, traveling-wave dielectrophoresis, and 2-D dielectrophoresis. Those who are skilled in the art of dielectrophoretic manipulation and dielectrophoretic separation may readily use and apply these methods for separating moieties of interest from a mixture in combination with the sample solution of the present invention. The following articles provide detailed descriptions of a number of dielectrophoretic manipulation and dielectrophoretic separation methods: Wang, et al., *Biochim. Biophys. Acta.* 1243:185-194 (1995), Wang, et al., *IEEE Trans. Ind. Appl.* 33:660-669 (1997) (various electrode structures, manipulation by dielectrophoresis and traveling wave dielectrophoresis); Wang, et al., *Biophys. J* 72:1887-1899 (1997) (concentration, isolation and separation using spiral electrodes using traveling wave dielectrophoresis); Wang, et al., *Biophys. J.* 74:2689-2701 (1998), Huang, et al., *Biophys. J.* 73:1118-1129 (1997) and Yang, et al., *Anal. Chem.* 71(5):911-918 (1999) (levitation, repulsion from electrodes and separation by dielectrophoretic/gravitational field-flow-fractionation); Gascoyne, et al., *IEEE Trans. Ind. Apps.* 33(3):670-678 (1997), Becker, et al., *Proc. Natl. Acad. Sci. USA* 92:860-864 (1995) and Becker, et al., *J. Phys. D: Appl. Phys.* 27:2659-2662 (1994) (trapping, repulsion, redistribution and separation, separation by dielectrophoretic migration, separation by dielectrophoresis retention); Huang, et al., *J. Phys. D: Appl. Phys.* 26:1528-1535 (1993) (transportation, separation and trapping by traveling-wave-dielectrophoresis); and Wang, et al., *J. Phys. D: Appl. Phys.* 26:1278-1285 (1993) (trapping, separation and repulsion, separation by dielectrophoretic migration). All the above cited papers are incorporated in the present application by reference. Other examples of manipulation and separation methods that are reported in the literature and may be adapted for manipulating moieties using the present methods include: separation of bacteria from blood cells, and of different types of microorganisms (Hawkes, et al., *Microbios.* 73:81-86 (1993); and Cheng, et al., *Nat. Biotech.* 16:546-547 (1998)); enriching CD34+ stem cells from blood (Stephens, et al., *Bone Marrow Transplantation* 18:777-782 (1996)); DEP collection of viral particles, sub-micron beads, biomolecules (Washizu, et al., *IEEE Trans. Ind. Appl.* 30:835-843 (1994); Green and Morgan, *J. Phys. D: Appl. Phys.* 30:L41-L44 (1997); Hughes, et al., *Biochim. Biophys. Acta.* 1425:119-126 (1998); and Morgan, et al., *Biophys J.* 77:516-525 (1999)); dielectrophoretic levitation for cell characterization (Fuhr, et al., *Biochim. Biophys. Acta.* 1108:215-233 (1992)); single-particle homogeneous manipulation (Washizu, et al., *IEEE Trans. Ind. Appl.* 26:352-358 (1990); Fiedler, et al., *Anal. Chem.* 70:1909-1915 (1998); and Müller, et al., *Biosensors and Bioelectronics* 14:247-256 (1999)); dielectrophoretic field cages (Schnelle, et al., *Biochim. Biophys. Acta.* 1157:127-140. (1993); Fiedler, et al. (1995); Fuhr, et al. (1995a); Fiedler, et al. (1998); Müller, et al. (1999)); traveling-wave DEP manipulation of cells with linear electrode arrays (Hagedorn, et al., *Electrophoresis* 13:49-54 (1992); Fuhr, et al., *Sensors and Actuators A:* 41:230-239 (1994); and Morgan, et al., *J. Micromech. Microeng.* 7:65-70 (1997)) All the above cited papers are incorporated in the present application by reference.

Dielectric Focusing Structures

Dielectric focusing structures refer to any electrode structure elements fabricated or machined onto a chip substrate that have the following properties. These electrode elements can produce electric fields in the spaces around the chip when they are connected with and energized with electrical signals. Such electric fields may be non-uniform AC electric fields, traveling-wave electric fields, or non-uniform traveling wave electric fields, or electric fields of any other configuration. These electric fields preferably can exert dielectrophoretic forces and traveling wave dielectrophoretic forces on the particles that are suspended or placed in the solutions that are in contact with the electrode elements. Such dielectrophoretic and/or traveling-wave dielectrophoretic forces can then direct or focus or move the particles onto certain specific locations.

In operation, a fluidic chamber is first constructed that includes a biochip of the present invention. A sample that includes particles such as cells is introduced into the chamber. The appropriate electrical signals are applied to the electrodes to produce an electrical field that exert dielectrophoretic and traveling-wave dielectrophoretic forces that can direct or focus or move the particles to the specific locations on the chip. Those locations correspond to the positions at which the ion-channel means are located.

Non-limiting examples of the dielectric focusing structures include spiral electrode structures, circular electrode structures, squared spiral electrode structures, traveling wave dielectrophoresis structures, particle switch structures, quadropole electrode structures, and electrorotation structures.

Spiral electrode structures include multiple, parallel, linear spiral electrode elements. For example, the structure can include three, four, five or even more, parallel, linear spiral elements. AC electrical signals of same frequency, but different phases are applied to these multiple electrode elements to generate a traveling wave electric field towards or away from the center of the electrode array. In order to produce such traveling wave electric field, phases of the signals applied to these electrode elements should be 0, 360/N, 2*360/N, . . . (N−1)*360/N, where N is the number of the spiral elements. The structure and operational principle of a spiral electrode array (N=4) is described in "Dielectrophoretic manipulation of cells using spiral electrodes by Wang et al., *Biophys. J.*, 72:1887-1899 (1997)", which is incorporated in its entirety by reference.

In operation, a fluidic chamber is first constructed that includes a biochip having a spiral electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the spiral electrode elements. The details of choosing such operation conditions for the maximum response effects in a 4-phase spiral electrode system are described and discussed in "Dielectrophoretic manipulation of cells using spiral electrodes by Wang et al., Biophys. J., 72:1887-1899 (1997)". Based on the details on this article, those who are skilled in dielectrophoresis and traveling-wave dielectrophoresis can readily choose the operation conditions for other spiral electrode structures with different numbers of the parallel elements. An ion-channel measuring means is located at the central region of the spiral electrode structures. For example, a hole of appropriate size and geometry is at the center of the spiral electrode. After the particles are moved or focused to the center of the spiral electrodes and over the hole at the center of the spiral electrode elements, appropriate electrophysiology measurements are performed on the particles to determine the electrical functions and properties of the ion channels (or ion transporters or other proteins or non-peptide entity that permit the passage of the ions) on the surface of the particles. In one example, electrophysiological measurement include the procedure of obtaining and testing high-resistance electrical seal between the cell and the chip or the hole, obtaining whole cell access by rupturing membrane patch in the hole, recording the whole-cell current through the ion channels located in the cell membrane under various voltage-clamp protocols.

Concentric circular electrodes are electrode structures that include multiple concentric circular electrode elements. The circular electrode elements are connected to external signal source through electrode lines cutting cross these circular elements. These electrode lines have to be fabricated into a different layer on the chip and have to be isolated from the circular elements. In order to produce a traveling electric field, the electrical signals applied to the circular elements have to be phase-sequenced. For example, the signals with the phase values of 0, 90, 180, 270 can be applied sequentially to the circular elements. If we number the circular elements from outermost element (as No. 1) to the innermost as 1, 2, 3, 4, 5, 6, . . . , then the electrode elements 1, 5, 9, . . . etc are connected with 0 phase signal, the elements 2, 6, 10, . . . etc are connected with 90 phase signal, the elements 3, 7, 11, . . . etc are connected with 180 phase signal, the elements, 4, 8, 12, . . . etc are connected with 270 phase signals. Other phase combinations can be used and applied so long as a complete phase sequence (0 to 360 degree) can be established over the electrode elements. For example, signals having phase values of 0, 120 and 240 degrees can be used to energize three neighboring electrode elements.

The operational principle of the concentric circular electrodes is similar to the spiral electrode elements (see, Wang et al., "Dielectrophoretic manipulation of cells using spiral electrodes by Wang et al., Biophys. J., 72:1887-1899 (1997)".

In operation, a fluidic chamber is first constructed including a biochip having a concentric electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the concentric electrodes. The details as for how to choose such operation conditions for the maximized response effects in a 4-phase spiral electrode structure are described and discussed in "Dielectrophoretic manipulation of cells using spiral electrodes by Wang et al., Biophys. J., 72:1887-1899 (1997)". Based on the details on this article, those skilled in dielectrophoresis and traveling-wave dielectrophoresis can readily choose the operation conditions for the concentric electrode structures. An ion-channel measuring means is located at the central region of the concentric electrode elements. For example, a hole of appropriate size and geometry is at the center of the concentric electrode structure. After the particles are moved or focused to the center of the spiral electrodes and over the hole at the center of the concentric circular electrode elements, appropriate electrophysiological measurements are performed on the particles to determine electrical functions or properties of the ion channels (or ion transporters or other proteins or non-peptide entity that permit the passage of the ions) on the surface of the particles.

Squared-spiral electrodes are electrode structures that include multiple squared-spiral electrode elements. The operation principle of the squared-spiral electrodes is similar to that of a spiral electrode structure, and the traveling wave dielectrophoretic forces produced by the squared spiral electrodes are directed to be normal the linear electrode segments in these electrode elements.

In operation, a fluidic chamber is first constructed including a biochip having a squared-spiral electrode structure. A sample that includes particles such as cells is introduced into the chamber. The electrical signals of appropriate phase, voltage and frequencies are applied to the electrodes to produce an electrical field that exert dielectrophoretic and traveling-wave dielectrophoretic forces that can direct or focus or move the particles to the center regions of the squared-spiral electrode structures. The details as for how to choose such operation conditions for the maximized response effects in a 4-phase spiral electrode structure are described and discussed in "Dielectrophoretic manipulation of cells using spiral electrodes by Wang et al., Biophys. J., 72:1887-1899 (1997)". Based on the details on this article, those skilled in dielectrophoresis and traveling-wave dielectrophoresis can readily choose the operation conditions for the squared-spiral structures. An ion-channel measuring means is located at the central region of the squared-spiral electrode elements. For example, a hole of appropriate size and geometry is at the center of the squared-spiral electrode structure. After the particles are moved or focused to the center of the squared spiral electrodes and over the hole at the center of the squared-spiral electrode elements, appropriate electrophysiological measurements are performed on the particles to determine electrical functions or properties of the ion channels (or ion transporters or other proteins or non-peptide entity that permit the passage of the ions) on the surface of the particles. In one example, electrophysiological measurement include the procedure of obtaining and testing high-resistance electrical seal between the cell and the chip or the hole, obtaining whole cell access by rupturing membrane patch in the hole, recording the whole-cell current through the ion channels located in the cell membrane under various voltage-clamp protocols.

Traveling Wave Dielectrophoresis Structures

Traveling wave dielectrophoresis structure generally refers to an electrode structure that can produce traveling wave electric fields and exert traveling wave dielectrophoresis forces on the particles. Examples of the traveling wave dielectrophoresis structures include, but not limited to, the spiral electrode structure, the squared electrode structure and the concentric circular electrode structures, particle switch structures. Another example of the traveling wave dielectrophoresis structures is a set of linear, parallel electrodes that can be energized with phase-sequenced signals and can induce traveling electric fields. A number of traveling wave dielectrophoresis structures are disclosed and described on the co-pending U.S. applications (Ser. No. 09/678,263), titled "AN APPARATUS FOR SWITCHING AND MANIPULATING PARTICLES AND METHOD OF USE THEREOF" by Wang et al., filed on Oct. 3, 2000, which is incorporated by reference in its entirety. Those electrode structures can be utilized for the manipulation and positioning of particles such as cells and cell fragments for ion channel or ion transport measurement described in this application. An ion-channel measuring means (or a means to measure electrical responses of ion channels, ion transporters and any other molecules or entities that permit ion passage across an enclosed membrane envelope or across a spread-out membrane area) is located at appropriate locations in respect to the traveling wave dielectrophoresis structures. For example, it is preferred that the ion channel measuring means are located at the regions where the particles can be manipulated into when appropriate electrical signals are applied.

In one specific embodiment, traveling wave dielectrophoresis structures take the form of a set of linear, parallel electrode elements. An ion-channel measuring means (or a means to measure electrical responses of ion channels, ion transporters and any other molecules or entities that permit ion passage across an enclosed membrane envelope or across a spread-out membrane area) is located on one end of the linear set of the electrodes. These structures are produced on a chip substrate. In the operation, a fluidic chamber is first constructed comprising this chip having the linear set of electrode elements. A sample that comprises particles such as cells is introduced into the chamber. The electrical signals of appropriate phases, voltages and frequencies are applied to the electrode elements to produce an electrical field that exert dielectrophoretic and traveling-wave dielectrophoretic forces that can direct or focus or move the particles to the end of the linear set of the electrodes (the end where an ion-channel measuring means is located). Those are skilled in dielectrophoresis and traveling-wave dielectrophoresis can readily choose the operation conditions for such linear parallel electrode structures. The ion channel measuring means, for example, may comprise a hole at the end of the linear set of the electrodes. After the particles are moved or focused to the center of the spiral electrodes and over the hole at the end of the linear electrode elements, appropriate electrophysiological measurements are performed on the particles to determine electrical functions or properties of the ion channels (or ion transporters or other proteins or non-peptide entity that permit the passage of the ions) on the surface of the particles. In one example, electrophysiological measurement include the procedure of obtaining and testing high-resistance electrical seal between the cell and the chip or the hole, obtaining whole cell access by rupturing membrane patch in the hole, recording the whole-cell current through the ion channels located in the cell membrane under various voltage-clamp protocols.

Particle Switch Structures

Particle switching structures generally refer to an electrode structure that can transport, switch, and move the particles in certain directions defined by the traveling wave electric fields generated by such particle switching electrodes when electrical signals of appropriate phase. A number of example for the particle switching structures are provided in the co-pending U.S. patent application Ser. No. 09/678,263, titled "AN APPARATUS FOR SWITCHING AND MANIPULATING PARTICLES AND METHOD OF USE THEREOF" by Wang et al., filed on Oct. 3, 2000. The U.S. patent application Ser. No. 09/678,263 also disclosed methods for manipulation, transportation, separation and positioning of particles such as cells by applying appropriate electrical signals. An ion-channel measuring means (or a means to measure electrical responses of ion channels, ion transporters and any other molecules or entities that permit ion passage across an enclosed membrane envelope or across a spread-out membrane area) is located at appropriate locations in respect to the particle switching structures. For example, it is preferred that the ion channel measuring means are located at the regions where the particles can be manipulated into when appropriate electrical signals are applied.

In operation, a fluidic chamber is first constructed including a biochip having particle-switch electrode structures. A sample that includes particles such as cells is introduced into the chamber. The electrical signals of appropriate phase, voltage and frequencies are applied to the particle switch structures to produce an electrical field that exert dielectrophoretic and traveling-wave dielectrophoretic forces that can direct or focus or move the particles to certain locations of the particle switching electrode structures where the ion-channel measuring means is located. The co-pending U.S. patent application Ser. No. 09/678,263, entitled "AN APPARATUS FOR SWITCHING AND MANIPULATING PARTICLES AND METHOD OF USE THEREOF" by Wang et al., filed on Oct. 3, 2000, disclosed details of the choice of appropriate electrical conditions for moving and transporting particles. The ion channel measuring means, for example, may comprise a hole located at appropriate positions with respect to the particle switching electrode structures. After the particles are moved or focused to the regions of ion channel measuring means and over the hole, appropriate electrophysiological measurements are performed on the particles to determine electrical functions or properties of the ion channels (or ion transporters or other proteins or non-peptide entity that permit the passage of the ions) on the surface of the particles. In one example, electrophysiological measurement include the procedure of obtaining and testing high-resistance electrical seal between the cell and the chip or the hole, obtaining whole cell access by rupturing membrane patch in the hole, recording the whole-cell current through the ion channels located in the cell membrane under various voltage-clamp protocols.

Electromagnetic Structures

Magnetic particles that are capable of being translocated in response to magnetic field and to electromagnetic forces can comprise any magnetic material (such as $\gamma Fe_2O_3$ and $Fe_3O_4$, $\gamma Fe_2O_3$ is the $\gamma$-phase of $Fe_2O_3$). Paramagnetic particles are preferred whose dipoles are induced by externally applied magnetic fields and return to zero when the external field is turned off. Suitable paramagnetic materials include, for example, iron compounds. Magnetic materials can be combined with other materials, such as polymers, in or on magnetic particles. Surfaces of magnetic particles of the present embodiment can optionally be coated with one or more compounds to facilitate attachment of specific binding members or to promote direct or indirect binding of particles such as cells or target cells. Magnetic particles that can be used in the present invention can be of any shape. Preferably magnetic particles are spherical or ellipsoid, but this is not a requirement of the present invention. The use of magnetic particles is well known in the biological and biochemical separation arts, and magnetic particles, including magnetic particles coupled to a variety of specific binding members are also commercially available (Dynal Biotech, Lake Success, N.Y.).

More than one preparation of magnetic particles can be used in the methods of the present invention. In embodiments using more than one preparation of magnetic particles, different magnetic particles can have different surface properties, such that they can bind different particles in a sample. In this way, more that one type of particles can be separated or positioned using the methods of the present invention. Different surface properties of magnetic particles can be conferred, for example, by coating the magnetic particles with different compounds, or by reversibly or irreversibly linking different specific binding members to the surfaces of the magnetic particles.

The particles to be manipulated or positioned can be coupled to the surface of the binding partner such as magnetic particles with any methods known in the art. For example, the particles such as cells can be coupled to the surface of the binding partner (e.g. magnetic particles) directly or via a linker. The particle can also be coupled to the surface of the binding partner (e.g. magnetic particles) via a covalent or a non-covalent linkage. Additionally, the particle can be coupled to the surface of the binding partner (e.g. magnetic particles) via a specific or a non-specific binding. The linkage between the particle and the surface of the binding partner (e.g. magnetic particles) can be a cleavable linkage, for example, a linkage that is cleavable by a chemical, physical or an enzymatic treatment.

Linkers can be any particle suitable to associate the particle (e.g., cells or cell fragments) and the binding partner (e.g. magnetic particles). Such linkers and linkages include, but are not limited to, amino acid or peptidic linkages, disulfide bonds, thioether bonds, hindered disulfide bonds, and covalent bonds between free reactive groups, such as amine and thiol groups. Other linkers include acid cleavable linkers, such as bismaleimideothoxy propane, acid labile-transferrin conjugates and adipic acid dihydrazide, that would be cleaved in more acidic intracellular compartments; cross linkers that are cleaved upon exposure to UV or visible light and linkers, such as the various domains, such as $C_H1$, $C_H2$, and $C_H3$, from the constant region of human $IgG_1$ (Batra et al., *Molecular Immunol.*, 30:379-386 ((1993)). In some embodiments, several linkers may be included in order to take advantage of desired properties of each linker. Other linkers, include trityl linkers, particularly, derivatized trityl groups to generate a genus of conjugates that provide for release of the particle at various degrees of acidity or alkalinity (U.S. Pat. No. 5,612,474). Additional linking particles are described, for example, in Huston et al., *Proc. Natl. Acad. Sci. U.S.A.*, 85:5879-5883 (1988), Whitlow, et al., *Protein Engineering*, 6:989-995 (1993), Newton et al., *Biochemistry*, 35:545-553 (1996), Cumber et al., *Bioconj. Chem.*, 3:397-401 (1992), Ladurner et al., *J. Mol. Biol.*, 273:330-337 (1997) and in U.S. Pat. No. 4,894,443. In some cases, several linkers may be included in order to take advantage of desired properties of each linker. The preferred linkages used in the present methods are those effected through biotin-streptavidin interaction, antigen-antibody interaction, ligand-receptor interaction, or nucleic complementary sequence hybridization. Linkers for binding a particle to a binding partner such as a microparticle and methods of coupling linkers to microparticles are further described in U.S. patent application Ser. No. 09/636,104, entitled "Methods for Manipulating Moieties in Microfluidic Systems", naming Xiaobo Wang, Lei Wu, Jing Cheng, Weiping Yang, and Junquan Yu as inventors and on filed Aug. 10, 2000 and corresponding PCT Application Number PCT/US00/25381, entitled "Method for Manipulating Moieties in Microfluidic Systems", filed Sep. 15, 2000, and naming Xiaobo Wang, Lei Wu, Jing Cheng, Weiping Yang, and Junquan Yu as inventors, and herein incorporated by reference in its entirety.

There are two general purposes for using magnetic particles in the present invention. The first is to bind to a particle (e.g. a cell containing ion channels in its plasma membrane) or target particle (e.g. a target cells within a cell mixture) to a magnetic particle for the purpose of separating the particle or target particle from other particles, such as in a population of particles in a sample mixture. The separation can be achieved using magnetic or electromagnetic elements, structures or means on, within or outside of a chip. The second is to position particles (e.g. the cells that contain ion channels in their plasma membranes) bound with magnetic particles in proximity of ion transport detection structures of the present invention. The positioning can be achieved using magnetic or electromagnetic elements, structures or means on, within or outside of a chip. In certain instances, the magnetic particles can aid in engaging a particle with such an ion transport detection structure. In one aspect of the present invention, particles (e.g. cells) are selectively attached to magnetic microparticles, such as through specific binding members, such as antibodies. The particles (e.g., cells) labeled with magnetic microparticles are then separated using electromagnetic elements of the present invention and can be manipulated or positioned at or near an ion transport measuring means. The particle (e.g. a cell) is engaged with such ion transport measuring means and one or more ion transport functions or properties can be determined.

In one aspect of the present invention, particles, such as cells, can express or over-express an exogenous surface peptide or over-express an endogenous surface protein, such as a cell surface marker not endogenous to the cell. A specific binding member bound to a magnetic particle would specifically bind with that cell and allow for that cell to be separated from a sample including a mixture of cells using electromagnetic elements. The magnetic particle bound to a particle (e.g. a cell) would also facilitate manipulation of the particle and positioning at or near an ion transport determination structure such as a hole or capillary. Particles such as cells having such cell surface markers can be made by introducing an expression vector into the cells. The expression vector would include a regulatory element such as a promoter operable in the host cell being used operably linked to a nucleic acid sequence encoding the exogenous or endogenous cell surface protein. Methods of making such constructs, introducing the vector into the cells and expression are known in the art.

In another aspect of the present invention, particles such as cells can co-express two proteins, one the exogenous cell surface marker or over-expressed endogenous cell surface marker discussed above and the second an exogenous ion transport protein or over-expressed endogenous ion transport protein. These particles such as cells thus express a surface marker that can be specifically bound with another particle such as a magnetic particle. These bound particles can be separated, manipulated and positioned with appropriate particle manipulation devices, such as magnetic, electromagnetic devices. The particles that are positioned in this way include the ion transport protein which can then be interrogated using structures and methods of the present invention.

In some cases, after manipulating or separating the particle-binding partner, for example, cell-magnetic micropar-ticle, the binding partners do not interfere with reactions or measurements the particles (e.g. cells) are to be subsequently involved in. Thus, it may not be necessary to decouple the particles (e.g. cells) from the magnetic particles. However, in other cases, it may be desirable or necessary to decouple the particles (e.g. cells) from the magnetic particles after the manipulating step. The nature of the decoupling step depends on the nature of the particle, the particular magnetic particle, the surface modification of the magnetic particle, in particular the specific binding partner, linker, or coupling agent that may be on the magnetic particle, and the manipulation step. In some cases, the condition of the decoupling step is the opposite of the conditions that favor the binding between the particle and the magnetic particle. For example, if a particle binds to the magnetic particle at a high salt concentration, the particle can be decoupled from the magnetic particle at a low salt concentration. Similarly, if a particle binds to the magnetic particle through a specific linkage or a linker, the particle can be decoupled from the magnetic particle by subjecting the linkage to a condition or agent that specifically cleaves the linker.

Paramagnetic particles are preferred whose magnetic dipoles are induced by externally applied magnetic fields and return to zero when external field is turned off. For such applications, commercially available paramagnetic or other magnetic particles may be used. Many of these magnetic particles are between below micron (for example, 50 nm-0.5 micron) and tens of microns. They may have different structures and compositions. One type of magnetic particles has ferromagnetic materials encapsulated in thin latex, for example, polystyrene, and shells. Another type of magnetic particles has ferromagnetic nanoparticles diffused in and mixed with latex for example polystyrene, surroundings. The surfaces of both these particle types are polystyrene in nature and may be modified to link to various types of molecules.

Separations, manipulations or positioning of particles such as target cells using magnetic particles are performed on electromagnetic chips, where the source of the electromagnetic force is in part separate from the chip and in part integral to the chip. An electrical current source is external to an electromagnetic chip of the present invention, allowing the operator to control the electromagnetic force, whereas the electromagnetic elements are fabricated onto the chip. The electromagnetic elements can produce magnetic fields and exert electromagnetic forces on magnetic particles. The electromagnetic elements can be of various structural geometries. For example, the electromagnetic elements can be a loop of conducting material, such as metal, that goes around a ferromagnetic body and that can be sputtered, electroplated, or deposited on a chip. An electromagnetic chip can have one or more electromagnetic units as described in the U.S. patent application Ser. No. 09/399,299, filed Sep. 16, 1999, naming Zhou et al. as inventors, and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Cheng, Weiping Yang, YuXiang Zhou, LiTian Liu, and JunQuan Xu as inventors, both herein incorporated by reference. For use of these electromagnetic chips for characterizing the ion channel responses in the method of the present invention, these electromagnetic chips may further comprise ion transport detection (or measuring) means. The ion transport detection structures are fabricated or made at appropriate locations with respect to the electromagnetic elements.

Other examples of such electromagnetic elements include, but not limited to, those described in the following articles such as Ahn, C., et al., *J. Microelectromechanical Systems*. Volume 5: 151-158 (1996); Ahn, C., et al., *IEEE Trans. Magnetics*. Volume 30: 73-79 (1994); Liakopoulos et al., in *Transducers* 97, pages 485-488, presented in 1997 International Conference on Solid-State Sensors and Actuators, Chicago, Jun. 16-19, 1997; U.S. Pat. No. 5,883,760 by Naoshi et al. The above publications are incorporated in the present application by reference. These publications, and the co-pending U.S. patent application Ser. No. 09/399,299, filed Sep. 16, 1999, and the and the U.S. Patent with Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Cheng, Weiping Yang, YuXiang Zhou, LiTian Liu, and JunXuan Xu, as inventors, both herein incorporated by reference, further disclose the materials, methods and protocols that may be used to fabricate the electromagnetic structures on a chip.

The electromagnetic chip can be fabricated on a number of materials such as ceramics, polymers, copolymers, plastics, rubber, silicon, or glass. An electromagnetic chip can be from about 1 mm$^2$ to about 0.25 m$^2$. Preferably, the size of the chips useable in the present methods is from about 4 mm$^2$ to about 25 cm$^2$. The shape of the chips useable in the present methods can be regular shapes such as square, rectangular, circular, or oval, or can be irregularly shaped. Chips useable in the methods of the present invention can have one or more wells or one or more channels that can be etched or bored into a chip or built onto the surface of a chip. For use of these electromagnetic chips for characterizing the ion channel responses in the method of the present invention, these electromagnetic chips may further comprise ion transport detection (or measuring) means. The ion transport detection structures are fabricated or made at appropriate locations with respect to the electromagnetic elements.

An electromagnetic chip can be a part of a chamber, where a chamber is a structure capable of containing a fluid sample. A chamber can comprise any fluid-impermeable material, for example, silicon, glass, metal, ceramics, polymers, plastics, acrylic, glass, etc. Preferred materials for a chamber include materials that do not interfere with electromagnetic manipulation of particles in a sample. The chamber can also include an ion transport-measuring device or element.

A chamber that comprises an electromagnetic chip with an ion-transport detection means useable in the methods of the present invention can comprise one or more ports, or openings in the walls of a chamber. Preferably, a port is of a shape and size that allows a conduit to engage a port for the dispensing of a sample into the chamber. A conduit can be any tube that allows for the entry of a fluid sample into the chamber. Preferred conduits for use in the present invention include tubing, for example, rubber or polymeric tubing, e.g., tygon or teflon or PEEK tubing. Alternatively, a port can provide an opening in a wall of a chamber for the dispensing of sample into the chamber by, for example, pipetting or injection.

Conduits that engage one or more ports of the sample can introduce a sample by means of a pump (for example, a peristaltic pump or infusion pump), pressure source syringe, or gravity feed. One or more reagents, buffers, or solutions, including, but not limited to, a population of magnetic particles, can be added to the chamber before, after, or concurrently with the addition of a sample to a chamber. It is also within the scope of the invention to mix the sample with a reagent, buffer, or solution, before adding the sample to the chamber. Such mixing can optionally occur in one or more conduits leading to a chamber, or in one or more reservoirs connected to conduits.

The chamber can be of any size or dimensions, and preferably can contain a fluid sample of between 0.001 microliter and 50 milliliters, more preferably between about 1 microliters and about 20 milliliters, and most preferably between about 10 microliters and about 10 milliliters. A chamber can comprise any suitable material, for example, silicon, glass, metal, ceramics, polymers, plastics, etc. and can be of a rigid or flexible material.

It is necessary to point out that for chambers with large volumes (up to 50 mL), chips of special geometries and configurations may have to be used. The chips may be fabricated on flexible materials so that the chips can be folded to form tube like chambers. Multiple chips may be configured into a same chamber. The electromagnetic elements may have to have certain configurations so that effective electromagnetic forces may be generated in the region of the interest in the chamber.

The manipulation and positioning of particles such as target cells on an electromagnetic chip requires the magnetic field distribution generated over microscopic scales. One approach for generating such magnetic fields is the use of microelectromagnetic units. Such units can induce or produce magnetic field when an electrical current is applied. The on/off status and the magnitudes of the electrical current applied to these units will determine the magnetic field distribution. The structure and dimension of the microelectromagnetic units may be designed according to the requirement of the magnetic field distribution. The examples of the electromagnetic units include, but not limited to, those described in the following articles such as Ahn, C., et al., *J. Microelectromechanical Systems*. Volume 5: 151-158 (1996); Ahn, C., et al., *IEEE Trans. Magnetics*. Volume 30: 73-79 (1994); Liakopoulos et al., in *Transducers* 97, pages 485-488, presented in 1997 International Conference on Solid-State Sensors and Actuators, Chicago, Jun. 16-19, 1997; U.S. Pat. No. 5,883,760 by Naoshi et al. Other examples of the electromagnetic units are provided in the co-pending U.S. patent application Ser. No. 09/399,299, filed Sep. 16, 1999, and the U.S. Patent with Ser. No. 09/685,410, filed Oct. 10, 2000, entitled "Individually Addressable Micro-Electromagnetic Unit Array Chips in Horizontal Configurations" and naming Lei Wu, Xiaobo Wang, Weiping Yang, YuXiang Zhou, LiTian Liu, and JunXuan Xu as inventors, both herein incorporated by reference.

Manipulation and positioning of particles includes the directed movement, focusing and trapping of magnetic particles. The motion of magnetic particles in a magnetic field is termed "magnetophoresis". Theories and practice of magnetophoresis for cell separation and other applications may be found in various literatures (for example, Magnetic Microspheres in Cell Separation, by Kronick, P. L. in Methods of Cell Separation, Volume 3, edited by N. Catsimpoolas, 1980, pages 115-139; Use of magnetic techniques for the isolation of cells, by Safarik I. And Safarikova M., in J. of Chromatography, 1999, Volume 722(B), pages 33-53; A fully integrated micromachined magnetic particle separator, by Ahn C. H. et al., in J. of Microelectromechanical systems, 1996, Volume 5, pages 151-157). Use of are electromagnetic chip to separate, manipulate or position particles bound to magnetic particles is disclosed in U.S. patent application Ser. No. 09/399,299, filed Sep. 16, 1999, naming Zhou et al. as in ventors, and U.S. patent application Ser. No. 09/685,410, filed Oct. 10, 2000, entitled "Individually Addressable Micro-Electromagnetic Unit Array Chips in Horizontal Configurations" and naming Lei Wu, Xiaobo Wang, Jing Chen, Weiping Yang, YuXiang Zhou, LiTian Liu, and JunXuan Xu as inventors, both herein incorporated by reference.

Micro-electromagnetic units are fabricated on substrate materials and generate individual magnetic fields when electric currents are applied. One example of the unit is a single loop of electrical conductor wrapped around a ferromagnetic body or core and connected to an electric current source through electronic switches. Such a loop may be a circle, ellipse, spiral, square, triangle or other shapes so long as a flow of electric current can be facilitated around the ferromagnetic body. If the loop is single, it should be complete or nearly complete. The loop may be in the form of a plurality of turns around the ferromagnetic body. The turns may be fabricated within a single layer of the microstructure, or, alternatively, each turn may represent a separate layer of the structure. The electric conductor may be a deposited conductive trace as in a electroplated, sputtered or deposited metallic structure, or the conductor can be formed within a semiconductor layer through selective doping. A preferred arrangement of array of a plurality of micro-electromagnetic units has a column and row structure of the form common in microelectronics. That is, the columns and rows are mutually perpendicular although the columns and rows can readily be offset at different angles (for example 80 degrees). For use of the electromagnetic chips for characterizing the ion channel responses in the methods of the present invention, the electromagnetic chips may further comprise ion transport detection (or measuring) means at appropriate locations with respect to the electromagnetic elements.

Other Structures

Quadropole Electrode Structures

Quadropole electrode structures refer to a structure that include four electrodes that are arranged around a locus such as a hole or capillary or a needle on or within a biochip or chamber. Appropriate electrical signals can be applied to such an electrode structure to produce dielectrophoretic forces on particles or the cells. For example, negative dielectrophoretic forces can be produced so that the particles are directed away from the electrode elements to the central regions between the electrode structures. An ion-channel measuring means (or a means to measure electrical responses of ion channels, ion transporters and any other molecules or entities that permit ion passage across an enclosed membrane envelope or across a spread-out membrane area) is located at appropriate locations in respect to the quadropole electrode structures. For example, it is preferred that the ion channel measuring means are located at the central regions between the quadropole electrode structures so that particles can be manipulated and positioned onto the central regions between the electrode structures. A number of quadropole electrode structures have been disclosed in the U.S. patent applications (Ser. No. 09/643,362), titled "APPARATUS AND METHOD FOR HIGH THROUGHPUT ELECTROROTATION ANALYSIS", filed on Aug. 22, 2000, naming Jing Cheng et al. as inventors, which is incorporated by reference in its entirety. It is particularly important to know that an array of quadropole electrode structures, coupled with appropriate ion-channel measuring means can be fabricated and produced on a single chip so that a number of individual cells or particles, which are located in each quadropole electrode structure, can be assayed and analyzed simultaneously with ion-channel measuring means. All the electrode structures described in this applications such as spiral electrode structures, circular electrode structures, squared spiral electrode structures, traveling wave dielectrophoresis structures, particle switch structures, quadropole electrode structures, electrorotation structures, dielectric focusing structures and other electrode structures that are not described here but with the capabilities for moving and directing particles or cells to certain defined locations can be fabricated into an array format on a biochip. Each of these electrode structure units within the array has an associated ion-channel measuring means structure. Such a biochip can be utilized for assaying and analyzing the functions and properties of ion channels or other ion-passage proteins or non-peptide entities that are located on in a number of individual cells or other particles.

In operation, a fluidic chamber is first constructed including a biochip supporting a quadropole electrode structure. A sample that includes particles such as cells is introduced into the chamber. The electrical signals of appropriate phase, voltage and frequencies are applied to the quadropole electrode structures to produce an electrical field that exert dielectrophoretic forces that can direct or focus or move the particles to certain locations of the quadropole electrode structures where the ion-channel measuring means is located. For example, particles can be directed to the central regions between the quadropole electrode elements. The ion channel measuring means, for example, may comprise a hole located at the center between the quadropole electrode structures. After the particles are moved or focused to the center regions and over the hole, appropriate electrophysiological measurements are performed on the particles to determine the electrical functions and properties of the ion channels (or ion transporters or other proteins or non-peptide entity that permit the passage of the ions) on the surface of the particles. In one example, electrophysiological measurement include the procedure of obtaining and testing high-resistance electrical seal between the cell and the chip or the hole, obtaining whole cell access by rupturing membrane patch in the hole, recording the whole-cell current through the ion channels located in the cell membrane under various voltage-clamp protocols.

Electrorotation Structures

Electrorotation structures refer to a structure that include four or more electrodes that are arranged around a locus such as a hole or capillary or a needle on or within a biochip or chamber. The electrorotation structure can produce a rotating electric field. Preferred electrorotation structures include a plurality of electrodes that are energized using phase-offset signals, such as 360/N degrees, where N represents the number of the electrodes in the electrorotation structure. A number of the electrorotation structures are disclosed in the U.S. patent application (Ser. No. 09/643,362) entitled "APPARATUS AND METHOD FOR HIGH THROUGHPUT ELECTROROTATION ANALYSIS", filed on Aug. 22, 2000, naming Jing Cheng et al. as inventors. A rotating electrode structure can also produce dielectrophoretic forces for positioning the particles the certain locations, such as the center between the electrodes, under appropriate electrical signals or excitations. For example, when N=4 and electrorotation structure corresponds to a quadropole electrode structure. For producing rotating electric field, phase-offset signals are needed to apply to the electrodes. For producing dielectrophoretic forces for positioning particles such as cells, either phase-offset signals or regular AC electric signals can be applied to the electrodes. When negative dielectrophoretic forces are used for positioning particles, particles are positioned to the central region between the electrode structures. When positive dielectrophoretic forces are used for positioning the particles, particles are positioned to the electrode edges. Thus, depending on which type of dielectrophoretic forces are used to position particles, the structures within an ion-channel measuring means are located on either the regions between the electrode structures or close to the electrode edges. An array of electrorotation electrode structures, coupled with appropriate ion-channel measuring means can be fabricated and produced on a single chip so that a number of individual cells or particles, which are positioned into each electrorotation electrode structure, can be assayed and analyzed simultaneously with ion-channel measuring means. The U.S. patent application (Ser. No. 09/643,362) entitled "APPARATUS AND METHOD FOR HIGH THROUGHPUT ELECTROROTATION ANALYSIS", filed on Aug. 22, 2000, naming Jing Cheng et al as inventors, disclosed a number of types of electrorotation electrode structure array.

In operation, a fluidic chamber is first constructed including a biochip supporting an electrorotation electrode structure. A sample that includes particles such as cells is introduced into the chamber. The electrical signals of appropriate phase, voltage and frequencies are applied to the electrorotation electrode structures to produce an electrical field that exert dielectrophoretic (and traveling-wave dielectrophoretic forces) that can direct or focus or move the particles to certain locations within the electrorotation electrode structures where the ion-channel measuring means is located. For example, particles can be directed to the central regions between the electrorotation electrode elements. The ion channel measuring means, for example, may comprise a hole located at the center between the electrorotation electrode structures. After the particles are moved or focused to the center regions and over the hole, appropriate electrophysiology measurements are performed on the particles to determine the electrical functions and properties of the ion channels (or ion transporters or other proteins or non-peptide entity that permit the passage of the ions) on the surface of the particles.

In some embodiments, it may be preferred that a number of concentric independent quadropole or electrorotation electrode structure unit can be used as the particle positioning means. In such a case, the particles will be positioned first by the outer quadropole electrode structure, moving to the central region between these outer electrode structures. The particles will then be further positioned with improved accuracy by other inner electrode structures. In an example of three concentric quadropole electrode structures, continuous positioning procedures can be undertaken, for example, first by the outermost electrode structure, then by the second outermost electrode structure, and finally by the innermost electrode structure.

All the electrode structures described in this application (for example spiral electrode structures, circular electrode structures, squared spiral electrode structures, traveling wave dielectrophoresis structures, particle switch structures, quadropole electrode structures, electrorotation structures, dielectric focusing structures) and other electrode structures that are not described here can be utilized for cell separation purposes with appropriate electrical signals applied onto them. Various dielectrophoresis separation techniques can be employed. Thus one embodiment of the biochip may comprise the following elements, a dielectrophoresis separation electrode structure, a particle positioning means, and an ion channel measuring means. The dielectrophoresis separation electrode structures can be coupled to the particle positioning means so that the target particles, after being separated from an original mixture sample on a dielectrophoresis separation electrode structure, can be positioned and manipulated to specific desired locations for ion channel measurement (or ion transport assay or other assays that are for determining the electrical properties and functions of ion passage proteins or entities that are located on the particle surfaces). Non-limiting examples of integrating the dielectrophoresis separation electrode structures and a particle switching structure (for positioning and transporting particles) can be found in the co-pending U.S. patent application Ser. No. 09/678,263, entitled "AN APPARATUS FOR SWITCHING AND MANIPULATING PARTICLES AND METHOD OF USE THEREOF" by Wang et al., filed on Oct. 3, 2000. Those who are skilled in dielectrophoresis and traveling wave dielectrophoresis can readily design various electrode structures that can be used for as dielectrophoresis separation electrode structures and particle positioning means.

DC Electric Field Induced Fluid Motion Structures

DC electric field induced fluid motion structures. When a DC electric is applied to a solution, under certain conditions, a fluid motion can be induced. For example, a DC electric field across a thin channel can cause fluid motion within the channel if the channel wall has appropriate charge distributions. Such a fluid motion could be an electroosmosis effect or electrophoretic effect. In another example, DC electric field may result in certain electrohydrodynamic effects. These electrohydrodynamic effects may result in the interaction between the applied DC electric field and the volume charges within the fluid. Such DC electric field induced fluid motion can be used for moving, transporting and manipulating and positioning particles.

In one example, a DC electric field induced fluid motion structure can be used for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric field is produced in the hole so that a fluidic motion is produced in the hole. The fluidic flow is along the direction from the top to the bottom. Such a flow in the hole would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiological measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single-channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration. In one exemplary method, a series of voltage pulses with different amplitudes (e.g., increasing amplitudes for each sequential pulse) having same or different time width may be used sequentially to act on the membrane patch whilst a continuous or intermittent monitoring of the resistance between the solutions on the top surface and the bottom surface of the chip is performed, until the membrane is ruptured (as monitored and optionally determined by the resistance between the solutions on the top surface and the bottom surface of the chip) at which time the voltage pulses are reduced or discontinued.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods. In one exemplary method, a series of negative-pressure pulses with different amplitudes (e.g., increasing amplitudes for each sequential pulse) having same or different time width may be used sequentially to act on the membrane patch whilst a continuous or intermittent monitoring the resistance between the solutions on the top surface and the bottom surface of the chip is performed, until the membrane is ruptured (as monitored by the resistance between the solutions on the top surface and the bottom surface of the chip). In another exemplary method, a negative pressure is continuously (i.e. no pulse intervals) applied from the bottom surface of the chip and the pressure amplitude is gradually increasing until the membrane rupture occurs (as monitored by the resistance between the solutions on the top surface and the bottom surface of the chip) at which time the voltage pulses are reduced or discontinued.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording.

Actual electronic recording of ion channel responses may depend on specific measurement protocols used. In one example, the resting membrane potential may be measured. In another example, a series of electronic voltage pulses may be applied to the membrane, and the current going through the ion channels located on the cell membranes is determined. This method is particularly useful for analyzing the electrophysiological properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Electroosmosis Structures

Electroosmosis refers to the fluid motion induced by the application of a DC electric field, typically a uniform DC field. The electroosmosis can be exploited for moving, transporting and manipulating and positioning particles. Electroosmosis structures refer to the structures that can generate electroosmosis effects. For example, when the ion transport measuring means comprises a hole through the chip and comprises electrodes or microelectrodes that are on both side of the chip and are in contact with the solutions at the two sides of the chip, the electroosmosis can be generated in the hole and the electroosmosis structure comprises the hole and the electrodes.

In one example, electroosmosis structure can be used for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric field is produced in the hole so that an electroosmosis effects may be generated in the hole. The fluidic flow is along the direction from the top to the bottom. Such a flow in the hole would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiological measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. All the methods described in the context of "DC electric field induced fluid motion structures" can be utilized.

Electrophoretic Structures

Electrophoresis refers to the motion of the charged particles (such as cells or cell fragments) under the application of a DC electric field, typically a uniform DC field. The electrophoresis can be exploited for moving, transporting and manipulating and positioning particles. Electrophoresis structures refer to the structures that can generate electrophoresis effects on charged particles. For example, when the ion transport measuring means comprises a hole through the chip and comprises electrodes or microelectrodes that are on both side of the chip and are in contact with the solutions at the two sides of the chip, the electrophoresis forces can be exerted on the charged particles near the hole or positioned over the hole and the electrophoresis structure comprises the hole and the electrodes.

In one example, electrophoresis structure can be used for positioning the particles and for enhancing the sealing between the particle surface and the ion transport measuring means. For simplicity, we discuss an example in which the particles that are being analyzed are mammalian cells. The ion transport measuring means in this example is a hole that is etched through the chip substrate, as exemplified in FIG. 1 and FIG. 2. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, a DC electric voltage is applied between the electrodes that are located on the top surface and the bottom surface of the chip. A DC field is produced in the regions near the hole. Such DC field may exert the electrophoresis forces on the particles, driving the cells towards the hole. Furthermore, the electrophoretic forces on the cell would result in a net pulling force on the cell so that the cell is pulled into the hole. During this process, a gradual sealing between the cell membrane and the hole on the chip occurs. Such a sealing will be monitored through the measurement of the total impedance between the solution over the chip and the solution below the chip. Depending on the specific electrophysiological measurement approach, certain impedance values may be required for achieving electronic sealing tight enough so that small electronic noises are produced. This process is similar to the electronic sealing procedure of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single-channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording.

Actual electronic recording of ion channel responses may depend on specific measurement protocols used. In one example, the resting membrane potential may be measured. In another example, a series of electronic voltage pulses may be applied to the membrane, and the current going through the ion channels located on the cell membranes is determined. This method is particularly useful for analyzing the electrophysiological properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Acoustic Structures

Acoustic structures refer to the structures that can generate acoustic field and thus exert acoustic forces on the particles. For example, a biochip could be made from a piezoelectric material and when electrical field is applied across the biochip, the mechanical vibrations can be generated on a biochip and an acoustic field can be generated in the solutions that are in contact with such a biochip. In this case, the piezoelectric structures include the biochip with its piezoelectric material and the electrodes on the chip.

Figure 2:
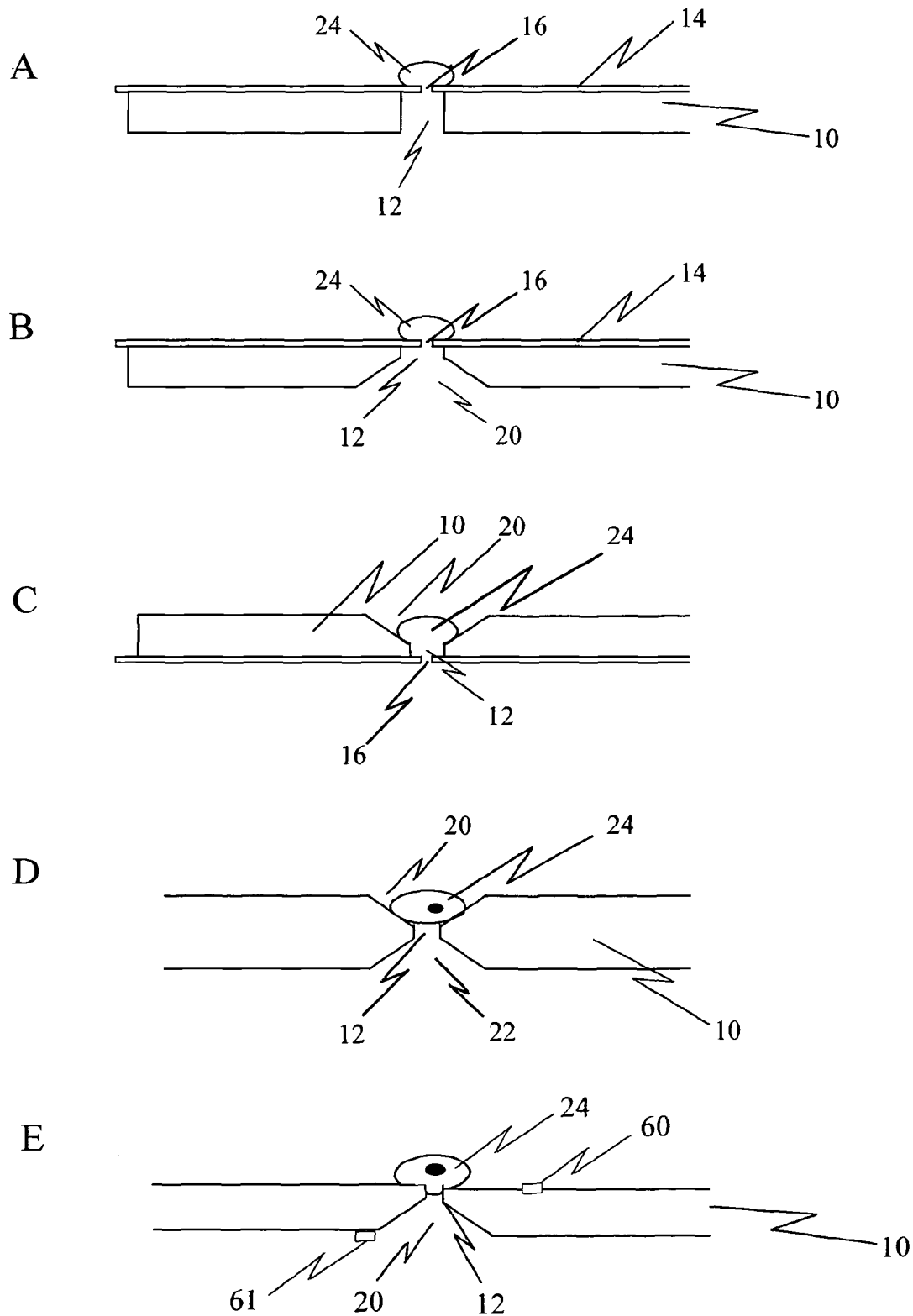
FIG. 2 depicts different configurations of substrates (10) and coatings (14) to form holes in the substrate (12) and holes in the coating (16).
Figure 3G:
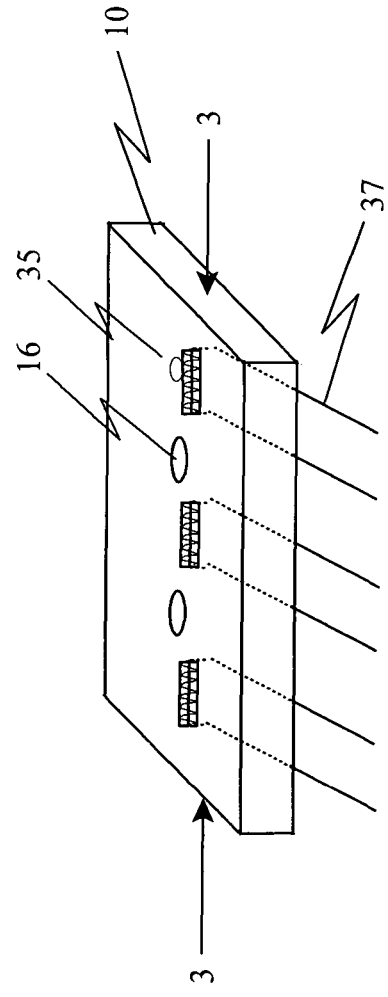
FIG. 3G depicts a biochip wherein electromagnetic structures (35) are provided on or within a biochip. Preferably, the electromagnetic structures are within the biochip.
Figure 3H:
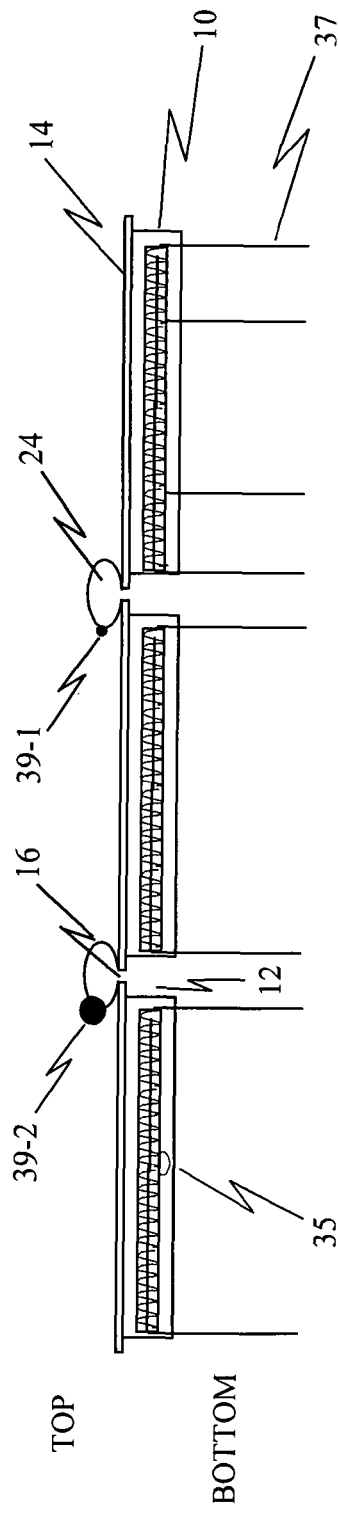
FIG. 3H is a cross section of the biochip of FIG. 3G along 3-3. Also shown are particles such as cells (24) engaged with the holes (16) that can be coupled or linked to a magnetic particle (1, 2) of small (1) or large (2) size.
Figure 4:
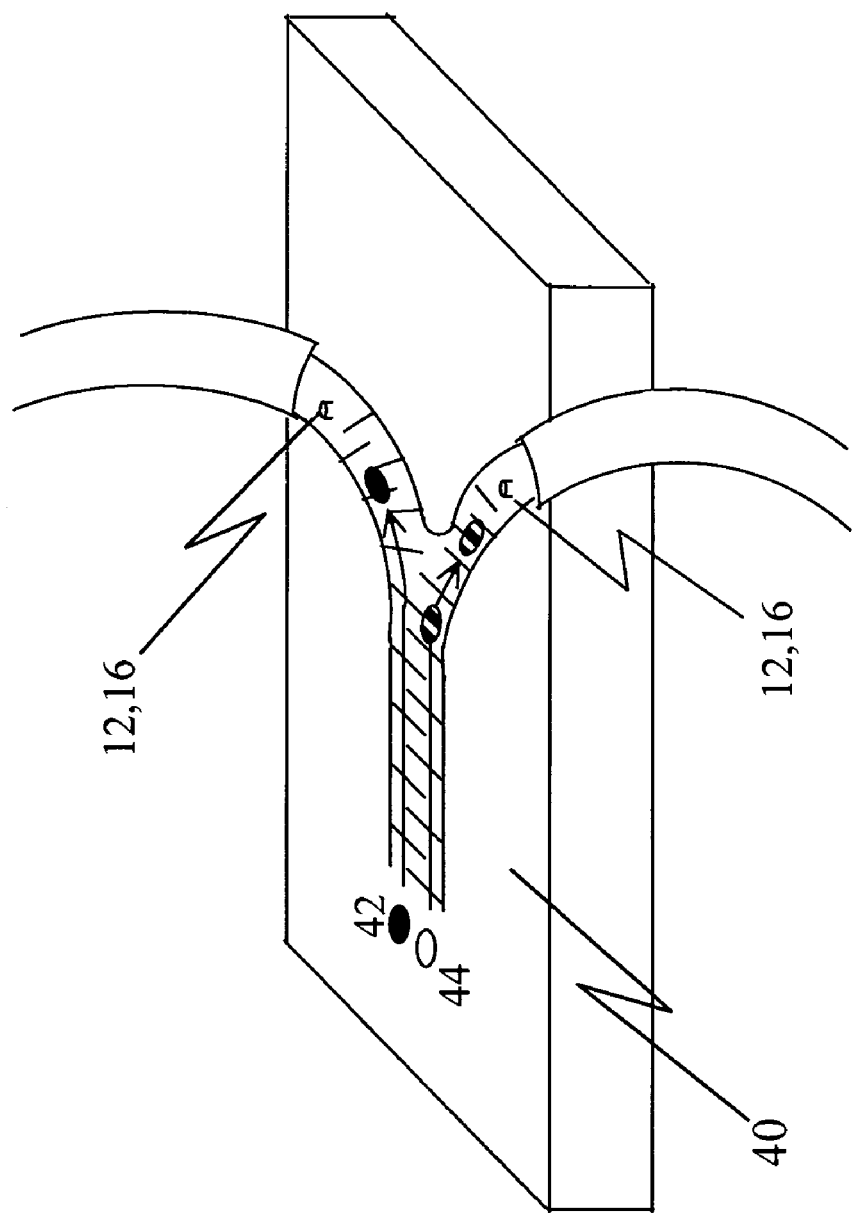
FIG. 4 depicts a particle switch (40) that can modulate the direction of travel of particles of different dielectric properties (42, 44) along a path and through a particle switch. The particle switch can include holes (12, 16) for use at least in part as ion transport measuring means. A sample can include a mixture of target particles and non-target particles. Target particles are preferably separated from or enriched from the non-target particles prior to measurements.

In one example, acoustic structure can be used for positioning the particles and for enhancing the sealing between the particle surface and the ion transport measuring means. For simplicity, we discuss an example in which the particles that are being analyzed are mammalian cells. The acoustic structure is a piezoelectric substrate with electrodes on both major surfaces and is located as the top plate of a chamber. The chamber bottom plate is a chip substrate for the ion transport measuring means, as illustrated in FIG. 1 and FIG. 2. In this example the ion transport measuring means is a hole that is etched through the chip substrate. An individual cell in the solution placed in chamber comprising the chip is positioned above the hole with various positioning means. For example, quadropole electrodes may be used to push the cell into the region between the four electrodes within the quadropole electrode structure.

After the cell positioning means moves the cell onto the hole, electric signals are applied between the electrodes that are located on the top surface and the bottom surface of the chip. Acoustic field is produced in the chamber. Standing wave acoustic fields or traveling wave acoustic fields could be produced. These acoustic fields may exert an acoustic force on the cell, driving it towards the hole. Furthermore, the acoustic force on the cell would result in a net pushing force on the cell so that the cell is pushed into the hole. During this process, a gradual sealing between the cell membrane and the hole on the chip occurs. Such a sealing will be monitored through the measurement of the total impedance between the solution over the chip and the solution below the chip. Depending on the specific electrophysiological measurement approach, certain impedance values may be required for achieving electronic sealing tight enough so that small electronic noises are produced. This gradual sealing is similar to the electronic sealing of the cell membrane onto a glass pipette tip that is widely used in electrophysiological ion channel recording.

The acoustic structure could also be attached onto the bottom plate of the chamber. The acoustic waves from such structures can be coupled through the chamber plate and into the solutions above the chamber plate. The acoustic wave or acoustic field in the solution could also be exploited for moving the particles and enhancing electronic sealing between the particle surface and the chip surfaces.

After the appropriate electronic sealing is achieved, various measurement methods can be implemented to recording the ion channel responses. Specific measurement methods utilized will depend on the type of ion channels and depend on whether single-channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods. In one exemplary method, a series of negative-pressure pulses with different amplitudes (e.g., increasing amplitudes for each sequential pulse) having same or different time width may be used sequentially to act on the membrane patch whilst a continuous or intermittent monitoring the resistance between the solutions on the top surface and the bottom surface of the chip is performed, until the membrane is ruptured (as monitored by the resistance between the solutions on the top surface and the bottom surface of the chip) at which time the voltage pulses are reduced or discontinued. In another exemplary method, a negative pressure is continuously (i.e. no pulse intervals) applied from the bottom surface of the chip and the pressure amplitude is gradually increasing until the membrane rupture occurs (as monitored by the resistance between the solutions on the top surface and the bottom surface of the chip) at which time the voltage pulses are reduced or discontinued.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact. This technique is referred as the "attached membrane patch" recording. Actual electronic recording of ion channel responses may depend on specific measurement protocols used. In one example, the resting membrane potential may be measured.

In another example, a series of electronic voltage pulses may be applied to the membrane, and the current going through the ion channels located on the cell membranes is determined. This method is particularly useful for analyzing the electrophysiological properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized. For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Negative Pressure Structures

Negative pressure structures refer to the structures that can generate negative pressures onto the cells or other particles and thus exert pressure forces on the particles. For example, fluidic pumps can be used for generating such negative pressures on the cells that are over a hole etched through a chip.

In one example, negative pressure structures can be used for positioning the particles and for enhancing the sealing between the particle surface and the ion transport measuring means. For simplicity, we discuss an example in which the particles that are being analyzed are mammalian cells. The negative pressure structure is a fluidic pump that is connected to the fluid in a chamber for ion channel measurement. The chamber bottom plate is a chip substrate for the ion transport measuring means, as illustrated in FIG. 1 and FIG. 2. In this example the ion transport measuring means is a hole that is etched through the chip substrate. An individual cell in the solution placed in chamber comprising the chip is positioned above the hole with various positioning means. For example, quadropole electrodes may be used to push the cell into the region between the four electrodes within the quadropole electrode structure. The fluidic pump is connected to the fluid below the ion channel measurement chip in a sealed fluidic circuit.

After the cell positioning means moves the cell onto the hole, fluidic pumps is set to certain flow rate to pull the fluid from the chamber to the pump for certain length time for achieving an electronic seal between the cell membrane and the surface of the hole. Such a fluidic withdrawal from the chamber may result in a pulling force on the cell (for example a negative pressure on the cell), driving the cell into the hole. During this process, a gradual sealing between the cell membrane and the hole on the chip occurs. Such a sealing will be monitored through the measurement of the total impedance between the solution over the chip and the solution below the chip. Depending on the specific electrophysiological measurement approach, certain impedance values may be required for achieving electronic sealing tight enough so that small electronic noises are produced. This gradual sealing is similar to the electronic sealing of the cell membrane onto a glass pipette tip that is widely used in electrophysiological ion channel recording.

After the appropriate electronic sealing is achieved, various measurement methods can be implemented to recording the ion channel responses. Specific measurement methods utilized will depend on the type of ion channels and depend on whether single-channel or whole-cell recording is used, and depend on what functions or properties the measurements are targeted for. Those who are skilled in ion channel recording may determine specific methods that may be used for specific ion channels. In the following, we describe several whole-cell recording approaches. In one example, the whole-cell recording is performed on the cell after the membrane patch that has been pulled into the hole on the chip is ruptured. There may be various methods for rupturing such membrane patches and the electronic sealing between the cell membrane and the holes is maintained during the rupturing process.

As an example, one method for rupturing such membrane patches may be the application of an electrical voltage pulse applied to the electrodes that are in contact with the solutions on the top surface of the chip and the electrodes that are in contact with the solutions on the bottom surface of the chip. Appropriate voltage-pulse amplitudes and durations are required for making such membrane ruptures. Such a rupturing method is similar to the electrical voltage pulse method for rupturing membrane patch in a glass capillary that is used to manually operated patch clamp methods. Those who are skilled in ion channel recording may determine the electronic pulse conditions in terms of the pulse amplitude and pulse duration. In one exemplary method, a series of voltage pulses with different amplitudes (e.g., increasing amplitudes for each sequential pulse) having same or different time width may be used sequentially to act on the membrane patch whilst a continuous or intermittent monitoring the resistance between the solutions on the top surface and the bottom surface of the chip is performed, until the membrane is ruptured (as monitored by the resistance between the solutions on the top surface and the bottom surface of the chip) at which time the voltage pulses are reduced or discontinued.

As another example, a method may be the application of a negative pressure pulse applied from the bottom surface of the chip so that the pulse of pulling force is applied to the membrane patch inside the hole. Appropriate negative pressure-pulse amplitudes and durations are required for making such membrane ruptures. Such a rupturing method is similar to the negative pressure pulse method for rupturing membrane patch in a glass capillary that is used to manually operated patch clamp methods. In one exemplary method, a series of negative-pressure pulses with different amplitudes (e.g., increasing amplitudes for each sequential pulse) having same or different time width may be used sequentially to act on the membrane patch whilst a continuous or intermittent monitoring the resistance between the solutions on the top surface and the bottom surface of the chip is performed, until the membrane is ruptured (as monitored by the resistance between the solutions on the top surface and the bottom surface of the chip) at which time the voltage pulses are reduced or discontinued. In another exemplary method, a negative pressure is continuously (i.e. no pulse intervals) applied from the bottom surface of the chip and the pressure amplitude is gradually increasing until the membrane rupture occurs (as monitored by the resistance between the solutions on the top surface and the bottom surface of the chip) at which time the voltage pulses are reduced or discontinued.

In another ion channel whole-cell recording method, the membrane is actually not ruptured. However, perforation agents such as nystatin or amphotericin B may be used to form pores or perforations on the membrane patch. These perforation agents may be introduced into the hole from the bottom surface side of the chip. The use of these perforation agents for making pores on the membrane patch in the hole of the chip is similar to the use of such agents for making pores on the membrane patch inside the glass capillary. Those who are skilled in ion channel recording may readily choose the concentrations of such agents for making perforations in the cell membranes.

In another ion channel whole-cell recording method, the membrane is actually not ruptured, nor perforated. In this case, the membrane patch remains intact and is sealed against the ion transport detection structures. If the ion transportation detection structure is a hole on an ion-channel chip, the membrane patch is made in contact with the surfaces of the hole having a very large sealing resistance (e.g., Giga-Ohm) between the solutions at the two ends of the hole. In this way, the whole cell remains relatively intact. This technique is referred as the "attached membrane patch" whole-cell recording. Thus, the electrical voltages applied between the electrodes that are in contact with the solutions at the two ends of the hole are applied to the membrane patch in the hole and to the large-area membrane surface, which are the areas other than the membrane patch. Recording data needs to be carefully analyzed to take into account such recording mode.

In another ion channel recording method, we would be recording the ion channel activities for the ion channels that are located in the membrane patch. In this case, the membrane is actually not ruptured, nor perforated. Indeed, the membrane patch remains intact while other parts of the cells are ruptured or removed from the attached membrane patch. In this way, the "inner surface" of the attached membrane patch that is in contact with the cytoplasm before the removal of other parts of the cells is now made in contact with external cell bathing medium. Again, the membrane patch needs to have a very high resistance sealing (e.g. giga ohm sealing) against the measurement structures. Thus, the measured current response from the membrane patch corresponds to the ion channel activities from single or multiple ion-channels or ion transporters that are located in the membrane patch. This is a "single-channel recording" technique.

Actual electronic recording of ion channel responses may depend on specific measurement protocols used. In one example, the resting membrane potential may be measured. In another example, a series of commanding electronic voltage pulses may be applied to the membrane, and the current going through the ion channels located on the cell membranes is determined. This method is particularly useful for analyzing the electrophysiological properties of voltage-gated ion channels. In another example, the current going through the ion channels on the membranes is measured as a function of the concentrations of the specific chemical ligands or chemical molecules in the solution. The specific chemical ligands or molecules are in the solutions above the chip. Such a method is particularly useful for ion-channels that are extra-cellular ligand-gated ion channels. The specific chemical ligands or molecules are in the solutions below the chip and are in contact with intracellular space through the holes on the chip. Such a method is particularly useful for ion-channels that are intracellular ligand-gated ion channels. The above-mentioned methods can also be utilized for measuring the current or other electrical parameters for the ion transporters. It is important to know that if the ion transporter involves the use of energy sources such as ATP, then the ATP molecules should be added into the solutions. For non-energy associated ion transporters, appropriate solutions should also be utilized.

For other specific types of ion channels such as stretch-gated ion channels, appropriate mechanical stresses should be applied to the cell that has been patch clamped. The electronic current or other electronic parameters may be measured as a function of the mechanical stresses that are applied or as a function of whether the stretch force is applied to the ion channels.

Horizontal Positioning Means and Vertical Positioning Means

The particle positioning means can be horizontal positioning means or vertical positioning means. Horizontal positioning means allow a particle to be moved over the surface of a chip, such as at least in the X-Y axis where gravity is in the Z-axis. Horizontal positioning means are exemplified but not limited to traveling wave dielectrophoresis structures, dielectric focusing structures, spiral electrodes, concentric electrodes and particle switch structures that can guide the path of a particle to an ion transport measuring means. Vertical positioning means allow a particle to be drawn towards a ion transport measuring means, such as a hole, such as at least in the Z-axis where gravity is also in the Z-axis. Vertical positioning means are exemplified but not limited to acoustic structures, electroosmotic structures, electrophoretic structures and negative pressure structures. Horizontal positioning means such as dielectric focusing structures, spiral electrodes, concentric electrodes, quadropole electrode structures and electrorotation electrode structures may also be used for vertical positioning of a particle (e.g. a cell).

In general, a chip can have a major surface, onto which a sample that can include particles such as cells is introduced. The chip preferably has one or more particle positioning means provided integral to the chip. The forces acting on the particles in any direction within a plane parallel to the major surface are horizontal forces whereas the forces acting on cells in a direction approximately normal to the major surface are vertical forces.

The particles such as cells to be analyzed may initially be randomly distributed above the surface of a chip, such as in a fluidic chamber above the chip. Thus, it can be desirable if forces generating means could produce forces in the horizontal plan, the vertical plane or both. In this way, these forces can be used for rapid, efficient and effective positioning of the particles. In one preferred aspect of the present invention, both horizontal positioning means and vertical positioning means are included in whole or in part within or on a chip or can be provided in whole or in art on or within ancillary structures, such as a fluidic chamber or housing.

These force-generating means can be integral, such as a single type of structure element can be used for generating both a horizontal force and a vertical force, but that need not be the case and separate structures can be used. For example, the force generating means can be separate, for example, one structure can be used for producing one or more vertical forces and the other type for producing one or more horizontal forces. The force generating means can include two or more structures, each of the structures optionally capable of producing both horizontal and vertical forces on the particles to be positioned. In the alternative, at least one of the structures is capable of producing at least one horizontal force and at least one vertical force. Such structures can be used in combination with other structures.

In general, certain forces generated by force generating means can have both horizontal and vertical force components. The forces with both vertical and horizontal components can be generated by a single type of force generating structure or by multiple structures. Such force generating structures can have a single or multiple types of signal application modes. In one aspect of the present invention, the horizontal force is generated, preferably primarily generated, by one structural element and the vertical force is generated, preferably primarily generated, by a second type of structural element, but that need not be the case. In one aspect of the present invention, the horizontal and vertical forces can be generated by two or more force generating structures, each of which is capable of generating the forces in both horizontal and vertical directions. In the alternative, a combination of force generating structures can be used to produce forces in both the horizontal and vertical directions.

Ion Transport Measuring Means

Ion transport measuring means can be a structure that can be used to detect or measure one or more ion transport functions or properties. Preferred ion transport measuring means include patch clamp detection structures. Such patch clamp detection structures preferably include a hole or capillary that can contact a particle, such as a cell or a portion thereof, such as to form a seal between the membrane of the cell or portion thereof and the detection structure. This hole or capillary is preferably part of a patch clamp detection structure. Preferably a tight seal between the particle and the hole is obtained, preferably with mega ohm characteristics and more preferably with giga ohm characteristics. At least one electrode such as a recording electrode is also preferred, as is a detection device, such as device that can detect, monitor and preferably record a variety of electric parameters, such as electric current, voltage, resistance and capacitance of a membrane being patched, including a cellular membrane, an artificial membrane and the like. In one aspect of the present invention, an ion transport measuring means includes a wire that can be used in the ion transport detection methods. An ion transport detection means of the present invention can detect at least one ion transport function or property in whole cells or in portions thereof, such as in vesicles, blebs or patches of membranes.

As shown in FIG. 1, the ion transport detection means preferably includes holes that are provided in a substrate, and optionally with a coating to provide well-defined holes. The holes can be provided in any appropriate configuration, but are preferably provided as an array. The holes can be of any shape, but are preferably generally circular when viewed from the top or bottom. The holes can be of any shape when viewed from the side, but are preferably generally cylindrical or generally funnel shaped when viewed from that angle. The funnel shape can be preferred because this type of shape can be the result of etching procedures, particularly Deep Reactive Ion Etching (DRIE) of silicon.

The holes in the substrate can be of any appropriate size, but the opening that is to directly or indirectly contact the particle are generally between about 0.1 micrometers and about 100 micrometers in diameter and more preferably between about 0.5 micrometers and about 10 micrometers in diameter. In the aspect of the invention where funnel shaped holes are used, the widest diameter is preferably between about 0.2 micrometers and about 200 micrometers in diameter and more preferably between about 0.5 micrometer and about 20 micrometers in diameter.

Holes in the coating can generally be made more accurately and precisely due to the characteristics of the material and the thickness of the coating. These holes or apertures can be of any shape or size, as long as the holes, with or without the coating, allow adequate electronic seals (high resistance seals, e.g., mega ohms and giga ohms) between the membranes of the particles (e.g. cells, artificial vesicles) and the substrates or the holes for appropriate electrophysiological measurement of ion transports located in the membranes. The holes are preferably generally circular when viewed from the top or bottom. These holes are generally between about 0.1 micrometer and about 100 micrometers in diameter and more preferably between about 0.5 micrometers and about 10 micrometers in diameter. To achieve appropriate electronic seals between the membranes of the particles (e.g. cells, artificial vesicles) and the substrates or the holes, the holes should have appropriate geometry, surface texture (e.g. smoothness), electrical charge and/or surface hydrophilicity or hydrophobicity.

The holes in the substrate or coating can be made using any appropriate method for the material that makes up the substrate. Micromachining, laser ablation, molding, dry or wet etching or masking are methods that are preferable. In one aspect of the present invention, the holes in the substrate are made by first etching the substrate using chemicals, such as acid etching of glass or DRIE of silicon materials. Such etching can form the funnel structures (20, 22) as generally set forth in FIG. 2B, FIG. 2C and FIG. 2D.

Figure 5:
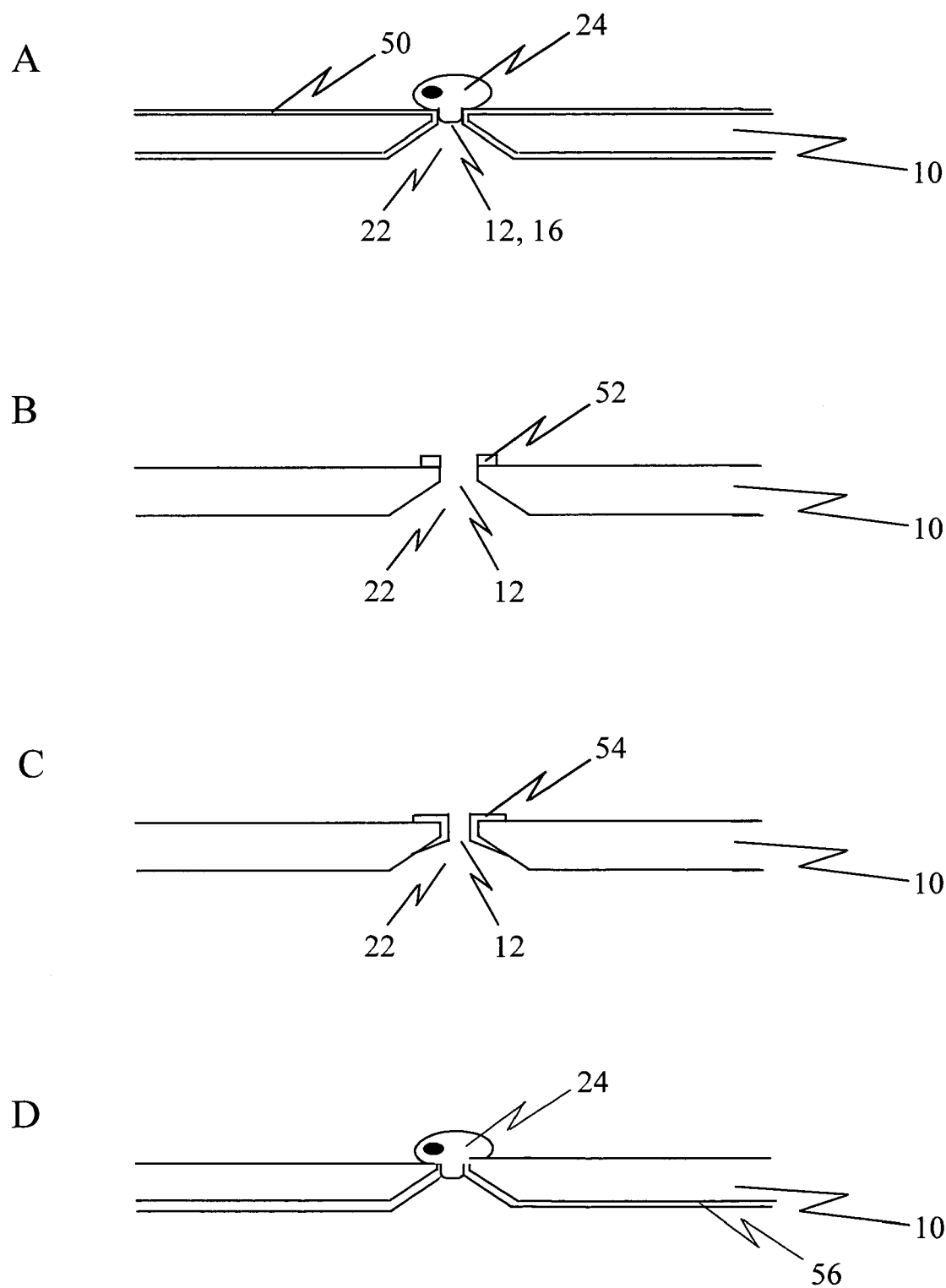
FIG. 5 depicts a structure such as depicted in FIG. 2B including a substrate (10) that defines a hole (12) with a funnel structure (22).

As shown in FIG. 5, the surfaces surrounding holes (optionally including the surfaces within the holes) can include additional coatings, such as particularly those set forth in FIG. 5A, FIG. 5B and FIG. 5C. The depicted coatings can be made of a variety of materials and are intended to increase the "strength" or "tightness" of the seal between the particle and the hole. In one aspect of the present invention, the coating (50, 52, 54) can be made of a polymer that expands or contracts as temperature changes, such as expanding when temperature increases. In that way, a particle can be contacted with a hole at a low temperature the temperature can then be changed so that the coating expands, and the seal between the cell and the hole becomes tighter. For patch clamp methods, the seal should have characteristics in the mega ohm range, and more preferably in the giga ohm range. A coating can be applied using methods known in the art, such as spraying, thermal oxidation, sputtering or spin casting. Preferred coating materials include plastics, polymers, molecular layers, metal oxides, glass, and silicon dioxide. In one alternative, hypertonic conditions can be used when a particle such as a cell is engaging a structure such as a hole, which causes the particle to shrink or crenate. A tight seal can be made by returning the surrounding medium to normal osmolarity or by making the environment hypotonic, causing the particles to expand. Preferred coatings include polyimide, polyethyleneimine, PDMS, paralyene, PMMA SU8 and the like. Some of these polymers can be elastic after being incorporated onto or within a chip. In this instance, when particles such as cells are being driven or aligned into or onto the aperture, the elastic property of the polymers can help to form a tight electric sealing between the particle and the polymer coating. These polymer coatings can help to reduce the noise coupling from the solution to the measurement electrodes and from the electrode to the air. The polymer coating or other coating can also reduce the electronic capacitance coupling between the solution baths on the top and bottom of the aperture or in certain instances sideways perfusion chambers to the measurement electrodes.

Alternatively, a coating can include specific binding members, such as ligands, receptors, antibodies or active fragments thereof. This is particularly true for the configurations set forth in FIG. 5B and FIG. 5C. The specific binding members can be specific or non-specific for a particle, such as a cell. For example, the specific binding members can be antibodies that recognize cell surface antigens or receptors or ligands that can bind a population of cells. In the alternative, the specific binding member can be specific for an antigen, preferably a cell surface antigen, that the cell would not normally express, but is that the cell has been engineered to express. In this way, particles, particularly cells or fragments thereof, could be localized at or near a hole based on the binding of particles to specific binding members that have been localized on the biochip. In the alternative, specific binding members that bind with non-specific cell surface antigens such as, for example, cell adhesion molecules including basement membrane proteins, fibronectin, integrins, or RGD-containing peptides or proteins or active fragments or portions thereof, can also be used. Furthermore, the specific binding members localized at or near the edges of the hole would tend to increase the "tightness" of the seal between the cell and the hole to form a tight patch clamp.

A coating that covers the surface of or surrounds an ion transport measuring means can be made by modification, such as by chemical modification or chemical treatment (for example, treated in acid, and/or base for specified lengths of time), of the substrate. For example, treatment of a glass chip comprising a hole through the chip as an ion transport measuring means with acid and/or base solutions may result in a cleaner and smoother surface in terms of surface texture for the hole. In addition, the treatment of the surface of a biochip or fluidic channel that comprises an ion transport measuring means (such as a hole or aperture) or treating the surface of a capillary with acid and/or base may alter the surface composition, and/or modify surface hydrophobicity and/or change surface charge density and/or surface charge polarity. Modifying the properties of the surface may facilitate electric seal or sealing between a particle surface and the ion transport measuring means.

Furthermore, a coating can be made by spraying, dipping or otherwise contacting liquid or semisolid material onto the substrate, wherein the material is then solidified such as through cooling, gelling, solidifying or polymerization. Another category of methods for producing a coating or functional layer on a biochip or other structure that comprises one or more ion channel measurement means is by physical means. For example, a biochip or other structure can be subjected to a baking procedure at a certain temperature for a certain length of time, which may result in some changes in surface compositions of the biochip or structure in the region of the ion transport measuring means. In another example, at least a portion of a surface of a biochip or other structure can be subjected a treatment by applying high energy radiation (including UV radiation), microwave radiation, oxygen plasma, reactive chemical compounds. In still another example, a surface or portion of a surface of a biochip made of glass may be subjected to a laser of appropriate wavelength and intensity so that the surface can be smoothed or polished.

Figure 6:
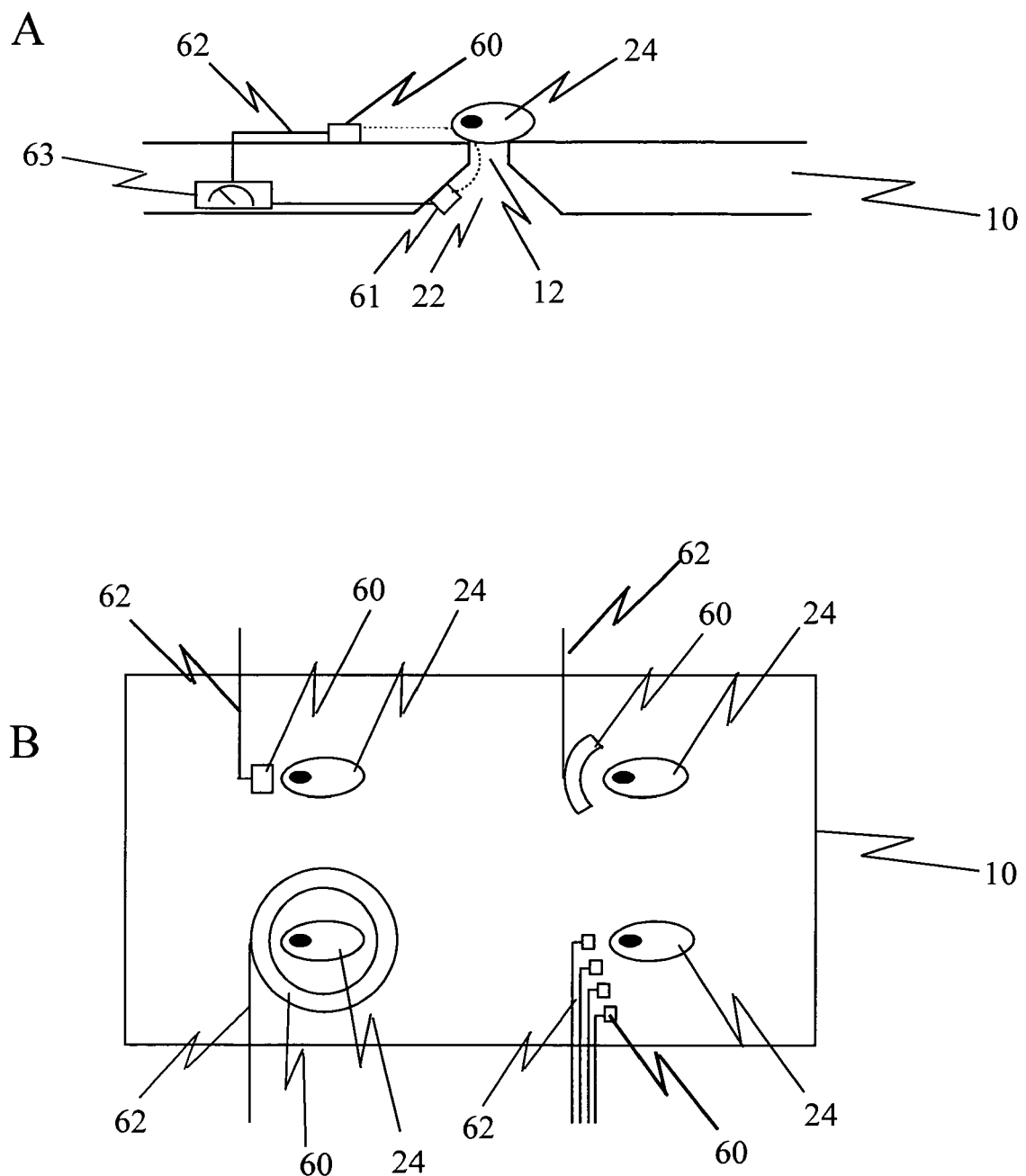
FIG. 6A depicts electrode structures (60, 61) present on either side of a hole (12,16) defined by a substrate (12) and depicted as including a funnel structure (24). The electrodes are positioned as to be on either side of particle, such as a cell (24). Electrical connection leads (62) connect the electrodes (60, 61) to a measuring device (63) that can measure and optionally record the electrical properties of the particle depicted by the dashed line, such as, for examples, electric current through the ion transports in the particle membrane under applied voltage conditions or the cell membrane potential under fixed current flow through the ion transports in the membrane. Measuring device (63) can be conventional electrophysiology measurement apparatus, such as commercialized by Axon Instruments Inc.
FIG. 6B depicts a variety of electrode structures as viewed from the top of FIG. 6A. In one aspect of the present invention, the electrode (60) can have any appropriate shape, such as square, circular or semi-circular. The electrode is preferably operably linked to at least one electrical connection lead (62). In one aspect of the present invention, there can be several electrodes, preferably independently attached to separate electrical connection leads so as to be independently addressable, that have different distances from a hole (12, 16). Depending on the conditions of a particular method or the electrical parameter being measured, such as voltage or current, electrodes of different shapes, sizes or geometries can be utilized. Although

The ion transport measuring means can also include an electrode. As depicted in FIG. 6, for example, electrode structures can be provided on either side of a particle such as a cell when engaged with a hole. The electrode structures are preferably made using conductive material such as metal, such as gold, and can be of any shape or size appropriate for the configuration of an ion transport measuring means, such as a patch clamp structure. The electrodes can be made using appropriate methods, such as masking, sputtering and the like. The proximity of the electrodes to each other and to the particle when engaged, preferably between about 10 micrometers and about 100,000 micrometers and can be optimized using routine experimentation. This range is not a limiting factor of the present invention and the range can be smaller or larger. The electrodes are preferably connected with electrical connection leads, which are preferably made of conductive materials and fabricated upon or within the biochip. Such fabrications are known in the art, such as in the fabrication of electronic chips. The electrical connection leads preferably directly or indirectly connect to a measuring device that can measure and optionally record a variety of electric measurements, such as current, voltage, resistance or capacitance.

In one aspect of the present invention, a chip can include application specific integrated circuits (ASIC). Typically, a patch clamp recorded ionic current is of a mall magnitude, such as in the pico Amp, nano Amp or micro Amp range. For accurate and precise measurement and recording of currents in these ranges, it is preferred to have the ASIC located within the closest distance from the particles such as cells that are being measured. This, it is preferred to have ASICs that can be incorporated at least in part onto or within a chip of the present invention. The ASIC can optionally include the same functions as a head-stage that is commonly used in traditional patch clamp recording systems, as they are known in the art.

ASIC can have one or more features, such as high input impedance and relatively small output impedance. In one aspect of the present invention, an ASIC can convert the electronic current to electronic voltage. There are certain advantages of having an ASIC integral at least in part to a chip or provided in the vicinity of a chip. One advantage is that the small distance from the source of the ionic current to the measurement circuit can reduce electronic noise which results in reduced signal loss. Another advantage is the reduction of stray capacitance effect, which is related to potentially long signal connection wires can be minimized. Also, the weak current signal can be converted to a voltage signal that can be connected to an appropriate signal amplifier.

In one embodiment of the present invention, an ASIC can convert an electronic current to an electronic voltage. In general, operational amplifiers are used for achieving such purposes. As known in the art of microelectronics, operational amplifiers typically have high input impedance; very large open-loop gains and can drive different kinds of impedance loads. Two modes of operational amplifiers can be designed to achieve conversion of electronic current to voltage, for example, resistive feedback and capacitive feedback. In the resistive feedback mode, the current is passed through "feedback resistor" and generates a voltage across the feedback resistor. This voltage can be monitored and recorded. In the capacitive feedback mode, the current is passed through the "feedback capacitor" to charge up the capacitor. Thus the voltage across the feedback capacitor will ramp up with time as a result of the current charging up the capacitor. Capacitive feedback mode has advantages including low electronic-noise but has disadvantages that the voltage across the capacitor cannot ramp forever in one direction so that a reset of this charging-voltage is needed once a while. Resistive feedback mode has the advantage that it does not require reset but it can have a relative large thermal noise component.

Those who are skilled in the art of microelectronics can readily design circuits for achieving the operational amplifiers with either resistive or capacitive feedback configurations or both, and can then realize and implement these circuit designs into Integrated Circuits.

A number of functions or features can be included into the ASIC. These may include:

(1) Potential-offset. In some applications, the electrolyte solution that is for bathing cells may be different from the electrolyte that is connected with the intracellular compartments. In one exemplary configuration, the ion-channel measuring means comprises an aperture etched through the chips. The cells are positioned over the aperture before seals are formed and the measurements are conducted for determining the voltage-current relationships between the electrodes located on the two sides of on the chips when a cell is positioned on the aperture with or without membrane patch being ruptured. In such a case, the electrolyte solutions on the topside of the chip may be different from those on the bottom side of the chip, thus producing an electrical-potential difference between the top-solutions and the bottom solutions. The potential-offset circuits will be able to offset this potential difference account the voltage or current clamp mode. Because different application setting may use different electrolyte solutions and may result in un-identical "potential-difference", the potential-offset circuit should be able to compensate these different values. The exact potential-offset values may be controlled externally or by applying external signals to the potential-offset circuits. Those who are skilled in the art of microelectronics and understanding the patch-clamp processes can readily design the circuitry for such potential-offset.

(2) Series resistance compensation. The solution resistances for the solution suspending and for the solution in the recording-aperture (again, we use the chips with apertures as examples only) present themselves as series resistors to the ion-channels that are being recorded for their activities. In order to have a fast amplifier response to achieve better temporal resolutions, these serial resistors should be compensated by certain ASIC. The ASIC may have separate circuits for compensating not only the bulk solution resistances but also the resistances in the aperture. In addition, the compensation values may be adjusted in both large-magnitude and small magnitude variations. Those who are skilled in the art of microelectronics and understanding the patch-clamp processes can readily design the circuitry for such series-resistor compensation.

(3) Membrane patch ZAP control. In one of the whole cell recording modes, the membrane patch within the recording-aperture (again, we are using the chips with apertures as an example only) is ruptured. One way to make this rupture is to apply a brief high voltage pulse in the range between 100 mV to 10,000 volts to the membrane via the recording electrodes. The ASIC may comprise a separate circuit that can deliver variable magnitude and variable duration of electric-potential pulses. The magnitude and temporal duration of the pulses can be changed by external means or by applying certain control signals externally. Those who are skilled in the art of microelectronics and understanding the patch-clamp processes can readily design the circuitry for such membrane-patch ZAP control circuits.

(4) Whole cell capacitance neutralization. The whole cell capacitance is acting in parallel to the ion-channels that are being measured. Such capacitances should be neutralized or compensated to achieve better temporal control and accurate measurement of the ionic current. The exact values of the neutralized capacitances may be different for different experiments. Thus, the ASIC may incorporate specific circuits for neutralizing or compensating such whole cell capacitance. The magnitude of the compensation capacitances can be changed by external means or by applying certain control signals externally. Those who are skilled in the art of microelectronics and understanding the patch-clamp processes can readily design the circuitry for such whole cell capacitance neutralization. In designing such circuits, the neutralization should be able to "be turned off" when the experiments were for evaluating or measuring the whole cell capacitances.

(5) The chip-capacitance compensation. The chip-capacitance is acting in parallel to the ion-channels that are being measured. (again, we use the chip with recording apertures as examples). Such capacitances should be compensated to achieve better temporal resolution to observe fast kinetic responses of the ion channels. The exact values of the compensated capacitances may be different from different experiments. Thus, the ASIC may incorporate specific circuits for compensating such chip-capacitances. The magnitude of the compensation capacitances can be changed by external means or by applying certain control signals externally. Those who are skilled in the art of microelectronics and understanding the patch-clamp processes can readily design the circuitry for such chip-capacitance compensation.

(6) High-quality low-pass filters. The recorded electrical signals tend to be noisy. Thus, appropriate electronic filters may be applied to filter out the high-frequency noises to obtain cleaner signals. For example, multiple-pole (e.g. 4-pole) Bessel filter may be used. The ASIC may comprise specific filter circuits. Those who are skilled in the art of microelectronics and understanding the patch-clamp processes can readily design such filters to remove/filter out the noises.

(7) Seal-Test. The patch-clamping recording requires high-resistance sealing between the cell membrane and the apertures in the chips (again, we are using the chips with apertures structures as examples only). It is desirable to have a specific circuit that can be operated to test whether a high resistance seal is formed. In the voltage-clamp mode, a small voltage (<10 mV, or ~10 mV) may be applied and then current responses are monitored. Before sealing, there may be relatively large current responses during to the current leaking through the hole. Yet after a high-resistance seal is achieved, the current will be quite small. The magnitude of the current is inversely proportional to the seal resistance. A current-pulse may also be applied in the current-clamp mode. In such a case, the voltage responses should be monitored. The ASIC may comprise specific circuits for such Seal-Test. Those who are skilled in the art of microelectronics and understanding the patch-clamp processes can readily design such pulse-generating and voltage/current monitoring circuits.

(8) Independent holding command. In some experiments, it may be desirable to have the ability to independently hold the voltage in the voltage-clamp mode or hold the current in the current-clamp mode. The ASIC may comprise a separate circuit for generating such independently controlled voltages or currents. Those who are skilled in the art of microelectronics and understanding the patch-clamp processes can readily design circuits for generating independently held voltage or current.

(9) Leak-subtraction. Since a perfect sealing between the membrane and the chip-recording apertures (again, we are using the chips with apertures as examples only) is nearly impossible, the leak current exists in many real recording setting. Such leak current is of linear voltage-current response in nature, thus a subtraction of such current may be desirable. The ASIC may comprise a specific circuit that can subtract such linear leak current components. Those who are skilled in the art of microelectronics and understanding the patch-clamp processes can readily design circuits for subtracting the leak currents.

Other Structures

The biochip of the present invention can also include additional structures. For example, a biochip can include a chamber that can include ports for the introduction and/or removal of materials. One aspect of such a chamber is provided in FIG. 14. In this figure, the biochip with holes is provided in a chamber such that fluidic space is provided above and below the chip so that fluid communication between the top chamber and bottom chamber when holes are not engaged with particles is possible. Particles such as cells are introduced into the upper chamber using an induction means. Induction means include pumps, microfluidic structures such as piezo dispenser, ink jet dispensers, solenoids and the like and can be the same or different from perfusion means. Induction means are used to introduce a sample to a chip or chamber, whereas perfusion means are used to introduce test chemicals or other moieties to a chip or chamber.

The particles are directed to ion transport measuring means using particle positioning means. The particle, such as a cell is then engaged with the structures of ion transport measuring means, such as a hole, using particle-manipulating means. The particle positioning means can also act to aid in forming a tight seal between the particle and the hole. For example, acoustic means, such as acoustic chips, can provide positive downward pressure on particles. In the alternative, electroosmotic force or electrophoretic force, such as electrodes operably engaged with an electric modulating device such as a reostat can be used to provide negative pressure on the particles. Furthermore, a fluidic means, such as a pump or microfluidics device can be used to provide negative pressure on the particle.

In operation, the particle manipulating means or fluidic means can be used to create a pulse such as an electric pulse or pressure pulse that rupture the membrane of a particle such as a cell to allow whole cell patch clamp recording.

In one aspect of the present invention, the perfusion means can be used to inject a sample into the chamber. The sample preferably includes a test compounds whose ion transport modulating activity is known or unknown. Changes in an ion transport function or property measured by ion transport measuring means with engaged particles is indicative of the ability of a test compound to modulate an ion transport function or property.

Figure 13:
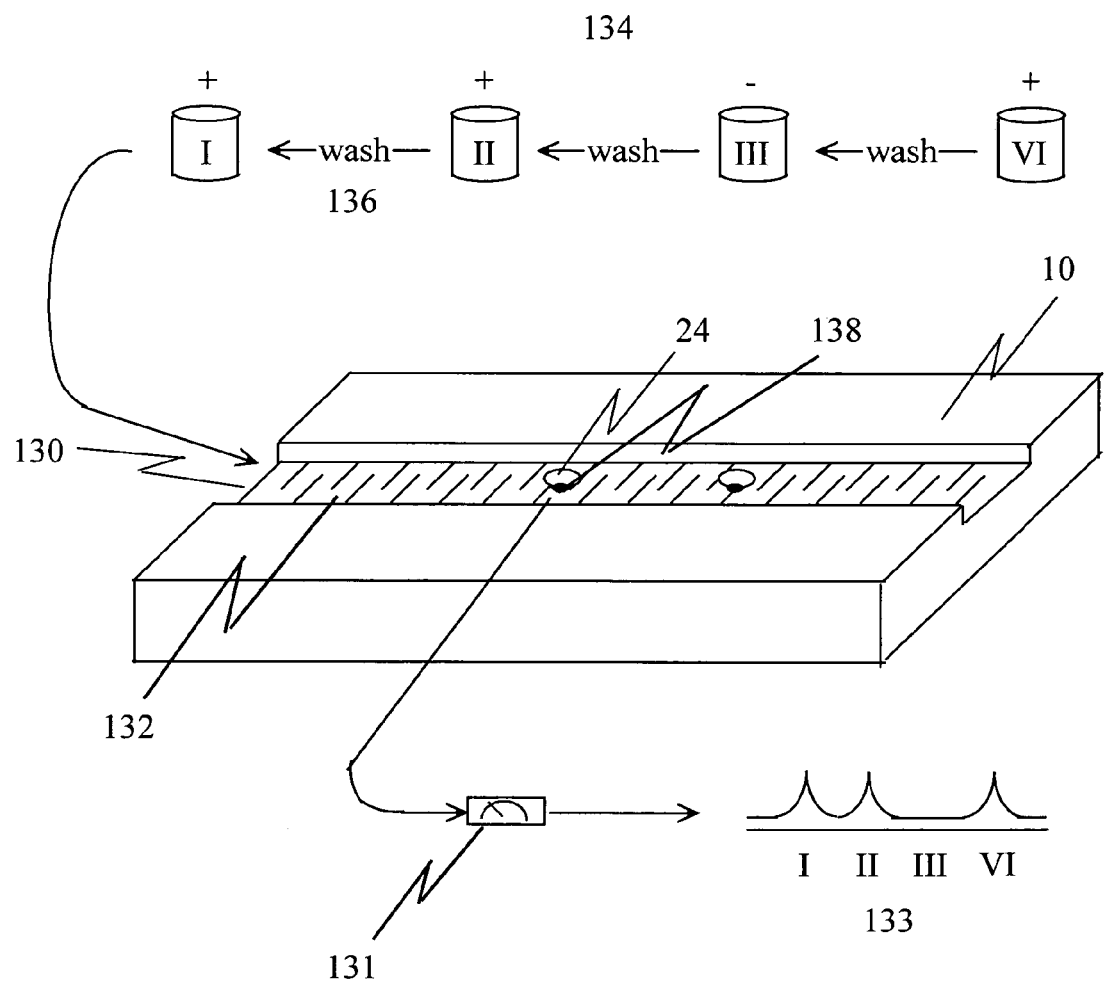
FIG. 13 depicts one preferred aspect of a flow through method for engaging particles such as cells (24) with ion transport measuring means (138). The depicted structure includes a channel (130), but the method depicted in FIG. 13 can be utilized on a biochip that does not include such channels (130). Particles such as cells (24) are positioned at or near ion transport measuring means (138) using particle positioning means (132) depicted here as traveling wave dielectrophoresis structures. The cells (24) engage the ion transport measuring means (138) and allow for detection on ion transport function or property via measuring devices (131) that can provide a readout (133). Samples (134) can be sequentially added to the biochip, such as through the channel (130) with or without dye solutions, reagent solutions including substrates (such as for enzymes), enzymes, or cells and the like, or washing solutions (136) in between the samples. The samples are sequentially contacted with the cells (24). The same cells can be tested with a given set of compounds. The modulation of ion transport function or property in response to these compounds is interrogated using ion transport measuring means (138), and the responses measured (131) and/or reported (133). Here, compounds I, II and IV increased ion transport function or property whereas compound III did not.

In one aspect of the present invention depicted in FIG. 13, a channel is formed that can include particle positioning means and ion transport measuring means. Particles engaged with the ion transport measuring means form patch clamps as discussed above. Test samples can be sequentially added to the channel in a flow-through manner, optionally with wash solutions in between. The responsiveness of the patch clamped particles to the test samples is measured. In this way, the same patch clamps are used to measure a plurality of samples.

Figure 14:
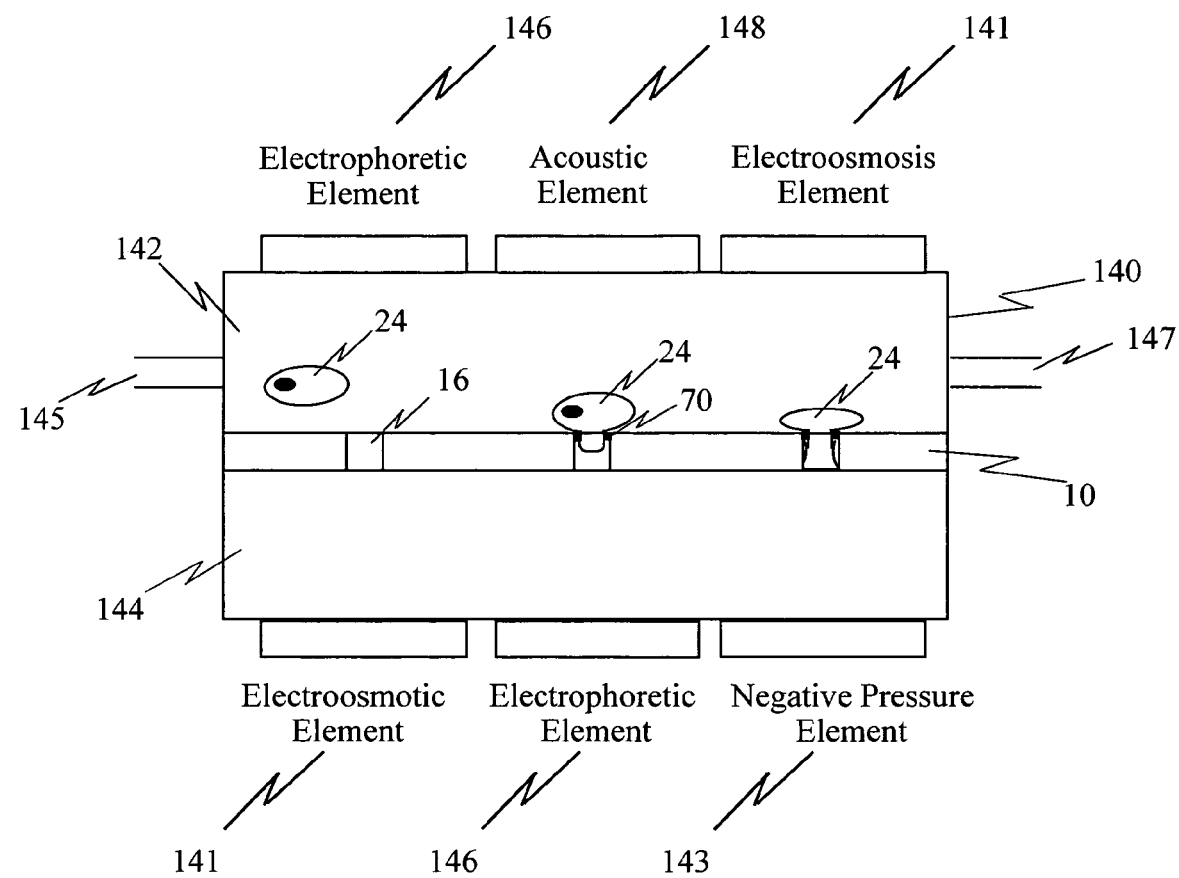
FIG. 14 depicts one aspect of the present invention wherein a substrate (10) with holes (16) is provided in a chamber (140) with an upper compartment (142) and a lower compartment (144) separated by a substrate layer with the holes. The holes (16) can be part of an ion transport detection structure. Capillaries or needles of the present invention can also be present or be substituted for the holes (16). The substrate (10) can include a variety of particle positioning means, particularly horizontal positioning means, such as but not limited to electromagnetic devices and dielectrophoretic devices (not depicted). The chamber (140) can include various particle positioning means, particularly vertical particle positioning structures, such as electrophoretic elements (146), acoustic elements (148), electroosmosis elements (141) and negative pressure elements (143). In operation, a sample that includes a particle such as a cell can be introduced into the chamber (140) by way of a conduit (145). The particle is positioned at or near the hole (16) by way of horizontal positioning structures. The particle is then aligned with the hole (16) using vertical positioning structures. The electric seal (70) between the particle and the hole can be enhanced using coatings, such as coatings including specific binding members or particle adhesion moieties, such a cell surface adhesion proteins, such as integrins or basement membrane proteins such as fibronectin. Other methods for enhancing the electric seal (70) between the particle and the hole can also be used. For example, chemical modification or treatment of the hole may be used to alter the hole surface properties, for example electrical charges, surface smoothness and/or surface compositions so that the altered surface properties allows better electrical seals (for example, higher resistance seal, shorter time to seal, more stable seal) between the particle and the hole. The particle can then be optionally ruptured, such as by the vertical positioning means such as pressure pulses. Preferably, the negative pressure element (143) performs this function, but that need not be the case. Alternatively ion-conducting holes can be made in the membrane by perforating agents such as but not limited to amphotericin B. At this point in time, ion transport functions or properties of the particle can be determined using methods of the present invention. In one aspect of the present invention, test compounds can be introduced via the inlet port (145) and effluent can be removed via the effluent port (147).

In another aspect of the present invention depicted in FIG. 14, a substrate (10) with holes (16) is provided in a chamber (140) with an upper compartment (142) and a lower compartment (144). The holes (16) can be part of an ion transport detection structure and capillaries or needles of the present invention can also be present or be substituted for the holes. (16) The substrate (10) can include a variety of particle positioning means, particularly horizontal positioning means, such as but not limited to electromagnetic devices and dielectrophoretic devices (not depicted). The chamber (140) can include various particle positioning means, particularly vertical particle positioning structures, such as electrophoretic elements (146), acoustic elements (148), electroosmosis elements (141) and negative pressure elements (143). In operation, a sample that includes a particle such as a cell can be introduced into the chamber (140) by way of a conduit (145). The particle is positioned at or near the hole (16) by way of horizontal positioning structures. The particle is then aligned with the hole (16) using vertical positioning structures. The electric seal (70) between the particle and the hole can be enhanced using coatings, such as coatings including specific binding members or particle adhesion moieties, such a cell surface adhesion proteins, such as integrins or basement membrane proteins such a fibronectin. The particle can then be optionally ruptured, such as by the vertical positioning structures such as by pressure pulses. Preferably, the negative pressure element (143) performs this function, but that need not be the case. At this point in time, one or more ion transport functions or properties of the particle can be determined using methods of the present invention. In one aspect of the present invention, test compounds can be introduced via the inlet port (145) and effluent can be removed via the effluent port (147).

In addition to particle positioning means such as those described herein, other particle manipulating means and structures can be incorporated in whole or in part or on a surface or in proximity with a surface of a chip. In one aspect of the present invention, mixtures of particles such as cells can be separated in accordance to certain forces such as those described herein, such as but not limited to pressure, dielectrophoresis or electromagnetic forces. Pressure systems that can be used in the present invention can include gating systems such as they are used in the art of fluorescence activated cell sorting (FACS). The separated particles can then be used for ion channel recording using appropriate structures provided on chips of the present invention. This type of format is particularly useful for handling mixtures of cells, such as cells provided from an organism including mammals and humans, particularly but not limited to primary cells, in which there are multiple cell types can be separated using structures of the present invention at least in part based on the physical properties of such cells. Such separation allows target cells to be separated or enriched prior to being engaged on an ion channel measuring structures such as those of the present invention and being interrogated using appropriate methods, such as those of the present invention. Alternatively, a population of cells can be directed to ion channel measuring structures such as those of the present invention and then engaged and interrogated as appropriate. In one aspect of the present invention, separated or enriched particles can be directed to different loci on a chip of the present invention using the positioning means of the present invention. Different physical properties of particles can be directed to such loci. At such loci, ion channel measuring structures can be present and the particles can be engaged and interrogated as appropriate. Thus, a single chip can be used to investigate members or subsets of a population of particles, such as a population of cells.

Furthermore, additional manipulation means can be incorporated at least in part within a chip, on a chip or in proximity to a chip of the present invention. These structures can be used for high-information content analysis of particles including cells. For example, on-chip, within-chip, partially within chip or off-chip means can be incorporated into a structure of the present invention to measure cellular responses by way of fluorescence or other readouts, particularly optically based readouts. In one aspect of the present invention, either before, during, or after patch clamp recording, other cellular events can be monitored, preferably using optical methods such as fluorescence. For example, a variety of intracellular phenomena are linked to ion channel activity. One such phenomenon is the modulation of calcium ion levels, in particular free calcium ion levels, within the cell. A variety of fluorescent markers are available that have differential fluorescence when bound with calcium. Examples include Fura1 and Fura2. Other ions can be investigated as well. Thus, particles such as cells can be loaded with such fluorescent markers and the particles can be interrogated with electromagnetic radiation, such as light, of appropriate character to allow the fluorescent markers to be activated. Appropriate light detecting means, such as CCDs optionally coupled with wave-guides, can be used to collect the emission of such fluorescent markers to provide readouts of such markers. In that way, multiple phenomena can be measured using methods of the present invention. Such measurements can be simultaneous with the ion channel detection of the present invention or can be separated in space and/or time. Other methods, such as the use of FRET based systems to measure polarization of membranes can also be used (see, for example, U.S. Pat. No. 5,661,035 issued Aug. 26, 1997 to Tsien and Gonzalez and U.S. Pat. No. 6,107,066 issued Aug. 22, 2000 to Tsien and Gonzalez.)

Other cellular events, such as membrane trafficking, protein-protein interactions, protein translocation, diffusion of second messenger molecules inside the particle such as a cell or sub-compartments of the particle such as a cell can be monitored by way of fluorescence based detection technologies such as fluorescent resonance energy transfer (FRET), fluorescence polarization (FP) and fluorescence lifetime methods. Appropriate detection structures can be used to detect, measure, and analyze the information generated by such methods.

A number of targets or phenomenon can be analyzed using such fluorescence based screening. These include but are not limited to morphology changes, viability, apoptosis, cellular differentiation, cytoskeletal changes, cell-cell interactions, chemotaxis, spatial distribution changes such as receptor trafficking, receptor internalization or processing, capping or complex formation.

Furthermore, other measurements of particles can be measured using appropriate methods, preferably optical and optionally fluorescence-based methods. For example, the motion or change of morphology of particles such as cells can be measured using appropriate methods. Preferred measurements include but not limited to, cell motility and neurite extension.

In one aspect of the present invention, ion channel recoding of a particle can be coupled with fluorescence imaging, such as high-resolution fluorescence imaging, of a single or multiple targets in the context of particles, particularly intact particles such as intact cells. Such multiple determinations allow for high information content screening of cellular and sub-cellular events as well as high throughput screening. In this aspect of the present invention, increasing the number of assays being performed on a sample, particularly those that are performed substantially in multiple sub-cellular localizations at the same time, generate a wealth of information beyond the traditional single assay used in high throughput screening methods known in the art.

Multiple, functional screenings can be performed simultaneously, near-simultaneously or separated by time and space on the same particles such as cells. In one aspect of the present invention, a system can be used to perform such assays. Such systems would include the appropriate chip, ancillary reagents, fluidic capabilities, readers, data collection structures and data processing structures, such as those including one or more Central Processing Units (CPUs) and appropriate hardware and software. Preferably, the individual cell based, multiplexed optical cellular measurements allow for locating and eliminating fluorescent or optical artifacts and backgrounds, allows for measuring of biological variability of individual cells rather than investigating populations of cells and the isolation and measurement of sub-populations of particles such as populations and sub-populations of cells.

In one aspect of the present invention, particles such as cells that have been interrogated and the results recorded for ion channel currents can be further analyzed by a variety of methods. For example, a single-particle such as single-cell PCR can be used to determine genetic (DNA or RNA) information of the particle, or by a single-particle or single-cell gene expression assay or protein detection assay. These types of analysis and/or gene expression analysis can be performed on the same chip as the ion channel chip or another chip or alternative structure, such as a chip or other structure in communication with the ion channel chip, such as via fluid communication by way of appropriate conduits, such as channels, tubes, troughs or the like can be used. These types of analysis can be performed using methods known in the art or adaptable to the chip environment and structure.

If such analyses are performed on a chip, then appropriate structures and reagents can be utilized. For example, manipulation means such as particle transportation, lyses, molecular extraction, molecular separation can be used. One expel is that after on-chip ion channel recording is performed, an on chip PCR or RT-PCR method can be performed in situ. Preferably, specific genetics information of the particle such as the cell, determined by appropriate methods such as the use of primers to be used in the PCR reactions, is amplified. After this step, the PCR product, such as amplified nucleic acids such as DNA, can be optionally transported to a detection unit and/or optionally analysis unit on the same chip, a different chip or another structure. (FIG. 21) The genetic information provided within the nucleic acid molecule can then be decoded and analyzed using methods known in the art. Transportation of moieties can be accomplished by any appropriate structure and method that can be utilized to transport samples such as fluids. Preferred methods include microfluidics such as the transfer of materials via channels, conduits, troughs, tubing and the like.

Microfluidics can be provided on, within or partially within a chip of the present invention. Such microfluidics can be utilized in order to facilitate the automation and throughput of assays that utilize a chip of the present invention. For effective delivery of sample and reagents, such as a particle sample such as a sample including a cell or cells, perfusion buffer or test compounds, into a chip of the present invention, or a chip-chamber combination, a variety of microfluidic structures can be used. Preferred microfluidic structures are channels, troughs or tubing. Such structures can be made using methods known in the art, such as etching, machining or in one alternative to such methods, by selected polymerization (see, for example, U.S. Provisional Patent Application No. 60/258,281 filed Dec. 26, 2000). As set forth in FIG. 17 and FIG. 18, channels are one preferred microfluidic structure of the present invention, particularly the structural configuration set forth in FIG. 18 where microfluidic channels are incorporated onto or within, at least in part, a chip. These channels can be fabricated onto or at least in part within the substrate of a chip of the present invention. Alternatively, such structures can be added onto the chip of the present invention. The channels can be made of various materials, such as but not limited to plastics, rubbers, PDMS, polyimide, paralyene, SU8, glass, $Al_2O_3$ and the like. The flow of fluid within these channels can be driven by a variety of forces, including capillary flow, positive pressure, negative pressure, electroosmosis, electrophoresis or electrohydrodynamics forces. Appropriate structures can provide the forces, such as pumps, syringes, piezo injectors or dispensers, electric fields, impellers or other structures known in the art, particularly the art of microfluidic circuits.

In one preferred aspect of the present invention, various structural elements useful for microfluidics can be incorporated in whole or in part on or within a chip or provided off-chip. Such elements include but are not limited to pumping mechanisms; electrodes to drive electric-filed induced fluid flow, valves and the like. Such structures can be manufactured using methods known in the art, particularly by MEMS technologies, machining or etching.

Figure 17:
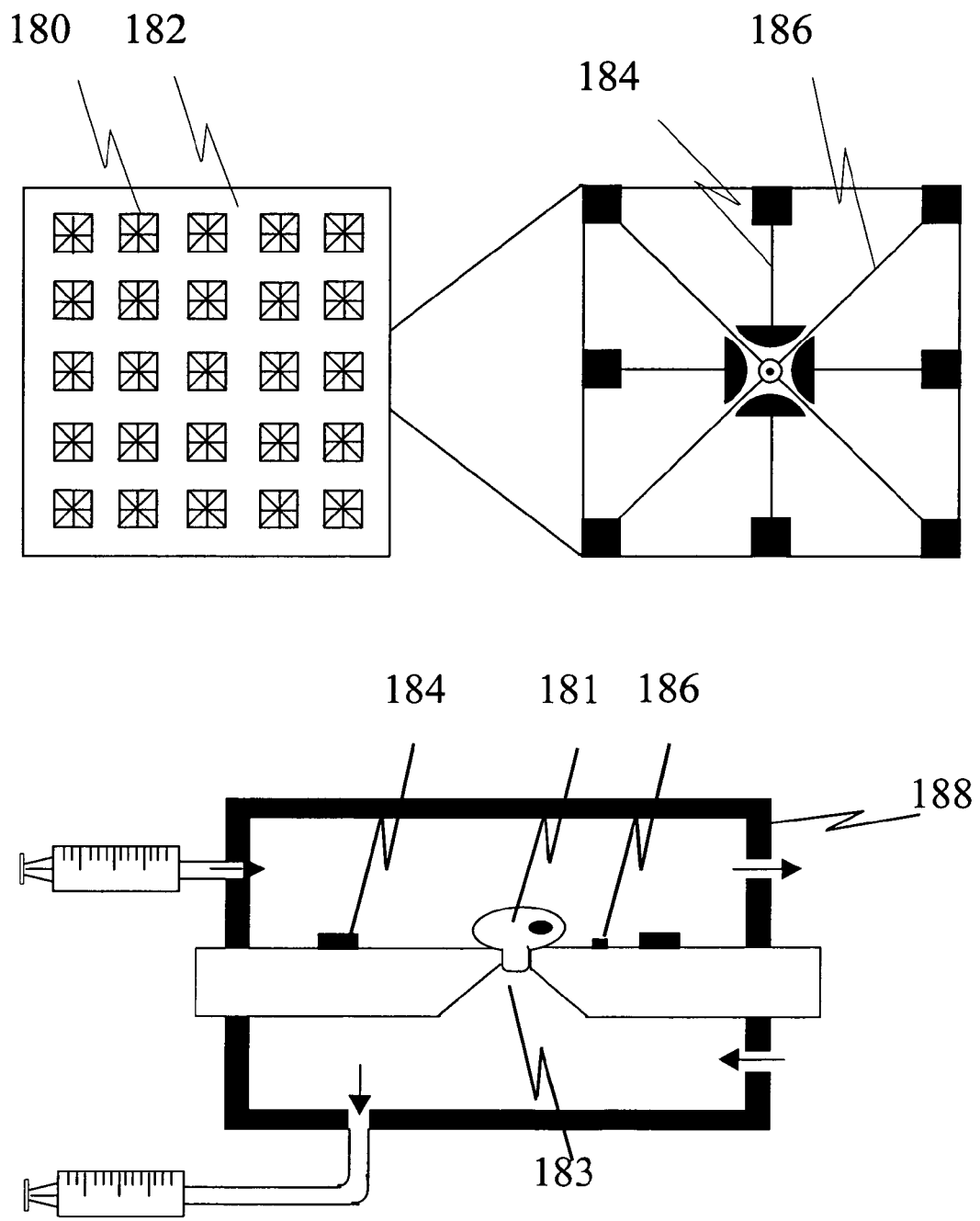
FIG. 17 depicts a chip (180) of the present invention that includes an array (182) of long-range (184) and short-range (186) particle positioning means around a hole on a chip optionally within a chamber (188). Each depicted unit in the array is a measurement unit. Short-range particle positioning means are most effective at a range of less than about 100 micrometers, more typically less than about 40 micrometers. Long-range particle positioning means are most effective at a distance of between greater than about 20 micrometers and less than about 10 centimeters, typically between greater than about 50 micrometers and less than about 1 centimeter or about 5 millimeters. In operation, the long-range (184) particle positioning means are used to localize a particle such that the short-range (186) particle positioning means can localize the particle within a range (181) at the hole (183) such that ion channel determinations can be made. In the instance depicted, the long-range (184) and short-range (186) particle positioning means operate on dielectrophoresis principles. In certain aspects of the present invention, the top chamber can be a single chamber for all of the measurement units, or the top chamber can be multiple discrete units. Such multiple discrete units can engage one or several particles, depending on the number of holes and ion transport detection structures provided. In the aspect where there are individual cells in a measurement unit, then the bottom chamber should be separate and discrete for each measurement unit so that microfluidics using pumps, tubing and the like can be individually monitored and manipulated, and individual recording electrodes and electrical connection leads can be provided. Although the long-range and short-range particle positioning means are depicted as the same configuration in this figure, different configurations can be utilized and can be designed depending on the conditions, target particles and assays to be performed.

One aspect of the present invention is depicted in FIG. 17. This figure depicts a chip-based cartridge where an individual chip includes multiple, addressable units. Each unit includes a cell positioning structure that can exert physical forces to position particles such as cells into the center or pre-designated location of an individual unit. At the center of the pre-designated location of the unit is located an ion channel measuring structure such as an aperture. The particles that have been positioned onto the aperture are then measured or assayed for their ion channel activities. Each unit preferably has separate fluidic control circuits that are optionally interfaced with the environment outside of the chamber.

Figure 18:
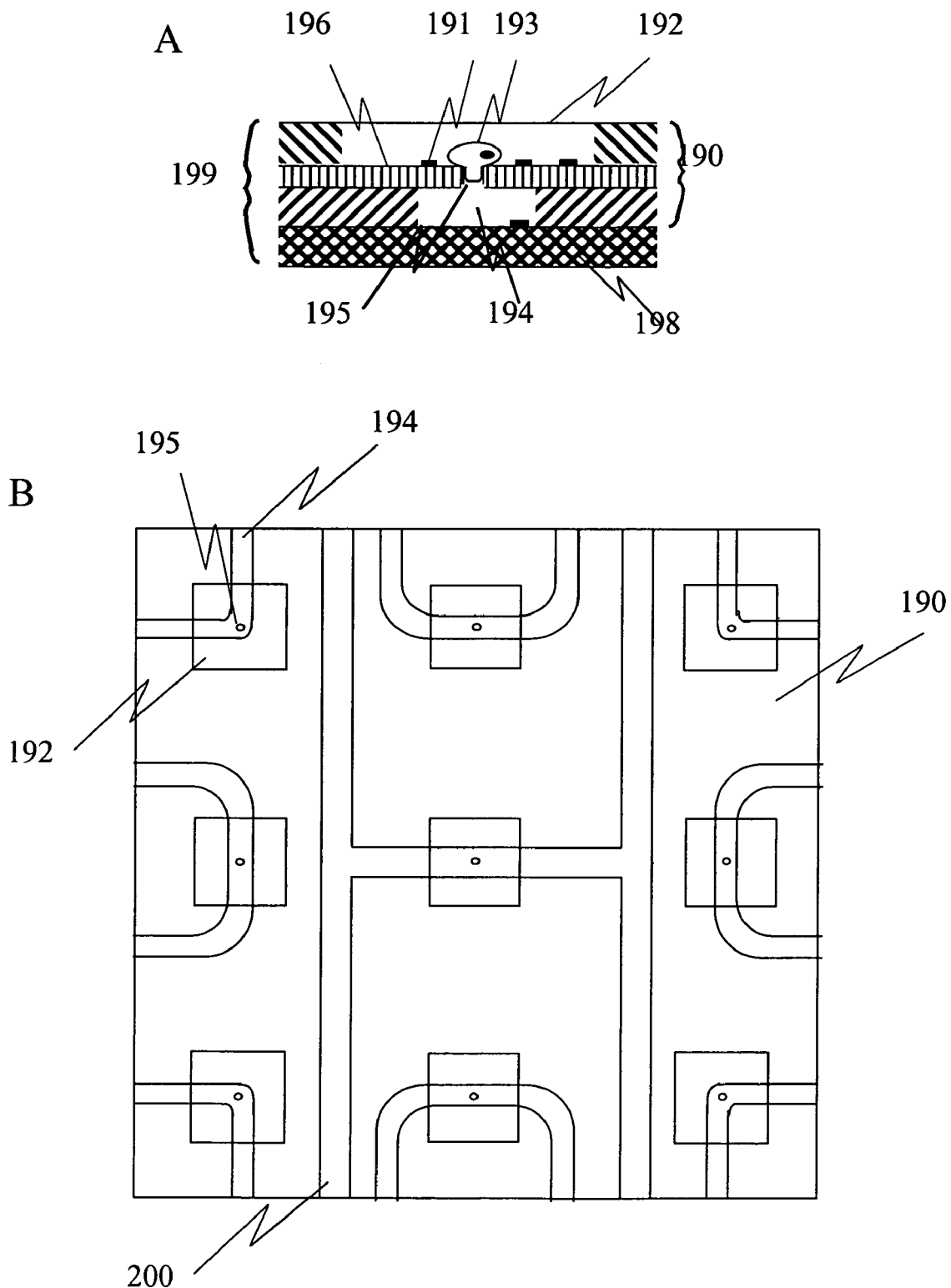
FIG. 18 depicts a modified configuration from that depicted in FIG. 17.

A modification of the chip depicted in FIG. 17 is depicted in FIG. 18. In FIG. 18, duel channels for the chambers. This configuration is more flexible than that depicted in FIG. 17 because a variety of microfluidic circuits can be provided on a chip and channels can optionally link the individual units. FIG. 18 depicts an alternative configuration depicted in FIG. 17. FIG. 18 depicts chambers (190) being formed by a top channel (192) and a bottom channel (194) that can be made using appropriate methods such as etching, machining or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel detecting structure, such as an aperture (195). A plurality of units (199) can be combined to make an array of units (200) on a chip. Microfluidic connections, such as tubing such as TEFLON™ tubing, can be used to connect the top channel and/or lower channel to the environment external to the chip.

As discussed herein, chip configurations can have an upper chamber and a lower chamber, wherein the chamber can take the form of a channel. The chambers can be open, such as in the form of a trough, or closed such as in the configuration of a tube or pipe. In the alternative, the chambers can form open or closed wells which are larger in size and volume than channels (see, for example, distinction between FIG. 17 and FIG. 18). In one aspect of the present invention, a chip can include a top well that is an open chamber, a bottom chamber that is sealed with a connection such as tubing that connects to a pressure source. Another aspect of the present invention includes a chip, a top sealed chamber that is connected to external fluidic sources by tubing and a bottom sealed chamber that is connected to an external pressure source. Other combinations of open or closed chambers or channels, connection to outside fluidic control devices and fluidic control devices can be used and are apparent to one skilled in the art. Different configurations can be used for different application.

For research instrument and apparatus uses and configurations, a chip that includes an open top chamber, sealed bottom chamber connected to a negative pressure source is preferred. Optionally, other components can be includes, such as a pressure source and electronic apparatus, such as headstage, amplifier and the like.

For safety screening such as cardiac safety screening uses and configurations, a chip with a preferably closed top chamber with tubing inlets, bottom chambers with tubing connected to negative pressure sources and cultured cells as the source for the safety screening test along with a library of the safety testing compounds is preferred. The tubing inlet can be handled to connect to the source of the cultured cells and also to storage structures, such as microplates, microtiter plates or tubes can be directly or directly made. Safety testing refers to the realization that many drugs on the market can unexpectedly modulate ion channel activity non-specifically and can unexpectedly interfere with ion channel activity in non-target tissues such as cardiac tissues. Examples include the popular drugs Seldane™ and cyclosporin that have exhibited unintended modulation of ion channel activity, particularly in cardiac tissues. This phenomenon is of particular concern when the drug does not target ion channel activity as its intended target. Preferred ion channels to investigate for safety screens are HERG and MIRP, which are present in hart and brain tissues and interact together to form active ion channels. Other ion channels include KvLQT and Mink, Kv1.5, Kv2.1 and Kv6.2, and Kv4.3 etc.

For primary screening and secondary screening applications such as for screening for drug candidates, a chip that includes a top chamber, preferably closed but optionally open, can be fitted with a number of inlet tubing. The bottom chambers, preferably closed, can be fitted with multiple tubing connected to pressure sources such as negative pressure sources. The chambers can be connected to cultured cells provided in an appropriate vessel, such as a plate and a library of compounds provided in one or more appropriate containers, such as wells of plates such as microtiter plates or independent tubes. Primary screening refers to the initial testing of a large collection of chemical entities against an ion channel target for desired modulation using a specific assay format. Secondary screening refers to the testing of focused libraries of chemical entities constructed using the knowledge obtained from primary screening to find related compounds that have improved properties.

In one aspect of the present invention, a chip or a chip-chamber combination with or without ancillary structures can be provided in an anti-vibration chamber or structure. Such a chamber can be desirable to minimize shaking of a particle-aperture seal. Motion of a substrate such as a table that is in contact with a chip or ancillary structures can lead to decreased strength of such a seal and lead to increased noise in an ion transport assay. Anti-vibration cambers or structures can include heavy air tables such as those made of stone or metal that resist vibration associated with bumping or movement of buildings. Alternatively, an anti-vibration camber can include a camber filled with a fluid that can act to dampen vibrations, or combinations of such structures and methods.

In addition to particles such as cells or subcellular structures or vesicles, synthetic membranes can also be used in the present invention. For example, synthetic membranes such as lipid bilayers that include ion channels or other ion transporting molecules can be used in the present invention. Such lipid bilayers with and without such molecules can be made using methods known in the art.

In addition, noise reduction in an assay can be accomplished in the present invention based on electrode configuration, structure and materials. For example, ground electrodes in contact with a solution bath are called reference electrodes. In such a case, these types of electrodes are preferably Ag/AgCl or other materials suitable for such reference electrodes. Ag/AgCl can be readily fabricated by way of fabrication methods known in the art. For example, we could use photolithography method to pattern a thin silver film (deposited via various means such as evaporation, or sputtering) to form required electrode geometry. The silver electrode is then processed to become Ag/AgCl by electrochemically reacting the Ag electrodes in an appropriate solution containing chloride ions. Preferred reference electrodes can maintain a constant electrode/solution interface potential difference, or junction potential, relatively independent of the electric current driven through the reference electrodes.

Whereas the reference electrodes are preferably made with suitable materials such as Ag/AgCl for their desired electrochemical properties, the electrodes for injecting current or clamping voltages may also be made of these materials (e.g. Ag/AgCl).

In some embodiments, it is possible that the electrodes for positing the cells or particles via electrical forces (e.g. dielectrophoresis forces, traveling-wave dielectrophoresis forces, electrophoresis forces or electro-osmosis forces) are also used as the electrodes for recording the ion currents for the ion transports. But this does not have to be the case. In other embodiments, the electrodes for positioning of the cells or particles may be different from the electrodes for recording ion currents for the ion transports.

Many of the assays, structures and methods described herein relate to whole cell methods. As described further herein, single-cannel recording or other modes of recording are addressed by the present invention.

In one aspect of the present invention, the members of an array of measuring units can have a common or separate bath cambers and/or microfluidic channels. For example, as depicted in FIG. 17 and FIG. 18, one preferred aspect of the present invention allows units to be addressed by common or separate microfluidic channels by way of microfluidic circuitry.

In another aspect of the present invention, an array of biosensors can be made with synthetic or biological membranes in which ion transports or any ion-conducting pathways reside. Opening, closing or other functions and properties of the ion transports or ion-conducting pathways are linked to the detection of a target molecule, pathogen or other substance. Such detection can be of chemical, physical, biochemical or biophysical or the like in nature, such as the binding of a target molecular to a senor molecular device linked to ion transport detection microdevice described in this invention. Such device allows for highly sensitive single molecule detection of substance in a high throughput low noise manner.

Channel Structures in General

Figure 19:
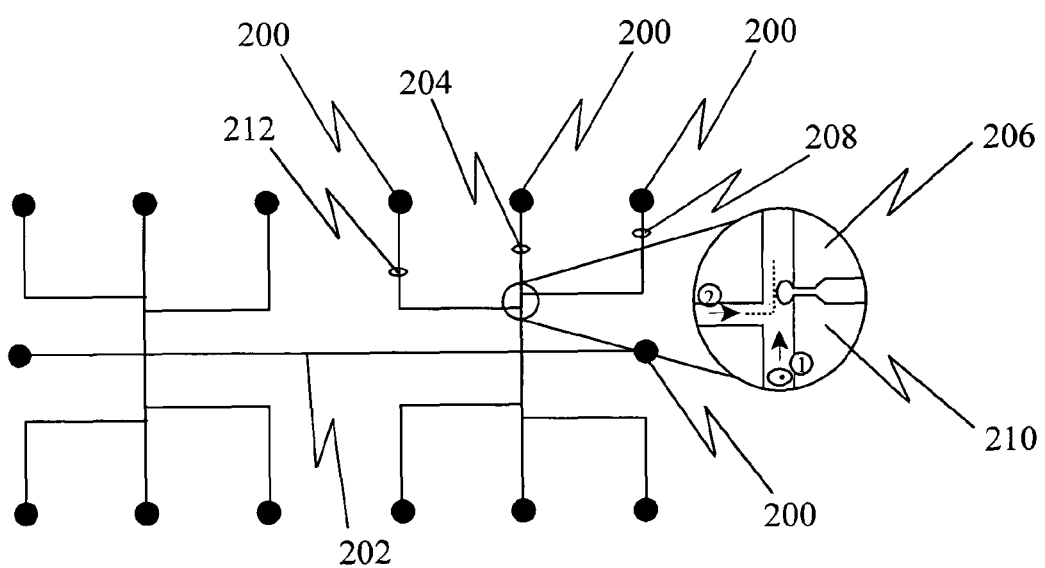
FIG. 19 depicts a top view of a chip of the present invention where the aperture or hole of an ion channel or ion transport detection structure is provided on the side of a channel rather than through the substrate. Additional particle positioning means besides the special confinement by the channels for this type of patch-clamp-in-a-channel technology can be provided near the aperture, but is optional.
Figure 20:
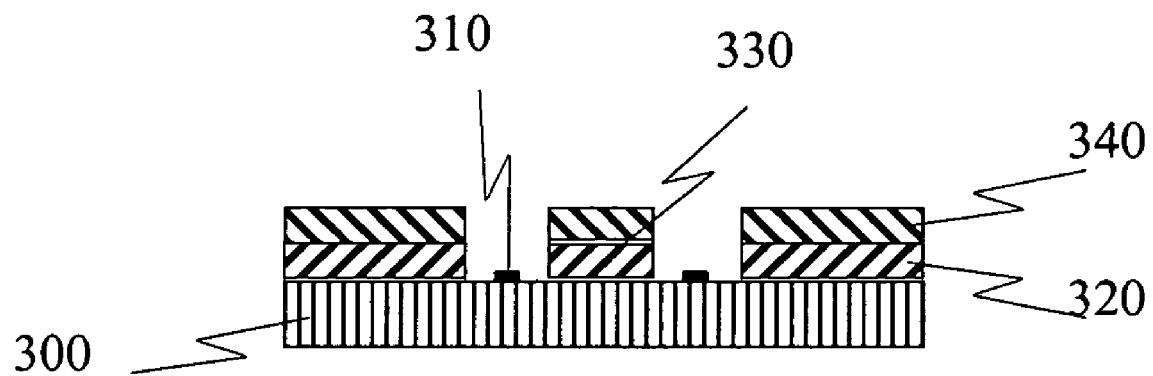
FIG. 20 depicts a cross section of one aspect of an ion transport recording chip depicted in FIG. 19 where the method of manufacture is diagrammatically shown. In one aspect of the present invention, a conduit is made using sacrificial layer methods. One preferred method is wire sacrificial methodologies such as they are known in the art, such as by the use of copper wire.

In one aspect of the present invention, microfluidic channels can be used to form at least one chamber of an ion transport function detection unit of the present invention. In this aspect of the present invention, open or closed channels can be made on chips using methods known in the art, such as machining, molding or polymerization. A closed channel can be made by overcoating a channel or providing a layer of material on top of an open channel, such as a layer of polymer or glass, such as a film of polymer or a thin sheet of glass, such as a coverslip. Subchannels can connect channels to form apertures for use in the methods of the present invention in any orientation, preferably parallel to the surface of the wafer. Alternatively, branch points in a matrix of channels can be used to trap particles such as cells in this type of configuration. FIG. 19 and FIG. 20 depict two configurations for such devices of the present invention.

Generally, particles are transported through main fluidic channels by forces such as positive or negative pressure, or acoustic or dielectrophoretic forces or other appropriate forces are used to draw cells into branch microfluidic channels where one or more recording sites, such as sites including apertures and ion channel detection structures are present. Cells can be stopped by dielectrophoretic, acoustic or other forces close to the recording site, which is preferably a hole in the side of a wall of a microfluidic channel. Pressure such as positive pressure or negative pressure or other appropriate forces can be used to seal the particle such as a cell to a hole or aperture to form Giga Ohm seals. Sealed membranes are then ruptured by electric zap and/or negative or positive pressure or other means such as chemical or enzymatic means to generate whole cell configurations. Patch clamp recording are then performed for each recording unit. Each branch microfluidic channel can have multiple recording sites. One main microfluidic channel can have many branch microfluidic channels. And one chip can have multiple main microfluidic channels.

The structures depicted in FIG. 19 and FIG. 20 can be manufactured using a variety of appropriate methods. For example, a substrate can be provided and prepared for further processing such as sputtering or etching. The electrodes, such as recording electrodes, DEP electrodes, acoustic electrodes or other appropriate electrodes can be fabricated by way of sputtering or other deposition of conductive materials such as metals, preferably gold. The first half of channel layer is fabricated using SU8, polyimide or other polymers or any etchable materials by masking. The sacrificial layer is then fabricated using masking and sputtering of appropriate removable materials. The second half of channel layer is then deposited using the methods used for the first channel layer. The sacrificial layer is then etched away using appropriate methods, such as chemical etching. The resulting structures can be linked by leads within, partially within or on the chip using appropriate connections as described herein or known in the art.

Channel Structures in Dual Vertical Configuration

One aspect of the present invention is a biochip that includes channels or chambers that can be connected in a vertical configuration by way of a hole that can function as an ion transport detection structure. For example, as set forth in FIG. 18A and FIG. 18B, chambers (190) are formed by a top channel (192) and a bottom channel (194). The channels can be made using appropriate methods such as etching, machining, subtractive etching or polymerization. The channels are preferably closed, but can also be in an open configuration, in particular the top channel (192). The channels are separated by a barrier (196) and are preferably provided on a substrate (198). Particle positioning means (191) can be present to guide a particle, such as a cell (193), to an ion channel detecting structure, such as an aperture (195).

Preferably, the structure depicted in FIG. 18A can be made using MEMS technologies in whole or in part. For example, the substrate can be provided and the electrode sputtered using appropriate metals, preferably a metal relatively resistant to sacrificial etching. The bottom channel can be formed by sputtering of subtractive material, such as copper and the lower layer can be provided by methods such as sputtering or masking. The lower layer can be made of any appropriate material, such as polymerized materials or resist. The middle layer is then provided by appropriate methods, such as sputtering, polymerizing or masking. The middle layer is preferably made of material resistant to subtractive etching. The hole is preferably left my masking but can also be made using machining or other appropriate methods. The hole allows etching materials, such as acids, reach into and create the bottom channel by way of subtractive etching. The top channel can be formed by providing an additional layer of material, such as polymerized materials or resist which can be deposited by appropriate methods such as sputtering or masking. The particle positioning means can be made by depositing appropriate materials, such as conductive materials or magnetic or magnetizable materials, using appropriate methods, such as sputtering. The particle positioning means can be coated with another material to prevent direct contact between a sample and these structures. Such material is preferably an insulating material and can be provided using appropriate methods, such as polymerizing, masking or sputtering. Optionally, the top channel can be covered with another structure to form a closed channel. The top channel can be covered with appropriate materials such as thin films of polymers or copolymers, such as cycloolefins or cycloolefin copolymers, or cover slips such as those made of glass or other appropriate materials.

As shown in FIG. 18B, the upper channel can take the configuration of a stand-alone well. In the alternative, the wells can be connected by way of channels that interconnect the wells, preferably through the upper layer of material (such interconnecting channels are not shown). Such interconnections are not necessary but can be desirable. In one aspect of the present invention, the interconnections are not present and the upper channels form wells, much like microtiter wells. These wells can have particle positioning structures such as but not limited to those depicted in FIG. 17. Dispensation methods known in the art, such as pipettes, syringes or other dispensing methods and structures can be used to dispense particles, cells, media, reagents compounds and the like into the well. Alternatively, these wells can be connected to one or more other wells which allows for a flow-through arrangement such that a variety of wells can be provided the same or different materials. In one aspect of the present invention, the wells are not formed and the upper and lower channels spatially intersect without the additional volume of the well structure. Thus, in FIG. 18B, the top channel structure is depicted as a well. Rather than a well, channel structures as depicted for the bottom channels can be provided. This type of configuration would reduce the assay volume of an assay and allow for flexibility in designing and performing assays using these structures.

The lower channels are depicted in configurations that allow for the introduction and removal of materials from the locus of the ion transport detection means. This flow-through allows for the exchange of materials and washing steps during the performance of an assay. The upper channels can be configured in the same or similar way.

Channel Structures in Horizontal Configurations

As depicted in FIG. 19 and FIG. 20, channel-channel intersections can be in a horizontal configuration. FIG. 19 depicts a top view of a chip of the present invention where the aperture or hole of an ion channel or ion transport detection structure is provided on the side of a channel rather than through the substrate. FIG. 20 depicts a cross section of one aspect of a chip depicted in FIG. 19 where the method of manufacture is diagrammatically shown. In one aspect of the present invention, a conduit is made using sacrificial layer methods. One preferred method is wire sacrificial methodologies such as they are known in the art, such as by the use of copper wire.

The structure depicted in FIG. 19 and in cross section in FIG. 20, is one preferred aspect of the present invention wherein the channels are provided side-by-side and are connected by conduits. These smaller channels are used to trap particles such as cells and act as a hole as part of an ion transport detection structure of the present invention. The channels and conduits can be made using any appropriate methods in the art and as discussed herein, preferably MEMS based methods. Preferably, the channels are made using sputtering, polymerizing or other methods. The conduits are preferably made using sacrificial methods, such as sacrificial wire methods.

The tree structure of FIG. 19 allows for a variety of assay formats. The ports (200) allow for materials to be provided to channels and manipulated. For example, reagents can be provided into the channels via ports and the flow of materials in the channels can be regulated by altering the pressure (positive, negative or neutral) applied to the port. Valves can be provided to regulate the flow and pressure at or near such ports (200). The central trunk (202) preferably includes cells that can be transported down the stems (204) to the reaction region (206). The reaction region can include a branch that allows particles to be engaged with a hole. Particles in the reaction region can be engaged with a conduit (210) by having negative pressure applied to the particle positioning channel (208). Reagents such as test compounds can be provided to the reaction region through a reagent channel (212). The channels that modulate the positioning of cells can include particle positioning means and particle separating means. For example, the central trunk (202) can be used to separate cells from a population based on their physical properties, such as dielectrophoretic characteristics. Cells at the branch points can be drawn down the stems (204) to the reaction regions (206) by pressure or other forces, such as electrophoresis. In the alternative, dielectrophoretic structures can guide cells to the reaction region (206). Once in the reaction region, particle positioning forces such as negative pressure by the particle positioning channel (208). One stem may have multiple recording sites each represented by the structure in the blown-up region of FIG. 19.

FIG. 20 is a cross section through FIG. 19 at Z-Z. This cross section is instructive as to methods of making these structures. First, a substrate (300) is provided. On the substrate electrodes for particle positioning means or ion transport detection structures (310) are provided, such as through sputtering. A first layer (320) is provided such as through sputtering, polymerizing, making or other appropriate methods. The sacrificial layer (330) is then provided, such as copper, which can be provided by sputtering or by a wire or similar structure. The second channel layer (340) is then provided, which can be the same or different from the first layer. The sacrificial layer can be digested, such as by acid washing for a sacrificial layer of copper, to form a conduit (210). Rather than being provided at the outset of this procedure, the electrodes (310) can be provided at this point in time, such as through sputtering or other appropriate methods. Optionally, a cover can be provided to make covered channels, but that is not a requirement of the present invention.

Alternatives to the horizontal-horizontal configuration and vertical-vertical configuration discussed above, vertical-horizontal configurations and other three-dimensional configurations can be made.

Channel Structures in Three-Dimensional Configurations

Rather than horizontal-horizontal or vertical-vertical configurations, channels can be made in three-dimensional matrices using appropriate methods. Conduits can be provided between the channels using sacrificial layers as discussed herein. Preferably, a network of channels can be created using sacrificial methods, such as wire subtractive methods. Such sacrificial methods can be combined with other manufacturing methods, such as machining, polymerizing or MEMS technologies. In this aspect of the invention, channels and conduits can be mapped out in three dimensional space using wires or other similar structures that are susceptible to subtractive methods, such as acid degradation. The wires can be imbedded in appropriate material, such as insulating material such as resist or polymerized materials. The imbedding material can be provided in one step, such as in a mold, or in layers. In the latter instance, channels and conduits can be formed using sputtering, masking and other methods.

Channel Structures in High Information Content Screening Configurations

Figure 21:
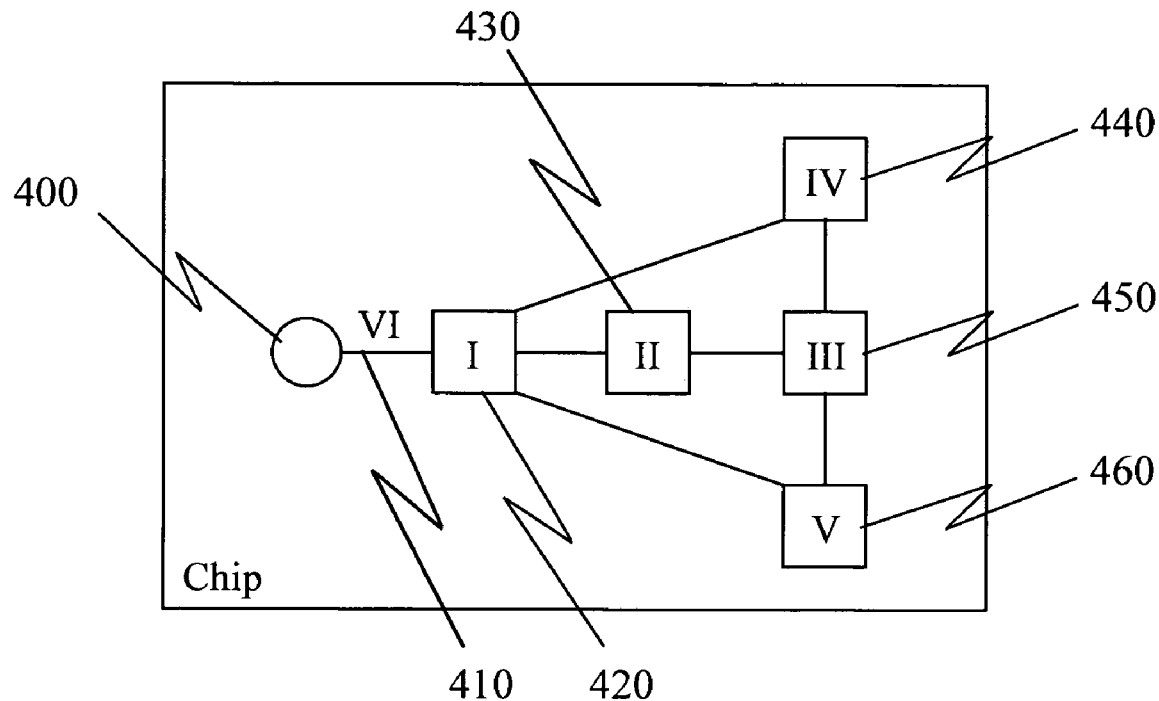
FIG. 21 depicts a multi-functional biochip useful for high information content screening. Samples are provided at port (400). Particles in the same are transported and optionally separated along a channel (410) that can include particle separating structures such as dielectrophoretic structures. Particles can be transferred from the port to the first chamber by particle manipulating means or structures, including pressure or gravity flow of fluids. A first chamber (or well) (420) is provided, which in the depicted configuration is a cell viability test, such as through optical detection methods of dye exclusion. Any appropriate test can take place in the first chamber, but the viability test is depicted for clarity. A second channel can connect the first chamber to other chambers where other tests can be performed. For example, the cells in the first chamber can be transported an ion transport detection unit (430) or other units, such as fluorescent units (450), genomics units (460) or proteomics units (440). The ion transport unit includes ion transport detection structures as described herein, in particular as depicted in FIG. 17, FIG. 18, FIG. 19 or FIG. 20. Optional particle separation units can be provided within, or after each chamber or units that performs detection functions.

FIG. 21 depicts a multi-functional biochip useful for high information content screening. Samples are provided at port (400). Particles in the same are transported and optionally separated along a channel (410) that can include particle separating structures such as dielectrophoretic structures. Particles can be transferred from the port to the first chamber by particle manipulating means or structures, including pressure or gravity flow of fluids. A first chamber (or well) (420) is provided, which in the depicted configuration is a cell viability test, such as through optical detection methods of dye exclusion. Any appropriate test can take place in the first chamber, but the viability test is depicted for clarity. A second channel can connect the first chamber to other chambers where other tests can be performed. For example, the cells in the first chamber can be transported an ion transport detection unit (430) or other units, such as fluorescent units (450), genomics units (460) or proteomics units (440). The ion transport unit includes ion transport detection structures as described herein, in particular as depicted in FIG. 17, FIG. 18, FIG. 19 or FIG. 20. Optional particle separation units can be provided within, or after each chamber or units that performs detection functions.

The different units can be connected to detection devices and structures appropriate for the readout of that unit. For example, for dye exclusion tests for viability, optical methods would be useful to detect the presence and location of dyes such as trypan blue within cells. In some units such as viability units, particles such as cells should remain intact. In other units, such as genomics units or proteomics units, particles such as cells should be lysed.

The fluorescence unit can be used to detect the fluorescence readout of several different tests as described herein, such as protein-protein interactions utilizing FRET applications, membrane potential readouts using FRET applications, ion sensitive fluorescent dyes such as fura2 or fura3, enzyme activity using fluorescent readouts and the like.

The proteomics unit can have a variety of tests, such as affinity reactions such as specific binding reactions, such as receptor ligand or antigen antibody reactions in order to detect the presence and optionally amount of a protein in a sample. Such systems can be based in silico as are known in the art. Particles such as cells can be interrogated as whole cells, or can be lysed to release contents such that the cytoplasmic and internal structures such as nuclei can be interrogated.

The genomics unit can include a variety of structures and methods. Whole particle, such as whole cell, applications include in situ hybridization, such as FISH. Alternative methods include ex vivo hybridization methods that have a particle such as cell being lysed prior to being interrogated. The nucleic acid molecules of a cell, including DNA, RNA and combinations thereof can be interrogated using a variety of methods as they are known in the art. Preferably, in silico methods, such as gene chips known in the art (see, Affimatrix patents and literature) can be used.

Thus, using High information content screening (HCS) of the present invention, a single sample can be provided and interrogated for a variety of particle properties and functions. The information generated by these systems can be collected, compared and utilized in bioinformatic applications, such as drug discovery, pharmacogenomics or pharmacokinetics.

Methods of Use

The present invention also includes a method of detecting at least one ion transport function or property of a particle that includes: contacting a sample comprising at least one particle with the biochip of the present invention and positioning said at least one particle at or near said ion transport measuring means. An ion transport function or property of the sample is then measured using the ion transport measuring means. The sample can be any appropriate sample, but preferably includes a biological sample that includes particles, preferably a cell or population of cells.

A sample solution can optionally be added to a sample before a sample is deposited on a biochip of the present invention or in a chamber that includes a biochip of the present invention. When a sample solution is use, the sample and sample solution can be incubated together for any length of time before adding the sample solution-sample mixture to a chamber for separation, from less than one second to several hours or even days. Sample or sample-sample solution mixing can occur in a conduit that leads to the chamber. Alternatively, a sample can optionally be added to a chamber and a sample solution can be added to the chamber subsequently. It is also possible to add a sample solution to a chamber before adding the sample to a chamber.

A sample, an optional sample solution, and optionally, solutions, buffers, preparations, or reagents, can be added to a chamber by any convenient means, such as transfer with a pipette, injection with a syringe, gravity flow through a conduit, such as tygon, teflon, PEEK tubing, through a microfluidic channel etc. Preferably a sample and other reagents such as solutions, buffers, preparations, or reagents are added to a chamber in a continuous flow mode, in which a continuous stream of fluid is injected or pumped into at least one inlet port, and non-retained sample components and fluids exit the chamber via at least one outlet port.

The particles are directed towards holes on a biochip by particle positioning means. The particles then engage such holes and an electronic seal is formed. One or more functions or properties of one or more ion transports are then determined using the structures and methods described herein. Such determinations are preferably made using patch clamp methods or whole cell methods, but other ion transport assay methods can be used.

Generally, the methods of the present invention provide the following characteristics, but not all such characteristics are required such that some characteristics can be removed and others optionally added: 1) the introduction of particles into a chamber that includes a biochip of the present invention, 2) positioning particles at or near an ion transport detection structure, 3) electronic sealing of the particle with the ion transport detection structure and 4) performing ion transport recording.

There a two general purposes for using magnetic particles or dielectric responsive particles in the present invention. The first is bind to a particle for the purposes of separating a particle from other particles, such as in a population of particles in a sample mixture. The second is to position particles in proximity of ion transport detection structures of the present invention. In certain instances, the magnetic particles or dielectric responsive particles can aid in engaging a particle with such an ion transport detection structure. In one aspect of the present invention, particles are selectively attached to magnetic microparticles or dielectric responsive particles, such as through specific binding members, such as antibodies. The particles labeled with magnetic microparticles or dielectric responsive particles are then separated using electromagnetic elements or dielectrophoretic or dielectric elements of the present invention and can be manipulated or positioned at or near an ion transport detection structure. The particle is engaged with such ion transport detection structure and an ion transport function or property can be determined.

In one aspect of the present invention, particles, such as cells, can express an exogenous surface peptide or over-express an endogenous surface protein, such as a cell surface marker not endogenous to the cell. A specific binding member bound to a magnetic particle would specifically bind with that cell and allow for that cell to be separated from a sample including a mixture of cells using magnetic or electromagnetic elements. The magnetic particle bound to a particle would also facilitate manipulation of the particle and positioning at or near an ion transport determination structure such as a hole or capillary. In the alternative, particles having dielectric properties such as latex or polymeric beads can be used instead of magnetic beads and dielectrophoretic or dielectric separating, manipulating and positioning structures can be used in place of the electromagnetic structures. Particles having such cell surface markers can be made by introducing a vector such as a plasmid into a cell. The vector would include a regulatory element such as a promoter operable in the host cell being used operably linked to a nucleic acid molecule encoding the exogenous cell surface protein. Methods of making such constructs, transfection and expression are known in the art.

In another aspect of the present invention, particles such as cells can co-express two proteins, one the exogenous cell surface marker or over-expressed endogenous cell surface marker discussed above and the second an exogenous ion transport protein or over-expressed endogenous ion transport protein. These particles thus have a marker that can be specifically bound with another particle such as a magnetic particle or dielectric responsive particle. These bound particles can be separated, manipulated and positioned with appropriate particle manipulation devices, such as magnetic, electromagnetic and/or dielectrophoretic devices. The particles that are positioned in this way include the ion transport protein which can then be interrogated using structures and methods of the present invention.

A number of patch-clamp recording modes, including whole cell recording, macro-patch recording (including without limitation inside-out, outside-in and cell attached configurations), single channel recording (including without limitation inside-out, outside-in and cell-attached configurations) can be performed on the chips of the present invention. In one preferred aspect of the present invention, the following order of operations can be used for a whole cell recording using a chip configuration depicted in FIG. 17 or FIG. 18. Fluids are loaded into the bottom chamber such that the aperture or hole is filled. Cells are loaded onto the top chamber and the particles such as cells are positioned to the locations just over the aperture or hole using one or more of horizontal and vertical positioning. Electronic engagement of the particles with the aperture to form Giga Ohm sealing by way of negative pressure driven processes are used to form a tight seal between the particle, such as a cell membrane, and the aperture or hole. The membrane of the particle is ruptured by an electronic zap, a pulse of negative pressure or the addition of appropriate chemicals to digest or break of the membrane within a patch or combinations of such methods. Electronic recording of ion channel activity progresses and the top chamber is optionally perfused. In the cell-attached recording configuration, after the formation of a seal such as a Giga Ohm seal, there is no absolute need for rupturing of the membrane. Electronic recording is made directed on the attached whole cell rather than a patch or portion thereof.

Particularly for high throughput and high informational assays, software systems that can be coupled with a chip of the present invention are desirable. The software can also be coupled to image analysis of cellular phenomenon described herein, particularly optical imaging based on fluorescent based assays. The software is preferably configured to measure electrophysiology and/or patch clamp data information to look for readouts, such as curves, that are out of the ordinary. For example, an active ion channel or ion transport molecule in a membrane provides for a signature profile under a given set of conditions. One example of such a profile for whole-cell or multiple channel assays is a curve that exhibits an activation phase, an inactivation phase, a deactivation phase and optionally a desensitization phase. Parameters for measure include the peak amplitude, duration and time constants. For single channel application, the open duration, open probability, noise analysis, gating current, latency, open time, dwell time, burst length, time interval omission, close time or statistical analysis of distributions of one or more of the above can be measured. When an ion channel or ion transport molecule is contacted with a test chemical or test ligand or other environmental condition, the curves and/or parameters can change. Also, the fluorescent or other optical signal can change as well. The software systems of the present invention are capable of determining and storing reference profiles and compare them to experimental profiles. This comparison can be used to identify, preferably automatically, chemical or ligands or conditions that can alter ion channel or ion transport activity. As the amount of information within the software system grows, preferably in the form of an addressable database, the software system can become more powerful and approach artificial intelligence in power. For example, with a large database of structures and profile, a software system having artificial intelligence capabilities can be used to predict the activity of chemicals or ligands based on their structure based on historical performance of other chemicals or ligands.

Such software systems can also be used to classify channel responses. Different classes of ion channels or ion transport molecules have different signature responses or responses to certain ligands, chemical or environmental conditions. Families of ion channels or ion transport molecules can be categorized based on these profiles. Furthermore, based on historical or taught limits such as gating, hits and misses can be determined by such software systems based on deviation from standard profiles or historical data.

In one aspect of the present invention, chips of the present invention can be used to measure endocytosis, exocytosis, mitosis or blebbing of membranes, particularly using whole particle or whole cell configurations of the present invention. These biological phenomena result in the change of the surface area of a particle or cell. As the surface area of a particle or cell attached to a whole cell patch configuration of the present invention change, the measured capacitance also changes. Because there is no readily available, simple or readily automatable methods for measuring these biological phenomenon, the present invention provides methods for readily measuring these phenomenon that are related to normal cellular functions and tissue specific functions such as neurotransmitter release and uptake. By measuring the change of cellular capacitance using methods such as patch claiming methods of the present invention, a quantitative approach to measuring these biological phenomena are provided. High throughput assay s for endocytosis and exocytosis using the present invention can provide a cost effective and automatable alternative to existing methods. Such capacitance measurement can be performed using structures of the present invention, such as those depicted in FIG. 17 and FIG. 18. With a cell or particle electronically engaged onto the measurement chip, a total cell membrane capacitance can be measured by measuring the impedance between the top chamber and the bottom chamber. The cell or particle can be subjected to certain stimulation, such as regents by a perfusion process or by electronic or other environmental stimulation to result in a chain of cellular biological reaction events. Such a chain of molecular reaction events can lead to endocytosis or exocytosis or, when appropriate, blebbing.

The structures and method of the present invention are well-suited for use in primary or secondary screening in the pharmaceutical or biopharmaceutical industries and are also applicable to safety screening and target identification. The present invention can be adapted for use in primary screening where a compound library is tested against certain in channels or ion transport targets to screen for a hit that has modulatory effects, preferably modulatory effects, on the ion channel or ion transport activities. The present invention can also be used for secondary screening to confirm or otherwise further investigate the primary hits determined using the primary screening methods. Preferably, the chemical structures obtained from the primary hits are further investigated using additional information. For example, the same or different screen can be used to further investigate hits from a primary screen. Repeating a screen adds reliability to the screening procedure whereas the use of multiple screens, such as against different targets or against the same target only under different conditions can provide highly useful information for drug screening purposes. Safety screening, as discussed herein, can be used to identify potential toxic effects or adverse effects of leading drug candidates, drugs in the regulatory approval process or approved drugs.

The structures and methods of the present invention can also be used for performing sequences of nucleic acid molecules such as DNA or RNA or both in single, double or triple stranded configurations or combinations thereof. In such cases, nucleic acid segments can be pulled through an aperture on a chip by a controlled force such as positive or negative pressure, electrophoretic or electroosmotic forces, or the activity of an ion channel or ion transport molecule that accepts a nucleic acid molecule or enzyme such as polymerases, topoisomerases, helicases etc. When different bases or base pairs to through the aperture, the impedance between the top chamber and the bottom chamber would vary according to the type of bases or base pairs, such as A, G, T, C, U and others, going through the aperture. Preferably, the degree and duration of the block of impedance signals is measured to discriminate between different base pairs or bases. In this way, the impedance sequence would be a direct reflection of the nucleic acid sequences being pulled or being pushed through an aperture. Preferably, such nucleic acid molecules are manipulated with physical forces exerting on the segments driving and/or pulling such molecules through the aperture. In one aspect of the present invention, step-wise cleavage of individual bases with a nucleic acid molecule can be utilized. Each cleaved base is driven through an aperture and the impedance readout can be used for sequence nucleic acid segments.

In one aspect of the present invention, membranes such as artificial membranes or other membranes can be used as a biosensor. For example, a membrane with an inserted ion channels or ion transport molecules can be immobilized over an aperture. These ion channels or ion transport molecules may have specific electric-current responses to target analytes to be detected or senses. Thus, when a sample potentially containing a target analyte is flown over the membrane, the target analyte, if present, will alter the ion channel response. In this way, the chips and methods of the present invention can be used as specific detection tools for monitoring target analytes and other molecules. Preferred targets include analytes of interest, including but not limited to biomolecules, pesticides, toxins, poisons, venoms, drugs, drugs of abuse and analogues, precursors or metabolites thereof. These devices and methods may have a very high sensitivity for detecting target analytes and could represent a low cost alternative to other detection methodologies.

One application of such ion channel chips is for agricultural applications. Plant ion channels in guard cells and root systems are known in the art. These ion channels have been found to play important roles in regulating water conservation, nutrient absorption and other plant functions. High throughput identification of molecules that modulate these channels can help to develop agri-chemicals that can help plants withstand unfavorable environmental conditions such as draught or to identify ion channels that can be engineered into plants and expressed to alter their ability to withstand environments such as draught or absorb nutrients.

II. Methods of Modifying an Ion Transport Measuring Means to Enhance Electrical Sealing The present invention also includes methods of modifying an ion transport measuring means to enhance the electrical seal of a particle or membrane with the ion transport measuring means. Ion transport measuring means includes, as nonlimiting examples, holes, apertures, capillaries, and needles. "Modifying an ion transport measuring means" means modifying at least a portion of the surface of a chip, substrate, coating, channel, or other structure that comprises or surrounds the ion transport measuring means. The modification may refer to the surface surrounding all or a portion of the ion transport measuring means. For example, a biochip of the present invention that comprises an ion transport measuring means can be modified on one or both surfaces (e.g. upper and lower surfaces) that surround an ion transport measuring hole, and the modification may or may not extend through all or a part of the surface surrounding the portion of the hole that extends through the chip. Similarly, for capillaries, pipettes, or for channels or tube structures that comprises ion transport measuring means (such as apertures), the inner surface, outer surface, or both, of the channel, tube, capillary, or pipette can be modified, and all or a portion of the surface that surrounds the inner aperture and extends through the substrate (and optionally, coating) material can also be modified.

As used herein, "enhance the electrical seal", "enhance the electric seal", "enhance the electric sealing" or "enhance the electrical sealing properties (of an ion transport measuring means)" means increase the resistance of an electrical seal, increase the efficiency of obtaining a high resistance electrical seal (for example, reducing the time necessary to obtain one or more high resistance electrical seals), or increasing the probability of obtaining a high resistance electrical seal (for example, the number of high resistance seals obtained within a given time period).

The method comprises: providing an ion transport measuring means and treating the ion transport measuring means to enhance the electrical sealing properties of the ion transport measuring means. Preferably, treating an ion transport measuring means to enhance the electrical sealing properties results in a change in surface properties of the ion transport measuring means. The change in surface properties can be a change in surface texture, a change in surface cleanness, or a change in surface electric charge on the surface of the ion transport measuring means. In some preferred aspects of the present invention, a substrate or structure that comprises an ion transport measuring means is subjected to chemical treatment (for example, treated in acid, and/or base for specified lengths of time). For example, treatment of a glass chip comprising a hole through the chip as an ion transport measuring means with acid and/or base solutions may result in a cleaner and smoother surface in terms of surface texture for the hole. In addition, treating a surface of a biochip or fluidic channel that comprises an ion transport measuring means (such as a hole or aperture) or treating the surface of a pipette or capillary with acid and/or base may alter the surface composition, and/or modify surface hydrophobicity and/or change surface charge density and/or surface charge polarity.

Preferably, the altered surface properties improve or facilitate a high resistance electric seal or high resistance electric sealing between the surface-modified ion transport measuring means and a membranes or particle.

In practice, in preferred aspects of the present invention the method comprises providing an ion transport measuring means and treating the ion transport measuring means with one or more of the following: heat, a laser, microwave radiation, high energy radiation, salts, reactive compounds, oxidizing agents (for example, peroxide, oxygen plasma), acids, or bases. Preferably, an ion transport measuring means or a structure (as nonlimiting examples, a structure can be a substrate, chip, tube, or channel, any of which can optionally comprise a coating) that comprises at least one ion transport measuring means is treated with one or more agents to alter the surface properties of the ion transport measuring means to make at least a portion of the surface of the ion transport measuring means smoother, cleaner, or more electronegative.

An ion transport measuring means can be any ion transport measuring means, including a pipette, hole, aperture, or capillary. An aperture can be any aperture, including an aperture in a channel, such as within the diameter of a channel (for example, a narrowing of a channel), in the wall of a channel, or where a channel forms a junction with another channel. (As used herein, "channel" also includes subchannels.) In some preferred aspects of the present invention, the ion transport measuring means is on a biochip, on a planar structure, but the ion transport measuring means can also be on a non-planar structure.

The ion transport measuring means or surface surrounding the ion transport measuring means modified to enhance electrical sealing can comprise any suitable material. Preferred materials include silica, glass, silicon, plastic materials, polydimethylsiloxane (PDMS), or oxygen plasma treated PDMS. In some preferred aspects of the present invention, the ion transport measuring means comprises SiOM surface groups, where M can be hydrogen or a metal, such as, for example, Na, K, Mg, Ca, etc. In such cases, the surface density of said SiOM surface groups (or oxidized SiOM groups ($SiO^-$)) is preferably more than about 1%, more preferably more than about 10%, and yet more preferably more than about 30%. The SiOM group can be on a surface, for example, that comprises glass, for example quartz glass or borosilicate glass, thermally oxidized $SiO_2$ on silicon, deposited $SiO_2$, polydimethylsiloxane (PDMS), or oxygen plasma treated PDMS.

In preferred embodiments, the method comprises treating said ion transport measuring means with acid, base, salt solutions, oxygen plasma, or peroxide, by treating with radiation, by heating (for example, baking or fire polishing) by laser polishing said ion transport measuring means, or by performing any combinations thereof.

An acid used for treating an ion transport measuring means can be any acid, as nonlimiting examples, HCl, $H_2SO_4$, $HSO_4$, $HNO_3$, $NaHNO_3$, HF, $H_3PO_4$, HBr, HCOOH, or $CH_3COOH$ can be. The acid can be of a concentration about 0.1 M or greater, and preferably is about 0.5 M or higher in concentration, and more preferably greater than about 1 M in concentration. Optimal concentrations for treating an ion transport measuring means to enhance its electrical sealing properties can be determined empirically (see examples). The ion transport measuring means can be placed in a solution of acid for any length of time, preferably for more than one minute, and more preferably for more than about five minutes.

An ion transport measuring means can be treated with a base, such as a basic solution, that can comprise, as nonlimiting examples, NaOH, KOH, $Ba(OH)_2$, LiOH, CsOH, or $Ca(OH)_2$. The basic solution can be of a concentration of about 0.01 M or greater, and preferably is greater than about 0.05 M, and more preferably greater than about 0.1 M in concentration. Optimal concentrations for treating an ion transport measuring means to enhance its electrical sealing properties can be determined empirically (see examples). The ion transport measuring means can be placed in a solution of base for any length of time, preferably for more than one minute, and more preferably for more than about five minutes.

Where treatments such as baking, fire polishing, or laser polishing are employed, they can be used to enhance the smoothness of a glass or silica surface. Where laser polishing of a chip or substrate is used to make the surface surrounding an ion transport measuring means more smooth, it can be performed on the front side of the chip, that is, the side of the chip or substrate that will be contacted by a sample comprising particles during the use of the ion transport measuring chip or device.

Appropriate temperatures and times for baking, and conditions for fire and laser polishing to achieve the desired smoothness for improved sealing properties of ion transport measuring means can be determined empirically. Conditions for baking and laser polishing glass chips and fire polishing capillaries are also provided in the examples herein.

In some aspects of the present invention, it can be preferred to rinse the ion transport measuring means, such as in water (for example, deionized water) or a buffered solution after acid or base treatment, or treatment with an oxidizing agent, and, preferably but optionally, before using the ion transport measuring means to perform electrophysiological measurements on membranes, cells, or portions of cells. Where more than one type of treatment is performed on an ion transport measuring means, rinses can also be performed between treatments, for example, between treatment with an oxidizing agent and an acid, or between treatment with an acid and a base. An ion transport measuring means can be rinsed in water or an aqueous solution that has a pH of between about 6.5 and about 8.5, and more preferably between about 6.8 and about 8.2. Nonlimiting examples of suitable aqueous solutions for rinsing ion transport measuring means can include salt solutions (where salt solutions can range in concentration from the micromolar range to 5M or more), biological buffer solutions, cell media, or dilutions or combinations thereof. Rinsing can be performed for any length of time, for example from minutes to hours.

Some preferred methods of treating an ion transport measuring means to enhance its electrical sealing properties include one or more treatments that make the surface more electronegative, such as treatment with a base. Base treatment can optionally be combined with one or more other treatments, such as, for example, treatment with heat (such as by baking or fire polishing) or a laser, or treatment with acid, or both. Optionally, one or more rinses in water, a buffer, or a salt solution can be performed before or after any of the treatments. For example, after manufacture of a glass chip that comprises one or more holes as ion transport measuring means, the chip can be baked, and subsequently incubated in a base solution and then rinse in water or a dilution of PBS. In another example, after manufacture of a glass chip that comprises one or more holes as ion transport measuring means, the chip can be baked, subsequently incubated in an acid solution, rinsed in water, incubated in a base solution, and finally rinsed in water or a dilution of PBS.

In some aspects of the present invention, it can be preferable to store an ion transport measuring means that has been treated to have enhanced sealing capacity in an environment having decreased oxygen or carbon dioxide relative to the ambient environment. This can preserve the enhanced electrical sealing properties of the ion transport measuring means. Such an environment can be, for example, water, a salt solution (including a buffered salt solution), acetone, a vacuum, or in the presence of one or more drying agents or under nitrogen or an inert gas. Where an ion transport measuring means or structure comprising an ion transport measuring means is stored in water or an aqueous solution, preferably the pH of the water or solution is greater than 4, more preferably greater than about 6, and more preferably yet greater than about 7. For example, an ion transport measuring means or a structure comprising an ion transport measuring means can be stored in a solution having a pH of approximately 8.

The present invention also includes methods of shipping or transporting ion transport measuring means modified by the methods of the present invention to have enhanced electric sealing properties and structures comprising ion transport means that have been modified using the methods of the present invention to have enhance electric sealing properties. Such ion transport measuring means and structures comprising ion transport measuring means can be shipped or transported in closed containers that maintain the ion transport measuring means in conditions of low $CO_2$ or air. For example, the ion transport measuring means can be submerged in water, acetone, alcohol, buffered solutions, salt solutions, or under nitrogen ($N_2$) or inert gases (e.g., argon). Where the ion transport measuring means or structure comprising an ion transport measuring means is stored in water or an aqueous solution, preferably the pH of the water or solution is greater than 4, more preferably greater than about 6, and more preferably yet greater than about 7. For example, an ion transport measuring means or a structure comprising an ion transport measuring means can be shipped in a solution having a pH of approximately 8.

The present invention also includes ion transport measuring means treated to have enhanced electrical sealing properties, such as by methods disclosed herein. The ion transport measuring means can be any ion transport measuring means, including those disclosed herein. The present invention also includes chips, pipettes, substrates, and cartridges, including those disclosed herein, comprising ion transport measuring means treated using the methods of the present invention to have enhanced electrical sealing properties.

The present invention also includes methods of using ion transport measuring means and structures comprising ion transport measuring means, such as biochips, to measure ion transport activity or functions of one or more particles, such as cells. The methods include: contacting a sample comprising at least one particle with an ion transport measuring means that has been modified to have enhance the electrical seal of a particle or membrane with the ion transport measuring means, engaging at least one particle or at least one membrane on or at the modified ion transport measuring means, and measuring at least one ion transport function or property of the particle or membrane. The methods can be practices using the methods and devises disclosed herein. Generally, the methods of the present invention provide the following characteristics, but not all such characteristics are required such that some characteristics can be removed and others optionally added: 1) the introduction of particles into a chamber that includes a biochip of the present invention, 2) optionally positioning particles at or near an ion transport detection structure, 3) electronic sealing of the particle with the ion transport detection structure, and 4) performing ion transport recording. Methods known in the art and disclosed herein can be performed to measure ion transport functions and properties using modified ion transport measuring means of the present invention, such as surface-modified capillaries, pipette, and holes and apertures on biochips and channel structures.

III An Array of Microfabricated Capillaries Optionally with Electrodes and Methods of Use The present invention also includes a biochip that includes an array of capillaries, wherein members of said array comprises an ion transport measuring structure.

Figure 15:
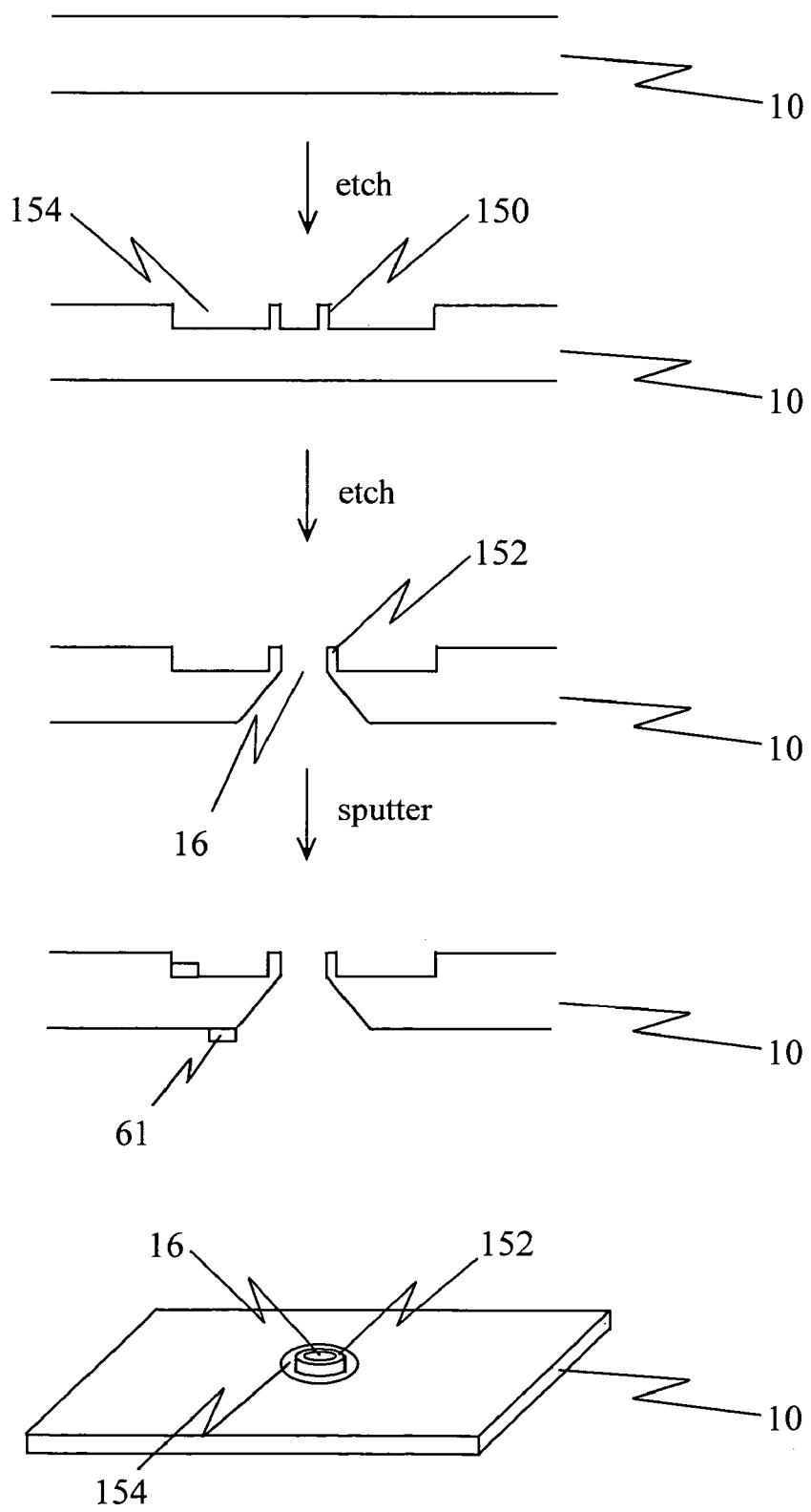
FIG. 15 depicts the manufacture of a capillary of the present invention that can be used as an ion transport detection structure in a manner generally depicted in FIG. 9. The process starts with providing a substrate (10), which is then etched to form protrusions (150) that will form a capillary structure (52). This etching forms a trench (154) that defines the protrusion (150) or capillary (152). Further etching from the other side of the substrate forms a hole (16) that can have a funnel shape. Deposition (e.g. sputtering) and photolithographic processing of conductive material can be used to provide electrode structures (61) for use in ion transport function or property determinations using methods of the present invention. In one aspect of the present invention, the protrusion (150) can be hollow and be open or closed at the top of the structure.

As depicted in FIG. 15, the present invention can include capillary structures that are useful in the present invention. These capillary structures can be provided in an array on a substrate. The substrate can be of any appropriate size, but preferably, the substrate is between about 1 mm$^2$ and about 2,500 cm$^2$, having a density of capillary structures between about 1 and about 2,500 capillary structures per mm$^2$. The capillary structures can be any appropriate distance apart, but are preferably between about 20 micrometers and about 10 cm apart.

Figure 9:
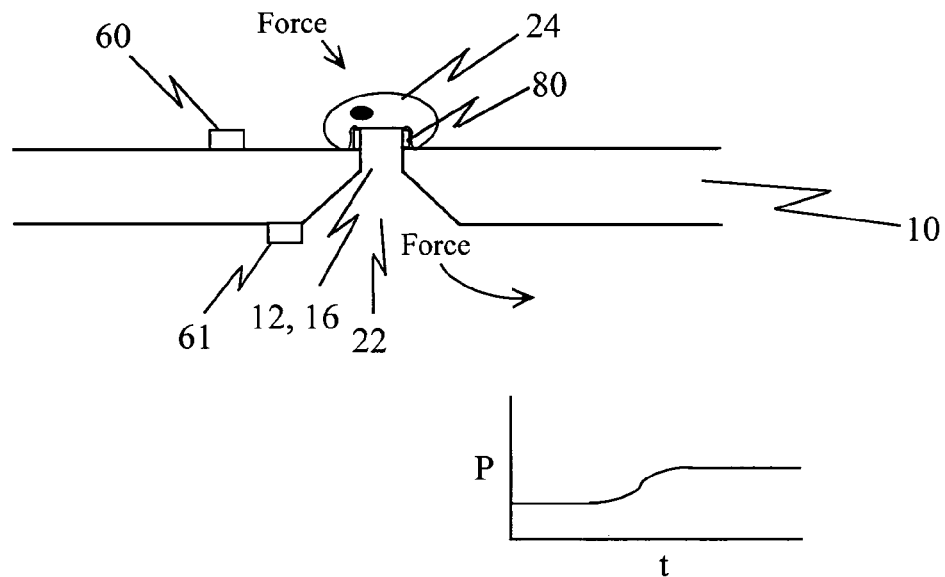
FIG. 9 depicts the operation of the structure depicted in FIG. 8 or FIG. 15.
Figure 9:
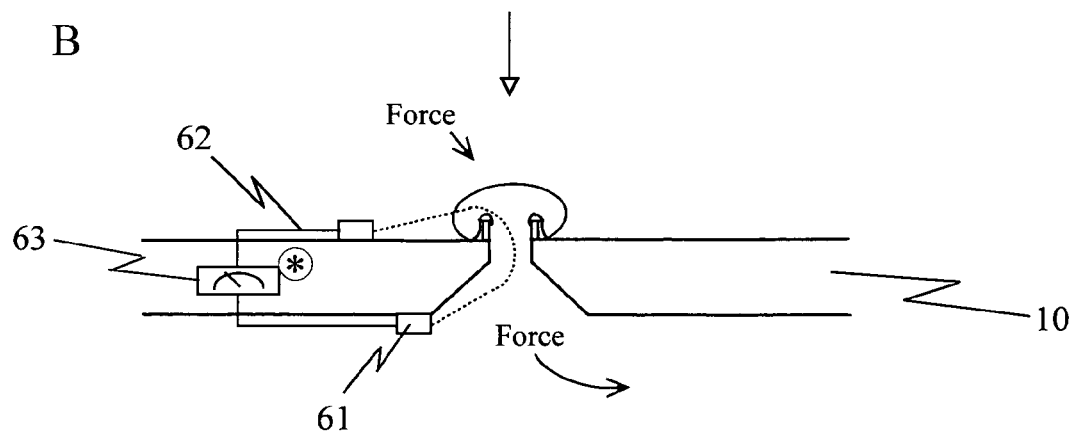
Figure 10:
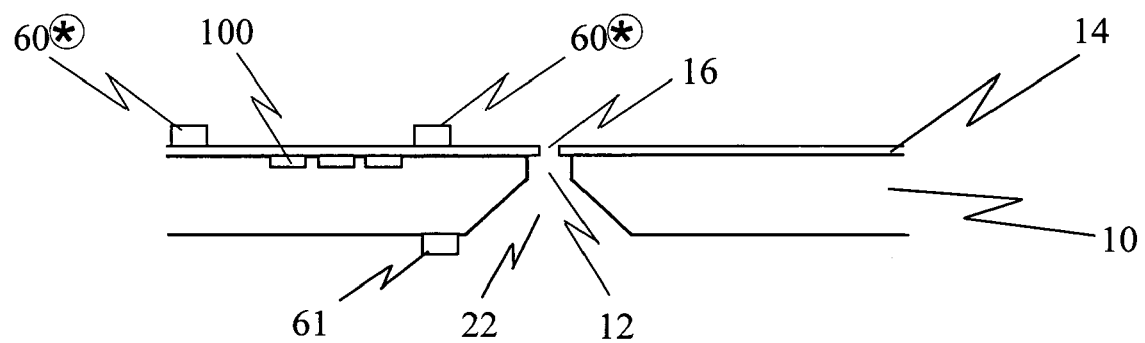
FIG. 10 depicts one preferred aspect of the present invention. In cross section a substrate (10) with a coating (14) is shown with a hole (12) in the substrate and a hole (16) in the coating with a funnel structure (22) and fitted with electrodes (60, 61). Also depicted are particle positioning means (100), which in this case are depicted as traveling wave dielectrophoresis structures (100).
Figure 11:
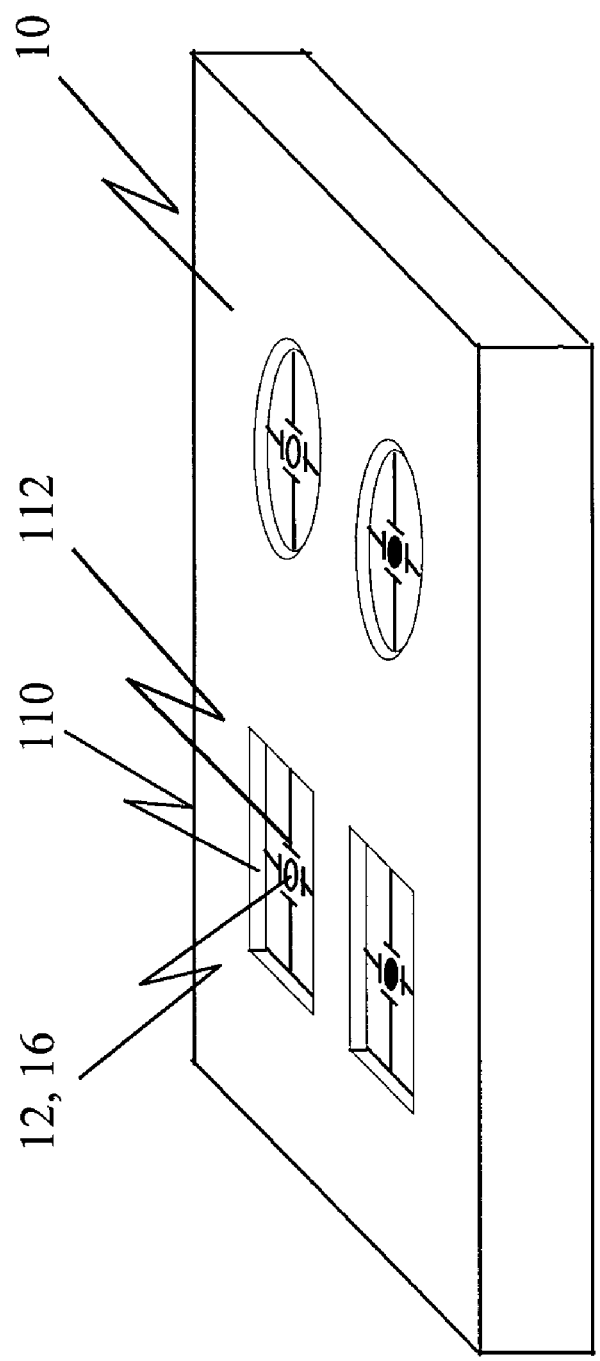
FIG. 11 depicts one aspect of the present invention wherein wells (110) are formed on a substrate (10). The wells can be of any appropriate shape, such as but not limited to the circles and squares depicted. The wells can be made using appropriate methods, such as a machining or etching. The wells preferably, but optionally, include particle positioning means (112). The wells are reminiscent of wells of a microtiter plate, but are preferably much smaller. In this way, a particle or population of particles, such as cells, can be added into the well or wells using introduction or dispensation methods and technologies appropriate for the type of particles being used. Also, appropriate introduction or dispensation methods and technologies can be used to add reagents, such as test reagents, to the wells. Appropriate dispensation methods include piezo dispensers, ink jet technologies, pipetters, micropipetters, electrophoretic dispensations, connected tubings, other microfluidics methods and devices and the like, such as they are known in the art or later developed. For example, the introduction methods could be realized through microfluidic channels in which electroosmotic pumping or pressure driven pumping of the fluid is utilized. A number of examples of traveling wave dielectrophoretic structures are provided herein and in U.S. patent application Ser. No. 09/678,263 and U.S. patent application Ser. No. 09/679,024.
Figure 12:
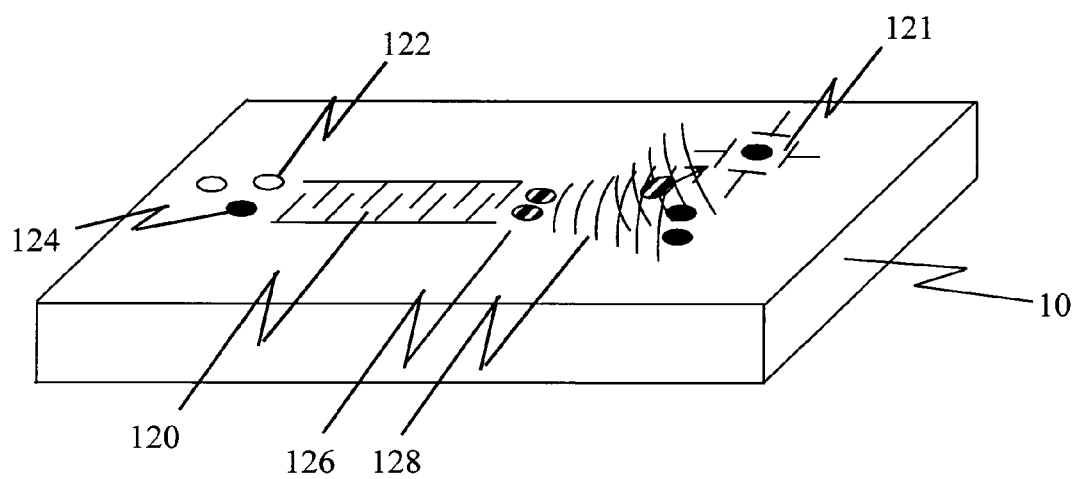
FIG. 12 depicts one preferred aspect of the present invention that includes particle separation structures along with particle positioning means. In this figure, a substrate (10) is fitted with traveling wave dielectrophoretic structure (120) that can separate particles (122, 124) of differing dielectric properties and/or other properties, such as live cells (122) and dead cells (124) which can be visualized using trypan blue exclusion or other viability dyes. The separated cells (126) are subject to one or more particle positioning means, such as a particle switch (128) which can further separate members of a population of cells (122, 124) and direct the desired population of cells to an ion transport measuring means (121). The cell directed to the ion transport measuring means is then engaged therewith for ion transport functional analysis.

FIG. 15 depicts the manufacture of a capillary of the present invention that can be used as an ion transport detection structure in a manner generally depicted in FIG. 9. The process beings with providing a substrate (10), which is then etched to form protrusions (150) that will form a capillary structure (52). This etching forms a trench (154) that defies the protrusion (150) or capillary (152). Further etching from the other side of the substrate forms a hole (16) that can have a funnel shape. Sputtering of conductive material can be used to provide electrode structures (61) for use in ion transport function or property determinations using methods of the present invention.

Capillary structures can have modified structures, such as surfaces that have been modified by the present invention to have enhance electrical seal properties. For example, capillaries can have surfaces that have been smoothed by heat or laser treatment, and/or treated with acid, base, or both to clean the surfaces or alter their electrical charge, such as by the methods disclosed herein.

The present invention also includes a method of detecting at least one ion transport function or property of a particle that includes contacting a sample comprising at least one particle with the biochip that includes capillary structures. Positioning the at least one particle at or near said ion transport measuring means and measuring an ion transport function or property of the sample or particle using said ion transport measuring means. This method is generally depicted in FIG. 9.

Figure 7:
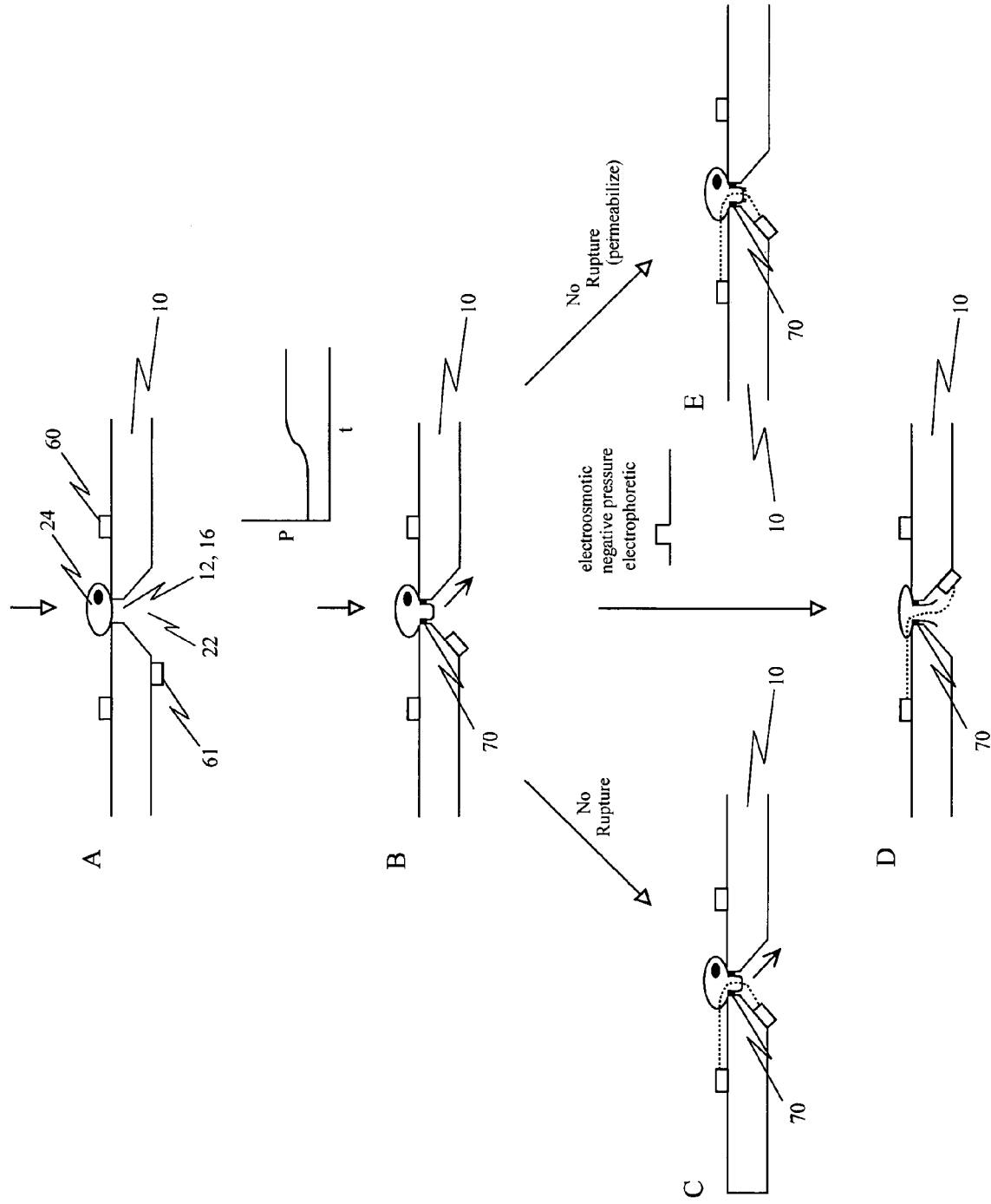
FIG. 7A depicts a process of the present invention wherein a particle (24) such as a cell engages a hole (12, 16) on a biochip of the present invention including a substrate (10) and electrodes (60, 61). The particle (24) has preferably been localized at or near the hole (12, 16) using particle positioning means (not shown). As depicted in FIG. 7B, once engaged, a portion of the particle (24) is moved into the space of the hole (12, 16) using appropriate forces, such as acoustic forces to push the cell (24) into the hole (12, 16) or electroosmotic, electrophoretic or negative pressure to pull the cell (24) into the hole (12, 16). Appropriate structures, such as acoustic structures, electroosmotic structures, electrophoretic structures or negative pressure structures can be provided on or near the biochip or a chamber connected thereto to allow for operations thereof. A good seal (70) between the substrate or coating thereon and the cell is preferable. Depending on the electric parameters being measured, mega ohm or giga ohm sealing between the particle and the hole is preferred.
FIG. 7C depicts the rupturing of the membrane of the cell using a pulse of force, such as negative pressure or electric field pulse. When the electric field pulse is applied, a strong electric field is applied to the membrane patch in the hole causing the rupture of the membrane. A negative pressure pulse would result in a ruptured membrane as well. A good seal (70) between the substrate or coating thereon and the cell is preferable.
Figure 8:
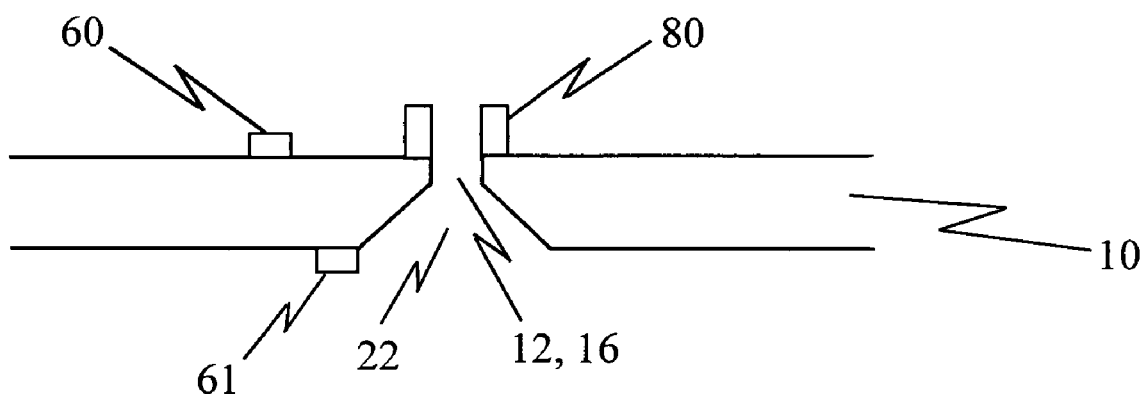
FIG. 8 depicts a structure of the present invention that includes protrusions or wires (80) that can be singular, partially circumnavigate or circumnavigate with regard to the hole (12, 16). The use of these structures is depicted in FIG. 9.

FIG. 9 depicts the operation of the structure depicted in FIG. 15. In FIG. 9A, a particle (24) such as a cell, is engaged with the capillary structure. This is preferably accomplished by applying a positive or negative force, such as depicted in FIG. 7. The particle, such as a cell, is ruptured, such as through a pulse of force, to form a patch clamp. The electrical connection leads (62) from the electrodes (60, 61) connect to a measuring device (63) that can monitor and optionally record the electric properties in the circuit completed as depicted by the dashed line. Optionally, other ion transport function or property determinations can be made using this structure. For example, whole cell determinations, patch clamp determinations, voltage gated determinations and ligand gated determinations and other ion transport assay methods described herein can also be made.

V An Array of Microfabricated Needle Electrodes on a Biochip and Methods of Use The present invention also provides a biochip that includes an array of needle electrodes wherein members of said array comprise an ion transport measuring means. The biochip can provide needle electrodes that are associated with a capillary or a hole on said biochip. In the alternative, the needle electrodes can penetrate a particle. The particle is preferably a cell or vesicle.

As depicted in FIG. 8, FIG. 9, FIG. 16A and FIG. 16B, the present invention can include needle electrode structures that are useful in the present invention. These needle electrode structures can be provided in an array on a substrate. The substrate can be of any appropriate size, but preferably, the substrate is between about 1 mm$^2$ and about 2,500 cm$^2$, having a density of needle electrodes between about 1 and about 2,500 needle electrodes per mm$^2$. The needle electrodes can be any appropriate distance apart, but are preferably between about 20 micrometers and about 10 cm apart.

Figure 16A:
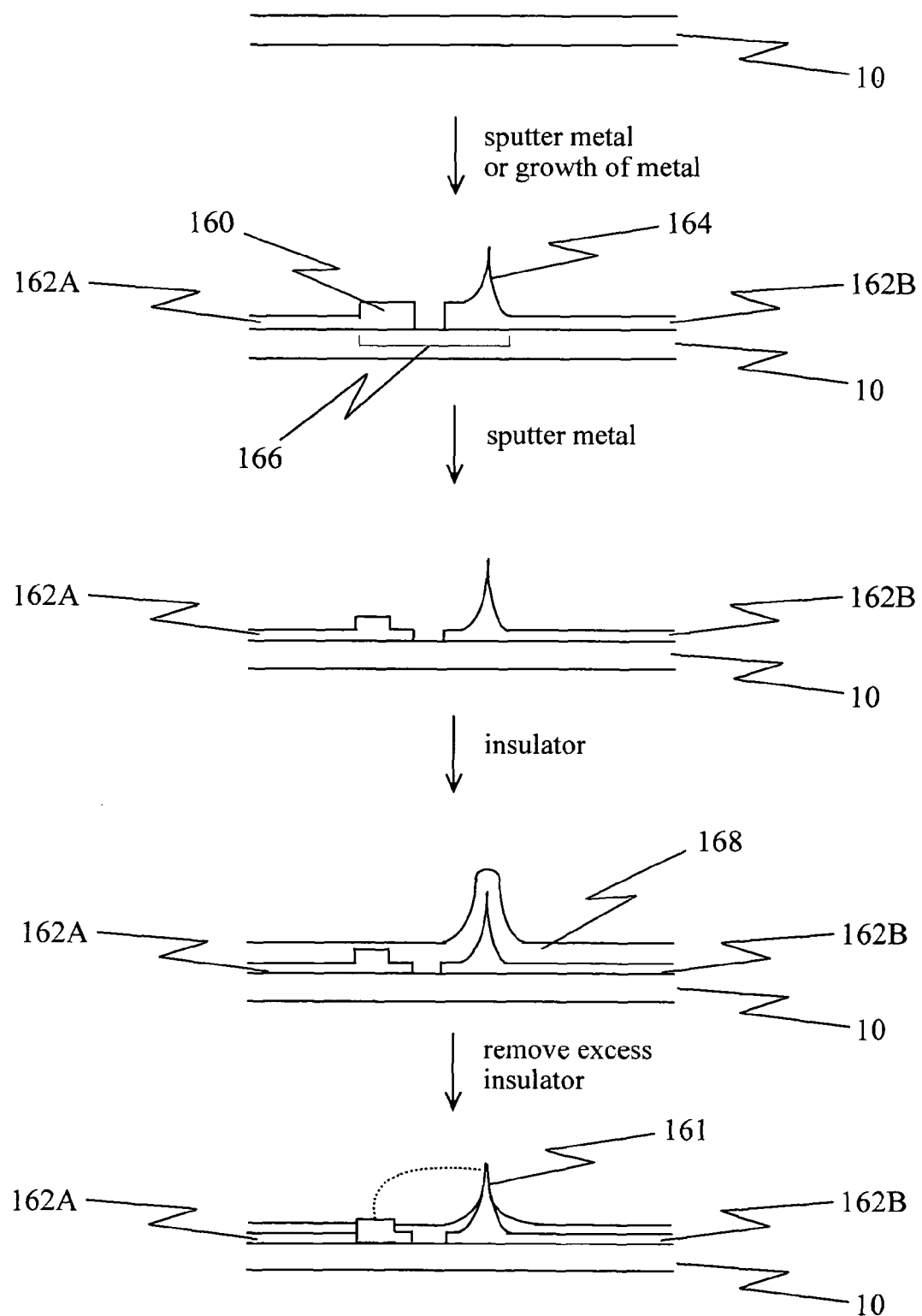
FIG. 16A depicts the manufacture of such a structure. A substrate (10) is provided, upon which a conductive material (160) is provided using, for example, sputtering, chemical growth, electrochemical growth or other growth methods. The conductive material provides an electrode portion (166) operably connected to a needle structure (164). Optionally, a button (162) of conductive material can be added to the electrode portion (166) via sputtering. An insulating material (168) such as $SiO_2$ or resist is then added over the conductive material (160) via sputtering, evaporation or other appropriate methods. Photolithographic methods and other patterning techniques can be used for these procedures. Excess insulating material is then removed by appropriate methods such as masked etching which results in a needle structure of the present invention (161). Electrical measurements can be made between the electrode portion (166) and the needle structure (164) as depicted by dashed lines. The needle structure can be connected to electrical connection leads (162) using appropriate methods, such as sputtering of conductive material at appropriate times during the manufacture of the device. Those skilled in microfabrication can choose appropriate protocols and materials for making these devices.

FIG. 16A depicts the manufacture of such a structure. A substrate (10) is provided, upon which a conductive material (160) is provided using sputtering. The conductive material provides an electrode portion (166) operably connected to a needle structure (164). Optionally, a button (162) of conductive material can be added to the electrode portion (166) via sputtering. An insulating material (168) such as resist is then added over the conductive material (160) via appropriate methods. Excess insulating material is then removed by appropriate methods such as masked etching which results in a needle structure of the present invention (161). Electrical measurements can be made between the electrode portion (166) and the needle structure (164) as depicted by dashed lines. The needle structure can be connected to electrical connection leads (162) using appropriate methods, such as sputtering of conductive material at appropriate times during the manufacture of the device.

The present invention also includes a method of detecting at least one ion transport function or property of a particle that includes contacting a sample comprising at least one particle with the biochip that includes needle electrode structures such as in an array. Positioning the at least one particle at or near said ion transport measuring means and measuring an ion transport function or property of the sample or particle using said ion transport measuring means. This method is generally depicted in FIG. 16B.

Figure 16B:
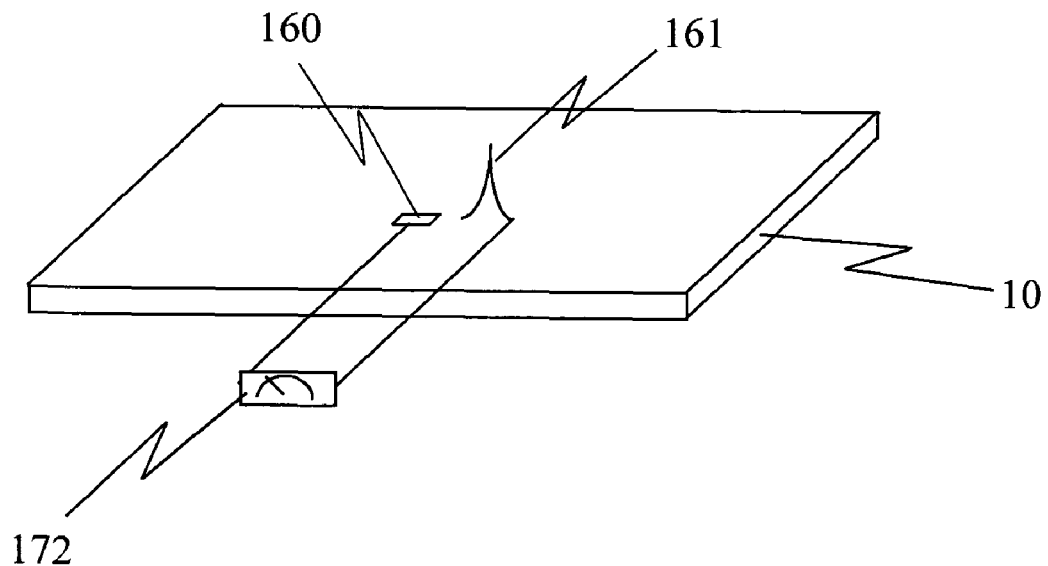
FIG. 16B and FIG. 16C depicts the use of the device of FIG. 16A in an ion transport function or property determination. The needle structure (161) is contacted with a sample including a particle (24) such as a cell. The cell is positioned at or near the needle structure such as by horizontal positioning structures (not depicted). The particle is then impaled upon the needle structure such as by vertical positioning structures (not depicted). The electric seal between the particle and the needle structure can be enhanced using specific binding members at a location corresponding to the juncture of the particle with the needle structure. Ion transport function or property determinations can be made using methods of the present invention by measuring the electrical properties between the electrode portion and the needle structure as depicted by the dashed line which completes the depicted circuit that includes an electrical measuring device (172) and an electrical source (174). Specific patterning methods such as photolithography can be used for producing electrode structures (160) at locations on the substrate.
Figure 16C:
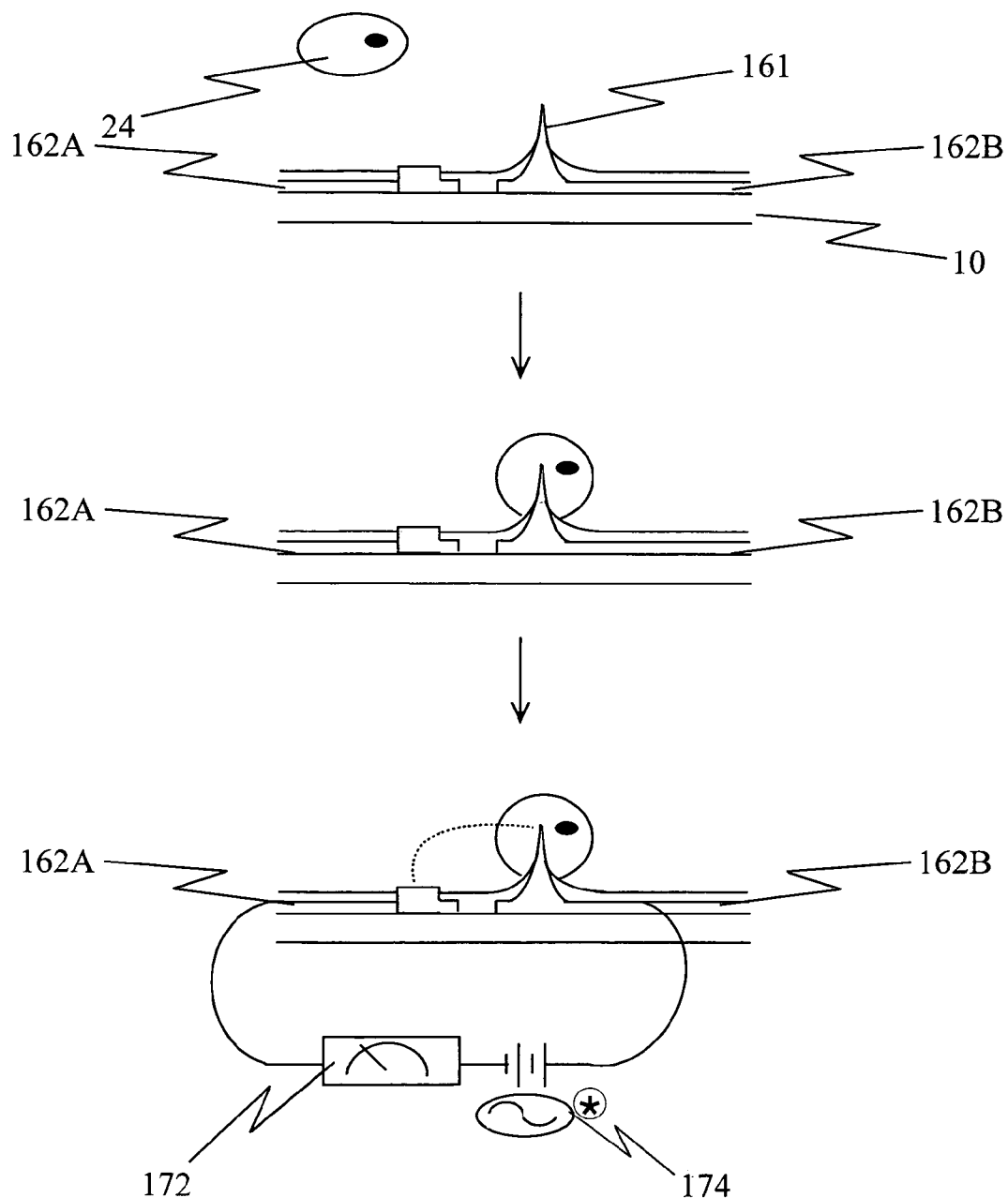

FIG. 16B depicts the use of the device of FIG. 16A in an ion transport function or property determination. The needle structure (170) is contacted with a sample including a particle (24) such as a cell. The cell is positioned at or near the needle structure such as by horizontal positioning structures (not depicted). The particle is then impaled upon the needle structure such as by vertical positioning structures (not depicted). The electric seal between the particle and the needle structure can be enhanced using specific binding members at a location corresponding to the juncture of the particle with the needle structure. Ion transport function or property determinations can be made using methods of the present invention by measuring the electrical properties between the electrode portion and the needle structure as depicted by the dashed line which completes the depicted circuit that includes an electrical measuring device (172) and an electrical source (174).

Various specific ion transport assay methods can be used for determining ion transport functions or properties. These include but are not limited to patch clamp recording, whole cell recording, perforated patch or whole cell recording, whole cell recording, vesicle recording, outside out or inside out recording, single channel recording, artificial membrane channel recording, voltage gated ion transport recording, ligand gated ion transport recording, energy requiring ion transporters (such as ATP), non energy requiring transporters, toxins such a scorpion toxins, viruses, ligand perfusion, stretch gated (fluid flow or osmotic) and the like. See, generally Neher and Sakman, Scientific American 266:44-51 (1992); Sakman and Neher, Ann. Rev. Physiol. 46:455-472 (1984); Cahalan and Neher, Methods in Enzymology 207:3-14 (1992); Levis and Rae, Methods in Enzymology 207:14-66 (1992); Armstrong and Gilly, Methods in Enzymology 207:100-122 (1992); Heinmann and Conti, Methods in Enzymology 207:131-148 (1992); Bean, Methods in Enzymology 207:181-193 (1992); Leim et al., Neurosurgery 36:382-392 (1995); Lester, Ann. Rev. Physiol 53:477-496 (1991); Hamill and McBride, Ann. Rev. Physiol 59:621-631 (1997); Bustamante and Varranda, Brazilian Journal 31:333-354 (1998); Martinez-Pardon and Ferrus, Current Topics in Developmental Biol. 36:303-312 (1998); Herness, Physiology and Behavior 69:17-27 (2000); Aston-Jones and Siggins, www.acn-p.org/GA/GN40100005/CH005.html (Feb. 8, 2001); U.S. Pat. No. 6,117,291; U.S. Pat. No. 6,107,066; U.S. Pat. No. 5,840,041 and U.S. Pat. No. 5,661,035; Boulton et al., Patch-Clamp Applications and Protocols, Neuromethods V. 26 (1995), Humana Press, New Jersey; Ashcroft, Ion Channels and Disease, Cannelopathies, Academic Press, San Diego (2000); Sakman and Neher, Single Channel Recording, second edition, Plenuim Press, New York (1995) and Soria and Cena, Ion Channel Pharmacology, Oxford University Press, New York (1998), each of which is incorporated by reference herein in their entirety.

V. An Array of Microfabricated Holes on a Biochip and Method of Use

The present invention also includes a biochip that includes an array of holes through the biochip. Preferably, the holes have negatively charged surfaces when the biochip is in contact with measurement solutions and are capable of engaging a particle such as a biological cell, a vesicle and/or a membrane organelle with high resistance electrical seal. The particle is preferably a cell or vesicle, but that need not be the case. In one preferred embodiment of a biochip of the present invention, the biochip comprises an array of holes through the biochip, wherein the hole surface has optionally been treated in acidic, and/or basic solutions and is capable of engaging a particle such as a biological cell, a vesicle and/or a membrane organelle with high resistance electrical seal.

In some preferred embodiments of the present invention, a biochip that comprises an array of holes has a surface that has been modified to increase the electrical seal of a particle with holes on the chip, such as by methods disclosed herein. In some preferred embodiments, a biochip that comprises an array of holes has been treated with base, and, preferably, rinsed with water or a salt solution such as dilute PBS. Optionally but preferably, in these embodiments the biochip has also been baked or laser polished, and optionally treated with acid prior to base treatment.

As depicted in FIG. 1, FIG. 2, and FIG. 5, the present invention can include holes that are useful in the present invention. These holes can be provided in an array on a substrate. The substrate can be of any appropriate size, but preferably, the substrate is between about 1 $mm^2$ and about 2,500 $cm^2$, having a density of holes between about 1 and about 2,500 holes per $mm^2$. The holes can be any appropriate distance apart, but are preferably between about 20 micrometers and about 10 cm apart.

FIG. 1 depicts one aspect of a biochip of the present invention. A substrate (10) made of appropriate material, such as fused silica, glass, silica, $SiO_2$, silicon, plastics, polymers or a combination or combinations thereof can define holes (12) that form at least in part ion transport measuring means of the present invention. Optionally, a coating (14) such as a polymer coating can be placed on top of the surface of the substrate. The coating can include functional groups to aid in the localization and immobilization particles at or near the holes (12). Such functional groups can include, for example, specific binding members that can facilitate such localization or immobilization of particles. The coating can also define holes (16) that can functionally engage the holes (16) defined by the substrate (10). In one aspect of the present invention, such holes (12) in the coating (14) are preferable because the accuracy and precision for machining or molding such holes in the coating is better suited for the coating (14) rather than the substrate (10). For example, it is more efficient, accurate and precise to manufacture holes in the thin coating (14) rather than the relatively thick substrate (10). This is particularly true when the coating (14) is made of polymers whereas the substrate (10) is made of harder materials that may be less suitable for machining, etching or molding, such as silica. FIG. 1A depicts a biochip of the present invention optionally with a coating. FIG. 1B depicts a cross section of FIG. 1A along A-A showing the coating in place.

FIG. 2 depicts different configurations of substrates (10) and coatings (14) to form holes in the substrate (12) and holes in the coating (16). FIG. 2A depicts the biochip of FIG. 1A with a cell (24) engaged thereto. FIG. 2B depicts a substrate (10) with a coating (14), wherein the substrate has been machined or etched to form a funnel shaped structure (20) continuous with a hole in the substrate (10). This funnel shaped structure (20) allows for less rigorous manufacturing parameters as compared to the straight walled holes (12) depicted in FIG. 2A. A cell (24) is depicted engaged on the structure of FIG. 2B. FIG. 2C depicts the structure of FIG. 2B inverted with a cell (24) engaged thereto. FIG. 2D depicts a structure having a double funnel structure (20, 22) that defines a hole (14) in the substrate (10). Although holes of particular shapes and dimensions are depicted, the holes can be of any appropriate shape or dimensions. Shapes of holes can be geometric or non-geometric, such as circular, oval, square, triangular, pentagonal, hexagonal, heptagonal, octagonal or the like. Non-geometrical shapes such as kidney bead or other shapes are also appropriate. Geometric shapes can have the advantage of allowing higher density packing of holes, such as in a honey-comb configuration. The diameter or cross section of the holes at the portion where a particle is contacted can be any appropriate size, but is preferably between about 0.1 micrometer and about 100 micrometers, more preferably between about 1 micrometer and about 10 micrometers.

FIG. 5 depicts a structure such as depicted in FIG. 2B including a substrate (10) that defines a hole (12) with a funnel structure (22). FIG. 5A depicts such a structure with a coating (50) over all surfaces. The coating can be made of appropriate materials, such as polymers or functional coatings that can allow for immobilization of materials such as biological moieties or chemical moieties. The coating can also include binding members, such as specific binding members, such as antibodies, that can facilitate the localization or immobilization of particles such as cells at or near the hole (12). In one aspect of the present invention, the coating is made of a polymer that has the characteristic of changing size with temperature. By increasing in size, the polymer can promote the formation of an efficient seal between a particle (24) such as a cell and the hole. In FIG. 5B the coating (52) is depicted as being localized to an area in close proximity to the hole (12) in the substrate. In one aspect of the present invention, the coating in this configuration includes specific binding members present on particles such as cells. In FIG. 5C the coating is depicted as being localized to the hole (12) and optionally surrounding areas. This configuration can promote a strong seal between the cell and the hole (12). In one aspect of the present invention, the substrate (10) is made of silicon. The substrate (10) is then heated to make a structure that includes the substrate (10) of silicon and a coating (50) of silicon dioxide.

The present invention also includes a method of detecting at least one ion transport function or property of a particle, including contacting a sample comprising at least one particle with a biochip including an array of holes, positioning the at least one particle at or near said ion transport measuring means; and measuring one or more ion transport functions or properties of the particles or sample using said ion transport measuring means. This method is generally depicted in FIG. 6 and FIG. 7.

FIG. 6A depicts electrode structures (60, 61) present on either side of a hole (12,16) defined by a substrate (12) and depicted as including a funnel structure (24). The electrodes are positioned as to be on either side of particle, such as a cell (24). Electrical connection leads (62) connect the electrodes (60, 61) to a measuring device (63) that can measure and optionally record the electrical properties of the particle depicted by the dashed line, such as, for examples, electric current through the ion transports in the particle membrane under applied voltage conditions or the cell membrane potential under fixed current flow through the ion transports in the membrane. Measuring device (63) can be conventional electrophysiology measurement apparatus, such as models available from Axon Instruments Inc. Various ion transport assay methods can be achieved with these or other electrophysiology apparatuses. FIG. 6B depicts a variety of electrode structures as viewed from the top of FIG. 6A. In one aspect of the present invention, the electrode (60) can have any appropriate shape, such as square, circular or semi-circular. The electrode is preferably operably linked to at least one electrical connection lead (62). In one aspect of the present invention, there can be several electrodes, preferably independently attached to separate electrodes so as to be independently addressable, that are different distances from a hole (12, 16). Depending on the conditions of a particular method or the electrical parameter being measured, such as voltage or current, electrodes of different shape, size or geometries can be utilized. Although FIG. 6B is viewed from the top of FIG. 6A, similar structures can be provided as electrode (61) as viewed from the bottom of FIG. 6B. The electrode (61) can be provided in or outside of the funnel structure (22) when present.

FIG. 7A depicts a process of the present invention wherein a particle (24) such as a cell engages a hole (12, 16) on a biochip of the present invention including a substrate (10) and electrodes (60, 61). The particle (24) has preferably been localized at or near the hole (12, 16) using particle positioning means (not shown). As depicted in FIG. 7B, once engaged, a portion of the particle (24) is moved into the space of the hole (12, 16) using appropriate forces, such as acoustic forces to push the cell (24) into the hole (12, 16) or electroosmotic, electrophoretic or negative pressure to pull the cell (24) into the hole (12, 16). Appropriate structures, such as acoustic structures, electroosmotic structures, electrophoretic structures or negative pressure structures can be provided on or near the biochip or a chamber connected thereto to allow for operation thereof. A good seal (70) between the substrate or coating thereon and the cell is preferable. Depending on the electric parameter being measured, mega ohm or giga ohm sealing between the particle and the hole is preferred. FIG. 7C depicts the rupturing of the membrane of the cell using a pulse of force, such as negative pressure or electric field pulse. When the electric filed pulse is applied, a strong electric filed is applied to the membrane patch in the hole causing rupture of the membrane. A negative pressure pulse would result in a ruptured membrane as well. A good seal (70) between the substrate or coating thereon and the cell is preferable.

VI. Examples (V.1) Investigation of the Effects of Surface Treatment on the Cell Giga-Ohm Seal Using Conventional Glass Capillary Electrodes A systematic investigation was performed in order to understand the physicochemical mechanism of giga-ohm seal between cell membrane and glass capillary. Patch-clamp glass capillaries from World Precision Instruments (WPI, Item No. PG52150-4) having ID (0.86 mm) and OD (1.5 mm) were pulled on a micropipette puller (Sutter Instruments Co., Flaming/Brown Micropipette Puller, Model P-97) and then polished on a WPI microscope (Item No. H602) under the polishing wire (WPI item no.: MF200-H3) connected to a Micro-Forge (WPI item no.: MF 200). The polishing, also referred to as "fire-polishing", resulted in a tip outer diameter of ~3 μm and ID of 1-1.5 μm. These glass capillaries were subjected to a variety of surface treatments and then tested for their ability to form giga-ohm seals using a model cell system—RBL-1 (rat blood leukocytes) cells. The results are summarized in Table 1-4 where the seal percentage is defined as the ratio of the number of giga-ohm seals obtained (several giga-ohm to about 20 giga-ohm) to the total number of glass capillaries tested under a specific surface treatment.

Table 1 summarizes the effect of acid treatment on seal formation. Whilst FPP (freshly pulled and polished pipette) had an overall seal percentage over 80%, acid treatments of these pipettes gave significantly lower percentages of giga-ohm seals (0% to 30%). On the other hand, acid-treated surfaces were re-activated or significantly-improved (50%-86%) by a number of follow-up treatments such as base-treatment or $Ca^{2+}$ treatment. Some other follow-up treatments 3-aminopropyltrimeth-oxysilane (APS), sol-gel, organic epoxide had little effect on the acid-treated surfaces in terms of their capability to form a giga-ohm seal.

Table 2 summarizes the effect of exposure of FPPs (Freshly Pulled and polished Pipettes) to room air or $CO_2$ on seal formation. It can be concluded that prolonged exposure to the air and/or $CO_2$ results in a significant reduction of the giga-ohm seal percentage (0%-50%). Again, like the acid-treated capillaries, the air-exposed or $CO_2$ treated pipettes were re-activated or significantly improved in sealing ability by a number of follow-up treatments such as base treatment, $Ca^{2+}$ treatment, and/or simply placing in water. In most cases, re-fire-polishing the pipette tip restored its sealability. On the other hand, treatment of FFPs in $HCO_3^-$ solution abolished their sealability, while storage of pipettes in a room air depleted of $CO_2$ preserved their sealability.

Table 3 summarizes effects of some other treatments. Storing the glass capillaries in 100 mM PBS (phosphate buffered saline) did not greatly affect their sealability whilst PE (phosphatidyl-ethonolamine) treatment inactivated all the capillaries tested.

Based on these investigations, we can conclude that whilst acid-treatment or $CO_2$ treatment may result in the inability of glass capillaries to form giga-ohm seals ("inactivation"), base-treatment and $Ca^{2+}$ treatment (and sometimes treatment with de-ionized $H_2O$) are able to restore the giga-ohm sealing capabilities. In addition, treatment or storage of FPPs in $H_2O$ was able to retain the sealability of the pipettes for over five months.

To further investigate the effects of various treatments on surface charge-properties of the glass capillaries, electro-osmosis experiments were performed on the glass capillaries. In these experiments, the glass capillaries were filled with electrolytes that were colored with a small amount of colored ink. These capillaries were placed in a beaker containing the same electrolytes as those in the capillaries (but without colored ink). DC electrical voltages were applied to the platinum wire electrodes in the glass capillaries and in the beaker. By observing the movement of colored electrolyte solutions in the glass capillaries, we could deduce the polarities of fixed charge on the tip of the capillaries. The results are summarized in Table 4. There is a correlation between the charge polarity and the percentage of giga-ohm seals, for example, negative surface charge on the glass capillaries correlates to improved sealing rate whilst a positive charge or no-charge or little negative charge correlates to a decreased sealing percentage.

To further investigate the effect of these acid/base treatments on the surface charge properties of glass capillaries, electroosmosis flow experiments were performed with fused silica capillaries that were treated with various acid and base solutions using a DMSO elution time as an indicator of the capillaries' surface charge. The capillaries were 50 micron in inner diameter and about 68 cm long. The length between the sample loading port to the detector is about 46 cm. Typically, the buffer used for electroosmosis testing is a $\frac{1}{10}^{th}$-PBS (phosphate buffered saline, pH=7.2, diluted in a de-ionized water in a ratio of 1 to 9 for PBS to water). A DC voltage of 20 kV is applied, resulting a typical current of about 25 µA. A neutral molecule marker DMSO is used and injected to measure the electro-osmosis effect in fused silica capillaries. Table 5 summaries the results of various electro-osmosis flow tests. Several conclusions can be drawn from these measurements:

(1) For fused silica capillaries, base-treatment would result in an increase in electro-osmosis mobility while acid-treatment would result in a decrease (or even reversal) in electro-osmosis mobility. Based on the electro-osmosis flow direction, it was determined that the surface charge in these fused silica capillaries is negative. Thus, a base treatment would result in an electrically more-negative surface or an increased surface negative charge density. On the other hand, an acid treatment would lead to a reduction in the surface negative charge and in some cases (not shown here) an acid treatment would cause a reversal of electro-osmosis flow direction, indicating a positively-charged surface.

(2) The electro-osmosis velocity for fused silica capillaries after the treatment with acid or base depends on how the capillaries are stored, rinsed or processed. For example, as shown in Table 5, a silica capillary treated/rinsed in 5 N NaOH (~9 min) followed by a $\frac{1}{10}^{th}$-PBS rinse (~9 min) would give an electro-osmosis mobility that is 30% higher than that of fresh capillaries. On the other hand, a silica capillary treated/rinsed in 5N NaOH (~9 min) followed by a $H_2O$ rinse (~9 min) and a $\frac{1}{10}^{th}$-PBS rinse (~9 min) would give an electro-osmosis mobility that is only about 8% higher than that of fresh capillaries. This indicates that the surface charge density values on these fused silica capillaries change with time and are also dependent on what solutions that have been introduced into the capillaries for rinse/treatment or storage. 5N NaOH treated capillaries have an increased negative surface charge density. The negative surface charge density was decreased when a capillary was rinsed or treated with $\frac{1}{10}^{th}$-PBS solution and decreased even more if a de-ionized $H_2O$ rinse was also used. The effect of treatment/rinsing conditions on electro-osmosis mobility (and on surface charge density of capillaries) has been studied and published in an article by Williian J. Lambert and David L. Middleton, entitled "pH hysteresis effect with silica capillaries in capillary zone electrophoresis", in Analytcal Chemistry, vol. 62, pages 1585-1687, 1990. These effects are related to the mechanisms through which a silica surface acquires negative charge. At high pH (for example, pH>5), the ionization of the surface silanol groups (SiOH) is increased, leading to more $SiO^-$ groups and more negative surface charge density. At low pH (for example pH<3), the ionization of the surface silanol group is suppressed, leading to less number of $SiO^-$ group and a reduced negative surface charge. Thus, the surface charge density of a fused silica capillary depends on the pH of the solution and also depends on whether the surface charge has reached an equilibrium state. The article by Williian J. Lambert and David L. Middleton, entitled "pH hysteresis effect with silica capillaries in capillary zone electrophoresis", in Analytical Chemistry, vol. 62, pages 1585-1687, 1990 further shows that the equilibration of the surface charge on the fused silica surface is a relatively slow process. In fact it may take several weeks at intermediate pH (for example pH=~4-6). On the other hand, re-equilibration to a pH where the surface become either fully (or nearly-fully) ionized (at a high pH, for example pH=12) or fully un-ionized (at a low pH, for example pH=2) appears to be rather rapid. Thus, in order to evaluate the effect of treatment of acidic solution or basic solution on a fused silica capillary on its surface charge density in terms of electro-osmosis mobility in a buffer with pH between about 7 and about 8, electro-osmosis mobility determination should be performed shortly after the silica capillary is treated in acidic or basic solutions. The time delay between electro-osmosis mobility determination and the treatment with acidic or basic solutions is preferably within 10 minutes and more preferably within 5 minutes, during which time the silica capillary is rinsed with or filled with or treated with the buffer in which the electro-osmosis mobility is determined.

The glass pipettes (or glass chips, as described below) used for ion channel patch clamping, at least in part because of the silanol group (SiOH) on the surface, will also exhibit a pH dependency for surface charge densities. However, because of their different molecular compositions from that of the fused silica capillaries and are thus expected to have different pH dependency for their surface charge densities. For example, K. D. Lukacs and J. W. Jorgeson demonstrated different pH dependencies for electroosmosis flow velocities for Pyrex glass and fused silica capillary in an article published in Journal of High Resolution Chromatography, Vol. 8, page 407, 1985. In this article, it was shown and demonstrated that Pyrex glass capillary has a higher electroosmotic velocity and has a larger negative surface density than those of a fused silica capillary.

Treating the glass pipettes (and/or glass chips) with acid and/or base solutions will also affect their surface charge densities. Furthermore, because $SiO_2$ are the major composition in glass pipettes or glass chips, and/or because SiOH is the major surface functional group on glass pipettes or glass chips, it is expected that base-treated glass would have a higher negative surface charge density while acid-treated glass would have a lower negative surface charge density. In addition, it is expected that surface charges on glass pipettes and/or glass chips are also dependent on whether the surfaces have reached equilibrium with solutions of different pH values, and thus dependent on how glass pipettes and/or glass chips are handled, stored or preserved after treatment.

In one experiment, freshly pulled glass pipettes were stored in de-ionized water for over five months and such de-ionized water preserved glass pipettes were tested for whole cell patch clamping with similar success rate in giga-Ohm seal and whole cell access to that obtained for freshly pulled pipettes. This indicates or suggests that de-ionized water (pH, ~8) storage does not seem to affect surface properties of glass pipettes much, or at least does not seem to affect those properties important to high resistance seals.

In another experiment, glass chips with ion transport measuring holes were treated in an acid solution (nitric acid, 6M, 4 h), followed by rinsing and treatment in de-ionized water (1 h) and then in base solution (NaOH, 5N, 45 min), and rinsing again in De-ionized water. Some of glass chips were then used for ion channel patch clamp recording directly and other chips were stored away for 1 month. It was found that de-ionized water preserved glass chips were tested for whole cell patch clamping with similar success rate in high resistance seal (for example, giga-ohm seal) and whole cell access to that obtained for glass chips that did not undergo water storage. This suggested that de-ionized water (pH, ~8) storage preserved those surface properties of glass chips important to high resistance seals.

The treatment method involving the use of acidic solutions and basic solutions can be applied to chips (or other forms of ion transport measuring components) made of various materials such as silica, glass, silicon, plastic materials, polydimethylsiloxane (PDMS) and oxygen plasma treated PDMS, or chips coated with various materials such as silica, glass, silicon, plastics, PDMS and oxygen plasma treated PDMS. Particularly, the treatment procedure can be applied to the chip with surface composition containing SiOM surface groups and $SiO_2$ groups. M can be a metal, such as, for example, Na, K, Ca, Mg, etc., or can be hydrogen. The surface density of SiOM groups (or oxidized SiOM groups ($SiO^-$)) and $SiO_2$ groups taken together on such chips may vary between as low as 0.01% to as high as near 100%. Preferably, however, the surface density of SiOM groups and $SiO_2$ groups taken together on such chips is more than about 1%, more preferably, more than about 10%, and even more preferably, more than about 30%.

All acidic solutions and basic solutions may be used for treatment methods described above. Acidic solutions can be chosen from a group consisting of, but not limited to, for example, HCl, $H_2SO_4$, $HNO_3$, HF, $H_3PO_4$, HBr, HCOOH, $CH_3COOH$. Basic solutions can be selected from the group consisting of, but not limited to, for example, NaOH, KOH, $NH_4OH$, $Ca(OH)_2$. Various concentrations of acid and base from as long as 1 mM to as high as 15 M can be used, provided such treatment would generate surface functional groups facilitating the electrical seal between the particle surface and the surface of the ion transport measuring means on the chip. Treatment time can vary from as short as 1 minute to as long as 24 hrs or days, even though it is expected that, at least for fused silica surfaces, the surface charge can reach an equilibrium determined by the treatment solution quite rapidly (for example, <2 hr) when the pH of the treatment solution is pH<2 or pH>12.

In brief summary, preferred treatment/storage conditions for patch-clamp glass pipettes include:

(1) Fresh-pulled polished pipettes—stored in de-ionized $H_2O$ (pH>4, typically pH greater than 7, in many cases, a pH of approximately 8)—

(2) Fresh-pulled polished pipettes—storage—Re-fire-polishing—use (3) Freshly-pulled polished pipettes—storage—NaOH treatment—de-ionized water—use (4) Fresh-pulled polished pipettes—storage—Acid treatment—NaOH treatment—de-ionized $H_2O$—use (5) Fresh-pulled polished pipettes—storage—Acid treatment—Ca 2+ treatment—de-ionized $H_2O$—use In addition, when pipettes need to be stored or shipped, they can be preserved and shipped in de-ionized $H_2O$. Pipettes have been shown to retain the same or similar sealability after being stored in de-ionized $H_2O$ for up to five months.

TABLE 1

Effects of acid treatment on giga-ohm seal ability.

| Treatment of pipette | Note | Total Seal | Total Number | Percentage |
|---|---|---|---|---|
| FPP | | 114 | 140 | 81% |
| HCl (3-6M, 1~17 h) | | 4 | 45 | 9% |
| $HNO_3$ (6 M, 17 h) | | 0 | 6 | 0 |
| $H_2SO_4$ (6 M, 17 h) | | 2 | 6 | 33% |
| HCl (3 M; 3 h) - RP (Re-polishing) | | 7 | 8 | 88% |
| HCl (3 M, 3 h) - NaOH (1M, 1 h) | | 3 | 5 | 60% |
| HCl (3 M, 3 h) - $Ca(OH)_2$ | 2 unstable | 4 | 8 | 50% |
| HCl (3 M, 3 h) - water (4 d) | | 3 | 11 | 27% |
| HCl (3 M, 3 h) - 3M $CaCl_2$ (5 h) | | 12 | 14 | 86% |
| HCl (3 M, 3 h) - 3M $MgCl_2$ (1 d) | | 3 | 8 | 38% |
| HCl (3 M, 3 h) - 3M $MnCl_2$ | | 4 | 13 | 31% |
| HCl (3 M, 3 h) Sol gel | | 2 | 36 | 6% |
| HCl (3 M, 3 h) - Si(Oet)4 + aminesilane | | 5 | 8 | 63% |
| HCl (3 M, 3 h) - organic epoxide | | 1 | 14 | 7% |

TABLE 1-continued

Effects of acid treatment on giga-ohm seal ability.

| Treatment of pipette | Note | Total Seal | Total Number | Percentage |
|---|---|---|---|---|
| HCl (3 M, 3 h) - APS(aminopropylsilane) | | 1 | 12 | 8% |

Note:
All treatments with solutions were performed on FPP pipettes.

TABLE 2

Effects of air-exposure or $CO_2$ on giga-ohm seal ability.

| Treatment | Note | Total Seal | Total Number | Percentage |
|---|---|---|---|---|
| FPP pipette | | 114 | 140 | 81% |
| Air/CR(clean Room, 1 d) | | 8 | 14 | 57% |
| Air (>2 d) | | 0 | 16 | 0 |
| CR (clean room, 2 d) | | 1 | 6 | 17% |
| $CO_2$ (3 h) | 2 unstable | 0 | 6 | 0% |
| 5% $CO_2$, 37° C. incubator (2-4 h) | | 0 | 7 | 0% |
| $NaHCO_3$, (pH = 7, 3 h) | | 1 | 6 | 17% |
| CR (7 d) - NaOH (1M, 30 min) | | 10 | 10 | 100% |
| CR (7 d) - $NH_4OH$ | | 3 | 3 | 100% |
| 5% $CO_2$, 37° C. incubator (4 h) - Water (21 h) | | 6 | 6 | 100% |
| Air (>2 d) stored over 10 M NaOH | | 11 | 12 | 92% |
| Air (1 wk) - 3 M $CaCl_2$ (5 h) | | 11 | 9 | 82% |
| CR - pH12 sol gel | | 6 | 15 | 40% |

Note:
All treatments with solutions were performed on FPP pipettes.

TABLE 3

Effects of other treatments on giga-ohm seal ability.

| Treatment | Note | Total Seal | Total Number | Percentage |
|---|---|---|---|---|
| FPP pipette | | 114 | 140 | 81% |
| 100 mM PBS | | 4 | 5 | 80% |
| PE | | 0 | 4 | 0 |

Note:
All treatments with solutions were performed on FPP pipettes.

TABLE 4

Surface charge determination for glass capillaries with a number of treatments

| Treatment | Seal number/ total number | Success rate | Electro-Osmosis-Flow determined surface charge |
|---|---|---|---|
| FPP pipette | 114/140 | 81.43% | Negative (−Ve) |
| HCl Acid (3 M, 3 h) | 4/45 | <9% | Positive (+Ve) |
| $HNO_3$ Acid (6 M, 17 h) | 0/6 | 0 | +Ve |
| Sulfuric acid (6 M, 17 h) | 2/6 | 33% | −Ve; Slow EOF |

TABLE 4-continued

Surface charge determination for glass capillaries with a number of treatments

| Treatment | Seal number/ total number | Success rate | Electro-Osmosis-Flow determined surface charge |
|---|---|---|---|
| HCl (3 M, 3 h) & 1M NaOH 1 h | 3/5 | 60% | −Ve |
| HCl (3 M, 3 h) & 3 M $Ca^{2+}$ (5 h) | 12/14 | 85% | −Ve (+Ve after EOF for 15 min) |
| 5% $CO_2$ 37° C. incubator (2-4 h) | 0/7 | 0 | +Ve |

Note:
All treatments with solutions were performed on FPP pipettes.

TABLE 5

Electrosomosis flow time for a fused silica capillary with a number of acid and/or treatments. The buffer used for electroosmosis test was $1/10^{th}$-PBS diluted in de-ionized water (1:9 for PBS:de-ionized $H_2O$).

| Treatment | Electro-osmosis flow time (minutes) | Electro-osmosis mobility ($10^{-4}$ cm$^2$/(V sec) |
|---|---|---|
| Fused silica capillary | 4.63, 4.66, 4.7 | 5.63, 5.59, 5.54 |
| 1 N NaOH rinse: 5 min; $H_2O$ rinse: 30 min; 1/10 PBS rinse: 5 min | 4.55, 4.60, 4.68 | 5.73, 5.67, 5.57 |
| 5 N NaOH rinse: 9 min; 1/10 PBS rinse: 9 min | 3.55, 3.60 | 7.34, 7.24 |
| 5 N NaOH rinse: 9 min; $H_2O$ rinse: 9 min; 1/10 PBS rinse: 9 min | 4.30, 4.30 | 6.06, 6.06 |
| 1 N HCl: 9 min; 1/10 PBS rinse: 9 min | 5.26, 5.08, 4.96, 4.91 | 4.95, 5.13, 5.25, 5.31 |
| 1 N HCl: 17 min; $H_2O$ rinse: 16 min; 1/10 PBS rinse: 12 min | 4.76, 4.83, 4.70 | 5.48, 5.40, 5.55 |
| 5 N $HNO_3$: 9 min; 1/10 PBS rinse: 11 min | 5.66, 5.33, 5.10, 5.37 | 4.60, 4.89, 5.11, 4.85 |

Note:
All treatments with solutions were performed on fused silica capillaries.

(V.2) Chip Fabrication (V.2.1) Example One
Silicon-Wafer Based Ion Channel Chips For descriptive purposes, we refer to the major-surface side of the wafer that has the ion channel recording aperture after fabrication as the front side and the other major-surface side as the backside. The brief summary of the fabrication process is as follows. The silicon wafer is first grown with a thin layer $SiO_2$ and/or $Si_3N_4$, which is then patterned with squared-shaped (or other regular or irregular-shaped) opening to serve as a hard mask for backside etching to produce an opening. Anisotropic etching of the silicon wafer (<100>-oriented silicon) using KOH solutions produces a square-shaped hole on the backside with an angle of 54.7 degrees. Etching condition and time are carefully controlled so that etching will leave 5-10 micron thickness of silicon from the front-side of the wafer. It is this 5-10 micron thick region over which the ion channel apertures are produced. After removing the $SiO_2$ and/or $Si_3N_4$ mask layer from the backside, a photoresist is then coated on the front-side of the wafer and is patterned with circular-openings of <1 micron to 3 microns in diameter for producing ion-channel measurement apertures. Deep reactive ion etching (a dry etching method) is then used to etch the photoresist-patterned silicon wafer from the front side to produce ion-channel measurement apertures. The etching time and conditions are controlled so that the ion channel apertures are completely etched through the 5-10 micron thickness of silicon. After the ion-channel aperture is produced, the wafer is then thermally oxidized to produce a layer of $SiO_2$. The thermal oxidation process is controlled so that the final ion-channel measuring aperture is in the range of <0.5 micron and 2.5 micron in diameter. The preferred thickness of thermal oxidation layer is 0.2~3 microns Depending on whether the positioning structures are incorporated onto these chips, the wafer is then directly diced to make individual chips, or processed to make the positioning electrodes on the front side. For example, quadrapole electrode structures can be used as the positioning structures. The examples of quadrapole electrodes include, but not limited to, the polynomial electrodes, as described in "Electrode design for negative dielectrophoresis", by Huang and Pethig, in Measurement Science and Technology, Vol. 2, pages 1142-1146, and a number of electrodes disclosed in U.S. patent application (Ser. No. 09/643,362), titled "Apparatus and method for high throughput electrorotation analysis, filed on Aug. 22, 2000, naming Jing Cheng et al as inventors, which is incorporated by reference in its entirety. Standard photolithography procedures can be utilized in making such positioning electrodes. During fabrication of such positioning electrodes, it is necessary to ensure that the ion channel recording apertures are not covered, or blocked. Thorough cleaning and stripping is used to remove any deposited materials in the apertures. Alternatively, the ion channel apertures may be protected by, for example, first filling the ion channel recording apertures with materials that can be later removed, then going through the electrode-fabrication, and lastly removing the filling-materials. After the positioning electrodes are fabricated, the wafers are diced into individual chips.

(V.2.2) Example Two

SOI (Silicon-on-Insulator) Wafer Based Chips

As an alternative to the silicon wafer, a silicon-on-insulator wafer is used for producing ion channel chips. These wafers have a silicon-dioxide ($SiO_2$) layer in the middle, sandwiched between silicon layers on two sides. Looking at such a wafer in a cross-sectional view, a top silicon layer of certain thickness (e.g., 5 microns), a thin middle $SiO_2$ layer, and a bottom silicon layer (e.g. several hundred microns). Fabrication of ion channel chips using such SOI wafers follows a similar procedure to that used for silicon wafers, except for several specific differences.

Figure 22A:
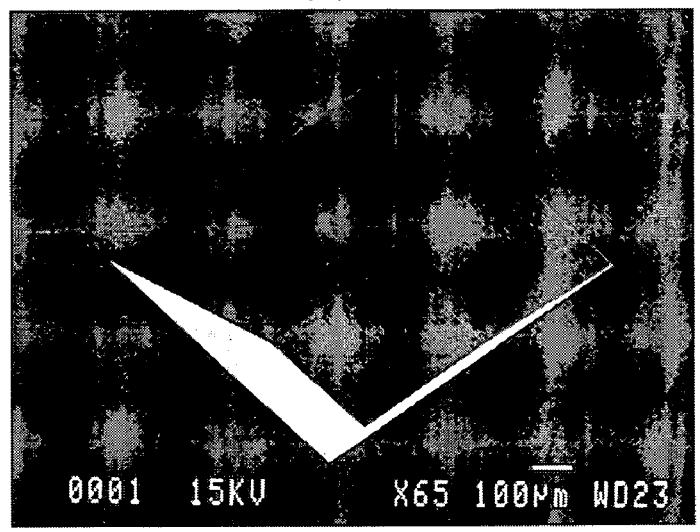
FIG. 22A shows an SEM (scanning electron microscopy) image of the backside opening on a silicon biochip for ion transport measurement and detection.
Figure 22B:
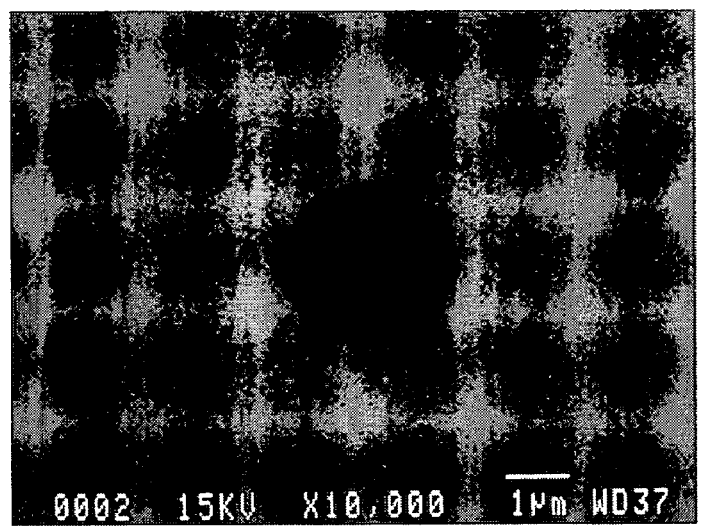
FIG. 22B shows an SEM image of an ion transport measurement aperture or hole fabricated on the front side of a silicon biochip.
Figures 23A, 23B:
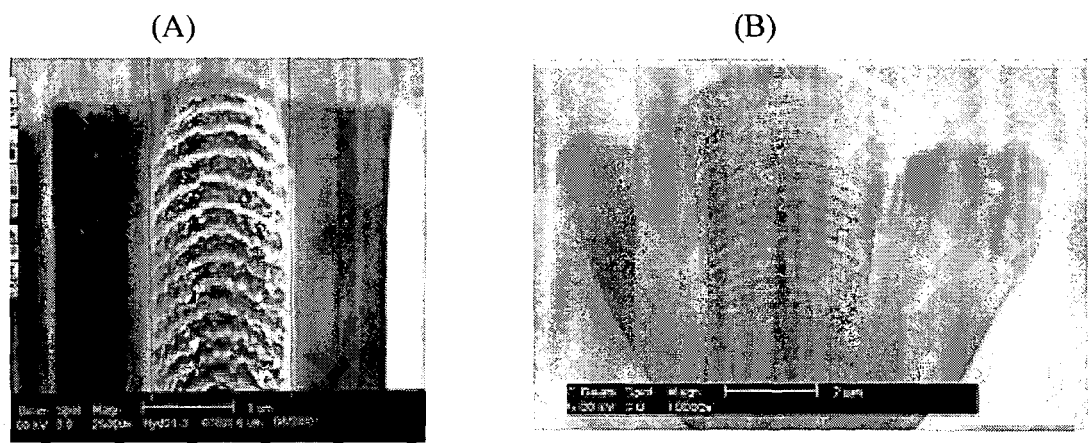
FIGS. 23A and 23B shows the cross-sectional SEM images of ion-transport or ion-channel measurement holes made on silicon substrates prior to the oxidation and after oxidation.

The brief summary of the fabrication process is as follows. The SOI wafer is first grown with a thin layer $SiO_2$ and/or $Si_3N_4$, which is then patterned with square-shaped (or other regular or irregular-shaped) opening to serve as a hard mask to produce an opening using backside etching. Anisotropic etching of the backside silicon (with <100>-orientation) with an angle of 54.7 degree is performed using KOH solutions. This step differs from the procedure for a solid silicon wafer, because the backside wet etching of silicon in this case would "stop automatically" at the middle $SiO_2$ layer, because the etching rate for $SiO_2$ is significantly lower than for etching the silicon layer. Thus, the etching time is not as critical as that used for a solid silicon wafer, for which special care is taken to ensure that the etching would leave 5-10 micron thick silicon from the front side. FIG. 22A shows an SEM image of the backside opening for an ion-channel chip. After removing the $SiO_2$ and/or $Si_3N_4$ mask layer, a photoresist is coated on the front-side of the wafer and is then patterned with circular openings of <1 micron to 3 micron in diameter for producing ion-channel measurement apertures. Deep reactive ion etching (RIE, a dry etching method) is used to etch the photoresist-patterned silicon wafer from the front side to produce ion-channel measurement apertures (FIG. 22B). Again, because of a much lower etching rate for $SiO_2$ than for silicon, the deep RIE would automatically "stop" at the middle $SiO_2$ layer. After deep RIE for ion channel apertures, a wet etching step (using, e.g. HF) is used to remove the middle $SiO_2$ layer. After the ion-channel aperture is produced and the middle $SiO_2$ layer is removed, the wafer is thermally oxidized to produce a coating layer of $SiO_2$. The thermal oxidation process is controlled so that the final ion-channel measuring apertures should be in the range of <0.5 micron and 2.5 micron in diameter. The cross-sectional images of ion-channel measurement apertures prior to the oxidation and after oxidation are shown in FIGS. 23A and 23B.

Figure 24:
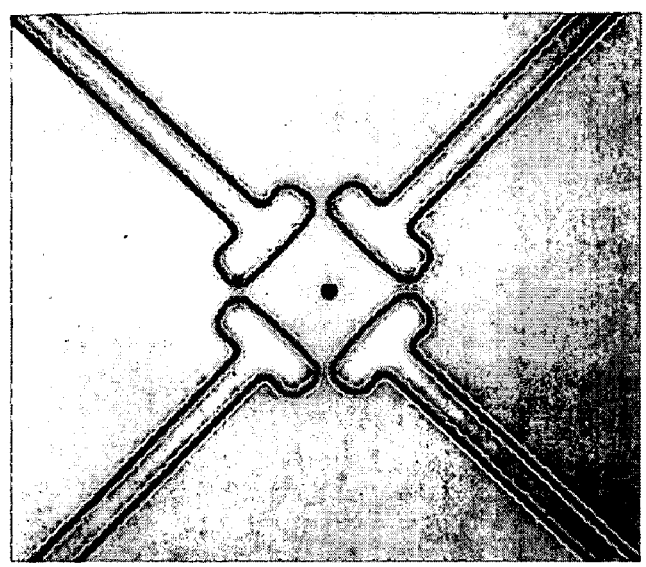
FIG. 24 shows a microscopic image of an ion transport measurement hole (or an ion channel recording hole) surrounded by a quadropole electrode structure for particle positioning.

Depending on whether the positioning structures are incorporated onto these chips, the wafer is then directly diced to make individual chips, or processed to make the positioning electrodes on the front side. For example, quadrapole electrode structures can be used as the positioning structures. The examples of quadrapole electrodes include, but not limited to, the polynomial electrodes, as described in "Electrode design for negative dielectrophoresis", by Huang and Pethig, in Measurement Science and Technology, Vol. 2, pages 1142-1146, and a number of electrodes disclosed in U.S. patent application (Ser. No. 09/643,362), titled "Apparatus and method for high throughput electrorotation analysis, filed on Aug. 22, 2000, naming Jing Cheng et al as inventors, which is incorporated by reference in its entirety. Standard photolithography procedures can be utilized in making such positioning electrodes. During fabrication of such positioning electrodes, it is necessary to ensure the ion channel recording apertures are not covered, or blocked. Thorough cleaning and stripping is used to remove any deposited materials in the apertures. Alternatively, the ion channel apertures may be protected by, for example, first filling the ion channel recording apertures with materials that can be later removed, then going through the electrode-fabrication, and lastly removing the filling-materials. After the positioning electrodes are fabricated, the wafers are diced into individual chips. FIG. 24 shows a microscopy image of an ion channel recording aperture surrounded by one type of positioning electrode structure.

(V.2.3) Example Three

Glass Chips

In the third example, glass is used as substrate material for making ion channel chips. The technique of "laser ablation" is used to produce ion channel recording apertures on the glass substrates. During laser ablation, a process called "photo dissociation" takes place when an excimer laser beam with certain energy densities (energy fluence with unit $J/cm^2$) hits the glass substrate. Because the short pulse duration of the laser, there is minimal thermal effect on the glass substrate from the laser-glass interaction. Instead, laser energy is absorbed directly by the electrons of the surface layers of atoms so that the bonds between atoms break, thereby removing layers of materials from the glass substrate. The absorption layer may be sub-micron. By using multiple pulses of laser beams, laser ablation can remove many microns of glass from the substrate. Because laser ablation only occurs at the path of the focused laser beam, a circular laser beam would result in a cylinder-shaped, near-cylinder-shaped, or truncated-cone-shaped hole produced on the glass. Further details about excimer laser and laser ablation can be found in the article by Patzel R and Endert H, titled "Excimer lasers: Once a scientific tool, the excimer laser now fills many roles", in "The Photonics Design and Applications Handbook, Book 3", pages H-239-248, published by Laurin Publishing Co., Inc., 1996.

The laser ablation effect is highly dependent on the wavelength of the laser. For example, both Argon/Fluoride 193 nm laser and Kr/Fluoride 248 nm laser may be used for processing various glass substrates. However, for a number of glass substrates, the energy transfer between the laser and the glass substrates for 248 nm laser may not be as efficient as 193 nm, and the inefficient energy between the laser and the glass substrates may result in certain undesired effects, e.g., cracking on the glass may occur during the laser ablation process. 193 nm and 248 nm lasers are examples of lasers that can be used for processing the glass substrates. Lasers of other wave lengths may also be used. In addition to the laser wavelength, other parameters or conditions that need to be carefully chosen during laser ablation include the laser pulse duration, interpulse time, duty cycle, laser energy density (fluence) and number of pulses. For a given glass type of given thickness, those who are skilled in laser ablation can readily determine and choose appropriate laser wavelengths and laser ablation conditions for producing holes or apertures of specified geometries. Alternatively, empirical testing could be used to find optimized conditions for parameters such as laser wavelength, energy density, pulse duration, duty cycle, for producing holes on given types of glasses.

Figure 25:
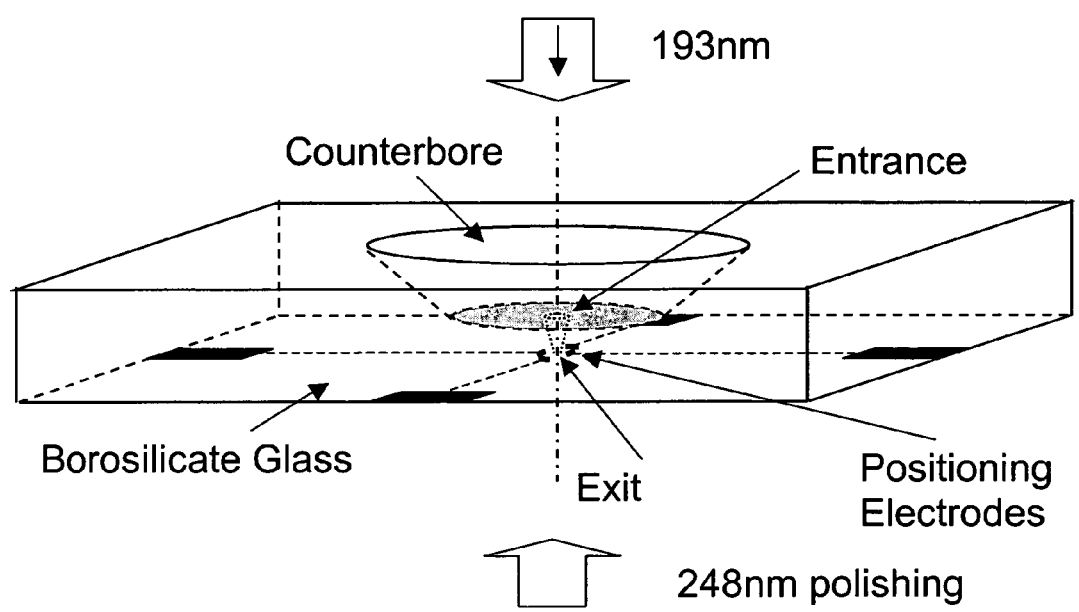
FIG. 25 shows a schematic representation of the laser ablation used to make ion transport measurement holes or ion channel recording holes on a solid substrate (for example glass).
Figure 26A:
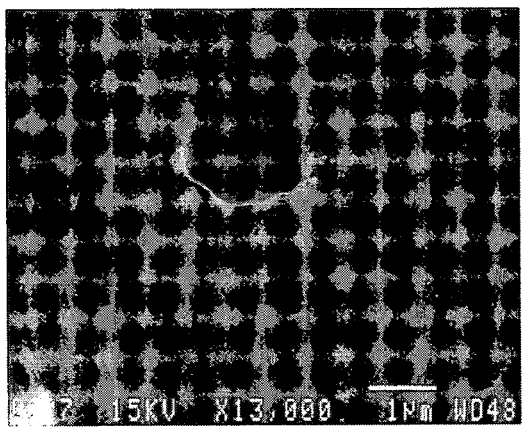
FIG. 26 shows SEM images of counter-pore (A) and entrance hole (A) and exit hole (B) for a glass biochip produced using laser ablation.
FIG. 26C shows an SEM image of two counter-pores and entrance hole for a glass biochip with double counter-pore configuration.
Figure 26B:
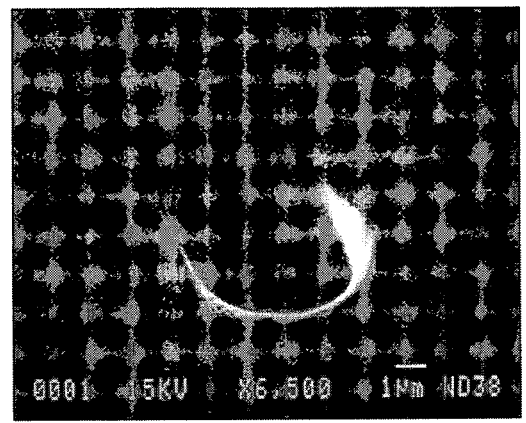

For the glass chips produced for our ion channel applications, both 193 nm and 248 nm lasers were used. Several types of glass were used in the fabrication, Corning AF-45 ($SiO_2$, 50.4%; $B_2O_3$, 12.5%; $Na_2O$, 0.2%; $Al_2O_3$, 11.6%; BaO 24.1%), Corning 0211 ($SiO_2$, 64%; $B_2O_3$, 9%; ZnO, 7%; $K_2O$, 7%; $Na_2O$, 7%; $TiO_2$, 3%; $Al_2O_3$, 3%), Erie D263 (composition unknown) and Corning 7740 ($SiO_2$, 80.6%; $B_2O_3$, 13%; $Na_2O$, 4%; $Al_2O_3$, 2.3%). The glass substrates were rectangular in shape, varying from 9 mm by 9 mm to 22 mm by 60 mm, and had thickness between 100 micron and 170 micron. These geometries and dimensions are not limiting factors for use of the glass substrates for making the ion channel chips. Indeed, substrates of other regular or irregular shapes, other sizes, other thickness may also be used. For processing for ion channel holes, a 75 micron diameter counter-pore is first made by using a laser beam with a larger diameter ablating the glass substrate from the back side. This is followed by a second laser beam of smaller diameter that is focused on the exit hole, on the other surface. The number of laser pulses and laser beam energy are controlled so that the first laser ablation process leaves behind about 30 micron thick glass and the second laser ablation process can go through the remaining 30 micron. For the second laser ablation, the laser beam comes in at an angle so that the entrance hole from the counter-pore is larger (e.g., 6~8 micron) than the exit hole (e.g., ~1.3±0.2 micron) giving a cone shaped carve-out. The schematic representation of the laser ablation used to make such ion channel recording apertures is shown in FIG. 25. The scanning electron micrographs of the counter-pore, entrance hole and exit hole for a glass chip are shown in FIG. 26. The size and geometry of the counter-pores and the ion channel recording apertures, and the procedure described above are the one that has been used for making glass chips. But these conditions and procedures are not the limiting factors of the present invention. For example, other procedure of laser ablation may also be used for producing the ion channel recording apertures on glass chips.

(V.3) Giga-Ohm Seal and Whole Cell Recording on Ion Channel Chips that were Treated or Surface-Modified with a Number of Conditions (V.3.1) Silicon Wafer Based Chips and SOI Wafer Based Chips To mimic the surface compositions of conventional glass capillary electrodes, ion channel chips made from silicon and SOI wafers were coated with Borosilicate glass using vapor phase deposition. Two tubes of patch clamp glass capillaries (Type 7052 or 7056 glass) were melted and used as the target during glass deposition. Coating was done from both front and back sides of the ion channel chips. Coating thickness was 3000 to 10,000 Å. Prior to use in the ion channel recording, the Borosilicate coating was "flamed" (flame annealed) using a propane torch (propane flame) to relax the stress on the glass. Such a "burning" process simulates the fire polishing procedure for the patch pipettes.

Figure 27:
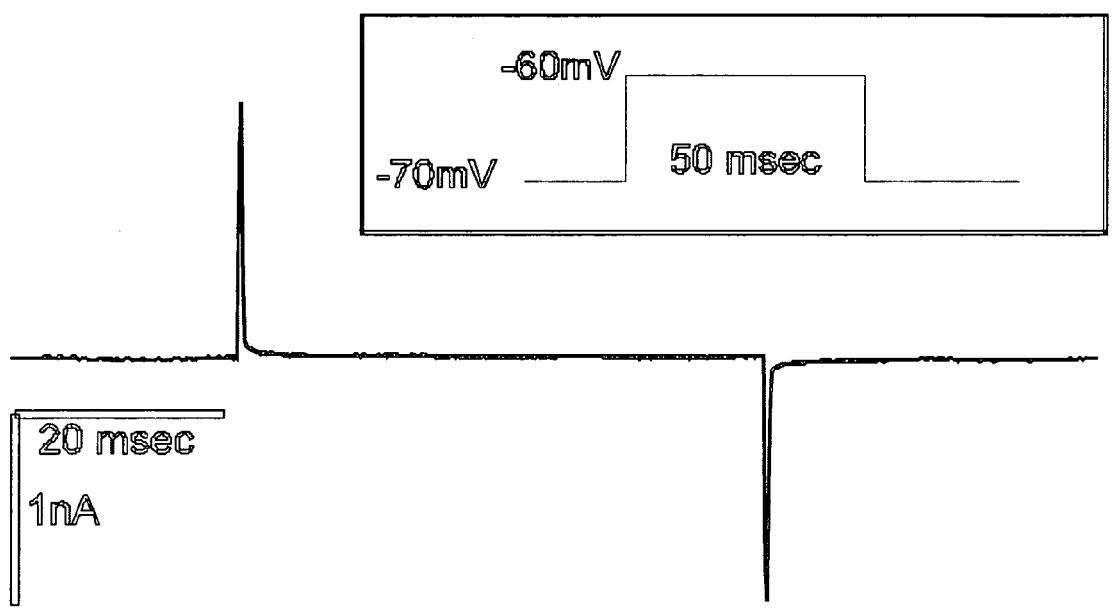
FIG. 27 shows an example of the current recorded in response to a voltage step (from −70 mV to −60 mV, pulse width of 50 ms) for a RBL-1 cell engaged with a hole on a silicon wafer based chip that has been deposited with a layer of Borosilicate glass.

In one example, for a silicon-wafer-based chip with a 2-2.5 micron aperture, after coating with 3000 Å of Borosilicate glass, a 2 giga-ohm seal was obtained on a RBL-1 cell. In the experiment, a RBL-1 cell was sucked into the ion channel recording aperture with a negative pressure (around −30 torr) the resistance quickly rose to 2 giga-ohm after the negative pressure was released. The seal-formation process was quite similar to that with a patch pipette. FIG. 27 shows an example of the current record in response to a voltage step (from −70 mV to −60 mV, pulse width of 50 ms) for this cell.

In another example, for a SOI-wafer-based chip with a 1.5 micron aperture coated with 3000 Å of Borosilicate glass, a high giga-ohm (40 giga ohm) seal was achieved. In the experiment, a RBL-1 cell was sucked into the ion channel recording aperture with a negative pressure (>−50 torr). Repeated suction and release eventually formed the 40 giga-ohm seal.

Figures 28A, 28B:
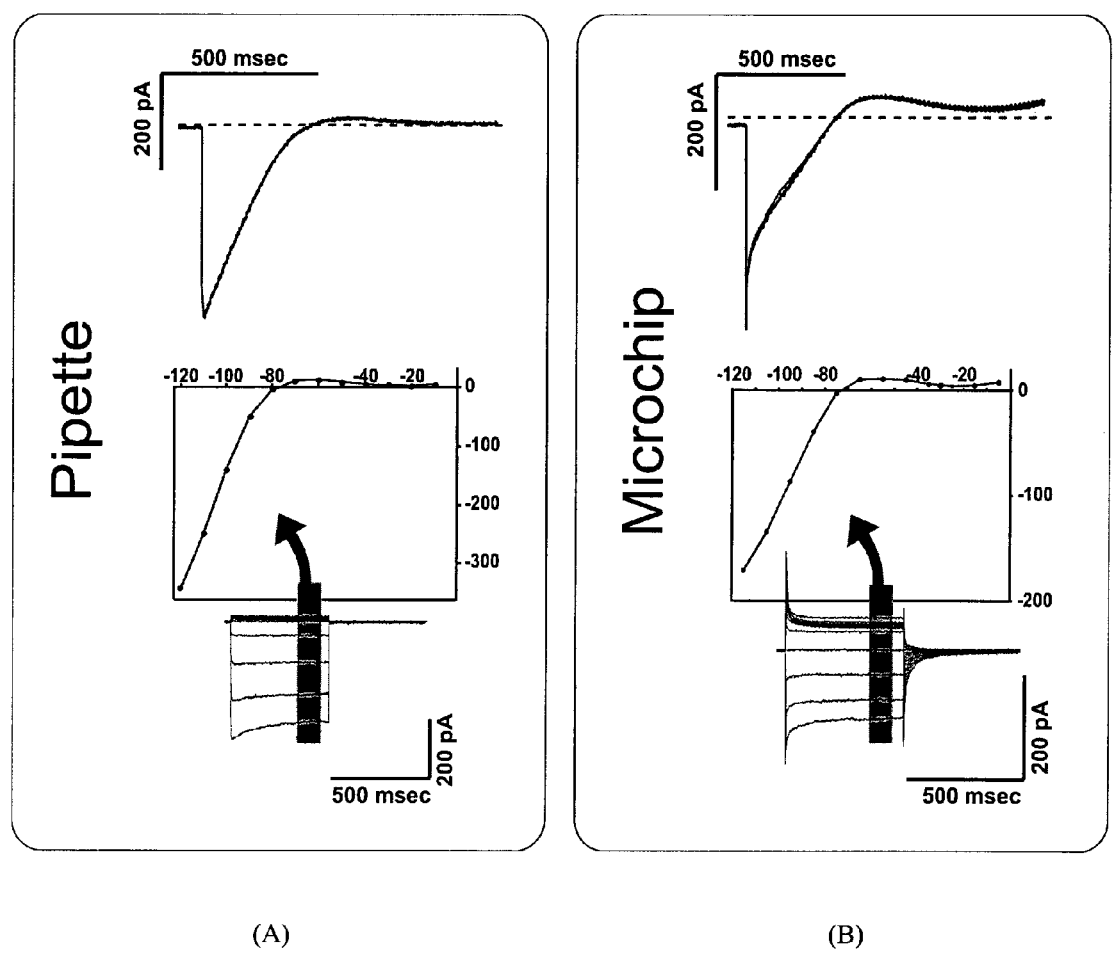
FIGS. 28A and B shows a comparison for the whole cell currents for two RBL-1 cells recorded using a conventional patch-clamp glass capillary electrode (panel A) or a biochip made from SOI (silicon-on-insulator) wafer (panel B).

In still another example, for a SOI-wafer-based chip with a 1.5 micron aperture coated with 3000 Å of Borosilicate glass, a whole cell access and recording was achieved. In the experiment, a RBL-1 was sucked into the ion channel recording aperture with a negative pressure (sloping from −30 to −150 torr). The seal resistance increased after the cell was in position with suction applied, and when it reached about 120 M-ohm, the membrane patch within the measurement aperture ruptured and electrical signals at the bottom chamber were applied to the cell interior via the ion channel recording aperture. This whole cell access is also sometimes called a "break-in". With subtraction of leakage current, the ion channel current from this RBL-1 cell was recorded with a voltage-ramp protocol and with a voltage-step protocol. FIGS. 28A and B shows a comparison for the whole cell currents for two RBL-1 cells recorded using a patch-clamp glass capillary electrode (panel A) or a SOI-based ion channel chip (panel B). On top is shown the current responses for a ramping voltage protocol in which the voltage applied across the cell membrane linearly varied with time from −120 mV to 60 mV at a rate of 120 mV/second. Significant current was observed at voltages far below −80 mV, and near-zero current was measured at voltage between 0 and −40 mV. The bottom panel shows the current record in response to a protocol in which a family of voltage steps (−80 mV holding potential, stepped for 500 msec at 2 sec intervals to between −120 mV and +60 mV in 20 mV increments) was applied across the cell membrane. The steady state current values for such voltage step signals are plotted in the middle of the panels A & B as a function of the voltage step amplitude. Again, significant current was observed at voltages below −80 mV, and near-zero current was measured at voltage between 0 and −40 mV. Clearly, there is a good match between current responses obtained with a patch pipette electrode and with a glass-coated chip.

(V.3.2) Glass Chips (V.3.2.1) Glass-Chip Baking

Glass chips were baked in a muffle furnace at certain temperatures to release the stress within the glass (in particular in the regions close to the ion transport measuring means) and to clean the chips by combustion of any organic "dirt" substances. First, the temperature of the furnace was raised to the desired value (e.g. 630° C.). The glass chip placed on a flat surface was then introduced into the furnace and baked for a specified length of time. During this time period, the temperature of the furnace returned to the desired value and was maintained within 1° C. accuracy. The baking time is typically set at 30 min. For 0211 glass, a baking temperature between 570° C. and 630° C. was used. For D263 glass, a baking temperature of 635° C. was used. For AF45, a baking temperature of 720° C. was used. Baking of glass chips may not be a necessary step for chip treatment. For glass chips that were processed with certain wavelength lasers, stress within the chips may not be a serious problem for chip handling and mounting. Glass cleaning may use other methods. Yet, in some instances, the glass baking seemed to increase the overall success rate of sealing. A wide range of baking temperatures can be used for cleaning the chips and for releasing the stress within the glass. If the baking time is quite short, then even temperatures higher than the softening point may be used.

(V.3.2.2) Surface Treatment

A number of surface treatment protocols were tested.

Figure 29:
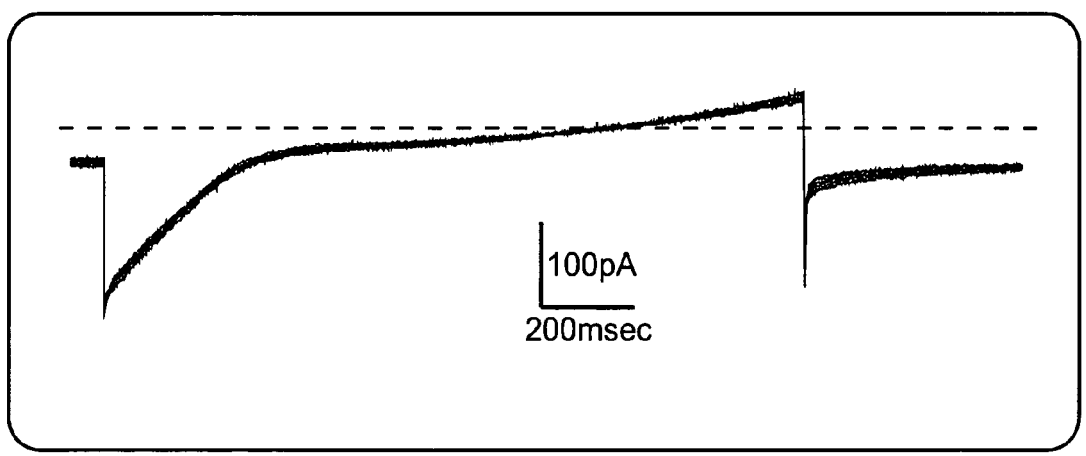
FIG. 29 shows the whole cell recording from an RBL-1 cell using a glass biochip for a voltage ramp protocol. The glass chip was baked at 570° C. for about 1 h and stored in de-ionized $H_2O$ for about 2 hrs.

(1) $H_2O$ storage and treatment. After baking, the glass chips were stored in de-ionized $H_2O$ for many hours (ranging from less than 1 hour to over 2 days). Using this protocol, we achieved a 2 Giga-ohm seal for a RBL-1 cell on a D263 glass chip that was baked at 570° C. for one hour and stored in $H_2O$ for ~2 hours. A good whole cell recording was achieved. However, the same treatment condition did not result in giga-ohm seal for another 7 chips. The whole cell recording on a RBL-1 cell on this chip for a ramping voltage protocol, in which the voltage applied across the cell membrane linearly varied with time from −120 mV to 60 mV at a rate of 120 mV/second, is shown in FIG. 29. $H_2O$ storage or treatment also improved the sealing properties of glass chips, even without baking of the glass chips beforehand.

Figure 30:
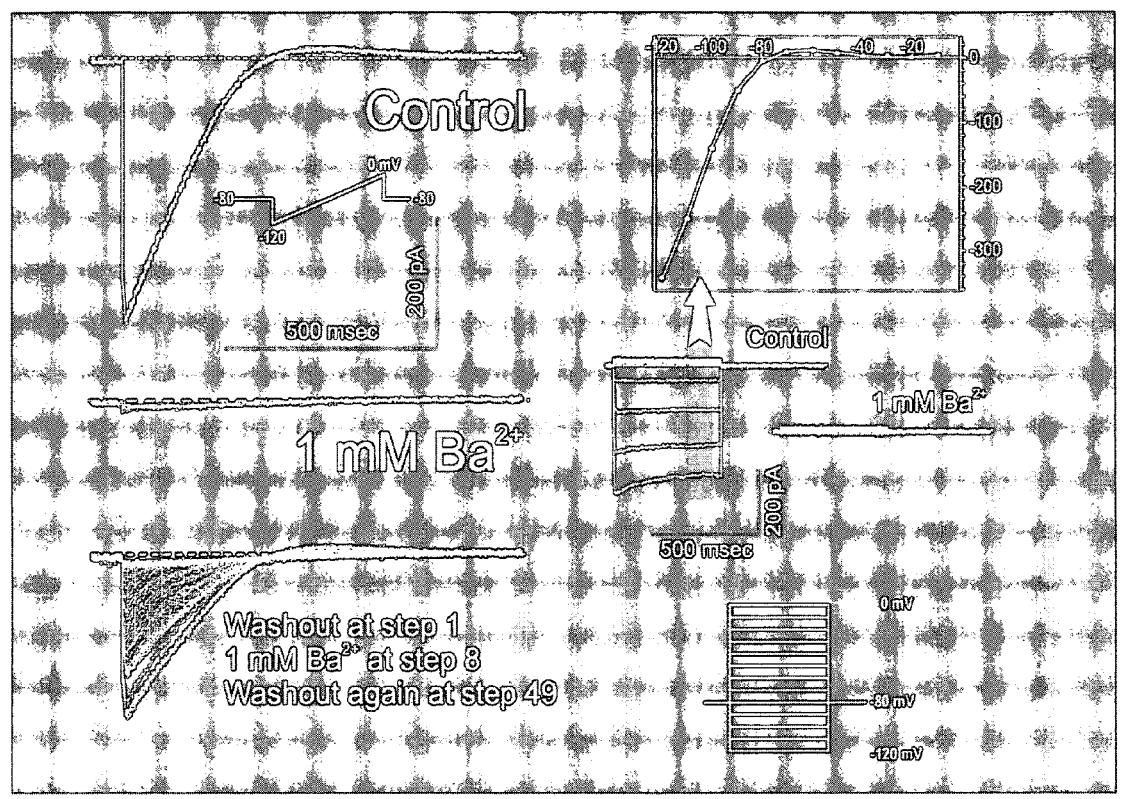
FIG. 30 shows the whole cell recording from an RBL-1 cell obtained with a conventional patch clamp glass capillary electrode.
Figure 31:
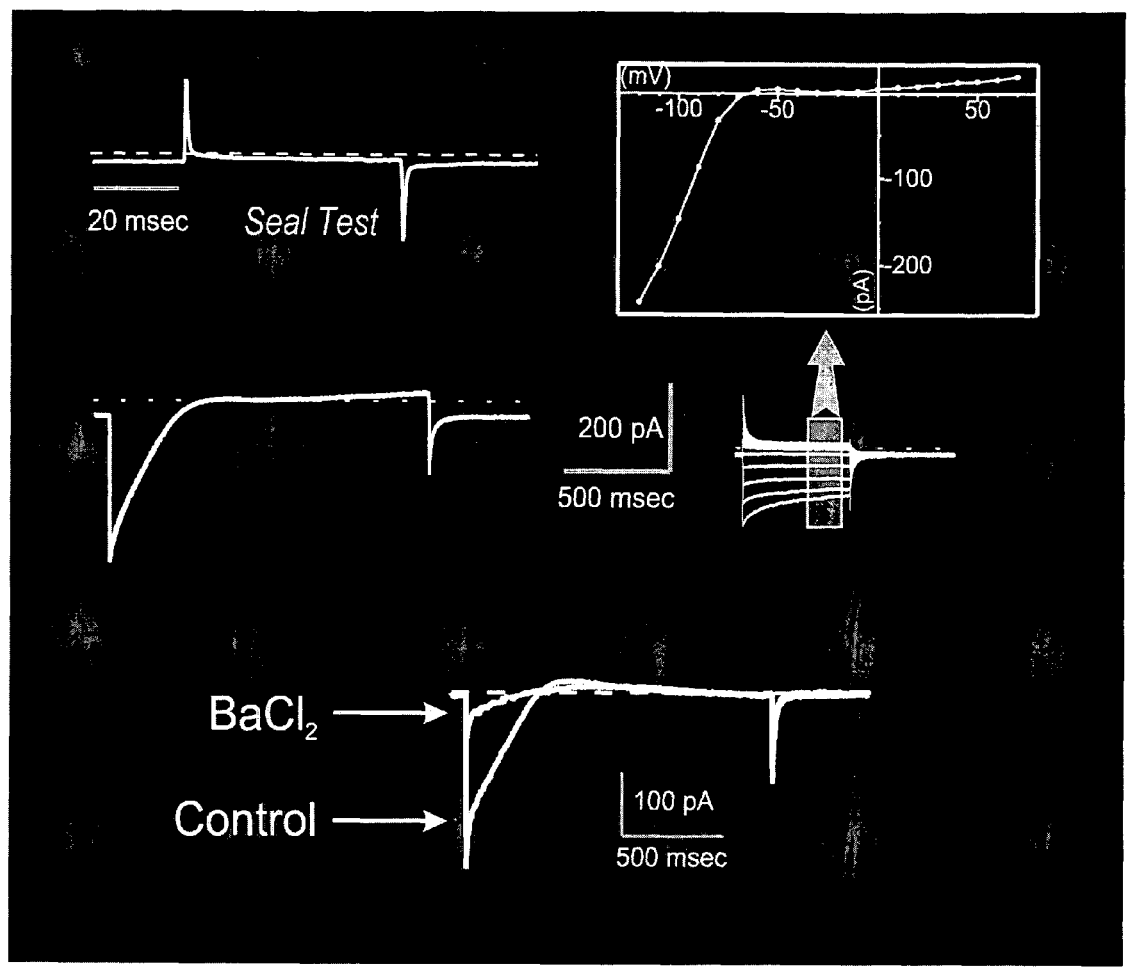
FIG. 31 shows the whole cell recording from an RBL-1 cell using a glass biochip that was treated in a basic solution followed by H$_2$O storage/treatment.

(2) Base treatment followed by $H_2O$. After baking, the glass chips were treated in a NaOH solution (1M to 5M) for 10 to 300 minutes (typically 30 min), and were then transferred into de-ionized $H_2O$ for storage/treatment. For glass chips made of either D263 or 0211 glasses, after they were treated by this method, we achieved a seal rate of about 50%. A sample whole cell recording is shown in FIG. 31 in comparison with the whole cell recording obtained on conventional patch glass capillaries (FIG. 30). Similar to the results shown in FIG. 28, panels A and B, there is a good agreement in the whole cell recordings between those obtained on a conventional patch pipette and those on a glass chip. FIGS. 30 and 31 further demonstrate an inhibition of the whole-cell current by the addition of barium chloride, a known inhibitor of this ion channel.

Figure 32:
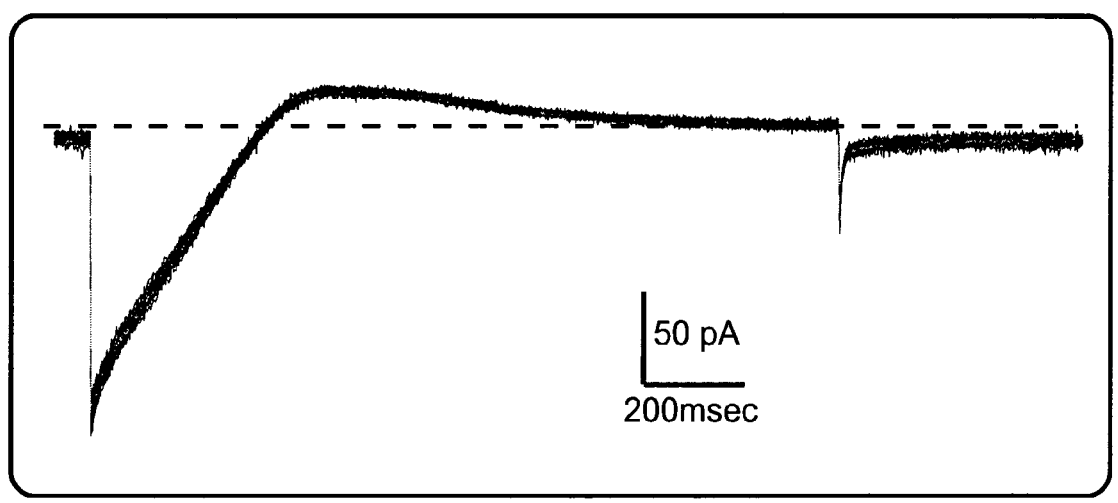
FIG. 32 shows an exemplary whole-cell recording for a RBL-1 cell recorded on a glass chip, that was baked and followed by treatment using acidic solution, basic solution and H$_2$O storage/treatment.
Figure 33:
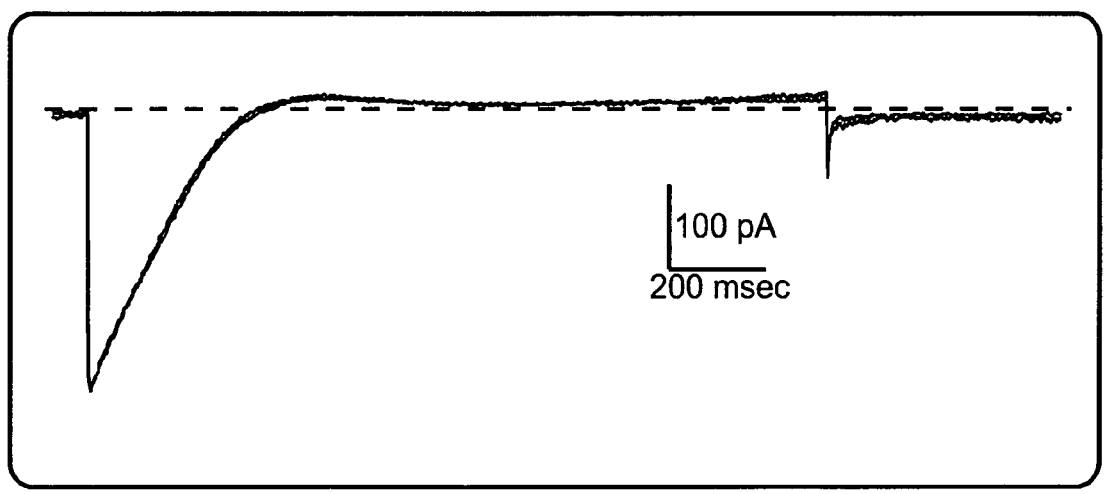
FIG. 33 shows an exemplary whole-cell recording from an RBL-1 cell recorded on a glass biochip without baking treatment but treated sequentially with acid, base, and H$_2$O.

(3) Acid treatment followed by base treatment and $H_2O$. With or without baking the chips, the glass chips were first treated with $HNO_3$ (6 M) for 4 or 5 hours, then treated with NaOH (5M) for 30-45 minutes, and were then transferred into de-ionized $H_2O$ (pH=6-7) for storage/treatment. For glass chips (made from 0211 glass) baked at 630° C. followed by the above-described acid-base-treatment, we achieved 54% seal rate. FIG. 32 shows an exemplary whole-cell recording for a RBL-1 cell recorded on a glass chip, that was treated by this method. A ramping voltage protocol was used for the recording in FIG. 32, in which the voltage applied across the cell membrane linearly varied with time from −120 mV to 60 mV at a rate of 120 mV/second. For glass chip (made from 0211 glass) without baking, we achieved 71% seal rate. An exemplary whole-cell recording for a RBL-1 cell recorded on such a glass chip is shown in FIG. 33. A ramping voltage protocol was used for the recording in FIG. 33, in which the voltage applied across the cell membrane linearly varied with time from −120 mV to 60 mV at a rate of 120 mV/second.

(4) Laser polishing followed by Acid treatment and then by base treatment. After the ion transport measuring hole on the glass chip was made, the area around the aperture on the front side of the chips was polished (and cleaned) with an excimer laser. Such laser polishing has several functions: smoothing the chip surfaces and smoothing ion transport measuring holes, removing or smoothing re-deposited glass material, and cleaning off any residual materials remaining on the glass surface. Using another treatment protocol, a non-sticky layer for cells was created on the top surface of the glass substrate using a coating (for example, polyethylene glycol (PEG) coated or bonded surface). In this case, laser polishing also removed the non-sticky surface layer only at the focused center area, creating a cell-sticky area with a polished glass surface surrounding the ion transport measuring hole and a non-sticky area surrounding the cell-sticky area. This surface pattern allows for effective positioning by DEP (dielectrophoresis) and other particle positioning means whilst retaining high cell stickiness near the ion transport measuring means. Laser polishing can also be used to pattern thin gold film surface electrodes while at the same time polishing the ion transport measuring hole area.

Figure 34:
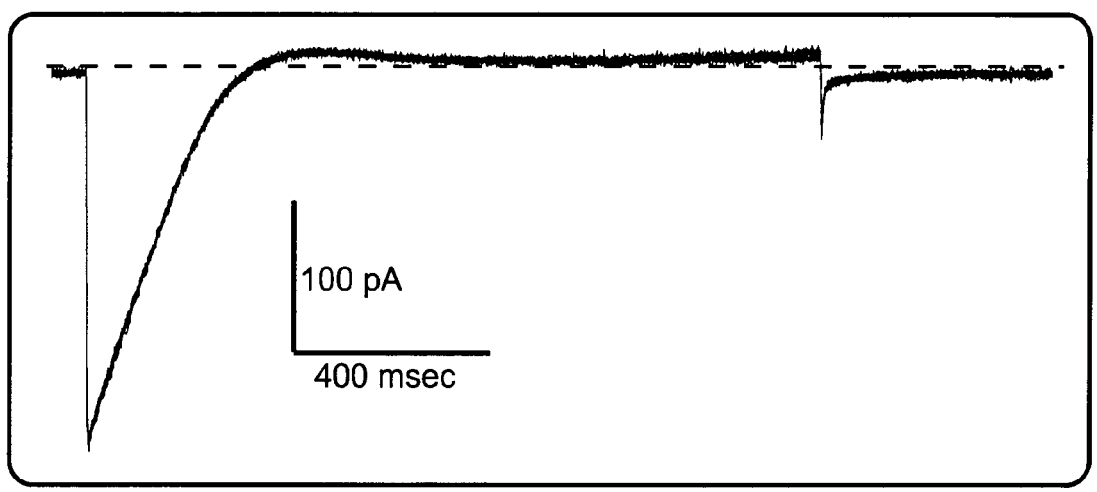
FIG. 34 shows an exemplary whole-cell recording for a RBL-1 cell recorded on a glass chip that was laser-polished on the side of chip surface corresponding to the extracellular chamber, followed by acid-base-water treatment.

The diameter of polished area was between 20 to 140 μm, although smaller or larger areas can also be used. The laser conditions (laser energy fluence, pulse number etc) used here were different from those used for laser ablation. Whilst those who are skilled in laser ablation of glass may readily determine appropriate laser-polishing conditions, these conditions may also be empirically determined by testing a range of conditions. For several types of glasses we tried, it was found that a 248 nm laser with certain energy fluence, attenuation degree, etc, provided the best polishing results. The laser-polished glass chips were then subjected to $HNO_3$ treatment and then NaOH treatment as described above. For such treatment protocols, a near-100% seal rate was achieved with the majority of the seal resistances in the high-giga ohm range (>4 giga-ohms). Exemplary whole cell recording is shown in FIG. 34. A ramping voltage protocol was used for the recording in FIG. 34, in which the voltage applied across the cell membrane linearly varied with time from −120 mV to 60 mV at a rate of 120 mV/second.

Examination of glass chips under optical microscopy revealed that acid treatment affects the glass surface by, at least in part, cleaning the surface. Glass chips that had gone through acid-base-$H_2O$ treatment appeared to be cleaner (sometimes much cleaner) than glass chips without the acid treatment step. In examples described above, nitric acid at a high concentration was used. Nitric acid at other concentrations and other acids (for example HCl) of different concentrations may also be used.

Base treatment appears to be an important step in modifying chip surface properties for enhancing or facilitating high resistance electric sealing between the hole on the chip and a cell membrane. In the examples described above, a high concentration of NaOH was used. NaOH at other concentrations and other base types (for example KOH) of different concentrations may also be used. Base treatment of glass surfaces results in a more negatively-charged surface. More negatively-charged surfaces appear to correlate with improved success rate in achieving high resistance electrical seals.

In addition to base treatment for obtaining a negative or more negatively charged surface on glass chips, other surface treatment or surface modification methods can also be used to obtain negatively charged surfaces. For glass chips, the negatively charged surface of the hole arises from or at least in part from negatively charged silanol groups. Glass chips or chips made of other materials, such as, but not limited to, plastics and polymers, can also be modified to contain a surface with other negatively charged chemical groups, such as, but not limited to, sulfate, phosphate, and carboxyl groups. One approach is to modify a surface by providing sulfate groups on the surface. In one strategy, the chip surface can first be pre-modified with vinyl groups and the negatively charged sulfate groups can then be added by co-polymerizing a neutral monomer (for example acrylamide) and a sulfate group containing monomer (for example 2-(sulfooxy)ethyl methacrylate ammonium) with pre-modified vinyl groups (as described in article entitled "Charged surface coating for capillary surface" by M. Huang, G. Yi, J. S. Bradshaw and M. L. Lee, Journal of Microcolumn Separations, volume: 5, page 199-205, 1993). In this way, the surface (negative) charge density can be controlled by using different ratios of acrylamide to 2-(sulfooxy)ethyl methacrylate ammonium. In addition, such negatively charged surface density is pH independent or nearly independent over a pH range between 3 and 9. Chips with different surface charge density values may be used and optimized for different types of the cells to facilitate high resistance electric seals.

In brief summary, preferred treatment/storage conditions for glass chips include:
(1) Glass chips—laser polishing—storage—NaOH treatment—de-ionized water
(2) Glass chips—laser polishing—storage—$Ca^{++}$ treatment—de-ionized water
(3) Glass chips—laser polishing—storage—Acid treatment—NaOH treatment—de-ionized water
(4) Glass chips—laser polishing—storage—Acid treatment—$Ca^{2+}$ treatment—de-ionized $H_2O$
(5) Glass chips—storage—baking—NaOH treatment—de-ionized water
(6) Glass chips—storage—baking—Acid treatment—NaOH treatment—de-ionized water
(7)—Glass chips—storage—baking—Acid treatment—$Ca^{2+}$ treatment—de-ionized water In addition, when glass chips are required to be stored and shipped, they can be preserved and shipped in de-ionized $H_2O$ with appropriate pH values or in a salt solution (e.g., PBS, a diluted form of PBS, such as 0.1×PBS, or concentrations of salt ranging from low (millimolar or less) to high molarity (such as, for example, 3 M $CaCl_2$)).

(V.3.2.3) Dielectrophoresis-Based Auto-Positioning

Figure 35A:
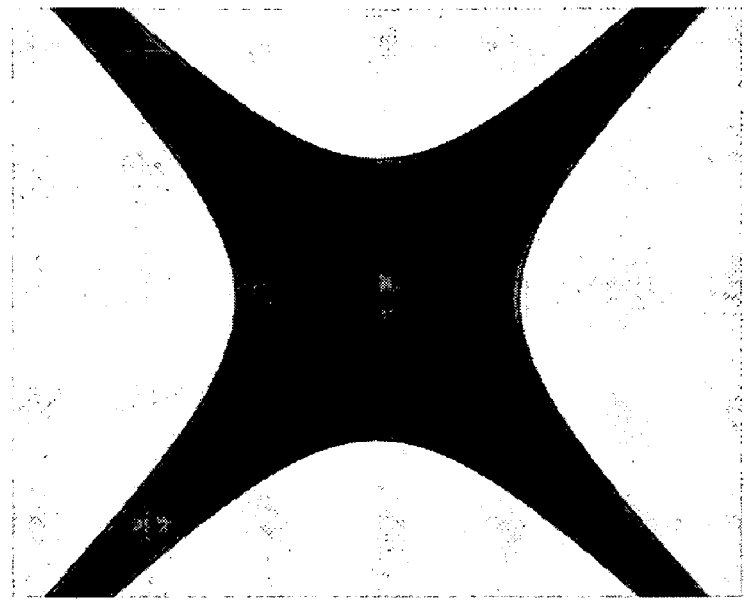
FIG. 35A shows the electrodes (light region) and the interelectrode spaces (dark region).
Figure 35B:
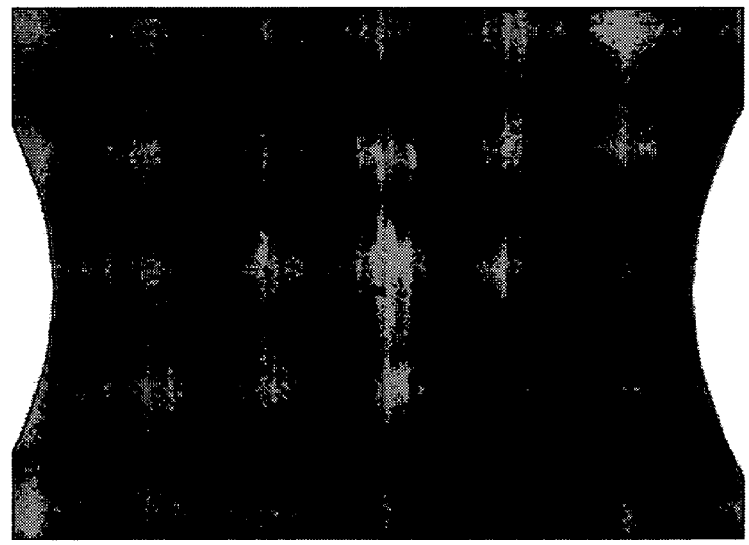
FIG. 35B shows the ion transport measuring hole in the central region of the interelectrode space.

Dielectrophoresis-based auto-positioning of cells was demonstrated on a glass-chip with a 150 micron polynomial electrode array (see FIG. 35) The light region on FIGS. 35A and 35B shows the electrodes and the dark region shows the interelectrode spaces, the center of which correspond the ion channel measuring aperture (or hole). The glass chip was made from a coverglass (made from 0211 glass)_, and was not polished by laser. The glass chip was baked at 630° C. for 1 hour and stored in de-ionized $H_2O$ for 2 days. Prior to use, the chip was treated with ~5 M NaOH for 15 minutes. The bottom chamber was filled with intra-cellular solution (in mM: 70 KCl, 70 K-Gluconate, 1.5 $MgCl_2$, 1 EGTA, 1 Mg-ATP, pH 7.2) and the solution was further pushed through the ion channel aperture to the top surface. The top chamber (>400 µL, <450 µL) was then filled with extra-cellular solutions (in mM: 150 NaCl, 10 HEPES, 10 Glucose, 4.2 KCl, 2 $CaCl_2$, 1.5 $MgCl_2$, pH 7.4). The chamber was then loaded onto the microscope stage for examination and the electrical connections for monitoring the seal process and recording whole-cell currents were made. The microscope lighting was turned off in order to avoid any heat-induced convection.

Figure 36:
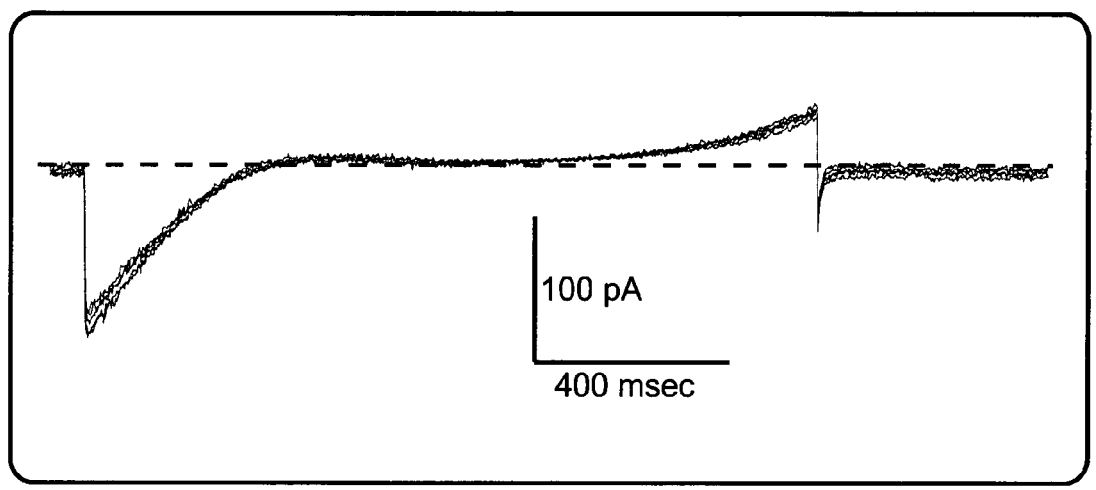
FIG. 36 shows the whole cell recording of a RBL-1 cell on a glass biochip after the cell was positioned with dielectrophoretic forces followed by a slight negative pressure applied to the ion transport recording hole from the bottom chamber (alternatively, a slight positive pressure can be applied to the hole from the top chamber).

10 µL of cell suspension (~2×10$^6$ cells per mL) was added into the chamber and immediately an AC electrical sine wave signal was applied continuously at 125 kHz and 3 V peak-to-peak to the positioning electrodes. With a slight negative pressure (~−20 torr) applied to the bottom chamber, the resistance between the top chamber and bottom chamber through the ion channel recording aperture was monitored. At one minute after AC signal application, the resistance across the top and bottom chamber jumped from 3 MOhm to about 20 MOhm. Turning on the microscope revealed that one cell had landed onto the ion channel recording aperture. The negative pressure (~−20 torr) was maintained and the resistance continued to increase until about 200 MOhm when the whole cell access was achieved. Seal properties continued to improve slightly even after whole-cell access. Whole cell recording was achieved (see FIG. 36). A ramping voltage protocol was used for the recording in FIG. 36, in which the voltage applied across the cell membrane linearly varied with time from −120 mV to 60 mV at a rate of 120 mV/second.

(V.4) Cartridge Construction

Figure 37:
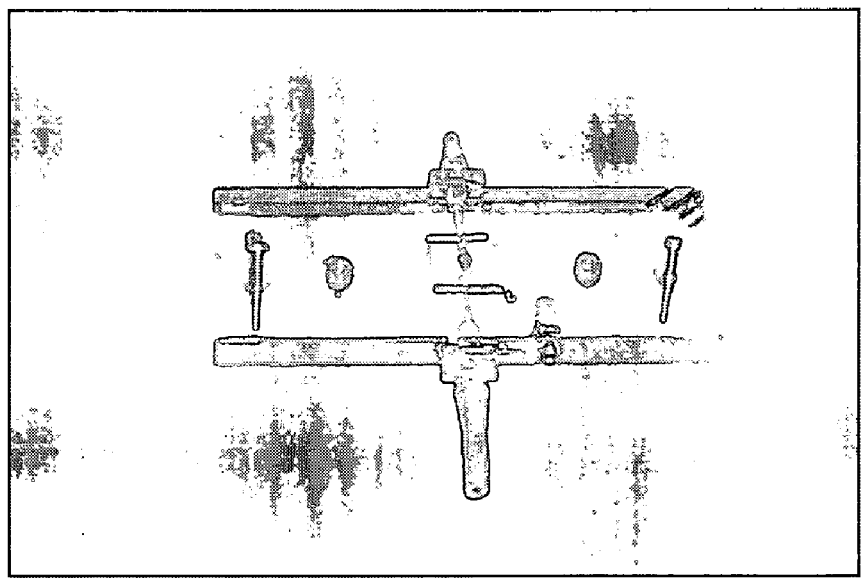
FIGS. 37A and 37B show the photographic images of various cartridges for testing ion channel biochips.
Figure 37:
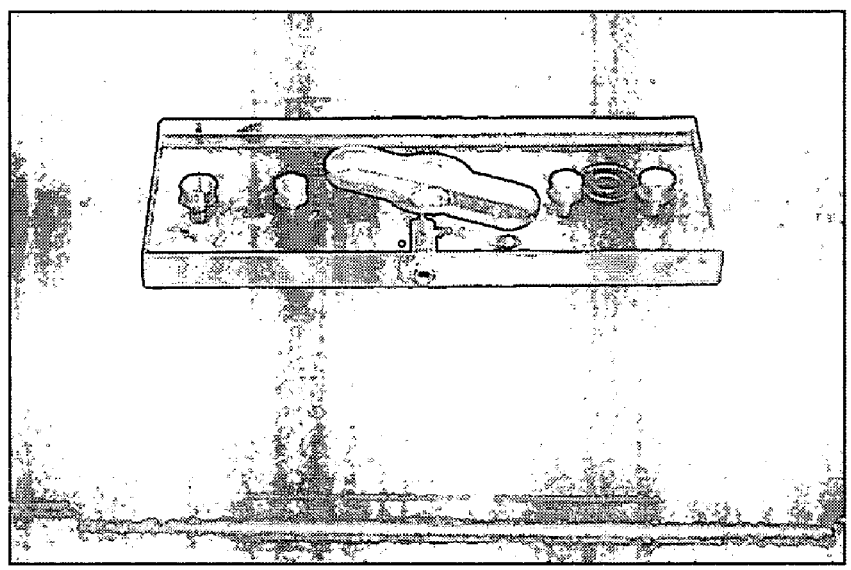

Various cartridge structures are tested and developed. FIGS. 37A and 37B show one of the examples. Several components are needed for constructing one chamber (called extracelluar chamber) above the ion channel chip and one chamber (called intracellular chamber) below the ion channel chip.

For the intracellular chamber, the component (shown in FIG. 37A) is made of a rectangular piece of polycarbonate plastic. Machine drilling is performed at the center locations of the two surfaces defined by its length and height along the direction of the width to produce two horizontal channels (of a diameter 1 mm) within the polycarbonate piece. The two channels are aligned and drilled to near the center of the piece, but not connected. Drilling is also made from the center of the top major surface of the rectangular piece in two diverging angles to meet the two horizontal channels. Thus, a continuous channel is formed, starting from one-side horizontal channel, to the upward-angled channel, to the opening on the major surface of the piece, to the other-side angled-channel, and ending at the other-side horizontal-channel. The opening at the center of a major surface of the polycarbonate piece is used to align with the back side of the ion channel recording aperture in the ion channel chip. For electrical connection to the intracellular chamber, an Ag/AgCl electrode wire (or other wires such as platinum wire or gold wire), used as the test or clamp electrode for patch-clamp recording, is introduced into this continuous channel.

For the extracellular chamber, the component (shown in FIG. 37B) is also made from a rectangular piece of polycarbonate plastic. Access to the top-side of the recording aperture of the ion channel chip is provided through a 3 mm hole on the bottom of the extracellular chamber. The chamber is then enlarged on the top side to contain a larger volume for the purpose of a) receiving an aliquot of cells, b) providing sufficient volume to make extracellular solution concentrations constant in spite of a small amount of intracellular solution that may leak through the recording aperture on the ion channel chip, c) hold a coverslip above the recording chamber to facilitate microscopic visualization, and d) provide access to the underside of the coverslip for delivery of cells and drugs with a pipette. The center of the opening (a 3 mm hole going through) is used to align with the ion channel recording aperture of an ion channel chip. A channel is drilled from the top surface on one side of the opening with an angle so that the channel will be ended on one of the sidewalls of the large openings. An Ag/AgCl electrode wire (or platinum wire, or gold wire), to function as the reference electrode during voltage-clamping, can be introduced into the opening via this channel.

For constructing the recording cartridge, a chip is sandwiched between top and bottom chamber pieces with PDMS molded seals on each side of the glass substrate, ensuring the through holes on the top chamber, the ion channel recording aperture on the chip and the opening on the bottom piece are perfectly aligned.

(V.5) Experimental Procedure

A typical experimental procedure is as follows. After mounting a chip onto the recording cartridge, the bottom chamber (i.e., the intracellular chamber) is first loaded with the intracellular solutions. The intracellular solution is then pushed through the ion channel recording aperture to reach the top chamber (i.e., the extracellular chamber) so that the ion channel recording aperture is filled with intracellular solutions. Immediately after that, the top chamber is loaded with extra-cellular solutions using a pipette. The cartridge is then loaded onto the microscope stage. Electrical connections from the intracellular electrodes and extracellular electrodes to the connections in the preamplifier head-stage are made. The resistance through the ion channel recording apertures is monitored with an AXON Instruments patch clamp amplifier (Axopatch 200B), Digidata 1320 computer interface and pClamp8 software. A small aliquot of cell suspension is then introduced into the top chamber. A slight negative pressure is applied to suck the cells onto the recording aperture. The landing of a cell on the aperture results in an immediate change in the resistance across the top and bottom chambers. Maintaining the negative pressure, or releasing and applying the negative pressure again facilitates sealing. Sealing resistance is continuously monitored throughout this procedure. After a giga-ohm seal is achieved, further increasing the pressure results in break-in and whole-cell access (i.e. membrane sealed within the ion channel recording aperture is ruptured by pressure). After compensating for the leakage resistance and capacitance, whole cell recordings can be made.

(V.6) Inverted Chamber

Figure 38:
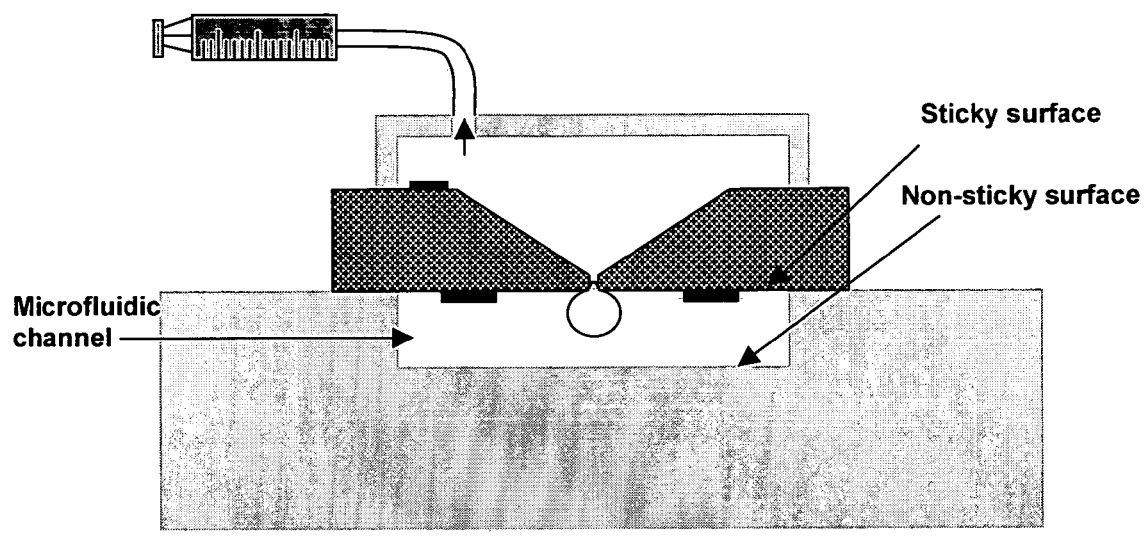
FIG. 38 shows a diagram of a cartridge that is operated isuch that the intracellular chamber is on the top of the biochip and the extracellular chamber now is below the biochip with hole opening downward from the top of the chamber.
Figure 39:
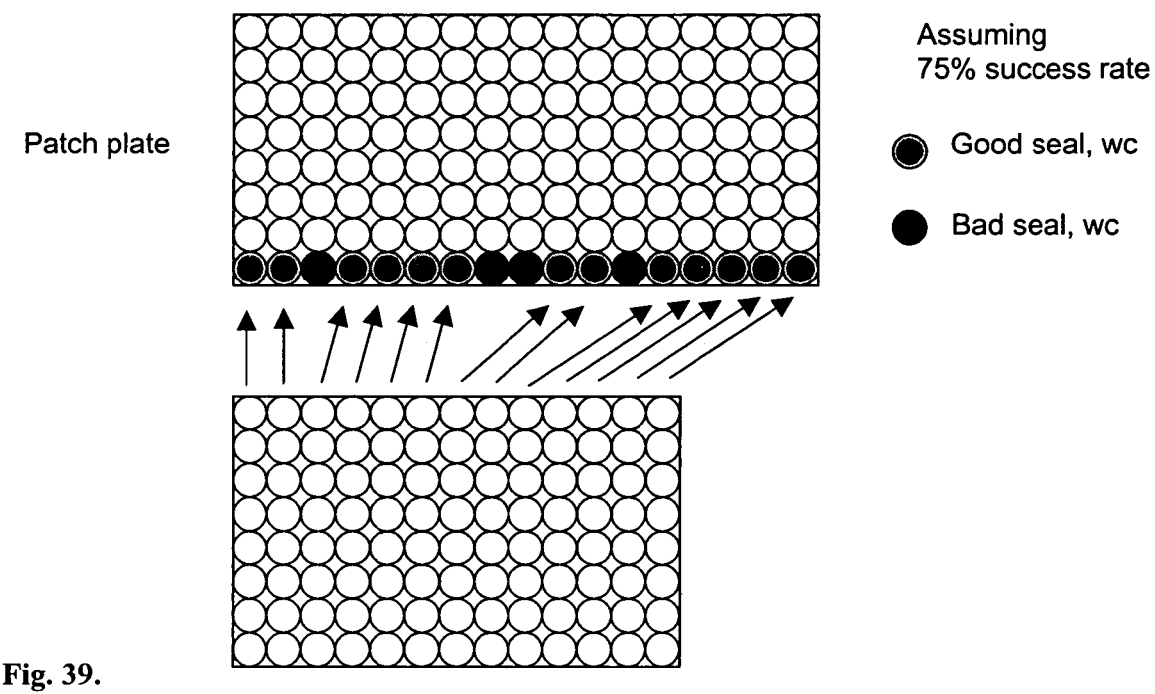
FIG. 39 illustrates the principle of a method for addressing the problem of relatively low success rate in patch clamping.

Ideally, it is required that the surface near the ion channel recording aperture be "sticky" to the cells for easy "sealing" and that the surface away from the recording aperture is "slippery" to facilitate positioning of the cells on chip by DEP (dielectrophoresis). In another design, the "aperture on a substrate" is inverted so that the intracellular chamber faces upward and the extracellular chamber now is inverted with aperture opening downward from the top of the chamber, as shown in FIG. 38. Cells are delivered through a microfluidic channel made from non-sticky materials such as PDMS, leaving the chip surface as modified or treated for sealing (e.g., sticky to the cells). When cells are delivered, they will settle down to the "slippery", bottom surfaces of the chamber due to sedimentation arising from gravity and will not move up to stick to the surface of the chip. Electrical signals are then applied to the positioning electrode structures on the chip so that the cells are positioned to the center, which is vertically aligned with and in close proximity to the ion channel recording aperture. After cells are positioned, a negative pressure is applied to suck the cells onto the recording aperture.

(V.7) Addressing Success Rate Problem

For drug screening, success rate is crucial because retesting unsuccessfully-assayed compounds is costly. The success rate is defined by the ratio of number of successful measurements to number of total measurements. For whole-cell recording of ion channel currents, the success rate is the percentage of successful whole cell recording with giga-ohm seals with respect to the total cells being measured. In many cases, over 90%, even close to 100%, success rate is required for compound screening and/or testing. For on-chip patch clamping, the success rate of seal formation and whole cell recording may be below 90%. To address this problem, an approach is devised to take advantage of the seal-testing in "patch clamping". FIG. 18 illustrates the principle of this method. Here, for testing 96 compounds with a device having 85% success rate, instead of using "8 by 12" plates, plates having "8 by 15" wells are made and used. Compounds are added row by row from a compound plate having 8×12 wells. Importantly, addition of compounds to the wells in the patch plate is controlled electronically so that only those wells that have been tested with successful sealing and whole cell access are used for screening. The wells with no or poor sealing, or without good whole cell access are skipped, i.e., no compounds are wasted. Because of 85% success rate in seal formation and whole cell access, a "8 by 15" plate will have 102 wells in which successful seal and whole cell access are achieved, providing enough number of wells for testing 96 compounds.

Figure 40:
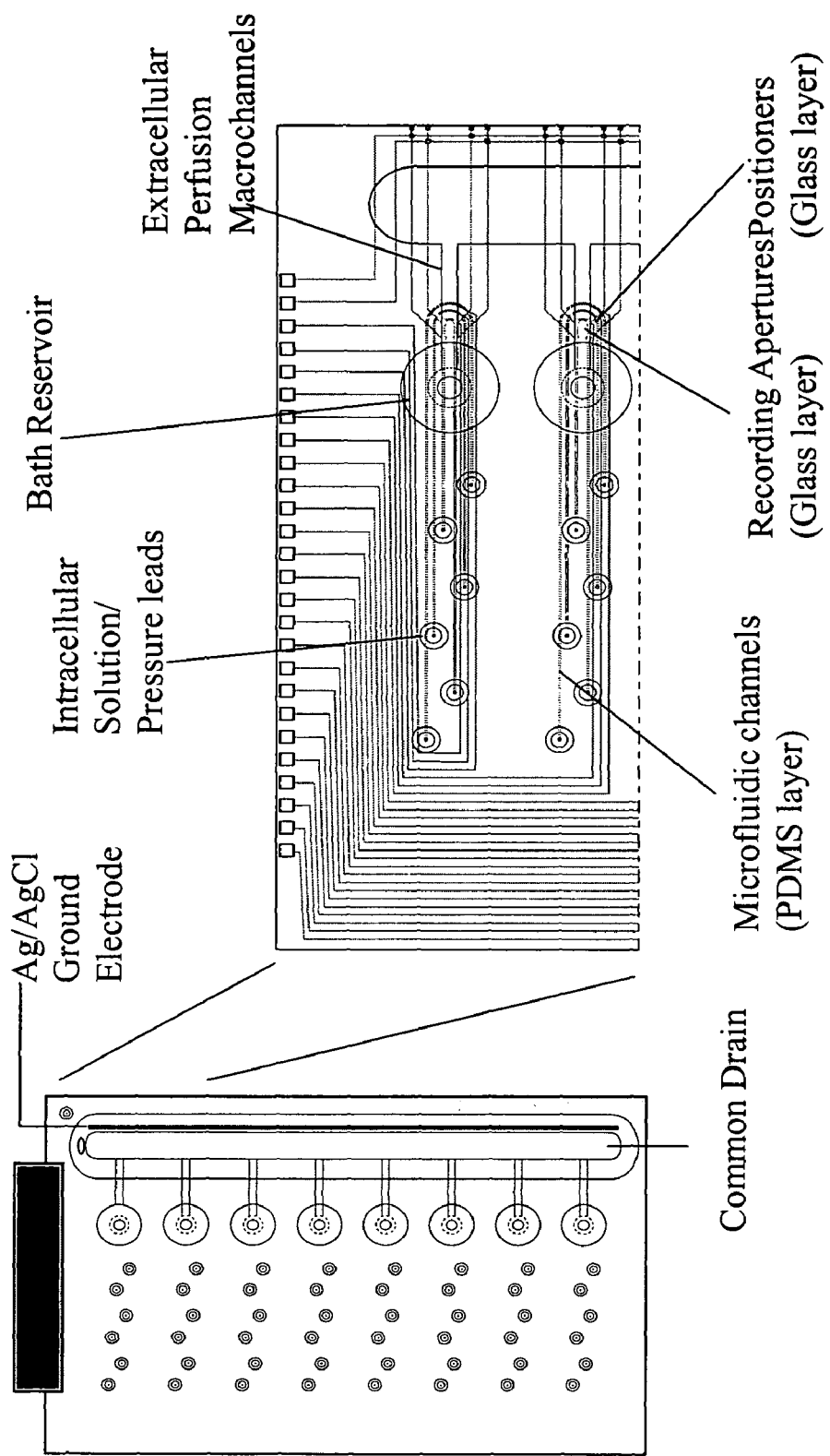
FIG. 40 shows the schematic drawing for a cartridge having eight ion transport recording wells.

An alternate design is proposed whereby multiple redundancy is provided at each well by placing multiple recording apertures into a fluidic path connecting an inflow well to an outflow well. In this format only 8 inflow wells are provided on a single cartridge and these 8 wells are arranged on a cartridge to facilitate delivery of compounds from a single row of a 96-well plate during drug screening. The multiple recording apertures per well ensure that at least one successful whole-cell access will be available for screening the compound. Multiple cartridges (12) may be used simultaneously to simultaneously screen an entire 96-well plate with high (near 100%) success rate. Such a cartridge may also be used to simultaneously record from all successful whole-cell accesses for each well to provide multiple data points from each inflow well, thereby reducing the costs of pharmaceutical secondary and safety screening. The outflow well of such cartridge may be shared among all the inflow wells and emptied by suction to prevent back-flow (see FIG. 40). The intracellular chamber may be perfused with microfluidics, with fluidic connections on the top side of the cartridge to reduce the chance of introducing bubbles into the microfluidic channels. Each microfluidic channel on the intracellular chamber contains an independently controlled test electrode printed onto the chip surface, and a common reference electrode exists in the extracellular chamber in the common outflow well. Positioning electrodes in the extracellular chamber are either printed onto the chip surface, or are embedded in the fluidic channel connecting the inflow well to the outflow well.

All headings are for the convenience of the reader and should not be used to limit the meaning of the text that follows the heading, unless so specified.

We claim:

1. A biochip, comprising:
   one or more holes that extends through said biochip,
   wherein when said biochip is in contact with a measurement solution, said holes have negatively charged surfaces and are capable of engaging particles or membranes with high resistance electric seals, wherein said resistance is between 1 mega ohm and 100 giga ohms,
   wherein said biochip comprises one or more materials selected from the group consisting of glass, quartz, silicon dioxide, silicon, plastics, polymers, polydimethylsiloxane (PDMS), oxygen plasma treated PDMS, and combinations thereof, and
   wherein said surfaces of said one or more holes comprise one or more SiOM groups or oxidized SiOM groups (SiO$^-$), where M is hydrogen or a metal, and the surface density of said SiOM groups and SiO$^-$ groups is more than about 10%.

2. The biochip of claim 1, wherein said surfaces of said one or more holes possess surface charge density approximately that or substantially equivalent to that of a capillary that has an electro-osmotic mobility between about $10^{-9}$ cm$^2$/(V sec) and about $10^{-4}$ cm$^2$/(V sec) in an aqueous solution that has an ionic concentration equivalent to that of a one in ten dilution of PBS in water, and a pH between about 7 and about 8.

3. The biochip of claim 1, wherein said surfaces of said one or more holes possess surface charge density approximately that or substantially equivalent to that of a capillary that has an electro-osmotic mobility between about $10^{-4}$ cm$^2$/(V sec) and about $3\times10^{-4}$ cm$^2$/(V sec) in an aqueous solution that has an ionic concentration equivalent to that of a one in ten dilution of PBS in water, and a pH between about 7 and about 8.

4. The biochip of claim 1, wherein said surfaces of said one or more holes possess surface charge density approximately that or substantially equivalent to that of a capillary that has an electroosmotic mobility between about $3\times10^{-4}$ cm$^2$/(V sec) and about $6\times10^{-4}$ cm$^2$/(V sec) in an aqueous solution that has an ionic concentration equivalent to that of a one in ten dilution of PBS in water, and a pH between about 7 and about 8.

5. The biochip of claim 1, wherein said biochip comprises one or more materials selected from the group consisting of silicon, plastics, polymers, polydimethylsiloxane (PDMS), oxygen plasma treated PDMS, and combinations thereof.

6. The biochip of claim 1, wherein the surface of said biochip comprises at least one chemical group selected from sulfate, phosphate, and carboxyl groups.

7. The biochip of claim 1, wherein said one or more holes is fabricated using laser ablation, laser drilling, or both.

8. The biochip of claim 1, wherein said biochip has been treated with oxygen plasma, reactive compounds, or radiation, or has been baked, fire polished, flame annealed, or laser polished.

9. The biochip of claim 8, wherein the front side surface of said biochip surrounding said at least one hole has been polished using a laser.

10. The biochip of claim 8, wherein said biochip has been baked.

11. The biochip of claim 1, wherein said one or more holes of said biochip have been treated with base, or treated with acid and with base.

12. The biochip of claim 11, wherein said one or more holes of said biochip have been treated with base.

13. The biochip of claim 12, wherein said base is selected from group consisting of NaOH, KOH, LiOH, CsOH, NaOH, Ba(OH)$_2$, Ca(OH)$_2$, and NH$_4$(OH).

14. The biochip of claim 12, wherein the base is a solution of a concentration of about 0.1 M or greater.

15. The biochip of claim 11, wherein said biochip has been treated with acid and then with base.

16. The biochip of claim 15, wherein said acid is selected from the group consisting of HCl, HF, HBr, HCOOH, HClO$_3$, H$_2$SO$_4$, NaHSO$_4$, H$_2$SO$_4$, or HNO$_3$.

17. The biochip of claim 15, wherein said acid is a solution having a concentration of greater than about 1M.

18. The biochip of claim 1, wherein said one or more holes is an array of holes.

19. The biochip of claim 18, wherein the size of said holes is between 0.5 micron and 5 microns.

20. A method of measuring ion transport activity of a particle, comprising:
    (a) contacting a sample comprising at least one particle with the biochip of claim 1;
    (b) engaging said at least one particle at said one or more holes; and
    (c) measuring ion transport activity of said at least one particle.

21. The biochip of claim 1, wherein the surface density of said SiOM groups and SiO$^-$ groups is more than about 30%.

22. The biochip of claim 1, further comprising a coating localized to the hole and optionally surrounding areas.

23. The biochip of claim 22, wherein the coating comprises a polymer that expands or contracts as temperature changes.

24. The biochip of claim 1, wherein said biochip has been laser-polished, treated with acid, then treated with base.

25. The biochip of claim 1, wherein said one or more holes of said biochip have been treated with H$_2$SO$_4$ and H$_2$O$_2$ and then with base.

26. A biochip, comprising:
    one or more holes that extends through said biochip,
    wherein when said biochip is in contact with a measurement solution, said holes have negatively charged surfaces and are capable of engaging particles or membranes with high resistance electric seals, wherein said resistance is between 1 mega ohm and 100 giga ohms,
    wherein said biochip comprises a polymer that comprises at least one negatively charged chemical group, and
    wherein said surfaces of said one or more holes possess surface charge density that is substantially pH independent over a pH range from 3 to 9.

27. The biochip of claim 26, wherein said biochip is coated with a polymer material that comprises at least one negatively charged chemical group.

28. The biochip of claim 27, wherein the coating comprises a polymer selected from the group consisting of polyimide, polyethyleneimine, PDMS, paralyene, and PMMA SU8.

29. The biochip of claim 26, wherein said one or more holes is fabricated using laser ablation, laser drilling, or both.

30. The biochip of claim 26, wherein said one or more holes of said biochip have been treated with acid, treated with base, or treated with acid and with base.

31. The biochip of claim 30, wherein said biochip has been treated with acid and then with base.

32. A method of measuring ion transport activity of a particle, comprising:

(a) contacting a sample comprising at least one particle with the biochip of claim 26;
(b) engaging said at least one particle at said one or more holes; and
(c) measuring ion transport activity of said at least one particle.

33. The biochip of claim 26, wherein said biochip has been laser-polished, treated with acid, then treated with base.

34. The biochip of claim 26, wherein said biochip has been treated with $H_2SO_4$ and $H_2O_2$ and then with base.

* * * * *